US012392775B2

(12) United States Patent
Oved et al.

(10) Patent No.: US 12,392,775 B2
(45) Date of Patent: Aug. 19, 2025

(54) MARKER COMBINATIONS FOR DIAGNOSING INFECTIONS AND METHODS OF USE THEREOF

(71) Applicant: MeMed Diagnostics Ltd., Tirat HaCarmel (IL)

(72) Inventors: Kfir Oved, Hof HaCarmel (IL); Eran Eden, Haifa (IL); Gali Kronenfeld, Tirat Carmel (IL); Olga Boico, Atlit (IL); Roy Navon, Tel-Aviv (IL); Assaf Cohen-Dotan, Natania (IL)

(73) Assignee: MeMed Diagnostics Ltd., Tirat HaCarmel (IL)

( * ) Notice: Subject to any disclaimer, the term of this patent is extended or adjusted under 35 U.S.C. 154(b) by 0 days.

(21) Appl. No.: 18/077,277

(22) Filed: Dec. 8, 2022

(65) Prior Publication Data

US 2023/0184760 A1   Jun. 15, 2023

Related U.S. Application Data

(62) Division of application No. 17/007,095, filed on Aug. 31, 2020, now abandoned, which is a division of application No. 15/531,747, filed as application No. PCT/IL2015/051201 on Dec. 10, 2015, now abandoned.

(60) Provisional application No. 62/136,725, filed on Mar. 23, 2015, provisional application No. 62/090,606, filed on Dec. 11, 2014.

(51) Int. Cl.
G01N 33/569 (2006.01)

(52) U.S. Cl.
CPC . *G01N 33/56911* (2013.01); *G01N 33/56966* (2013.01); *G01N 33/56983* (2013.01); *G01N 2800/26* (2013.01); *G01N 2800/60* (2013.01)

(58) Field of Classification Search
None
See application file for complete search history.

(56) References Cited

U.S. PATENT DOCUMENTS

| | | |
|---|---|---|
| 5,639,617 A | 6/1997 | Bohuon |
| 5,910,421 A | 6/1999 | Small, Jr. et al. |
| 6,077,665 A | 6/2000 | Welrich et al. |
| 6,136,526 A | 10/2000 | Venge |
| 6,210,661 B1 | 4/2001 | Enssle et al. |
| 6,709,855 B1 | 3/2004 | Stanton et al. |
| 6,756,483 B1 | 6/2004 | Bergmann et al. |
| 6,953,435 B2 | 10/2005 | Kondo et al. |
| 7,115,717 B2 | 10/2006 | Mori et al. |
| 7,132,246 B2 | 11/2006 | Bergmann et al. |
| 7,153,662 B2 | 12/2006 | Bergmann et al. |
| 7,157,081 B2 | 1/2007 | Bergmann et al. |
| 7,598,031 B2 | 10/2009 | Liew |
| 7,629,116 B2 | 12/2009 | Ott |
| 7,892,539 B2 | 2/2011 | Winoto et al. |
| 8,021,836 B2 | 9/2011 | Kolopp-Sarda et al. |
| 8,155,993 B2 | 4/2012 | de Nijs et al. |
| 8,465,951 B2 | 6/2013 | Rao et al. |
| 8,507,210 B2 | 8/2013 | Bergmann et al. |
| 8,563,476 B2 | 10/2013 | Lillard, Jr. |
| 8,697,370 B2 | 4/2014 | Kas et al. |
| 8,821,876 B2 | 9/2014 | Ginsburg et al. |
| 9,034,328 B2 | 5/2015 | Takahashi |
| 9,709,565 B2 | 7/2017 | Eden et al. |
| 9,726,668 B2 | 8/2017 | Oved et al. |
| 9,850,539 B2 | 12/2017 | Tsalik et al. |
| 10,010,252 B2 | 7/2018 | Ide et al. |
| 10,209,260 B2 | 2/2019 | Oved et al. |
| 10,303,846 B2 | 5/2019 | Eden et al. |
| 10,502,739 B2 | 12/2019 | Oved et al. |
| 10,859,574 B2 | 12/2020 | Oved et al. |
| 11,385,241 B2 | 7/2022 | Eden et al. |
| 11,466,331 B2 | 10/2022 | Oved et al. |
| 11,776,658 B2 | 10/2023 | Eden |
| 2002/0001402 A1 | 1/2002 | Berliner |
| 2002/0055176 A1 | 5/2002 | Ray |
| 2002/0059030 A1 | 5/2002 | Otworth et al. |
| 2004/0038201 A1 | 2/2004 | Nau et al. |
| 2004/0043379 A1 | 3/2004 | Hashimoto et al. |
| 2004/0171013 A1 | 9/2004 | Lilius et al. |
| 2004/0197769 A1 | 10/2004 | Wong et al. |
| 2004/0209307 A1 | 10/2004 | Valkirs et al. |
| 2005/0164238 A1 | 7/2005 | Valkiris et al. |
| 2005/0227223 A1 | 10/2005 | Miyawaki |
| 2005/0233395 A1 | 10/2005 | Weiser et al. |
| 2006/0040301 A1 | 2/2006 | Deirmengian |
| 2006/0052278 A1 | 3/2006 | Powell |
| 2006/0078998 A1 | 4/2006 | Puskas et al. |
| 2006/0099628 A1 | 5/2006 | Ching et al. |
| 2006/0246495 A1 | 11/2006 | Garrett et al. |
| 2007/0015172 A1 | 1/2007 | Zhang et al. |
| 2007/0184460 A1 | 8/2007 | Ching et al. |
| 2007/0231816 A1 | 10/2007 | Chaussabel et al. |
| 2007/0281319 A1 | 12/2007 | Kolopp-Sarda et al. |
| 2008/0020379 A1 | 1/2008 | Agan et al. |

(Continued)

FOREIGN PATENT DOCUMENTS

| | | |
|---|---|---|
| AU | 2012244350 | 11/2012 |
| CN | 1656378 | 8/2005 |

(Continued)

OTHER PUBLICATIONS

Van Deursen 2014, Heart Failure, vol. 7, p. 35-42).*

(Continued)

*Primary Examiner* — Agnieszka Boesen

(57) ABSTRACT

A method of determining an infection type in a subject is disclosed. The method comprises measuring the concentration of a first determinant selected from the group consisting of the determinants which are set forth in Table 1 and a second determinant selected from the group of the determinants which are set forth in Table 2 in a subject derived sample, wherein the concentration is indicative of the infection type.

8 Claims, 38 Drawing Sheets
(37 of 38 Drawing Sheet(s) Filed in Color)
Specification includes a Sequence Listing.

(56) References Cited

U.S. PATENT DOCUMENTS

| | | | |
|---|---|---|---|
| 2008/0064113 | A1 | 3/2008 | Goix et al. |
| 2008/0171323 | A1 | 7/2008 | Banchereau et al. |
| 2008/0261258 | A1 | 10/2008 | Smith et al. |
| 2009/0155180 | A1 | 6/2009 | Jump et al. |
| 2009/0203534 | A1 | 8/2009 | Hossain et al. |
| 2009/0246790 | A1 | 10/2009 | Cote et al. |
| 2010/0028874 | A1 | 2/2010 | Ramachandran et al. |
| 2010/0068147 | A1 | 3/2010 | Hibberd et al. |
| 2010/0143372 | A1 | 6/2010 | Yao et al. |
| 2010/0267569 | A1 | 10/2010 | Salmon et al. |
| 2010/0297611 | A1 | 11/2010 | Sambursky et al. |
| 2011/0059858 | A1 | 3/2011 | Kas et al. |
| 2011/0117563 | A1 | 5/2011 | Filipowicz et al. |
| 2011/0144914 | A1 | 6/2011 | Harrington |
| 2011/0166166 | A1 | 7/2011 | Henkin |
| 2011/0183856 | A1 | 7/2011 | Agan et al. |
| 2011/0225114 | A1 | 9/2011 | Gotthardt |
| 2011/0275542 | A1 | 11/2011 | Eden et al. |
| 2011/0312534 | A1 | 12/2011 | Kayser et al. |
| 2012/0114661 | A1 | 5/2012 | Ginsburg et al. |
| 2013/0166219 | A1 | 6/2013 | Shaw |
| 2013/0309168 | A1 | 11/2013 | Ho |
| 2014/0127827 | A1 | 5/2014 | Kim et al. |
| 2014/0206016 | A1 | 7/2014 | Lozano Sanchez et al. |
| 2014/0227324 | A1 | 8/2014 | Robinson et al. |
| 2014/0277284 | A1 | 9/2014 | Chen et al. |
| 2014/0349326 | A1 | 11/2014 | Ingber |
| 2015/0017630 | A1 | 1/2015 | Oved et al. |
| 2016/0041153 | A1 | 2/2016 | Brown et al. |
| 2016/0153993 | A1 | 6/2016 | Eden et al. |
| 2017/0030909 | A1 | 2/2017 | Oved et al. |
| 2017/0234873 | A1 | 8/2017 | Oved et al. |
| 2017/0235871 | A1 | 8/2017 | Eden et al. |
| 2017/0269081 | A1 | 9/2017 | Oved et al. |
| 2018/0074057 | A1 | 3/2018 | Eden et al. |
| 2018/0310854 | A1 | 11/2018 | Geva et al. |
| 2019/0011456 | A1 | 1/2019 | Oved et al. |
| 2019/0041388 | A1 | 2/2019 | Oved et al. |
| 2019/0085378 | A1 | 3/2019 | Eden et al. |
| 2019/0120837 | A1 | 4/2019 | Eden et al. |
| 2019/0161813 | A1 | 5/2019 | Oved et al. |
| 2019/0237156 | A1 | 8/2019 | Eden et al. |
| 2019/0242894 | A1 | 8/2019 | Oved et al. |
| 2019/0242895 | A1 | 8/2019 | Eden et al. |
| 2019/0271709 | A1 | 9/2019 | Eden et al. |
| 2019/0339189 | A1 | 11/2019 | Takeda et al. |
| 2020/0088728 | A1 | 3/2020 | Oved et al. |
| 2020/0124593 | A1 | 4/2020 | Oved et al. |
| 2020/0388347 | A1 | 12/2020 | Eden et al. |
| 2020/0393463 | A1 | 12/2020 | Oved et al. |
| 2020/0400668 | A1 | 12/2020 | Eden et al. |
| 2022/0011320 | A1 | 1/2022 | Eden et al. |
| 2022/0042994 | A1 | 2/2022 | Oved et al. |
| 2022/0236269 | A1 | 7/2022 | Eden et al. |
| 2022/0326256 | A1 | 10/2022 | Eden |
| 2022/0329345 | A1 | 10/2022 | Kaplan |
| 2022/0399074 | A1 | 12/2022 | Eden |
| 2023/0045305 | A1 | 2/2023 | Oved et al. |

FOREIGN PATENT DOCUMENTS

| | | |
|---|---|---|
| CN | 1751128 | 3/2006 |
| CN | 101208602 | 6/2008 |
| CN | 101479389 | 7/2009 |
| CN | 101523217 | 9/2009 |
| CN | 101541976 | 9/2009 |
| CN | 101611314 | 12/2009 |
| CN | 101617056 | 12/2009 |
| CN | 101617230 | 12/2009 |
| CN | 101622364 | 1/2010 |
| CN | 101790687 | 7/2010 |
| CN | 101932940 | 12/2010 |
| CN | 102081101 | 6/2011 |
| CN | 102257386 | 11/2011 |
| CN | 102301002 | 12/2011 |
| CN | 102858991 | 1/2013 |
| CN | 103097891 | 5/2013 |
| CN | 103119444 | 5/2013 |
| CN | 104126125 | 10/2014 |
| CN | 104159616 | 11/2014 |
| CN | 104204803 | 12/2014 |
| CN | 104204808 | 12/2014 |
| CN | 104969071 | 10/2015 |
| CN | 105556308 | 5/2016 |
| EP | 1489416 | 12/2004 |
| JP | 2005-106694 | 4/2005 |
| JP | 2007-518062 | 7/2007 |
| JP | 2008-502908 | 1/2008 |
| JP | 2011-069696 | 4/2011 |
| KR | 10-2016-0072626 | 6/2016 |
| RU | 2007122617 | 12/2008 |
| RU | 2011111875 | 10/2012 |
| UA | 78641 | 3/2013 |
| UA | 92843 | 9/2014 |
| WO | WO 95/29404 | 11/1995 |
| WO | WO 99/33965 | 7/1999 |
| WO | WO 99/60171 | 11/1999 |
| WO | WO 01/14535 | 3/2001 |
| WO | WO 2004/108899 | 12/2004 |
| WO | WO 2005/033327 | 4/2005 |
| WO | WO 2006/009702 | 1/2006 |
| WO | WO 2007/011412 | 1/2007 |
| WO | WO 2007/088355 | 8/2007 |
| WO | WO 2007/127801 | 11/2007 |
| WO | WO 2008/024642 | 2/2008 |
| WO | WO 2008/028489 | 3/2008 |
| WO | WO 2009/015821 | 2/2009 |
| WO | WO 2009/021521 | 2/2009 |
| WO | WO 2009/025743 | 2/2009 |
| WO | WO 2009/077864 | 6/2009 |
| WO | WO 2009/100907 | 8/2009 |
| WO | WO 2009/130176 | 10/2009 |
| WO | WO 2009/158521 | 12/2009 |
| WO | WO 2010/056637 | 5/2010 |
| WO | WO 2011/008349 | 1/2011 |
| WO | WO 2011/017682 | 2/2011 |
| WO | WO 2011/132086 | 10/2011 |
| WO | WO 2013/040062 | 3/2013 |
| WO | WO 2013/117746 | 8/2013 |
| WO | WO 2014/006408 | 1/2014 |
| WO | WO 2014/008545 | 1/2014 |
| WO | WO 2014/049255 | 4/2014 |
| WO | WO 2014/117873 | 8/2014 |
| WO | WO 2015/048098 | 4/2015 |
| WO | WO 2016/024278 | 2/2016 |
| WO | WO 2016/059636 | 4/2016 |
| WO | WO 2016/079219 | 5/2016 |
| WO | WO 2016/092554 | 6/2016 |
| WO | WO 2017/149547 | 9/2017 |
| WO | WO 2017/149548 | 9/2017 |
| WO | WO 2017/221255 | 12/2017 |
| WO | WO 2018/011795 | 1/2018 |
| WO | WO 2018/011796 | 1/2018 |
| WO | WO 2018/060998 | 4/2018 |
| WO | WO 2018/060999 | 4/2018 |

OTHER PUBLICATIONS

Landro et al. (Clinical and Experimental Immunology, 2008, vol. 152, p. 57-63).*

Landro 2008.*

Requisition by the Examiner Dated Mar. 2, 2023 From the Innovation, Science and Economic Development Canada, Canadian Intellectual Property Office Re. Application No. 3,015,043. (5 Pages).

Supplementary European Search Report and the European Search Opinion Dated Mar. 28, 2023 From the European Patent Office Re. Application No. 22204952.0. (12 Pages).

Abdel-Razik et al. "Diagnostic Utility of Interferon Gamma-induced Protein 10 kDa in Spontaneous Bacterial Peritonitis: Single-Center Study", European Journal of Gastroenterology & Hepatology, 27(9): 1087-1093, Sep. 2015.

(56) References Cited

OTHER PUBLICATIONS

Lighter et al. "Chemokine IP-10: an Adjunct Marker for Latent Tuberculosis Infection in Children", The International Journal of Tuberculosis and Lung Disease, 13(6): 731-736, Jun. 2009.
Punyadeera et al. "A Biomarker Panel to Discriminate Between Systemic Inflammatory Response Syndrome and Sepsis and Sepsis Severity", Journal of Emergencies, Trauma and Shock, 3(1): 26-35, Jan-Mar. 2010.
Quint et al. "Serum IP-10 as a Biomarker of Human Rhinovirus Infection at Exacerbation of COPD", Science Direct, Chest, 137(4): 812-822, Apr. 2010.
Ruhwald et al. "IP-10 Can Be Measured in Dried Plasma Spots in Patients with Chronic Hepatitis C Infection", PLoS ONE 7(9): e45181, 1-4, Sep. 14, 2012.
Requisition by the Examiner Dated Mar. 21, 2023 From the Innovation, Science and Economic Development Canada, Canadian Intellectual Property Office Re. Application No. 3,015,046. (6 pages).
English Summary and Translation Dated Sep. 13, 2023 of Notification of Office Action Dated Aug. 29, 2023 From the State Intellectual Property Office of the People's Republic of China Re. Application No. 202010370187.X. (3 pages).
Hearing Notice Dated Sep. 9, 2023 From the Government of India, Intellectual Property India, The Patent Office Re. Application No. 201727005513. (3 Pages).
Notice of Allowance Dated May 10, 2023 from the US Patent and Trademark Office Re. U.S. Appl. No. 17/875,467. (122 pages).
Wang et al. "The significance of MMP-8, MMP-9 and FFN levels in pregnant women with bacterial vaginosis", Maternal and Child Health Care of China, vol. 28, No. 28, 2013, pp. 4615-4617.
Notification of Office Action and Search Report Dated Dec. 9, 2022 From the State Intellectual Property Office of the People's Republic of China Re. Application No. 202010215941.2. (11 Pages).
Summary Dated Dec. 22, 2022 of Notification of Office Action and Search Report Dated Dec. 9, 2022 From the State Intellectual Property Office of the People's Republic of China Re. Application No. 202010215941.2. (4 Pages).
Hastie et al. "The Elements of Statistical Learning: Data Mining, Inference, and Prediction", Springer Series in Statistics, 2nd Ed., p. 1-745, 2001. (Part 1).
Hastie et al. "The Elements of Statistical Learning: Data Mining, Inference, and Prediction", Springer Series in Statistics, 2nd Ed., p. 1-745, 2001. (Part 2).
Ip et al. "Value of serum procalcitonin, neopterin, and C-reactive protein in differentiating bacterial from viral etiologies in patients presenting with lower respiratory tract infections", Diagnostic Microbiology and Infectious Disease, 59(2): 131-136, Oct. 2007.
Mount "Bioinformatics: Sequence and Genome Analysis", Chaps. 1-10: 1-564, 2001. (Part 1).
Mount "Bioinformatics: Sequence and Genome Analysis", Chaps. 1-10: 1-564, 2001. (Part 2).
Mount "Bioinformatics: Sequence and Genome Analysis", Chaps. 1-10: 1-564, 2001. (Part 3).
Pauksen et al. "Serum Mesurements of Human Neutrophil Lipocalin (HNL) Discriminate Between Acute Bacterial and Viral Infections", Scandinavian Journal of Clinical and Laboratory Investigation, 55(2):125-131, 1995.
Vapnik "Statistical Learning Theory", Adaptive and Learning Systems for Signal Processing, Communications, and Control, p. 1-732, 1998. (Part 1).
Vapnik "Statistical Learning Theory", Adaptive and Learning Systems for Signal Processing, Communications, and Control, p. 1-732, 1998. (Part 2).
Vapnik "Statistical Learning Theory", Adaptive and Learning Systems for Signal Processing, Communications, and Control, p. 1-732, 1998. (Part 3).
Vapnik "Statistical Learning Theory", Adaptive and Learning Systems for Signal Processing, Communications, and Control, p. 1-732, 1998. (Part 4).
English Summary Dated Dec. 29, 2022 of Notification of Office Action Dated Dec. 2, 2022 From the State Intellectual Property Office of the People's Republic of China Re. Application No. 202010370187.X. (1 Page).
CNKI "Clinical Study on the Level of Plasma Tumor Necrosis Factor-Related Apoptosis-Inducing Ligand (TRAIL) in Evaluating the Prognosis of Patients With Sepsis", CNKI Master's E-Journals, 5: 4-26, Apr. 16, 2014.
Notification of Office Action Dated Aug. 29, 2023 From the State Intellectual Property Office of the People's Republic of China Re. Application No. 202010370187.X. (3 Pages).
Official Action Dated Aug. 29, 2023 from the US Patent and Trademark Office Re. U.S. Appl. No. 17/372,575. (144 pages).
Fosgerau et al. "Interleukin-6 Autoantibodies are Involved in the Pathogenesis of a Subset of Type 2 Diabetes", Journal of Endocrinology,204: 265-273, 2010.
Gupta et al. "Dinstict Functions of Autoantibodies Against Interferon in Systemic Lupus Erythematosus", Arthritis & Rheumatology, 68(7): 1677-1687, Jul. 2016.
Meyer "Anti-CRP antibodies in Systemic Lupus Erythematosus", Joint Bone Spine, 77 384-389, Jun. 2, 2010.
Thermo Scientific "ELISA Technical Guide and Protocols", Thermo Scientific, TR0065.0, 2010 (14 Pages).
Decision to Refuse A European Patent Application Dated Mar. 15, 2023 From the European Patent Office Re. Application No. 17759389.4. (4 Pages).
Partial European Search Report and the European Search Opinion Dated Jan. 31, 2023 From the European Patent Office Re. Application No. 22169859.0. (13 Pages).
Official Action Dated Apr. 19, 2023 from the US Patent and Trademark Office Re. U.S. Appl. No. 17/507,994. (189 pages).
Kramer et al. "Development and Characerization of New Rat Monoclonal Antibodies for Procalcitonin", Analytical and Bionalytical Chemistry, 392: 727-736, Aug. 19, 2008.
Vermot-Desroches et al. "Characterization of Monoclonal Antibodies Directed Against Trail or Trail Receptors", Cellular Immunology, 236(1-2): 86-91, Jul.-Aug. 2005.
Requisition by the Examiner Dated Oct. 10, 2023 From the Innovation, Science and Economic Development Canada, Canadian Intellectual Property Office Re. Application No. 3,027,341. (5 Pages).
Official Action Dated Jul. 17, 2023 from US Patent and Trademark Office Re. U.S. Appl. No. 17/717,200. (133 pages).
Liu et al. "CXCL10/IP-10 in Infectious Diseases Pathogenesis and Potential Therapeutic Implications", Cytokine & Growth Factor Reviews, 22(3): 121-130, Jun. 2011.
CNKI English Translation of "Clinical Study on the Level of Plasma Tumor Necrosis Factor-Related Apoptosis-Inducing Ligand (TRAIL) in Evaluating the Prognosis of Patients With Sepsis", CNKI Master's E-Journals, 5: 4-26, Apr. 16, 2014.
Official Action Dated Aug. 2, 2023 from the US Patent and Trademark Office Re. U.S. Appl. No. 16/081,069. (36 pages).
Communication Pursuant to Article 94(3) EPC Dated Jul. 21, 2023 From the European Patent Office Re. Application No. 21178885.6 (6 Pages).
Notice of Allowance Dated Mar. 13, 2024 from the US Patent and Trademark Office Re. U.S. Appl. No. 17/372,575. (28 pages).
Communication Pursuant to Article 94(3) EPC Dated Jan. 31, 2024 From the European Patent Office Re. Application No. 17855163.6 (4 Pages).
Restriction Official Action Dated Feb. 1, 2024 from the US Patent and Trademark Office Re. U.S. Appl. No. 17/841,704. (6 pages).
"C-Reactive Protein", Australian Prescriber, 20(3): 74-76, Jun. 2007.
Official Action Dated Apr. 3, 2024 from the US Patent and Trademark Office Re. U.S. Appl. No. 17/507,994. (50 pages).
Official Action Dated Apr. 8, 2024 from the US Patent and Trademark Office Re. U.S. Appl. No. 17/010,912. (233 pages).
Requisition by the Examiner Dated Apr. 5, 2024 From the Innovation, Science and Economic Development Canada, Canadian Intellectual Property Office Re. Application No. 3,190,715. (3 Pages).

(56) References Cited

OTHER PUBLICATIONS

Haider et al. "C-Reactive Protein is Expressed and Secreted by Peripheral Blood Mononuclear Cells", Clinical and Experimental Immunology, 146: 533-539, 2006.
Stiver "The Treatment of Influenza With Antiviral Drugs", CMAJ, Canadian Medical Association, 168(1): 49-57, Jan. 7, 2003.
Suarez et al. "Superiority of Transcriptional Profiling Over Procalcitonin for Distinguishing Bacterial From Viral Lower respiratory Tract Infections in Hospitalized Adults", The Journal of Infectious Diseases, 212: 213-222, Jul. 15, 2015.
Notice of Allowance Dated Mar. 27, 2024 from the US Patent and Trademark Office Re. U.S. Appl. No. 17/717,200. (34 pages).
Official Action Dated Mar. 26, 2024 from the US Patent and Trademark Office Re. U.S. Appl. No. 18/230,718. (67 pages).
Askarieh et al. "Systemic and Intrahepatic Interferon-Gamma-Inducible Protein 10 kDa Predicts the First-Phase Decline in Hepatitis C Virus RNA and Overall Viral Response to Therapy in Chronic Hepatitis C", Hepatology, 51: 1523-1530, 2010.
Bartolome et al. "Interleukin-28B Polymorphisms and Interferon Gamma Inducible Protein-10 Serum Levels in Seronegative Occult Hepatitis C Virus Infection", Journal of Medical Virology, 88(2):268-274, Feb. 2016.
Feld et al. "Plasma Interferon-Gamma-Inducible Protein-10 Levels Are Associated with Early, but Not Sustained Virological Response during Treatment of Acute or Early Chronic HCV Infection", PLoS One 8(11): e80003, 1-11, Nov. 20, 2013.
Grebely et al. "Plasma Interferon-gamma-Inducible Protein-10 (IP-10) Levels During Acute Hepatitis C Virus Infection", Hepatology 57(6): 2124-2134, Jun. 2013.
Lagging et al. "IP-10 Predicts Viral Response and Therapeutic Outcome in Difficult-to-treat Patients with HCV Genotype 1 Infection", Hepatolgy 44(6): 1617-1625, Dec. 2006.
Sonneveld et al. "Pre-treatment Levels of IP-10 Predict Response to Peginterferon in HBeAg-positive Chronic Hepatitis B Patients 396", Hepatology 56(4): 386A-387A, Oct. 2012.
Decision on Rejection Dated Jan. 4, 2024 From the State Intellectual Property Office of the People's Republic of China Re. Application No. 202010370187.X and Its Machine Translation Into English. (9 Pages).
Communication Pursuant to Article 94(3) EPC Dated Oct. 30, 2023 From the European Patent Office Re. Application No. 17855164.4 (7 Pages).
Examination Report Dated Nov. 1, 2023 From the Australian Government, IP Australia Re. Application No. 2022200802. (6 Pages).
Communication Pursuant to Article 94(3) EPC Dated Apr. 8, 2024 From the European Patent Office Re. Application No. 22169859.0. (6 Pages).
Restriction Official Action Dated Nov. 27, 2023 from the US Patent and Trademark Office Re. U.S. Appl. No. 17/010,912. (8 pages).
English Summary Dated Jan. 25, 2024 of Decision on Rejection Dated Jan. 4, 2024 From the State Intellectual Property Office of the People's Republic of China Re. Application No. 202010370187.X (1 Page).
Official Action Dated Jun. 4, 2024 from the US Patent and Trademark Office Re. U.S. Appl. No. 16/081,069. (33 pages).
Communication Pursuant to Article 94(3) EPC Dated Jul. 9, 2024 From the European Patent Office Re. Application No. 15868614.7. (5 Pages).
Notice of Allowance Dated Oct. 10, 2024 from the US Patent and Trademark Office Re. U.S. Appl. No. 17/841,704. (20 pages).
Notification of Office Action and Search Report Dated Sep. 10, 2024 From the State Intellectual Property Office of the People's Republic of China Re. Application No. 202210796759.X and Its Translation into English. (26 Pages).
Consiglio et al. "BEAT: Bioinformatics Exon Array Tool to Store, Analyze and Visualize Affymetrix GeneChip Human Exon Array data from Disease Experiments", BMC Bioinformatics, 13 (Suppl 4): S21: 1-14, Mar. 28, 2012.
UCSC "UCSC Genome Browser on Human Feb. 2009 (GRCh37/hg19) Assembly", UCSC Genome Browserv409: 1P., Retrieved from Internet Jul. 7, 2021.
UCSI UCSI Genome Browser on Human Feb. 2009 GRCH37/hg19 Assembly, Human hg19 chr10:90579659-90611732 UCSC Genome Browser v409, Retrived from Internet: 1P., Dec. 7, 2021.
Communication Pursuant to Article 94(3) EPC Dated Oct. 11, 2024 From the European Patent Office Re. Application No. 21170448.1 (5 Pages).
Herbeuval et al. "CD4+ T-cell Death Induced by Infectious and Noninfectious HIV-1: Role of Type 1 Interferon-dependent, TRAIL/DR5-mediated apoptosis", Blood, Immunobiology, 106(10): 3524-3531, Nov. 15, 2005.
Notice of Allowance Dated Jun. 18, 2024 from the US Patent and Trademark Office Re. U.S. Appl. No. 18/230,718. (17 pages).
Notice of Allowance Dated Aug. 28, 2024 from the US Patent and Trademark Office Re. U.S. Appl. No. 17/507,994. (10 pages).
Official Action Dated May 9, 2024 from the US Patent and Trademark Office Re. U.S. Appl. No. 17/841,704. (166 pages).
Nicholson et al. "Late-Breaking Abstract: Plasma Level of TRAIL is Associated with Severity of Sepsis and Predicts Survival After Critical Illness", European Respiratory Journal, 48:OA3021, pp. 1-5, Nov. 2016.
Interview Summary Dated Jul. 26, 2024 from the US Patent and Trademark Office Re. U.S. Appl. No. 17/507,994. (2 pages).
Interview Summary Dated Nov. 27, 2024 from the US Patent and Trademark Office Re. U.S. Appl. No. 16/081,069. (16 pages).
Communication Pursuant to Article 94(3) EPC Dated Feb. 11, 2025 From the European Patent Office Re. Application No. 22204952.0 (6 Pages).
Notice of Allowance Dated Feb. 26, 2025 together with Interview Summary from the US Patent and Trademark Office Re. U.S. Appl. No. 16/081,069. (27 pages).
Requisition by the Examiner Dated Feb. 13, 2025 From the Innovation, Science and Economic Development Canada, Canadian Intellectual Property Office Re. Application No. 3,190,715. (5 Pages).
Secchiero et al. "Potential Prognostic Significance of Decreased Serum Levels of TRAIL after Acute Myocardial Infarction ", PLoS One, 4(2): e4442, pp. 1-6, Feb. 2009.
Van Houten et al. "A Host-Protein Based Essay to Differentiate Between Bacterial and iral Infection in Preschool Childres (Opportunity): A Double-Blind, Multicentre, Validation Study", XP085094723, The Lancet Infectious Diseases, 17(4): 431-440, Dec. 21, 2016.
Villar et al. "Biomarcadores Pronósticos de Gravedad Del Dengue", Biomedica, 33(1): 108-116, 2013.
"UCSC Genome Browser on Human (GRCh38/hg38)", UCSC Genome Browser, Version 440, Chr14:94109241-94118186, Retrieved From the Internet, 7 Pages, Jan. 12, 2022.
"UCSC Genome Browser on Human (GRCh38/hg38)", UCSC Genome Browser, Version 440, Chr17: 41754609-41786711, Retrieved From the Internet, 4 Pages, Jan. 12, 2022.
Advisory Action Before the Filing of An Appeal Brief Dated Dec. 23, 2019 From the US Patent and Trademark Office Re. U.S. Appl. No. 16/157,193. (3 pages).
Advisory Action Dated Mar. 9, 2022 from US Patent and Trademark Office Re. U.S. Appl. No. 16/081,906. (3 pages).
Advisory Action Dated Dec. 20, 2021 from US Patent and Trademark Office Re. U.S. Appl. No. 16/081,069. (7 pages).
Applicant-Initiated Interview Summary Dated Jul. 6, 2016 From the US Patent and Trademark Office Re. U.S. Appl. No. 14/377,887.
Applicant-Initiated Interview Summary Dated Feb. 10, 2020 From the US Patent and Trademark Office Re. U.S. Appl. No. 16/157,193. (3 pages).
Applicant-Initiated Interview Summary Dated Jul. 17, 2015 From the US Patent and Trademark Office Re. U.S. Appl. No. 13/090,893.
Applicant-Initiated Interview Summary Dated Feb. 22, 2017 From the US Patent and Trademark Office Re. U.S. Appl. No. 14/377,887. (3 Pages).
Applicant-Initiated Interview Summary Dated Oct. 26, 2017 From the US Patent and Trademark Office Re. U.S. Appl. No. 15/237,728. (3 pages).

(56) References Cited

OTHER PUBLICATIONS

Applicant-Initiated Interview Summary Dated Jul. 30, 2018 From the US Patent and Trademark Office Re. U.S. Appl. No. 15/641,400. (3 pages).
Communication of Notices of Opposition (R79(1) EPC) Dated May 4, 2022 From the European Patent Office Re. Application No. 17759388.6. (1 Page).
Communication Pursuant to Article 94(3) EPC Dated Jun. 2, 2021 From the European Patent Office Re. Application No. 17827121.9. (5 Pages).
Communication Pursuant to Article 94(3) EPC Dated Jun. 4, 2020 From the European Patent Office Re. Application No. 17759388.6. (3 Pages).
Communication Pursuant to Article 94(3) EPC Dated May 7, 2019 From the European Patent Office Re. Application No. 15831781.8. (3 Pages).
Communication Pursuant to Article 94(3) EPC Dated Dec. 9, 2016 From the European Patent Office Re. Application No. 13703112.6. (4 Pages).
Communication Pursuant to Article 94(3) EPC Dated Oct. 9, 2018 From the European Patent Office Re. Application No. 11748712.4. (8 Pages).
Communication Pursuant to Article 94(3) EPC Dated Nov. 12, 2020 From the European Patent Office Re. Application No. 17759389.4. (6 Page).
Communication Pursuant to Article 94(3) EPC Dated Jun. 17, 2016 From the European Patent Office Re. Application No. 11748712.4.
Communication Pursuant to Article 94(3) EPC Dated Mar. 17, 2021 From the European Patent Office Re. Application No. 15868614.7. (5 Pages).
Communication Pursuant to Article 94(3) EPC Dated Aug. 18, 2020 From the European Patent Office Re. Application No. 11748712.4. (3 Pages).
Communication Pursuant to Article 94(3) EPC Dated Sep. 23, 2022 From the European Patent Office Re. Application No. 17855163.6. (7 Pages).
Communication Pursuant to Article 94(3) EPC Dated Mar. 25, 2020 From the European Patent Office Re. Application No. 18162713.4. (5 Pages).
Communication Pursuant to Article 94(3) EPC Dated May 25, 2020 From the European Patent Office Re. Application No. 11748712.4. (7 Pages).
Communication Pursuant to Article 94(3) EPC Dated Sep. 25, 2020 From the European Patent Office Re. Application No. 17827122.7. (5 Pages).
Communication Pursuant to Article 94(3) EPC Dated Mar. 27, 2020 From the European Patent Office Re. Application No. 15868614.7. (6 Pages).
Communication Pursuant to Article 94(3) EPC Dated Jul. 31, 2019 From the European Patent Office Re. Application No. 18162713.4. (4 Pages).
Decision on Rejection Dated Aug. 30, 2022 From the National Intellectual Property Administration of the People's Republic of China Re. Application No. 201780073531.5 and Its Translation Into English. (13 Pages).
English Translation Dated May 10, 2022 of Examination Report Dated Apr. 14, 2022 From the Servico Publico Federal, Ministerio da Economia, Instituto Nacional da Propriedade Industrial do Brasil RE Application No. BR11 2017 002884 0. (3 Pages).
English Translation Dated Feb. 16, 2022 of Grounds of Reason of Rejection Dated Jan. 27, 2022 From the Korean Intellectual Property Office Re. Application No. 10-2017-7007002. (6 Pages).
European Search Report and the European Search Opinion Dated Oct. 6, 2021 From the European Patent Office Re. Application No. 21178885.6. (10 Pages).
European Search Report and the European Search Opinion Dated Jul. 14, 2021 From the European Patent Office Re. Application No. 21170448.1. (6 Pages).
European Search Report and the European Search Opinion Dated May 16, 2018 From the European Patent Office Re. Application No. 18162713.4. (7 Pages).
European Search Report and the European Search Opinion Dated Sep. 28, 2020 From the European Patent Office Re. Application No. 20164056.2. (10 Pages).
Examination Report Dated Oct. 6, 2017 From the Australian Government, IP Australia Re. Application No. 2013217935. (2 Pages).
Examination Report Dated Apr. 14, 2022 From the Servico Publico Federal, Ministerio da Economia, Instituto Nacional da Propriedade Industrial do Brasil RE Application No. BR11 2017 002884 0 together with an English Summary and Pending Claims. (8 Pages).
Examination Report Dated Feb. 19, 2022 From the Servico Publico Federal, Ministerio da Economia, Instituto Nacional da Propriedade Industrial do Brasil RE Application No. BR112014 019733.4. (4 Pages).
Examination Report Dated May 29, 2019 From the Australian Government, IP Australia Re. Application No. 2018202302. (5 Pages).
Examination Report Under Sections 12 & 13 of the Patents Act, 1970 and the Patents Rules, 2003 Dated Oct. 21, 2019 From the Government of India, Intellectual Property India, Patents, Designs, Trade Marks, Geographical Indications Re. Application No. 9122/DELNP/2012 (5 Pages).
Examination Report Under Sections 12 & 13 of the Patents Act, 1970 and the Patents Rules, 2003 Dated Mar. 26, 2018 From the Government of India, Intellectual Property India, Patents, Designs, Trade Marks, Geographical Indications Re. Application No. 9122/DELNP/2012. (7 Pages).
Examination Report Under Sections 12 & 13 of the Patents Act, 1970 and the Patents Rules, 2003 Dated Nov. 30, 2018 From the Government of India, Intellectual Property India, Patents, Designs, Trade Marks, Geographical Indications Re. Application No. 1780/MUMNP/2014. (7 Pages).
Examination Report Under Sections 12 & 13 of the Patents Act, 1970 and the Patents Rules, 2003 Dated Mar. 31, 2021 From the Government of India, Intellectual Property India, Patents, Designs, Trade Marks, Geographical Indications, The Patent Office Re. Application No. 201727005513. (7 Pages).
Examiner-Initiated Interview Summary Dated Nov. 27, 2017 From the US Patent and Trademark Office Re. U.S. Appl. No. 15/518,491. (2 pages).
Final Official Action Dated Sep. 3, 2021 From the US Patent and Trademark Office Re. U.S. Appl. No. 16/316,631. (37 Pages).
Final Official Action Dated Sep. 10, 2021 from the US Patent and Trademark Office Re. U.S. Appl. No. 16/081,069. (61 pages).
Final Official Action Dated Jun. 15, 2021 From the US Patent and Trademark Office Re. U.S. Appl. No. 16/334,033. (36 Pages).
Final Official Action Dated Nov. 29 together with Interview Summary Dated Nov. 14, 2021 from US Patent and Trademark Office Re. U.S. Appl. No. 16/081,906. (45 pages).
Final Official Action Dated Sep. 8, 2020 from the US Patent and Trademark Office Re. U.S. Appl. No. 16/687,726. (28 pages).
Grounds of Reason of Rejection Dated Jan. 27, 2022 From the Korean Intellectual Property Office Re. Application No. 10-2017-7007002. (6 Pages).
Hearing Notice Dated Jul. 16, 2019 From the Government of India, Patent Office, Intellectual Property Building Re. Application No. 1780/MUMNP/2014. (3 Pages).
International Preliminary Report on Patentability Dated Apr. 11, 2019 From the International Bureau of WIPO Re. Application No. PCT/IL2017/051088. (6 Pages).
International Preliminary Report on Patentability Dated Apr. 11, 2019 From the International Bureau of WIPO Re. Application No. PCT/IL2017/051089. (7 Pages).
International Preliminary Report on Patentability Dated Sep. 13, 2018 From the International Bureau of WIPO Re. Application No. PCT/IL2017/050270. (7 Pages).
International Preliminary Report on Patentability Dated Sep. 13, 2018 From the International Bureau of WIPO Re. Application No. PCT/IL2017/050271. (9 Pages).

(56) References Cited

OTHER PUBLICATIONS

International Preliminary Report on Patentability Dated Jun. 22, 2017 From the International Bureau of WIPO Re. Application No. PCT/IL2015/051201. (7 Pages).
International Preliminary Report on Patentability Dated Feb. 23, 2017 From the International Bureau of WIPO Re. Application No. PCT/IL2015/050823. (7 Pages).
International Preliminary Report on Patentability Dated Jan. 24, 2019 From the International Bureau of WIPO Re. Application No. PCT/IL2017/050780. (9 Pages).
International Preliminary Report on Patentability Dated Jan. 24, 2019 From the International Bureau of WIPO Re. Application No. PCT/IL2017/050781. (7 Pages).
International Preliminary Report on Patentability Dated Apr. 27, 2017 From the International Bureau of WIPO Re. Application No. PCT/IL2015/051024. (7 Pages).
International Search Report and the Written Opinion Dated Mar. 12, 2012 From the International Searching Authority Re. Application No. PCT/IB2011/001299.
International Search Report and the Written Opinion Dated Sep. 14, 2017 From the International Searching Authority Re. Application No. PCT/IL2017/050781. (12 Pages).
International Search Report and the Written Opinion Dated Jun. 15, 2017 From the International Searching Authority Re. Application No. PCT/IL2017/050270. (13 Pages).
International Search Report and the Written Opinion Dated Jun. 15, 2017 From the International Searching Authority Re. Application No. PCT/IL2017/050271. (16 Pages).
International Search Report and the Written Opinion Dated Sep. 18, 2017 From the International Searching Authority Re. Application No. PCT/IL2017/050780. (15 Pages).
International Search Report and the Written Opinion Dated Jan. 20, 2016 From the International Searching Authority Re. Application No. PCT/IL2015/051024.
International Search Report and the Written Opinion Dated Feb. 22, 2016 From the International Searching Authority Re. Application No. PCT/IL2015/051201.
International Search Report and the Written Opinion Dated Dec. 25, 2017 From the International Searching Authority Re. Application No. PCT/IL2017/051088. (9 Pages).
International Search Report and the Written Opinion Dated Dec. 28, 2017 From the International Searching Authority Re. Application No. PCT/IL2017/051089. (10 Pages).
International Search Report and the Written Opinion Dated Nov. 29, 2015 From the International Searching Authority Re. Application No. PCT/IL2015/050823.
International Search Report Dated Apr. 5, 2013 From the International Searching Authority Re. Application No. PCT/EP2013/052619.
Interview Summary Dated Feb. 1, 2021 From the US Patent and Trademark Office Re. U.S. Appl. No. 16/687,726. (2 Pages).
Interview Summary Dated Dec. 3, 2021 from US Patent and Trademark Office Re. U.S. Appl. No. 16/081,069. (3 pages).
Interview Summary Dated Oct. 14, 2020 from the US Patent and Trademark Office Re. U.S. Appl. No. 16/081,906. (3 pages).
Interview Summary Dated Feb. 22, 2022 from US Patent and Trademark Office Re. U.S. Appl. No. 16/081,906. (2 pages).
Interview Summary Dated Apr. 29, 2022 from US Patent and Trademark Office Re. U.S. Appl. No. 16/081,906. (2 pages).
Notice of Allowance Dated Feb. 7, 2022 from US Patent and Trademark Office Re. U.S. Appl. No. 16/336,528. (46 pages).
Notice of Allowance Dated Mar. 2, 2022 from US Patent and Trademark Office Re. U.S. Appl. No. 16/081,069. (10 pages).
Notice Of Allowance Dated Feb. 4, 2019 From the US Patent and Trademark Office Re. U.S. Appl. No. 15/503,439. (6 pages).
Notice of Allowance Dated Jan. 5, 2022 from US Patent and Trademark Office Re. U.S. Appl. No. 16/316,631. (9 pages).
Notice of Allowance Dated Sep. 10, 2020 from the US Patent and Trademark Office Re. U.S. Appl. No. 16/157,193. (13 pages).
Notice of Allowance Dated Mar. 16, 2022 from US Patent and Trademark Office Re. U.S. Appl. No. 16/998,006. (28 pages).
Notice of Allowance Dated Mar. 17, 2022 from US Patent and Trademark Office Re. U.S. Appl. No. 16/334,033. (29 pages).
Notice of Allowance Dated May 17, 2022 From the US Patent and Trademark Office Re. U.S. Appl. No. 16/081,906. (14 Pages).
Notice of Allowance Dated Apr. 19, 2021 from the US Patent and Trademark Office Re. U.S. Appl. No. 16/238,582. (22 pages).
Notice of Allowance Dated May 22, 2020 from the US Patent and Trademark Office Re. U.S. Appl. No. 16/355,984. (18 pages).
Notice Of Allowance Dated Jul. 29, 2019 From the US Patent and Trademark Office Re. U.S. Appl. No. 15/237,728. (21 pages).
Notice of Allowance Dated and Interview Summary Jul. 19, 2021 from the US Patent and Trademark Office Re. U.S. Appl. No. 16/687,726. (24 pages).
Notice of Non-Compliant Amendment Dated Aug. 4, 2015 From the US Patent and Trademark Office Re. U.S. Appl. No. 13/090,893.
Notice of Reason for Rejection Dated Nov. 12, 2019 From the Japan Patent Office Re. Application No. 2017-126712 and an English Summary. (3 Pages).
Notice of Reason for Rejection Dated Aug. 20, 2019 From the Japan Patent Office Re. Application No. 2017-507867 and Its Translation Into English. (5 Pages).
Notice of Reason(s) for Rejection Dated Dec. 7, 2021 From the Japan Patent Office Re. Application No. 2020-021606 and Its Translation Into English. (11 Pages).
Notice of Reason(s) for Rejection Dated Dec. 14, 2021 From the Japan Patent Office Re. Application No. 2020-109710 and Its Translation Into English. (7 Pages).
Notice of Reason(s) for Rejection Dated Jun. 15, 2021 From the Japan Patent Office Re. Application No. 2020-109710 and Its Translation Into English. (12 Pages).
Notice of Reasons for Rejection Dated Nov. 1, 2016 From the Japan Patent Office Re. Application No. 2014-556086 and Its Translation Into English. (12 Pages).
Notice of Reasons for Rejection Dated Apr. 2, 2019 From the Japan Patent Office Re. Application No. 2017-126712 and Its Translation Into English. (8 Pages).
Notice of Reasons for Rejection Dated Jun. 19, 2018 From the Japan Patent Office Re. Application No. 2017-126712 and Its Translation Into English. (9 Pages).
Notice of Reasons for Rejection Dated Apr. 20, 2021 From the Japan Patent Office Re. Application No. 2020-021606 and Its Translation Into English. (9 Pages).
Notice on Office Action and the Search Report Dated Feb. 25, 2015 From The State Intellectual Property Office of the People's Republic of China Re. Application No. 201180030792.1 and Its Translation Into English.
Notification of Lack of Unity and Search Report Dated Jan. 21, 2019 From the Federal Government Institution, Federal Institute of Industrial Property of the Federal Service for Intellectual Property, Patents and Trade Marks of the Russian Federation Re. Application No. 2017107750 and Its Translation of Office Action Into English. (12 Pages).
Notification of Office Action and Search Report Dated Dec. 2, 2022 From the State Intellectual Property Office of the People's Republic of China Re. Application No. 202010370187.X. (12 Pages).
Notification of Office Action and Search Report Dated Jul. 2, 2021 From the State Intellectual Property Office of the People's Republic of China Re. Application No. 201780055014.5. (23 Pages).
Notification of Office Action and Search Report Dated Aug. 3, 2021 From the State Intellectual Property Office of the People's Republic of China Re. Application No. 201780055347.8 and Its Translation of Office Action Into English. (26 Pages).
Notification of Office Action and Search Report Dated Jun. 3, 2021 From the State Intellectual Property Office of the People's Republic of China Re. Application No. 20180014541.1 and Its Translation Into English. (17 Pages).
Notification of Office Action and Search Report Dated Mar. 4, 2016 From the State Intellectual Property Office of the People's Republic of China Re. Application No. 201380019055.0.

(56) References Cited

OTHER PUBLICATIONS

Notification of Office Action and Search Report Dated Jan. 11, 2019 From the State Intellectual Property Office of the People's Republic of China Re. Application No. 201580055946.0. (5 Pages).
Notification of Office Action and Search Report Dated Feb. 13, 2017 From the State Intellectual Property Office of the People's Republic of China Re. Application No. 201380019055.0 and Its Translation of Office Action Into English. (10 Pages).
Notification of Office Action and Search Report Dated Jul. 13, 2021 From the State Intellectual Property Office of the People's Republic of China Re. Application No. 20180781584.9 and an English Summary. (4 Pages).
Notification of Office Action and Search Report Dated Mar. 15, 2022 From the State Intellectual Property Office of the People's Republic of China Re. Application No. 201780055347.8 and Its Translation of Office Action Into English. (28 Pages).
Notification of Office Action and Search Report Dated Feb. 19, 2019 From the State Intellectual Property Office of the People's Republic of China Re. Application No. 201580075265.0 and A Summary of the Notification of Office Action Into English.(7 Pages).
Notification of Office Action and Search Report Dated Jun. 19, 2018 From the State Intellectual Property Office of the People's Republic of China Re. Application No. 201580075265.0 and its English Summary. (14 Pages).
Notification of Office Action and Search Report Dated Apr. 20, 2022 From the National Intellectual Property Administration of the People's Republic of China Re. Application No. 201780073531.5 and Its Translation Into English Including Claims. (31 Pages).
Notification of Office Action and Search Report Dated Feb. 20, 2021 From the State Intellectual Property Office of the People's Republic of China Re. Application No. 201780014568.0 and Its Translation Into English. (22 Pages).
Notification of Office Action and Search Report Dated Dec. 23, 2021 From the State Intellectual Property Office of the People's Republic of China Re. Application No. 201780014541.1 and Its Translation of Office Action Into English. (14 Pages).
Notification of Office Action and Search Report Dated Jul. 28, 2020 From the State Intellectual Property Office of the People's Republic of China Re. Application No. 201810781584.9 and Its Translation of Office Action Into English. (17 Pages).
Notification of Office Action and Search Report Dated Oct. 30, 2017 From the State Intellectual Property Office of the People's Republic of China Re. Application No. 201610817276.8. (10 Pages).
Notification of Office Action and Search Report Dated Sep. 30, 2021 From the State Intellectual Property Office of the People's Republic of China Re. Application No. 201780073531.5 and Its Translation of Office Action Into English. (14 Pages).
Notification of Office Action Dated Sep. 1, 2021 From the State Intellectual Property Office of the People's Republic of China Re. Application No. 201780014568.0 and Its Translation Into English. (7 Pages).
Notification of Office Action Dated Jul. 2, 2019 From the State Intellectual Property Office of the People's Republic of China Re. Application No. 201580075265.0. (3 Pages).
Notification of Office Action Dated Dec. 3, 2021 From the State Intellectual Property Office of the People's Republic of China Re. Application No. 201780055014.5 and Its Translation Into English. (5 Pages).
Notification of Office Action Dated Jul. 3, 2015 From the State Intellectual Property Office of the People's Republic of China Re. Application No. 201380019055.0.
Notification of Office Action Dated Jun. 3, 2019 From the China National Intellectual Property Administration Re. Application No. 201610817276.8 and Its Translation Into English. (10 Pages).
Notification of Office Action Dated Aug. 4, 2016 From the State Intellectual Property Office of the People's Republic of China Re. Application No. 201380019055.0 and Its Translation Into English.
Notification of Office Action Dated Mar. 5, 2021 From the State Intellectual Property Office of the People's Republic of China Re. Application No. 201810781584.9 and Its Translation of Office Action Into English. (13 Pages).
Notification of Office Action Dated May 6, 2014 From The State Intellectual Property Office of the People's Republic of China Re. Application No. 201180030792.1 and Its Translation Into English.
Notification of Office Action Dated May 11, 2022 From the State Intellectual Property Office of the People's Republic of China Re. Application No. 201780014541.1 and Its Translation Into English. (11 Pages).
Notification of Office Action Dated Jun. 20, 2018 From the State Intellectual Property Office of the People's Republic of China Re. Application No. 201580055946.0 and Its Summary in English. (5 Pages).
Notification of Office Action Dated Jan. 21, 2016 From The State Intellectual Property Office of the People's Republic of China Re. Application No. 201180030792.1 and Its Translation Into English.
Notification of Office Action Dated Aug. 22, 2019 From the State Intellectual Property Office of the People's Republic of China Re. Application No. 201580055946.0. (3 Pages).
Notification of Office Action Dated Jan. 24, 2022 From the State Intellectual Property Office of the People's Republic of China Re. Application No. 201780014568.0 and its Translation into English. (9 Pages).
Notification of Office Action Dated Aug. 25, 2017 From the State Intellectual Property Office of the People's Republic of China Re. Application No. 201380019055.0. (6 Pages).
Notification of Office Action Dated Aug. 28, 2015 From The State Intellectual Property Office of the People's Republic of China Re. Application No. 201180030792.1 and Its Translation Into English.
Notification of Office Action Dated Aug. 30, 2018 From the State Intellectual Property Office of the People's Republic of China Re. Application No. 201610817276.8 and Its Translation Into English. (22 Pages).
Notification of Reexamination Dated Jan. 12, 2018 From the State Intellectual Property Office of the People's Republic of China Re. Application No. 2013800190 and Its Machine Translation into English.
Office Action Dated Feb. 18, 2019 From the Israel Patent Office Re. Application No. 250585 and Its Translation Into English. (6 Pages).
Office Action Dated Nov. 28, 2019 From the Israel Patent Office Re. Application No. 254095 and Its Translation Into English. (7 Pages).
Office Action Dated Feb. 29, 2016 From the Israel Patent Office Re. Application No. 233998 and Its Translation Into English.
Office Action Dated Jul. 30, 2020 From the Israel Patent Office Re. Application No. 261529 and Its Translation Into English. (5 Pages).
Office Action Dated Jul. 30, 2020 From the Israel Patent Office Re. Application No. 261530 and Its Translation Into English. (5 Pages).
Official Action Dated Sep. 1, 2015 From the US Patent and Trademark Office Re. U.S. Appl. No. 13/090,893.
Official Action Dated Feb. 3, 2020 From the US Patent and Trademark Office Re. U.S. Appl. No. 16/355,984. (24 pages).
Official Action Dated Apr. 4, 2016 From the US Patent and Trademark Office Re. U.S. Appl. No. 13/090,893.
Official Action Dated Jan. 4, 2019 From the US Patent and Trademark Office Re. Application No. 151713,722. (72 pages).
Official Action Dated Nov. 4, 2020 From the US Patent and Trademark Office Re. U.S. Appl. No. 16/238,582. (37 Pages).
Official Action Dated Mar. 5, 2020 From the US Patent and Trademark Office Re. U.S. Appl. No. 15/713,722. (24 pages).
Official Action Dated May 5, 2021 From the US Patent and Trademark Office Re. U.S. Appl. No. 16/336,528. (108 Pages).
Official Action Dated Feb. 6, 2018 From the US Patent and Trademark Office Re. U.S. Appl. No. 15/503,439. (63 pages).
Official Action Dated Nov. 7, 2016 From the US Patent and Trademark Office Re. U.S. Appl. No. 13/090,893. (26 pages).
Official Action Dated Jun. 9, 2022 from US Patent and Trademark Office Re. U.S. Appl. No. 17/007,095. (118 pages).
Official Action Dated Mar. 9, 2021 From the US Patent and Trademark Office Re. U.S. Appl. No. 16/316,631. (121 Pages).
Official Action Dated Jun. 10, 2013 From the US Patent and Trademark Office Re. U.S. Appl. No. 13/090,893.

(56) References Cited

OTHER PUBLICATIONS

Official Action Dated Mar. 10, 2021 From the US Patent and Trademark Office Re. U.S. Appl. No. 16/081,906. (127 Pages).
Official Action Dated Apr. 12, 2018 From the US Patent and Trademark Office Re. U.S. Appl. No. 15/518,491. (59 pages).
Official Action Dated Aug. 12, 2015 From the US Patent and Trademark Office Re. U.S. Appl. No. 14/377,887.
Official Action Dated May 12, 2017 From the US Patent and Trademark Office Re. U.S. Appl. No. 15/237,728. (27 pages).
Official Action Dated Apr. 13, 2016 From the US Patent and Trademark Office Re. U.S. Appl. No. 14/377,887.
Official Action Dated Mar. 13, 2014 From the US Patent and Trademark Office Re. U.S. Appl. No. 13/090,893.
Official Action Dated Apr. 15, 2019 From the US Patent and Trademark Office Re. U.S. Appl. No. 15/237,728. (16 Pages).
Official Action Dated Dec. 15, 2016 From the US Patent and Trademark Office Re. U.S. Appl. No. 14/377,887. (22 pages).
Official Action Dated May 15, 2018 From the US Patent and Trademark Office Re. U.S. Appl. No. 15/237,728. (55 pages).
Official Action Dated May 15, 2020 From the US Patent and Trademark Office Re. U.S. Appl. No. 16/238,582. (92 Pages).
Official Action Dated Oct. 15, 2019 From the US Patent and Trademark Office Re. Application No. 151713,722. (57 Pages).
Official Action Dated Nov. 16, 2018 From the US Patent and Trademark Office Re. U.S. Appl. No. 15/503,439. (41 pages).
Official Action Dated Sep. 16, 2019 From the US Patent and Trademark Office Re. U.S. Appl. No. 16/355,984. (44 pages).
Official Action Dated Dec. 17, 2018 From the US Patent and Trademark Office Re. U.S. Appl. No. 15/237,728. (39 pages).
Official Action Dated Nov. 18, 2016 From the US Patent and Trademark Office Re. U.S. Appl. No. 15/237,728. (33 pages).
Official Action Dated Sep. 18, 2019 From the US Patent and Trademark Office Re. U.S. Appl. No. 16/157,193. (30 pages).
Official Action Dated Oct. 20, 2020 From the US Patent and Trademark Office Re. U.S. Appl. No. 16/081,069. (112 Pages).
Official Action Dated Nov. 22, 2021 from the US Patent and Trademark Office Re. U.S. Appl. No. 16/998,006. (116 pages).
Official Action Dated Apr. 23, 2019 From the US Patent and Trademark Office Re. U.S. Appl. No. 16/157,193. (47 pages).
Official Action Dated Nov. 23, 2020 From the US Patent and Trademark Office Re. U.S. Appl. No. 16/355,984. (9 pages).
Official Action Dated Oct. 24, 2019 From the US Patent and Trademark Office Re. U.S. Appl. No. 15/531,747. (37 Pages).
Official Action Dated Jan. 26, 2017 From the US Patent and Trademark Office Re. U.S. Appl. No. 15/015,309. (45 pages).
Official Action Dated Mar. 26, 2015 From the US Patent and Trademark Office Re. U.S. Appl. No. 13/090,893.
Official Action Dated Mar. 26, 2020 From the US Patent and Trademark Office Re. U.S. Appl. No. 16/687,726. (47 pages).
Official Action Dated Apr. 30, 2018 From the US Patent and Trademark Office Re. U.S. Appl. No. 15/641,400. (62 pages).
Official Action Dated Dec. 30, 2020 from the US Patent and Trademark Office Re. U.S. Appl. No. 16/334,033. (112 pages).
Official Action Dated Mar. 30, 2018 From the US Patent and Trademark Office Re. U.S. Appl. No. 15/531,747. (67 pages).
Official Action Dated Mar. 31, 2020 From the US Patent and Trademark Office Re. U.S. Appl. No. 15/531,747. (21 pages).
Official Action Dated Dec. 6, 2022 from the US Patent and Trademark Office Re. U.S. Appl. No. 16/081,069. (20 pages).
Official Action Dated May 7, 2020 from the US Patent and Trademark Office Re. U.S. Appl. No. 16/157,193. (23 pages).
Opposition to European Patent No. 3423589 Memed Diagnostics Ltd. on Behalf of J.A. Kemp LLP Dated Apr. 21, 2022 From the European Patent Office Re. Application No. 17759388.6. (31 Pages).
Partial European Search Report and Provisional Opinion Dated Jun. 25, 2020 From the European Search Report Re. Application No. 20164056.2. (11 Pages).
Patent Examination Report Dated Feb. 8, 2021 From the Australian Government, IP Australia Re. Application No. 2015302870. (4 Pages).
Request for Examination Dated Jun. 18, 2019 From the Federal Government Institution, Federal Institute of Industrial Property of the Federal Service for Intellectual Property, Patents and Trade Marks of the Russian Federation Re. Application No. 2017107750 and Its Translation of Office Action Into English. (11 Pages).
Requisition by the Examiner Dated Oct. 4, 2019 From the Innovation, Science and Economic Development Canada, Canadian Intellectual Property Office Re. Application No. 2,863,819. (3 Pages).
Requisition by the Examiner Dated Nov. 5, 2021 From the Innovation, Science and Economic Development Canada, Canadian Intellectual Property Office Re. Application No. 2,968,650. (7 Pages).
Requisition by the Examiner Dated Dec. 7, 2020 From the Innovation, Science and Economic Development Canada, Canadian Intellectual Property Office Re. Application No. 2,863,819. (4 Pages).
Requisition by the Examiner Dated Jun. 7, 2022 From the Innovation, Science and Economic Development Canada, Canadian Intellectual Property Office Re. Application No. 2,968,650. (3 Pages).
Requisition by the Examiner Dated Feb. 9, 2022 From the Innovation, Science and Economic Development Canada, Canadian Intellectual Property Office Re. Application No. 2,954,601. (3 Pages).
Requisition by the Examiner Dated Nov. 9, 2018 From the Innovation, Science and Economic Development Canada, Canadian Intellectual Property Office Re. Application No. 2,796,666. (3 Pages).
Requisition by the Examiner Dated Jul. 15, 2022 From the Innovation, Science and Economic Development Canada, Canadian Intellectual Property Office Re. Application No. 3,133,249. (4 Pages).
Requisition by the Examiner Dated Jan. 18, 2018 From the Innovation, Science and Economic Development Canada, Canadian Intellectual Property Office Re. Application No. 2,796,666. (5 Pages).
Requisition by the Examiner Dated Feb. 21, 2019 From the Innovation, Science and Economic Development Canada, Canadian Intellectual Property Office Re. Application No. 2,863,819. (8 Pages).
Requisition by the Examiner Dated Jul. 30, 2021 From the Innovation, Science and Economic Development Canada, Canadian Intellectual Property Office Re. Application No. 2,954,601. (16 Pages).
Restriction Official Action Dated Apr. 2, 2020 From the US Patent and Trademark Office Re. U.S. Appl. No. 16/081,069. (7 Pages).
Restriction Official Action Dated Nov. 2, 2017 From the US Patent and Trademark Office Re. U.S. Appl. No. 15/531,747. (9 pages).
Restriction Official Action Dated Feb. 4, 2022 from US Patent and Trademark Office Re. U.S. Appl. No. 17/007,095. (6 pages).
Restriction Official Action Dated Dec. 5, 2019 From the US Patent and Trademark Office Re. U.S. Appl. No. 16/081,906. (9 pages).
Restriction Official Action Dated Nov. 8, 2018 From the US Patent and Trademark Office Re. U.S. Appl. No. 16/157,193. (5 pages).
Restriction Official Action Dated May 10, 2018 From the US Patent and Trademark Office Re. U.S. Appl. No. 15/713,722. (6 Pages).
Restriction Official Action Dated Sep. 10, 2020 from the US Patent and Trademark Office Re. U.S. Appl. No. 16/316,631. (6 pages).
Restriction Official Action Dated Feb. 13, 2013 From the US Patent and Trademark Office Re. U.S. Appl. No. 13/090,893.
Restriction Official Action Dated May 15, 2015 From the US Patent and Trademark Office Re. U.S. Appl. No. 14/377,887.
Restriction Official Action Dated Mar. 29, 2021 From the US Patent and Trademark Office Re. U.S. Appl. No. 16/081,069. (8 Pages).
Restriction Official Action Dated Nov. 29, 2019 From the US Patent and Trademark Office Re. U.S. Appl. No. 16/238,582. (7 pages).
Restriction Official Action Dated Jul. 30, 2020 from the US Patent and Trademark Office Re. U.S. Appl. No. 16/081,906. (7 pages).
Restriction Official Action Dated Aug. 31, 2017 From the US Patent and Trademark Office Re. U.S. Appl. No. 15/518,491. (6 pages).
Restriction Official Action Dated Dec. 9, 2020 from the US Patent and Trademark Office Re. U.S. Appl. No. 16/336,528. (7 pages).
Search Report and Opinion Dated Dec. 10, 2019 From the Servico Publico Federal, Ministerio da Economia, Instituto Nacional da

(56) References Cited

OTHER PUBLICATIONS

Propriedade Industrial do Brasil Re. Application No. BR112017002884-0 and Its Translation Into English. (7 Pages).
Search Report and Opinion Dated Aug. 20, 2019 From the Servico Publico Federal, Ministerio da Economia, Instituto Nacional da Propriedade Industrial do Brasil Re. Application No. BR112014 019733-4 and Its Summary in English. (4 Pages).
Search Report Dated May 6, 2014 From The State Intellectual Property Office of the People's Republic of China Re. Application No. 201180030792.1 and Its Translation Into English.
Second Notice Of Allowance Dated Dec. 12, 2018 From the US Patent and Trademark Office Re. U.S. Appl. No. 15/641,400. (7 pages).
Second Notice of Allowance Dated May 12, 2021 From the US Patent and Trademark Office Re. U.S. Appl. No. 16/355,984. (32 Pages).
Summons to attend Oral Proceedings Pursuant to Rule 115(1) EPC Dated Jun. 10, 2022 From the European Patent Office Re. Application No. 17759389.4, (5 Pages).
Supplementary European Search Report and the European Search Opinion Dated May 4, 2020 From the European Patent Office Re. Application No. 17855163.6. (9 Pages).
Supplementary European Search Report and the European Search Opinion Dated Mar. 15, 2018 From the European Patent Office Re. Application No. 15831781.8. (11 Pages).
Supplementary European Search Report and the European Search Opinion Dated Sep. 17, 2018 From the European Patent Office Re. Application No. 15868614.7. (18 Pages).
Supplementary European Search Report and the European Search Opinion Dated Feb. 18, 2020 From the European Patent Office Re. Application No. 17827121.9. (5 Pages).
Supplementary European Search Report and the European Search Opinion Dated May 18, 2020 From the European Patent Office Re. Application No. 17855164.4. (13 Pages).
Supplementary European Search Report and the European Search Opinion Dated Jan. 21, 2020 From the European Patent Office Re. Application No. 17827122.7. (9 Pages).
Supplementary European Search Report and the European Search Opinion Dated Jan. 28, 2020 From the European Patent Office Re. Application No. 17759389.4. (11 Pages).
Supplementary European Search Report and the European Search Opinion Dated Sep. 30, 2019 From the European Patent Office Re. Application No. 17759388.6. (11 Pages).
Supplementary Partial European Search Report and the European Provisional Opinion Dated Jun. 1, 2018 From the European Patent Office Re. Application No. 15868614.7. (23 Pages).
Supplementary Partial European Search Report and the European Provisional Opinion Dated Oct. 24, 2019 From the European Patent Office Re. Application No. 17759389.4. (15 Pages).
Technical Examination Report Dated Aug. 11, 2022 from the National Institute of Industrial Property of Brazil Re. Application No. BR 11 2017 002884 0 with an English Translation. (8 pages).
Translation Dated Sep. 4, 2017 of Notification of Office Action Dated Aug. 25, 2017 From the State Intellectual Property Office of the People's Republic of China Re. Application No. 201380019055.0.
Translation Dated Apr. 5, 2016 of Notification of Office Action Dated Mar. 4, 2016 From the State Intellectual Property Office of the People's Republic of China Re. Application No. 201380019055.0.
Translation Dated Jul. 10, 2019 of Notification of Office Action Dated Jul. 2, 2019 From the State Intellectual Property Office of the People's Republic of China Re. Application No. 201580075265.0. (1 Page).
Translation Dated Sep. 11, 2019 of Notification of Office Action Dated Aug. 22, 2019 From the State Intellectual Property Office of the People's Republic of China Re. Application No. 201580055946.0. (1 Page).
Translation Dated Mar. 20, 2019 of Notification of Office Action Dated Feb. 19, 2019 From the State Intellectual Property Office of the People's Republic of China Re. Application No. 201580075265.0. (5 Pages).
Translation Dated Nov. 21, 2019 of Reason for Rejection From the Japanese Patent Office Re. Application No. 2017-126712. (2 Pages).
Translation Dated Sep. 21, 2015 of Office Action Dated Jul. 3, 2015 From the State Intellectual Property Office of the People's Republic of China Re. Application No. 201380019055.0.
Translation Dated Jul. 22, 2021 of Notification of Office Action Dated Jul. 13, 2021 From the State Intellectual Property Office of the People's Republic of China Re. Application No. 20180781584.9. (2 Pages).
Translation Dated Sep. 22, 2019 of Search Report and Opinion Dated Aug. 20, 2019 From the Servi?o Publico Federal, Ministerio da Economia, Instituto Nacional da Propriedade Industrial do Brasil Re. Application No. BR112014019733-4 and Its Summary in English. (4 Pages).
Translation Dated Jul. 27, 2021 of Notification of Office Action Dated Jul. 2, 2021 From the State Intellectual Property Office of the People's Republic of China Re. Application No. 201780055014.5. (12 Pages).
Translation Dated Jan. 30, 2019 of Notification of Office Action Dated Jan. 11, 2019 From the State Intellectual Property Office of the People's Republic of China Re. Application No. 201580055946.0.(1 Page).
Translation of Notification of Office Action and Search Report Dated Oct. 30, 2017 From the State Intellectual Property Office of the People's Republic of China Re. Application No. 201610817276.8. (16 Pages).
Affymetrix "Whole-Transcript Expression Analysis", Affymetrix, 8 pages, 2007.
Alexander et al. "*Staphylococcus aureus* and *Salmonella enterica* Serovar Dublin Induce Tumor Necrosis Factor-Related Apoptosis-Inducing Ligand Expression by Normal Mouse and Hurnan Osteoblasts", Infection and Immunity, 69(3): 1581-1586, Mar. 2001.
Ali et al. "Reliability of Serum Procalcitonin Concentrations for the Diagnosis of Sepsis in Neonates", Egypt Journal of Immunology, 15(1): 75-84, 2008. Abstract only.
Altmann et al. "Elevated Cardiac Troponin I in Sepsis and Septic Shock: No Evidence for Thrombus Associated Myocardial Necrosis", PLOSE One, 5(2): 1-5, 2010.
Ammann et al. "Elevation of Troponin I in Sepsis and Septic Shock", Intensive Care Medicine, 27: 965-969, May 16, 2001.
Arshed et al. "Elevated Troponin I in the Absence of Coronary Artery Disease: A Case Report with Review of Literature", Journal of Clinical Medicine Research, 7(10): 820-824, Aug. 23, 2015.
Bai et al. "A New Early Diagnostic Marker for Inflammatory Diseases—sTREM-1", International Journal of Pathology and Clinical Medicine, 27(1): 73-76, Feb. 2007.
Barnhart et al. "Changes in Cellular mRNA Stability, Splicing, and Polyadenylation Through HuR Protein Sequestration by A Cytoplasmic RNA Virus", Cell Reports, XP055621573, 5(4): 909-917, Nov. 27, 2013.
Becker et al. "Procalcitonin in Sepsis and Systemic Inflammation: a Harmful Biomarker and a Therapeutic Target", British Journal of Pharmacology, 159: 253-264, 2010.
Bessiere et al. "Prognostic Value of Troponins in Sepsis: a Meta-Analysis", Intensive Care Medicine, 39: 1181-1189, Apr. 18, 2018.
Biezeveld et al. "Sustained Activation of Neutrophils in the Course of Kawasaki Disease: An Association with Matrix Metalloproteinases", Clinical & Experimental Immunology 141(1): 183-188, Jul. 2005.
Bloos et al. "Rapid Diagnosis of Sepsis"; Virulence, 5(1): 154-160, 2014.
Boldrick et al. "Stereotyped and Specific Gene Expression Programs in Human Innate Immune Responses to Bacteria", Proc. Natl. Acad. Sci. USA, PNAS, 99(2): 972-977, Jan. 22, 2002.
Bone et al. "Definitions for Sepsis and Organ Failure and Guidelines for the Use of Innovative Therapies in Sepsis", Chest, 101(6): 1644-1655, 1992.
Borjesson et al. "Insights Into Pathogen Immune Evasion Mechanisms: Anaplasma Phagocytophilum Fails to Induce An Apoptosis

(56) References Cited

OTHER PUBLICATIONS

Differentiation Program in Human Neutrophils", The Jurnal of Immunology, 174: 6364-6372, 2005.
Boser et al. "A Training Algorithm for Optimal Margin Classifiers", Proceedings of the 5th Annual ACM Workshop on Computational Learning Theory, COLT'92, Pittsburgh, PA, USA, Jul. 27-29, 1992, p. 144-152, Jul. 27, 1992.
Brost et al. "Differential Expression of the TRAIL/TRAIL-receptor System in Patients with Inflammatory Bowel Disease", Pathology—Research and Practice, 206(1):43-50, Jan. 15, 2010.
Cai et al. "The Study on the Relationship Between PCT and CRP in Infective Diseases", Journ al of Qiqihar University of Medicine, 32(5): 696-697, 2011.
Calvano et al. "A Network-Based Analysis of Systemic Inflammation in Humans", Nature, 437: 1032-1037, Oct. 13, 2005.
Carrol et al. "The Diagnostic and Prognostic Accuracy of Five Markers of Serious Bacterial Infection in Malawian Children With Sign of Severe Infection", PLoS ONE, 4(8): e6621-1-e6621-8, Aug. 2009.
Chagan-Yasutan et al. "Persistent Elevation of Plasma Osteopontin Levels in HIV Patients Despite Highly Active Antiretroviral Therapy", The Tohoku Journal of Experimental Medicine, 218(4): 285-292, Aug. 2009.
Chaussabel et al. "Analysis of Significance Patterns Identifies Ubiquitous and Disease-Specific Gene-Expression Signatures in Patient Peripheral Blood Leukocytes", Annals of the New York Academy of Sciences, 1062: 146-154, 2005.
Chaussabel et al. "Assessing the Human Immune System Through Blood Transcriptomics", BMC Biology, 8: 84-1-84-14, Jul. 1, 2010.
Chen et al. "Discordant Protein and mRNA Expression in Lung Adenocarcinomas", Molecular & Cellular Proteomics: MCP, 1(4): 304-313, Apr. 2002.
Chieux et al. "MxA Protein in Capillary Blood of Children With Viral Infections", Journal of Medical Virology, 59: 547-551, 1999.
Chieux et al. "The MxA Protein Levels in Whole Blood Lysates of Patients With Various Viral Infections", Journal of Virological Methods, 70: 183-191, 1998.
Consiglio et al. "BEAT: Bioinformatics Exon Array Tool to Store, Analyze and Visualize Affymetrix GeneChip Human Exon Array Data From Disease Experiments", BMC Bioinformatics, XP021117755, 13(Suppl.4): S21-1-S21-14, Mar. 28, 2012.
Corada et al. "Monoclonal Antibodies Directed to Different Regions of Vascular Endothelial Cadherin Extracellular Dornain Affect Adhesion and Clustering of the Protein and Modulate Endothelial Permeability", Blood, 97(6): 1679-1684, Mar. 15, 2001.
Cowland et al. "Molecular Characterization and Pattern of Tissue Expression of the Gene for Neutrophil Gelatinase-Associated Lipocalin from Humans", Genomics, 45:17-23,1997.
Cristianini et al. "An Introduction to Support Vector Machines and Other Kernel- -Based Learning Methods: Contents", Cambridge University Press, 4 P., 2000.
Crowe et al. "Quantitative Immunocytofluorographic Analysis of CD4 Surface Antigen Expression and HIV Infection of Human Peripheral Blood Monocyte/Macrophages", Aids Research and Human Retroviruses, 3(2): 135-145, 1987.
Cummins et al. "The TRAIL to Viral Pathogenesis: The Good, the Bad and the Ugly", Current Molecular Medicine, XP055056835, 9(4): 495-505, May 1, 2009.
De la Grange et al. "A New Advance in Alternative Splicing Databases: From Catalogue to Detailed Analysis of Regulation of Expression and Function of Human Alternative Splicing Variants", BMC Bioinformatics, 8: 180-1-180-14, Jun. 4, 2007.
Dirke et al. "TRAIL and DcR1 Expressions Are Differentially Regulated in the Pancreatic Islets of STZ-Versus CY-AppHed NOD Mice", Experimental Diabetes Research, Article ID 625813, pp. 1-11, 2011.
Duda et al. "Contents", Pattern Classification, 2nd Ed., 11 P., 2001.
Eberl et al. "A Rapid Crosstalk of Human gamma delta T Cells and Monocytes Drives the Acute Inflammation in Bacterial Infections", PLOS Pathogens 5(2): 1-16, 2009.

Falschlehner et al. "Following TRAIL's Path in the Immune System", Immunology, XP055056763, 127(2): 145-154, Jun. 1, 2009. Chapter 'TRAIL in Viral and Bacterial Infections'.
Feezor et al. "Molecular Characterization of the Acute Inflammatory Response to Infections With Gram-Negaitve Versus Gram-Positive Bacteria", Infection and Immunity, 71(10): 5803-5813, Oct. 2003.
Forde et al. "The Beneficial Pleiotropic Effects of Tumour Necrosis Factor-Related Apoptosis-Inducing Ligand (TRAIL) Within the Vasculature: A Review of the Evidence", Atherosclerosis, XP029468976, 247: 87-96, Available Online Feb. 9, 2016.
Furey et al. "Support Vector Machine Classification and Validation of Cancer Tissue Samples Using Microarray Expression Data", Bioinformatics, 16(10): 906-914, Oct. 2000.
Gaedtke et al. "Elevated Troponin is Associated with Mortality in Severe Sepsis and Septic Shock Patients", American Journal of Respiratory and Critical Care Medicine, 189: 1-2, 2014.
Greenspan et al. "Defining Epitopes: It's Not As Easy As It Seems", Nature Biotechnology, 17: 936-937, Oct. 1999.
Halminen et al. "Expression of MxA Protein in Blood Lymphocytes Discriminates Between Viral and Bacterial Infections in Febrile Children", Pediatric Research, 41(5): 647-650, May 1997.
Hanley et al. "A Method of Comparing the Areas Under Receiver Operating Characteristics Curves Derived From the Same Cases", Radiology, 148(3): 839-843, Sep. 1983.
Henriquez-Camacho et al. "Biomarkers for Sepsis"; BioMed Research International, 547818: 6 pages, 2014.
Herzig et al. "The Role of CXCL10 in the Pathogenesis of Experimental Septic Shock", Critical Care, 18(3): R113-1-R113-18, Jun. 2, 2014.
Hinson et al. "Viperin Is Highly Induced in Neutrophils and Macrophages during Acute and Chronic Lymphocytic Choriomeningitis Virus Infection", The Journal of Immunology, 184:5723-5731, 2010.
Hoffmann et al. "TRAIL Limits Excessive Host Immune Responses in Bacterial Meningitis", JCI The Journal of Clinical Investigation, 117(7): 2004-2013, Jul. 2, 2007.
Holland et al. "STAT3 Mutations in the Hyper-IgE Syndrome", The New England Journal of Medicine, 357(16): 1608-1619, Oct. 18, 2007.
Hu et al. "Gene Expression Profiles in Febrile Children With Defined Viral and Bacterial Infection", Proc. Natl. Acad. Sci. USA, PNAS, 110(31): 12792-12797, Published Online Jul. 15, 2013.
Ioannidis et al. "Plasticity and Virus Specifity of the Airway Epithelial Cell Immune Response During Respiratory Virus Infection", Journal of Virology, 86(10): 5422-36, Mar. 7, 2012.
Janols et al. "Lymphocyte and Monocyte Flow Cytometry Immunophenotyping as A Diagnostic Tool in Uncharacteristic Inflammatory Disorders", BMC Infectious Diseases, XP002663504, 10(205): 1-9, 2010. Abstract.
Jenner et al. "Insights Into Host Responses Against Pathogens From Transcriptional Profiling", Nature Review Microbiology, 3: 281-294, Apr. 2005.
Ju et al. "Research Progress of Some Inflammatory Markers in Infectious Diseases", Chinese Journal of Practical Internal Medicine, 30(Suppl.1): 80-81, Jun. 2010. With an English Translation.
Kaizer et al. "Gene Expression in Peripheral Blood Mononuclear Cells From Children With Diabetes", The Journal of Clinical Endocrinology & Metabolism, 92(9): 3705-3711, 2007.
Kang et al. "Low serum TNF-Related Apoptosis-Inducing Ligand (TRAIL) Levels Are Associated with Acute Ischemic Stroke Severity", Atherosclerosis, 240: 228-233, 2015.
Kawada et al. "Analysis of Gene-Expression Profiles by Oligonucleotide Microarray in Children With Influenza", Journal of General Virology, 87: 1677-1683, 2006.
Kichev et al. "Tumor Necrosis Factor-Related Apoptosis-Inducing Ligand (TRAIL) Signaling and Cell Death in the Immature Central Nervous System after Hypoxia-Ischemia and Inflammation", Journal of Biological Chemistry 289(13): 9430-9439, 2014.
Kohavi et al. "Wrappers for Feature Subset Selection", Artifical Intelligence, 97: 273-324, 1997.
Kotelkin et al. "Respiratory Syncytial Virus Infections Sensitizes Cells to Apoptosis Mediated by Tumor Necrosis Factor-Related

(56) References Cited

OTHER PUBLICATIONS

Apoptosis-Inducing Ligand", Journal of Virology, XP055056816, 77(17): 9156-9172, Aug. 12, 2003. Fig.5B.
Lampe et al. "Expression of the Interferon-Induced MxA Protein in Viral Encephalitis", Neuropathology and Applied Neurobiology, 29(3): 273-279, May 27, 2003.
Le Roux "Les Examens a Visee Etiologique Dans les Pneumopathies Communautaires de l'Enfant (Hors Imagerie) [Laboratory Investigations in Acute Lower Respiratory Tract Infections in Children]", Archives de Pediatrie, XP002663501, 5(Suppl.1): 28S-32S, 1998. Abstract.
Leibovici et al. "The Benefit of Appropriate Empirical Antibiotic Treatment in Patients with Bloodstream Infection", Journal of Internal Medicine, 244(5): 379-386, Nov. 1, 1998.
Liabeuf et al. "The Circulating Soluble TRAIL Is A Negative Marker for Inflammation Inversely Associated With the Mortality Risk in Chronic Kidney Disease Patients", Nephrology Dialysis Transplantation, XP055497900, 25(8): 2596-2602, Advance Access Publication Feb. 26, 2010. Abstract, p. 2597, Right col. 2nd Para, Figs.2, 3.
Liu et al. "Early Days: Genomics and Human Responses to Infection", Current Opinion in Microbiology, 9: 312-319, Available Online May 6, 2006.
Lloyd et al. "Modelling The Human Immune Response: Performance Of A 1011 Human Antibody Repertoire Against A Broad Panel Of Therapeutically Relevant Antigens", Protein Engineering, Design & Selection 22(3): 159-168, Oct. 29, 2008.
Ludwig et al. "Tumor Necrosis Factor Related Apoptosis Inducing Ligand: A Novell Mechanism for Bacillus Calmette Guerin Induced Antitumor Activity" Cancer Research 64: 3386-3390,May 15, 2004.
Malcolm et al. "Microarrays Analysis of Lipopolysaccharide-Treated Human Neutrophils", American Journal of Physiology, Lung Cellular & Molecular Physiology, 284(4): L663-L670, First Published Dec. 20, 2002.
Michowitz et al. "The Involvement of Tumor Necrosis Factor-Related Apoptosis-Inducing Ligand(TRAIL) in Atherosclerosis.", Journal of the American College of Cardiology, 45(7): 1018-1024, 2005.
Nakabayashi et al. "MxA-Based Recognition of Viral Illness in Febrile Children by A Whole Blood Assay", Pediatric Research, 60(6): 770-774, 2006.
Neu et al. "Expression of Tumor Necrosis Factor-Alpha-Related Apoptosis- Inducing Ligand and Its Proapoptotic Receptors Is Down-Regulated during Gastric Infection with Virulent cagA+/vacAsl+ *Helicobacter pylori* Strains", The Journal of Infectious Diseases 191(4): 571-578, Feb. 15, 2005.
New England Biolabs "New England Biolabs Catalog", New England Biolabs, 1-4 pages, 1996.
Ng et al. "IP-10 Is An Early Diagnostic Marker for Identification of Late-Onset Bacterial Infection in Preterm Infants", Pediatric Research, 61(1): 93-98, Jan. 2007.
Niederman "Biological Markers to Determine Eligibility in Trials for Community-Acquired Pneumonia: A Focus on Procalcitonin", Clinical Infectious Diseases, XP002670357, 47(Suppl.3): S127-S132, Dec. 2008.
Niessner et al. "Prognostic Value of Apoptosis Markers in Advanced Heart Failure Patients", European Heart Journal, XP055497907, 30(7): 789-796, Published Online Feb. 4, 2009. Abstract, Table 2, Fig.2.
Oda et al. "A Comprehensive Map of the Toll-Like Receptor Signaling Network", Molecular Systems Biology, 2(2006.0015): 1-20, Apr. 18, 2006.
Osmancik et al. "Prognostic Value of TNF-Related Apoptosis Inducing Ligand (TRAIL) in Acute Coronary Syndrome Patients", PLoS One, 8(2): e53860, 2013.
Oved et al. "A Novel Host-Proteome Signature for Distinguishing Between Acute Bacterial and Viral Infections", PLOS ONE, XP055456891, 10(3): e0120012-1-e120012-18, Mar. 18, 2015. Figs. 3C, 4.

Padlan "X-Ray Crystallography Of Antibodies", Advances In Protein Chemistry, 49: 57-133; 1996.
Paul et al. "Systematic Review and Meta-Analysis of the Efficacy of Appropriate Empiric Antibiotic Therapy for Sepsis", Antimicrobial Agents and Chemotherapy, 54(11): 4851-4863, Nov. 2010.
Pepe et al. "Combining Diagnostic Test Results to Increase Accuracy", Biostatistics, XP055033234, 1(2): 123-140, Jun. 2000.
Povoa et al. "C-Reactive Protein, An Early Marker of Community-Acquired Sepsis Resolution: A Multi-Center Prospective Observational Study", Critical Care, 15(4): R169-1-R169-10, Published Online Jul. 15, 2011.
Qian et al. "Identification of Genes Critical for Resistance to Infection by West Nile Virus Using RNA-Seq Analysis", Viruses, 5(7): 1664-1681, Jul. 8, 2013.
Radom-Aizik et al. "Effects of 30 Min. of Aerobic Exercise on Gene Expression in Human Neutrophils", Journal of Applied Physiology, 104: 236-243, 2008.
Ramilo et al. "Gene Expression Patterns in Blood Leukocytes Discriminate Patients With Acute Infections", Blood, 109(5): 2066-2077, Mar. 1, 2007.
RayBiotech "Mouse L308 Array, Membrane [AAM-BLM-1]1-Series-308-Label-Based-Mouse-Cytok", RayBiotech, XP055473187, Retrieved From the Internet, 7 P., May 7, 2018.
Rosseau et al. "Comparative Transcriptional Profiling of the Lung Reveals Shared and Distinct Features of *Streptococcus pneumoniae* and Influenza A Virus Infection", Immunology, 120: 380-391, 2006.
Rothstein et al. "Chronic Inhibition of Superoxide Dismutase Produces Apoptotic Death of Spinal Neurons", PNAS, (10): 4155-4159, May 1994.
Rudikoff et al. "Single Amino Acid Substitution Altering Antigen-Binding Specificity", PNAS, 79(6): 1979-1983, Mar. 1982.
Sasaki et al. "Differentiating Between Bacterial and Viral Infection by Measuring Both C-Reactive Protein and 2'-5'-Oligoadenylate Synthetase as Inflammatory Markers", Journal of Infection and Chemotherapy, XP055696216, 8(1): 76-80, Mar. 2002.
Secchiero et al. "Potential Prognostic Significance of Decreased Serum Levels of TRAIL After Acute Myocardial Infarction", PLoS ONE, XP055056988, 4(2): e4442-1-e4442-6, Feb. 16, 2009. Fig.1.
Shair et al. "Epstein-Barr Virus Latent Membrane Protein-1 Effects on Junctional Plakoglobin and Induction of a Cadherin Switch", Cancer Research, Cell, Tumor, and Stem Cell Biology, 69(14): 5734-5742, Jul. 15, 2009.
Sheyin et al. "The Prognostic Significance of Troponin Elevation in Patients with Sepsis: A Meta-Analysis", Heart & Lung, 44(1): 75-81, Jan.-Feb. 2015.
Shimetani et al. "Levels of Three Inflammation Markers, C-Reactive Protein, Serum Amyloid A Protein and Procalcitonin, in the Serum and Cerebrospinal Fluid of Patients With Meningitis", Scandinavian Journal of Clinical and Laboratory Investigation, XP008113027, 61(7): 567-574, 2001. Abstract.
Shommu et al. "Metabolomic and Inflammatory Mediator Based Biomarker Profiling as A Potential Novel Method to Aid Pediatric Appendicitis Identification", PLOS ONE, XP055692841, 13(3): e0193563-1-e0193563-13, Mar. 12, 2018.
Singer et al. "The Third International Consensus Definitions for Sepsis and Septic Shock (Sepsis-3)", Journal of the American Medical Association, JAMA, 315(8): 801-810, Feb. 23, 2016. Box 3, Fig.
Smith et al. "Quantitative Assessment of Human Whole Blood RNA as A Potential Biomarker for Infectious Disease", Analyst, 132: 1200-1209, First Published Oct. 31, 2007.
Sukumaran et al. "Early Transcriptional Response of Human Neutrophils to Anaplasma Phagocytophilum Infection", Infection and Immunity, 73(12): 8089-8099, Dec. 1, 2005.
Sullivan Pepe et al. "Combining Diagnostic Test Results to Increase Accuracy", Biostatistics, XP055033234, 1(2): 123-140, Jun. 1, 2000. Abstract, Section 2.4.
Tang et al. "Gene-Expression Profiling of Gram-Positive and Gram-Negative Sepsis in Critically Ill Patients", Critical Care Medicine, 36(4): 1125-1128, 2008.
Tang et al. "Hypoxic Preconditioning Enhances the Benefit of Cardiac Progenitor Cell Therapy for Treatment of Myocardial

(56) References Cited

OTHER PUBLICATIONS

Infarction by Inducing CXCR4 Expression", Circulation Research, XP055473182, 104(10): 1209-1216, May 22, 2009. Online Table 1.
Tang et al. "The Use of Gene-Expression Profiling to Identify Candidate Genes in Human Sepsis", American Journal of Respiratory and Critical Care Medicine, 176: 676-684, Originally Published Jun. 15, 2007.
ThermoFisher Scientific "Interferon Alpha Inducible Protein 27: IFI27", ThermoFisher Scientific, Product Details, 2 P., 2020.
ThermoFisher Scientific "Interferon Induced Protein 44 Like: IFI44L", ThermoFisher Scientific, Product Details, 2 P., 2020.
ThermoFisher Scientific "TaqMan Gene Expression Assay Solutions: Proven 5' Nuclease-Based Real-Time PCR Chemistry", Thermo Fisher Scientific, Applied Biosystems, 11 P., 2015.
Thivierge et al. "Eukaryotic Elongation Factor 1A Interacts With Turnip Mosaic Virus RNA-Dependent RNA Polymerase and VPg-Pro in Virus-Induced Vesicles", Virology, XP002663503, 377(1): 216-225, Jul. 2008. Abstract, p. 220, r-h col. Para 3-p. 222, r-h col. Para 1.
Tian et al. "Soluble Tumor Necrosis Factor Related Apoptosis Inducing Ligand Level as A Predictor of Severity of Sepsis and the Risk of Mortality in Septic Patients", PLOS One, XP055497898, 8(12): e82204-1-e82204-5, Dec. 12, 2013.
Tisato et al. "Low Circulating TRAIL Levels Are Associated With Increase of Resistin and Lipocalin-2/ngal Adipokines in Postmenopausal Women", Mediators of Inflammation, Article ID 5356020, 8 p. 2017.
Torkkola "Feature Extraction by Non-Parametric Mutual Information Maximization", Journal of Machine Learning Research, 3: 1415-1438, Mar. 2003.
Tsuji "TRAILing Gastrointestinal Pathogenesis", Journal of Gastroenterology and Hepatology, 18(7): 753-755, Published Online Jun. 10, 2003.
Tworoger et al. "Collection, Processing, and Storage of Biological Samples in Epidemiologic Studies: Sex Hormones, Carotenoids, Inflammatory Markers, and Proteomics as Examples", Cancer Epidemiol Biomarkers and Prevention, 15(9): 1578-1581, Sep. 2006.
UCSC "Human Gene IFI27 (ENST00000621160.5) From Gencode V39", Ucsc Browser, Retrieved From the Internet, 3 Pages, Last Updated Jan. 17, 2022.
UCSC "Human Gene IFIT1 (ENST00000371804.4) From Gencode V39", Ucsc Browser, Retrieved From the Internet, 4 Pages, Last Updated Jan. 17, 2022.
Ucsc "Ucsc Browser on Human Feb. 2009 (GRCh37/hg19) Assembly: Showing Location of Probes on the Affymetrix ExonChip Binding to Exons of ANKRD22", Ucsc Genome Browser, Version 387, XP055621243, Retrieved From the Internet, 7 P., Jan. 2009.
Ucsc "Ucsc Genome Browser on Human (GRCh38/hg38)", UCSC Genome Browser, Version 429, Chr10: 91152344-91163592, Retrieved From the Internet, 1 p. Apr. 14, 2022.
Ucsc "Ucsc Genome Browser on Human (GRCh38/hg38)", UCSC Genome Browser, Version 429, Chr14: 94577158-94582955, Retrieved From the Internet, 1 p. Apr. 14, 2022.
Ucsc "Ucsc Genome Browser on Human Feb. 2009 (GRCh37/hg19) Assembly: Showing Location of Probes on the Affymetrix ExonChip Binding to Exons of AIM2", Ucsc Browser, XP055621240, Retrieved From the Interent, 8 P., Jan. 2009.
Vogel et al. "Sequence Signatures and mRNA Concentration Can Explain Two-Thirds of Protein Abundance Variation in A Human Cell Line", Molecular Systems Biology, 6(Art.400): 1-9, Published Online Aug. 24, 2010.
Volpato et al. "Association of Tumor Necrosis Factor-Related Apoptosis-Inducing Ligand with Total and Cardiovascular Mortality in Older Adults", Atherosclerosis, 215: 452-458, 2011.
Wang et al. "Rotavirus Infection Alters Peripheral T-Cell Homeostasis in Children With Acute Diarrhea", Journal of Virology, 81(8): 3904-3912, Apr. 2007.
Whiteside et al. "Role of Human Natural Killer Cells in Health and Disease", Clinical and Diagnostic Laboratory Immunology, 1(2): 125-133, Mar. 31, 1994.
Wu "Increased Troponin in patients with Sepsis and Septic Shock: Myocardial Necrosis or Reversible Myocardial Depression", Intensive Care Medicine, 27: 959-961, 2001.
Xu et al. "Lipocalins as Biochemical Markers of Disease", Biochimica et Biophysica Acta, XP002376345, 1482(1): 298-307, Oct. 18, 2000.
Yamaji et al. "Significance of Eukaryotic Translation Elongation Factor 1A in Tobacco Mosaic Virus Infection", Archives of Virology, XP002663502, 155(2): 263-268, Feb. 2010. Abstract.
Yeung et al. "Serum Cytokines in Differentiating Between Viral and Bacterial Enterocolitis", Annals of Tropical Paediatrics, 24(4): 337-343, Published Online Jul. 18, 2013.
Zaas et al. "A Host-Based RT-PCR Gene Expression Signature to Identify Acute Respiratory Viral Infection", Science Translational Medicine, 5(203): 203ra126-1-203ra126-19, Sep. 18, 2013.
Zaas et al. "Gene Expression Signatures Diagnose Influenza and Other Symptomatic Respiratory Viral Infections in Humans", Cell Host & Microbe, XP002670360, 6(3): 207-217, Sep. 17, 2009. Abstract, p. 212, 1-h col. p. 213, 1-h col. Fig.4.
Zaas et al. "The Current Epidemiology and Clinical Decisions Surrounding Acute Respiratory Infections", Trends in Molecular Medicine, XP055522333, 20(10): 579-588, Published Online Sep. 5, 2014.
Zaas et al. Supplementary Materials for "A Host-Based RT-PCR Gene Expression Signature to Identify Acute Respiratory Viral Infection", Science Translational Medicine, 5(203): 203ra126-1-203ra126-21, Sep. 18, 2013.
Zhang "Research Progress of Interferon-Inducible Protein 10 and Its Effect in Newborn Infection Diagnosis", Chinese Journal of Neonatology, 4: 60-62, Jul. 15, 2013.
Zhang et al. "Expression of Tumor Necrosis Factor-Related Apoptosis-Inducing Ligand in Serum of Severe Hepatitis Patients with Nosocomial Infections and its Clinical Significance", Chinese Journal of Nosocomiology, 24, Abstract, 2012.
Zhu et al. "Use of Differential Display Analysis to Assess the Effect of Human Cytomegalovirus Infection on the Accumulation of Cellular RNAs: Induction of Interferon-Responsive RNAs", Proc. Natl. Acad. Sci. USA, XP002088235, 94(25): 13985-13990, Dec. 9, 1997. Abstract, Fig.2.
Zilliox et al. "Gene Expression Changes in Peripheral Blood Mononuclear Cells During Measles Virus Infection", Clinical and Vaccine Immunology, 14(7): 918-923, Jul. 2007.

\* cited by examiner

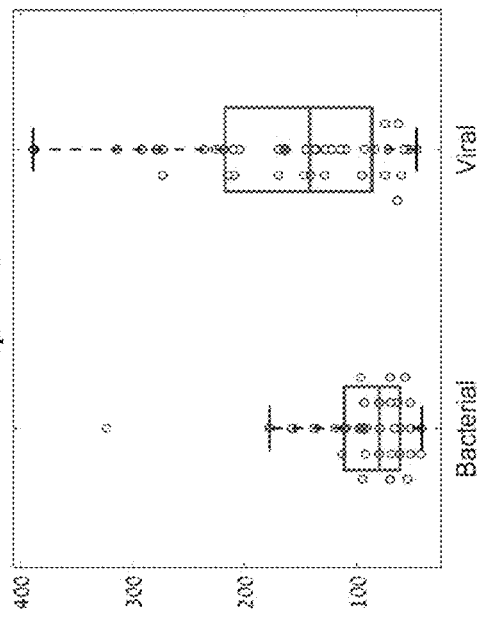
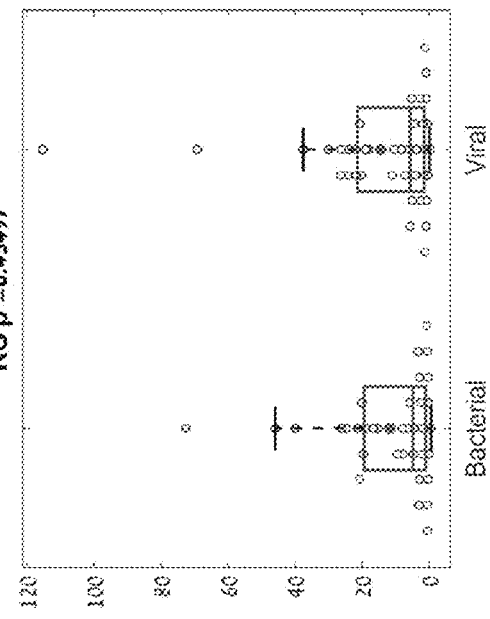
FIG. 7 cont.
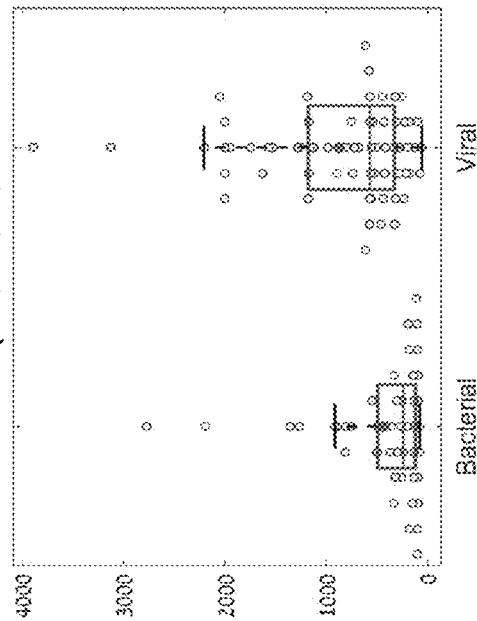
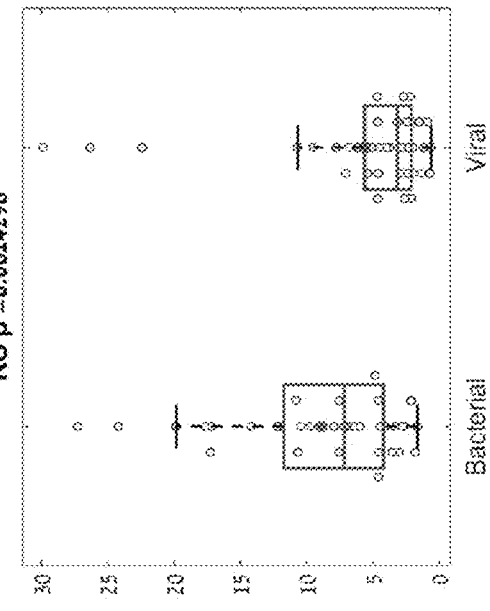

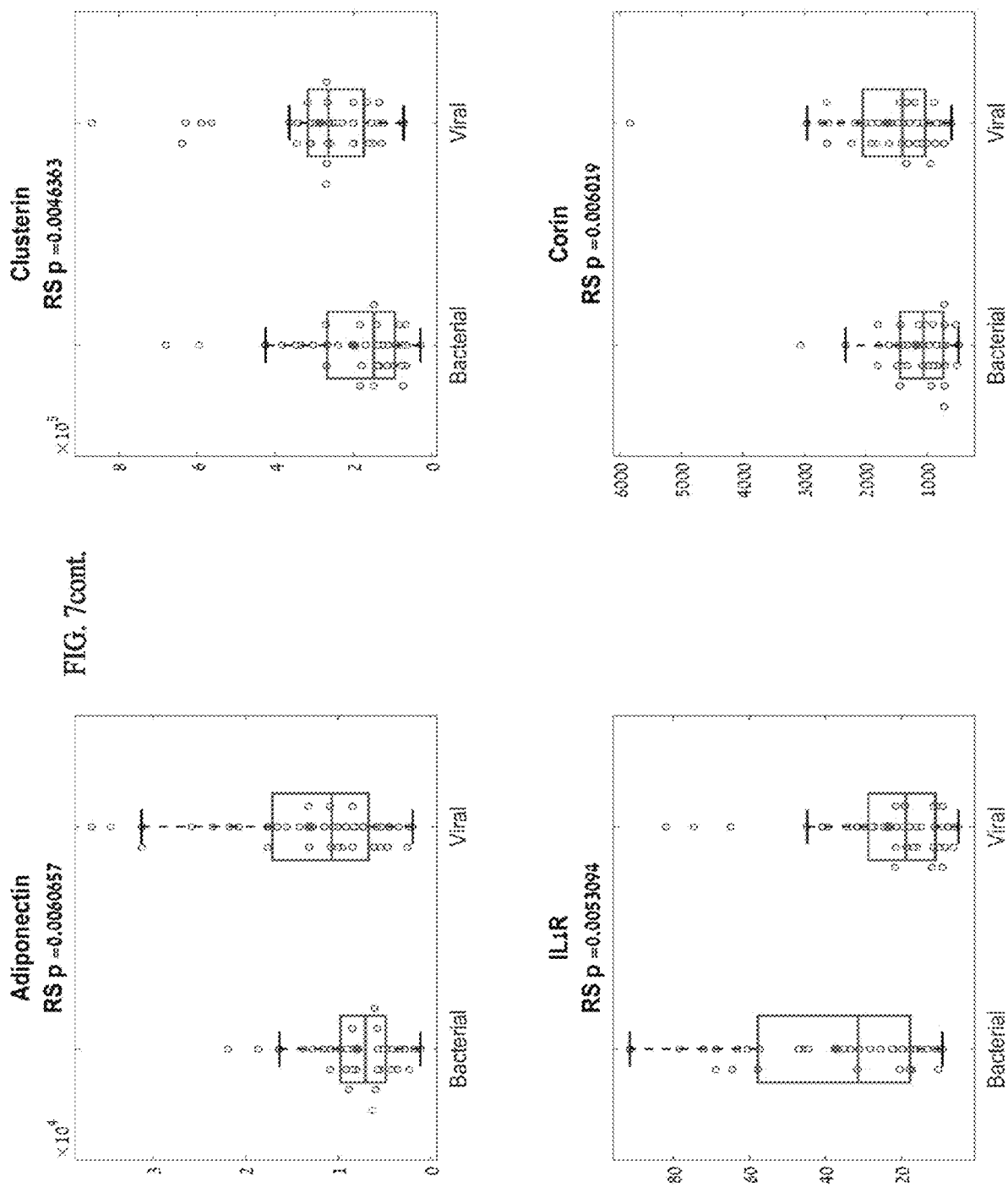
FIG. 7cont.

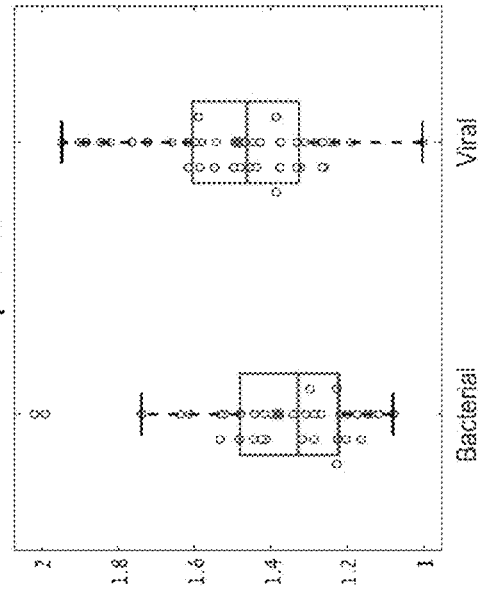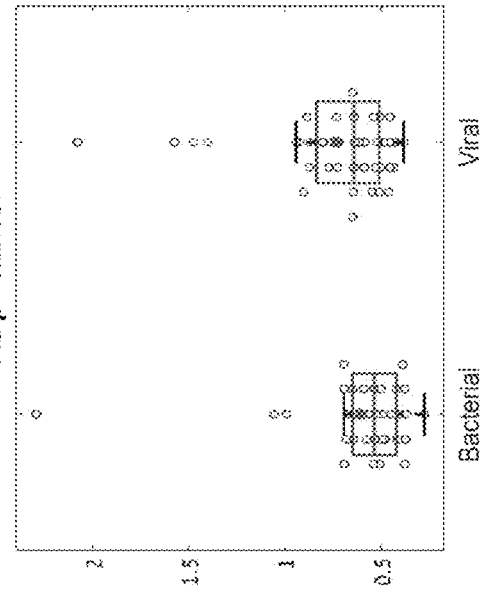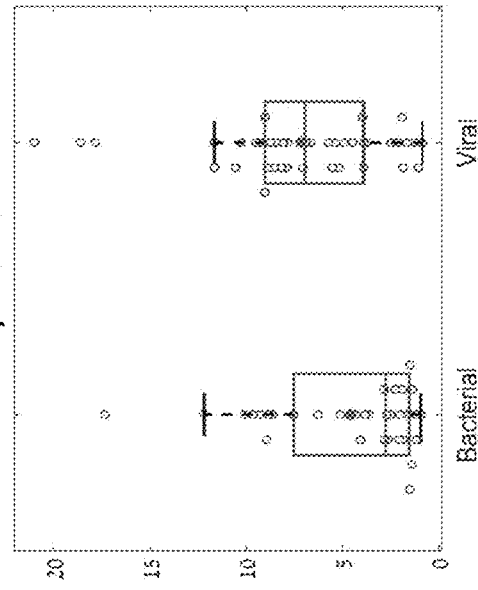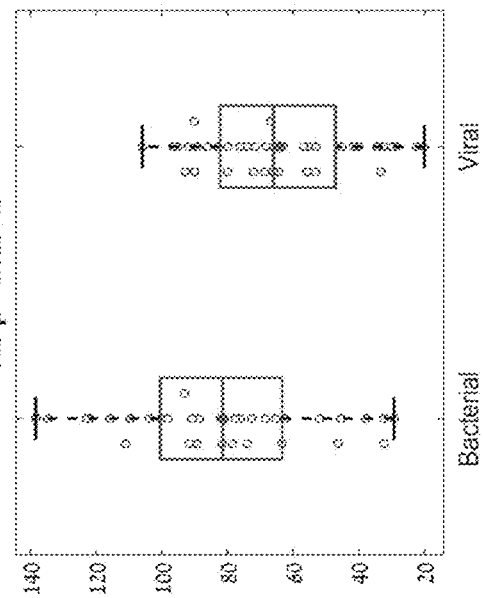
FIG. 7cont.

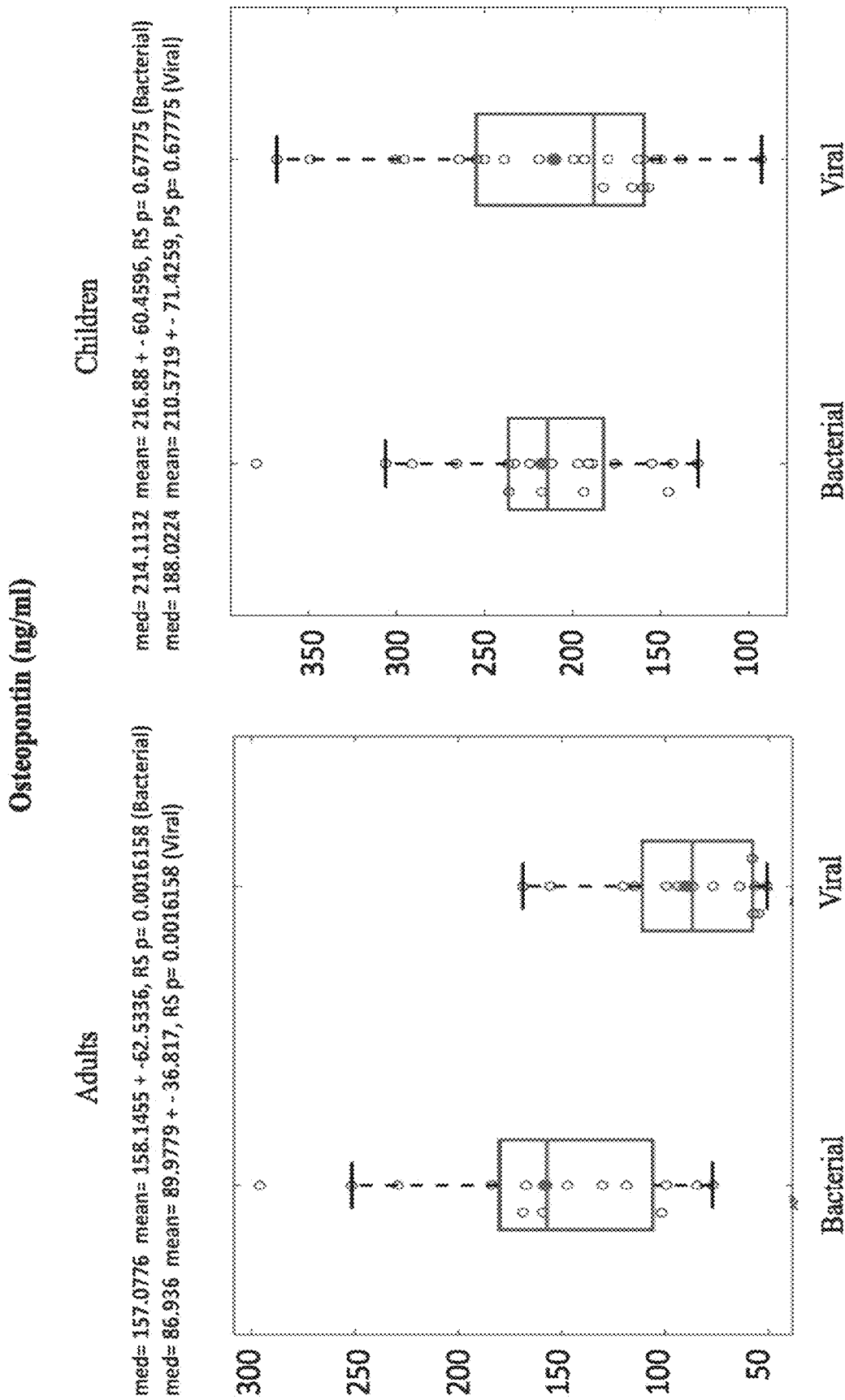

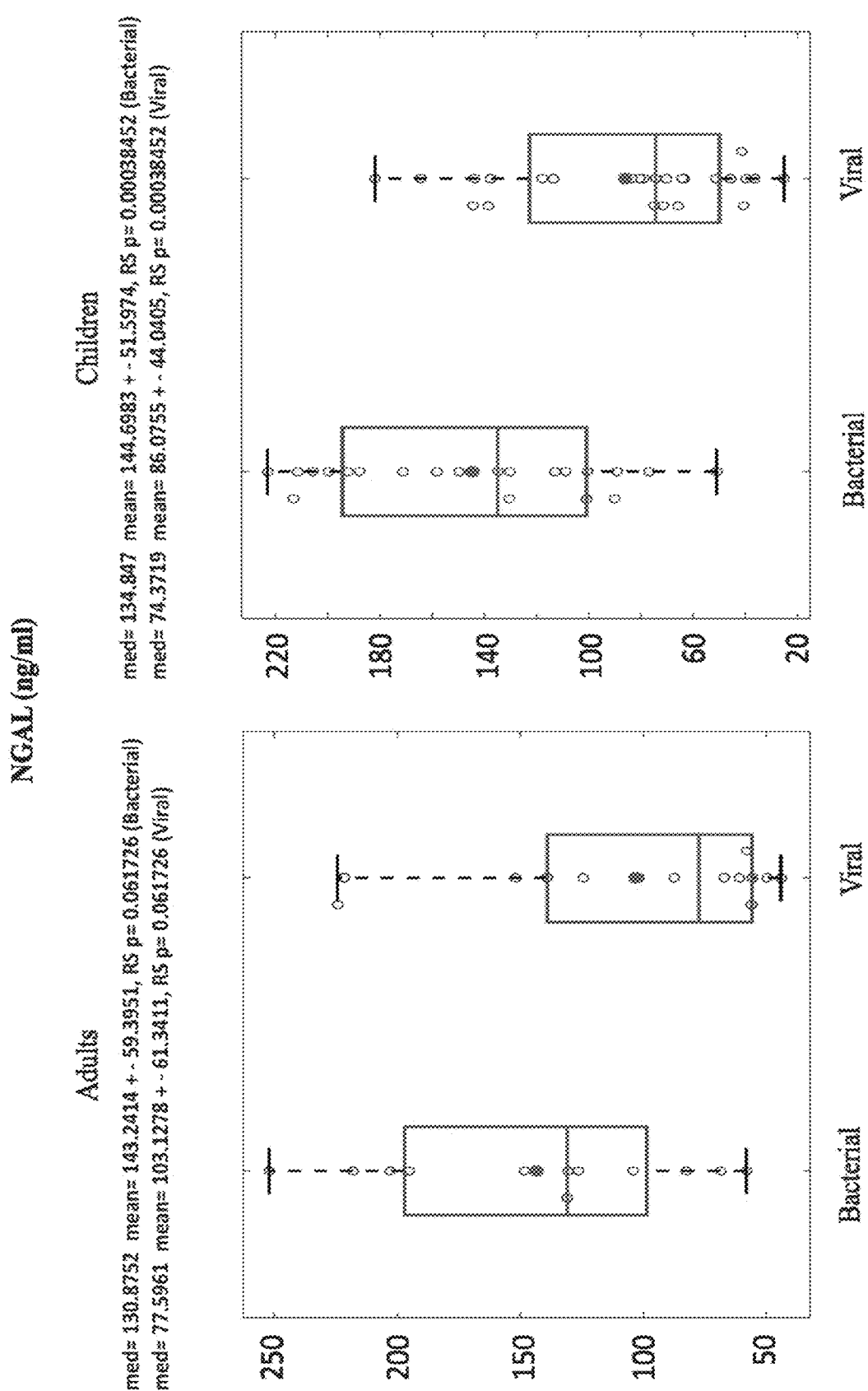

MARKER COMBINATIONS FOR DIAGNOSING INFECTIONS AND METHODS OF USE THEREOF

RELATED APPLICATIONS

This application is a division of U.S. patent application Ser. No. 17/007,095 filed on Aug. 31, 2020, which is a division of U.S. patent application Ser. No. 15/531,747 filed on May 31, 2017, which is a National Phase of PCT Patent Application No. PCT/IL2015/051201 having International Filing Date of Dec. 10, 2015, which claims the benefit of priority under 35 USC § 119(e) of U.S. Provisional Patent Application Nos. 62/136,725 filed on Mar. 23, 2015 and 62/090,606 filed on Dec. 11, 2014. The contents of the above applications are all incorporated by reference as if fully set forth herein in their entirety.

SEQUENCE LISTING STATEMENT

The XML file, entitled 94869SequenceListing.xml, created on Dec. 8, 2022, comprising 28,871 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to the identification of biological signatures and determinants associated with bacterial and viral infections and methods of using such biological signatures in the screening diagnosis, therapy, and monitoring of infection.

Antibiotics (Abx) are the world's most prescribed class of drugs with a 25-30 billion $US global market. Abx are also the world's most misused drug with a significant fraction of all drugs (40-70%) being wrongly prescribed (Linder, J. A. and R. S. Stafford 2001; Scott, J. G. and D. Cohen, et al. 2001; Davey, P. and E. Brown, et al. 2006; Cadieux, G. and R. Tamblyn, et al. 2007; Pulcini, C. and E. Cua, et al. 2007), ("CDC—Get Smart: Fast Facts About Antibiotic Resistance" 2011).

One type of Abx misuse is when the drug is administered in case of a non-bacterial disease, such as a viral infection, for which Abx is ineffective. For example, according to the USA center for disease control and prevention CDC, over 60 Million wrong Abx prescriptions are given annually to treat flu in the US. The health-care and economic consequences of the Abx over-prescription include: (i) the cost of antibiotics that are unnecessarily prescribed globally, estimated at >$10 billion annually; (ii) side effects resulting from unnecessary Abx treatment are reducing quality of healthcare, causing complications and prolonged hospitalization (e.g. allergic reactions, Abx associated diarrhea, intestinal yeast etc.) and (iii) the emergence of resistant strains of bacteria as a result of the overuse (the CDC has declared the rise in antibiotic resistance of bacteria as "one of the world's most pressing health problems in the $21^{st}$ century" (Arias, C. A. and B. E. Murray 2009; "CDC—About Antimicrobial Resistance" 2011)).

Antibiotics under-prescription is not uncommon either. For example up to 15% of adult bacterial pneumonia hospitalized patients in the US receive delayed or no Abx treatment, even though in these instances early treatment can save lives and reduce complications (Houck, P. M. and D. W. Bratzler, et al 2002).

Technologies for infectious disease diagnostics have the potential to reduce the associated health and financial burden associated with Abx misuse. Ideally, such a technology should: (i) accurately differentiate between a bacterial and viral infections; (ii) be rapid (within minutes); (iii) be able to differentiate between pathogenic and non-pathogenic bacteria that are part of the body's natural flora; (iv) differentiate between mixed co-infections and pure viral infections and (v) be applicable in cases where the pathogen is inaccessible (e.g. sinusitis, pneumonia, otitis-media, bronchitis, etc).

Current solutions (such as culture, PCR and immunoassays) do not fulfill all these requirements: (i) Some of the assays yield poor diagnostic accuracy (e.g. low sensitivity or specificity) (Uyeki et al. 2009), and are restricted to a limited set of bacterial or viral strains; (ii) they often require hours to days; (iii) they do not distinguish between pathogenic and non-pathogenic bacteria (Del Mar, C 1992), thus leading to false positives; (iv) they often fail to distinguish between a mixed and a pure viral infections and (v) they require direct sampling of the infection site in which traces of the disease causing agent are searched for, thus prohibiting the diagnosis in cases where the pathogen resides in an inaccessible tissue, which is often the case.

Consequentially, there still a diagnostic gap, which in turn often leads physicians to either over-prescribe Abx (the "Just-in-case-approach"), or under-prescribe Abx (the "Wait-and-see-approach") (Little, P. S. and I. Williamson 1994; Little, P. 2005; Spiro, D. M. and K. Y. Tay, et al. 2006), both of which have far reaching health and financial consequences.

Accordingly, a need exists for a rapid method that accurately differentiates between bacterial, viral, mixed and non-infectious disease patients that addresses these challenges.

WO 2013/117746 teaches signatures and determinants for distinguishing between a bacterial and viral infection.

Additional Background art includes Kfir et al., PLOS One, March 18, DOI:10.1371/journal.pone.0120012, 2015.

SUMMARY OF THE INVENTION

According to one aspect of the present invention there is provided a method of determining an infection type in a subject comprising measuring the concentration of a first determinant selected from the group consisting of the determinants which are set forth in Table 1 and a second determinant selected from the group of the determinants which are set forth in Table 2 in a sample derived from the subject, wherein the concentration is indicative of the infection type.

According to one aspect of the present invention there is provided a method of determining an infection type in a subject comprising measuring the concentration of at least two determinants which are set forth in Table 1 in a sample derived from the subject, wherein the concentration is indicative of the infection type.

According to one aspect of the present invention there is provided a method of distinguishing between a bacterial or mixed infection, and a viral infection in a subject comprising:

(a) measuring the concentration of a first determinant selected from the group consisting of the determinants which are set forth in Table 1 and a second determinant selected from the group of the determinants which are set forth in Table 2 in a sample derived from the subject;
(b) applying a pre-determined mathematical function on the concentrations of the determinants to compute a score;
(c) comparing the score to a predetermined reference value.

According to one aspect of the present invention there is provided a method of distinguishing between a bacterial or mixed infection, and a viral infection in a subject comprising:
(a) measuring the concentration of at least two determinants which are set forth in Table 1 in a sample derived from the subject;
(b) applying a pre-determined mathematical function on the concentrations of the determinants to compute a score;
(c) comparing the score to a predetermined reference value.

According to one aspect of the present invention there is provided a method of determining an infection type in a child, comprising measuring the concentration of the determinant neopterin and/or the determinant NGAL in a sample derived from the child, wherein the concentration is indicative of the infection type.

According to one aspect of the present invention there is provided a method of determining an infection type in an adult, comprising measuring the concentration of the determinant osteopontin in a sample derived from the adult, and at least one of the determinants set forth in Table 2, wherein the concentration is indicative of the infection type.

According to one aspect of the present invention there is provided a kit comprising a plurality of determinant detection reagents that specifically detect a first determinant selected from the group consisting of the determinants which are set forth in Table 1 and a second determinant selected from the group of the determinants which are set forth in Table 2.

According to one aspect of the present invention there is provided a kit comprising a plurality of detection reagents that specifically detect at least two determinants which are set forth in Table 1.

According to some embodiments, the first determinant is selected from the group consisting of a1 Acid Glycoprotein, Adiponectin, Angiogenin, Angiopoietin1, Angiopoietin2, APRIL, BAFF, BDNF, CD 23, CD14, CD142, CD27, CD95, Clusterin, Complement factor D, Corin, CXCL13, Cystatin C, Dkk1, E Cadherin, E Selectin, Endostatin, Fetuin A, GCP2, GDF15, ICAM1, IGFBP3, IL18, IL19, Leptin, Leptin R, LIGHT, MBL, MIF, MMP2, MMP3, MMP7, MMP8, Myeloperoxidase, Neopterin, NGAL, Osteopontin, Osteoprotegerin, P Selectin, PCSK9, Pentraxin3, Pro Cathepsin B, Progranulin, ProMMP10, Prostaglandin E2, RBP4, Resistin, SLPI, Substance P, TFPI, TGF B1, Thrombospondin2, Tie2, uPAR, VCAM1, VEGF C and Vitamin D Binding Protein.

According to some embodiments, the first determinant is selected from the group consisting of NGAL, Resistin, MMP8, Pentraxin3, E Selectin, MMP7, Myeloperoxidase, Osteopontin, PCSK9, Pro Cathepsin B, a1 Acid Glycoprotein, GDF15, Progranulin, Adiponectin, Clusterin, Corin, Neopterin, Cystatin C, CD27, E Cadherin, Complement factor D, IGFBP3, GCP2, RBP4, CD14 and ProMMP10.

According to some embodiments, the first determinant is NGAL, MMP8 or neopterin.

According to some embodiments, the first determinant is a polypeptide.

According to some embodiments, at least one of the at least two determinants is selected from the group consisting of a1 Acid Glycoprotein, Adiponectin, Angiogenin, Angiopoietin1, Angiopoietin2, APRIL, BAFF, BDNF, CD 23, CD14, CD142, CD27, CD95, Clusterin, Complement factor D, Corin, CXCL13, Cystatin C, Dkk1, E Cadherin, E Selectin, Endostatin, Fetuin A, GCP2, GDF15, ICAM1, IGFBP3, IL18, IL19, Leptin, Leptin R, LIGHT, MBL, MIF, MMP2, MMP3, MMP7, MMP8, Myeloperoxidase, Neopterin, NGAL, Osteopontin, Osteoprotegerin, P Selectin, PCSK9, Pentraxin3, Pro Cathepsin B, Progranulin, ProMMP10, Prostaglandin E2, RBP4, Resistin, SLPI, Substance P, TFPI, TGF B1, Thrombospondin2, Tie2, uPAR, VCAM1, VEGF C and Vitamin D Binding Protein.

According to some embodiments, at least one of the at least two determinants is selected from the group consisting of NGAL, Resistin, MMP8, Pentraxin3, E Selectin, MMP7, Myeloperoxidase, Osteopontin, PCSK9, Pro Cathepsin B, a1 Acid Glycoprotein, GDF15, Progranulin, Adiponectin, Clusterin, Corin, Neopterin, Cystatin C, CD27, E Cadherin, Complement factor D, IGFBP3, GCP2, RBP4, CD14 and ProMMP10.

According to some embodiments, at least one of the at least two determinants is NGAL, MMP8 or neopterin.

According to some embodiments, at least one of the at least two determinants is a polypeptide.

According to some embodiments, at least two determinants are polypeptides.

According to some embodiments, the determinant of Table 1 is selected from the group consisting of a1 Acid Glycoprotein, Adiponectin, Angiogenin, Angiopoietin1, Angiopoietin2, APRIL, BAFF, BDNF, CD 23, CD14, CD142, CD27, CD95, Clusterin, Complement factor D, Corin, CXCL13, Cystatin C, Dkk1, E Cadherin, E Selectin, Endostatin, Fetuin A, GCP2, GDF15, ICAM1, IGFBP3, IL18, IL19, Leptin, Leptin R, LIGHT, MBL, MIF, MMP2, MMP3, MP7, MMP8, Myeloperoxidase, Neopterin, NGAL, Osteopontin, Osteoprotegerin, P Selectin, PCSK9, Pentraxin3, Pro Cathepsin B, Progranulin, ProMMP10, Prostaglandin E2, RBP4, Resistin, SLPI, Substance P, TFPI, TGF B1, Thrombospondin2, Tie2, uPAR, VCAM1, VEGF C and Vitamin D Binding Protein.

According to some embodiments, the determinant of Table 1 is selected from the group consisting of NGAL, Resistin, MMP8, Pentraxin3, E Selectin, MMP7, Myeloperoxidase, Osteopontin, PCSK9, Pro Cathepsin B, a1 Acid Glycoprotein, GDF15, Progranulin, Adiponectin, Clusterin, Corin, Neopterin, Cystatin C, CD27, E Cadherin, Complement factor D, IGFBP3, GCP2, RBP4, CD14 and ProMMP10.

According to some embodiments, the determinant of Table 1 is selected from the group consisting of NGAL, MMP8 and Neopterin.

According to some embodiments, the second determinant is selected from the group consisting of CRP, TRAIL and IP-10.

According to some embodiments, the determinants comprise:
(i) CRP and NGAL;
(ii) CRP and MMP8;
(iii) CRP and neopterin;
(iv) TRAIL and NGAL;
(v) TRAIL and MMP8;
(vi) TRAIL and neopterin;
(vii) IP10 and NGAL;
(viii) IP10 and MMP8; or
(ix) IP10 and neopterin; or (x) Neopterin and PCT; or
(xi) NGAL and PCT.

According to some embodiments, the at least two determinants are:
(i) NGAL and MMP8;
(ii) NGAL and neopterin; or
(iii) neopterin and MMP8

According to some embodiments, the second determinant is TRAIL.

According to some embodiments, the concentration of the TRAIL is higher than a pre-determined threshold value, a bacterial infection is ruled out for the subject.

According to some embodiments, the concentration of the TRAIL is higher than a pre-determined threshold value, a viral infection is ruled in for the subject.

According to some embodiments, the method further comprises measuring the concentration of CRP and/or IP-10.

According to some embodiments, the method further comprises determining the concentration of at least one of the determinants set forth in Table 2.

According to some embodiments, no more than two determinants are measured.

According to some embodiments, no more than three determinants are measured.

According to some embodiments, no more than four determinants are measured.

According to some embodiments, the sample is whole blood or a fraction thereof.

According to some embodiments, the blood fraction sample comprises cells selected from the group consisting of lymphocytes, monocytes and granulocytes.

According to some embodiments, the blood fraction sample comprises serum or plasma.

According to some embodiments, the concentration of the determinant is determined electrophoretically or immunochemically.

According to some embodiments, the immunochemical detection is by flow cytometry, radioimmunoassay, immunofluorescence assay or by an enzyme-linked immunosorbent assay.

According to some embodiments, the concentration of the determinant is measured within about 24 hours after the sample is obtained.

According to some embodiments, the concentration of TRAIL is measured in a sample that was stored at 12° C. or lower, wherein the storage begins less than 24 hours after the sample is obtained.

According to some embodiments, the determinant of Table 1 is set forth in Table 5.

According to some embodiments, the determinant set forth in Table 5 is selected from the group consisting of NGAL, neopterin, and osteopontin.

According to some embodiments, the method further comprises age normalization of the determinant concentration.

According to some embodiments, the method further comprises stratifying the subject according to age and wherein the threshold is an appropriate age dependent threshold.

According to some embodiments, at least one of the determinants is a polypeptide.

According to some embodiments, the detection reagent is an antibody or fragment thereof.

According to some embodiments, the kit comprises antibodies that detect no more than 10 determinants.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

IN THE DRAWINGS

Figure 1:
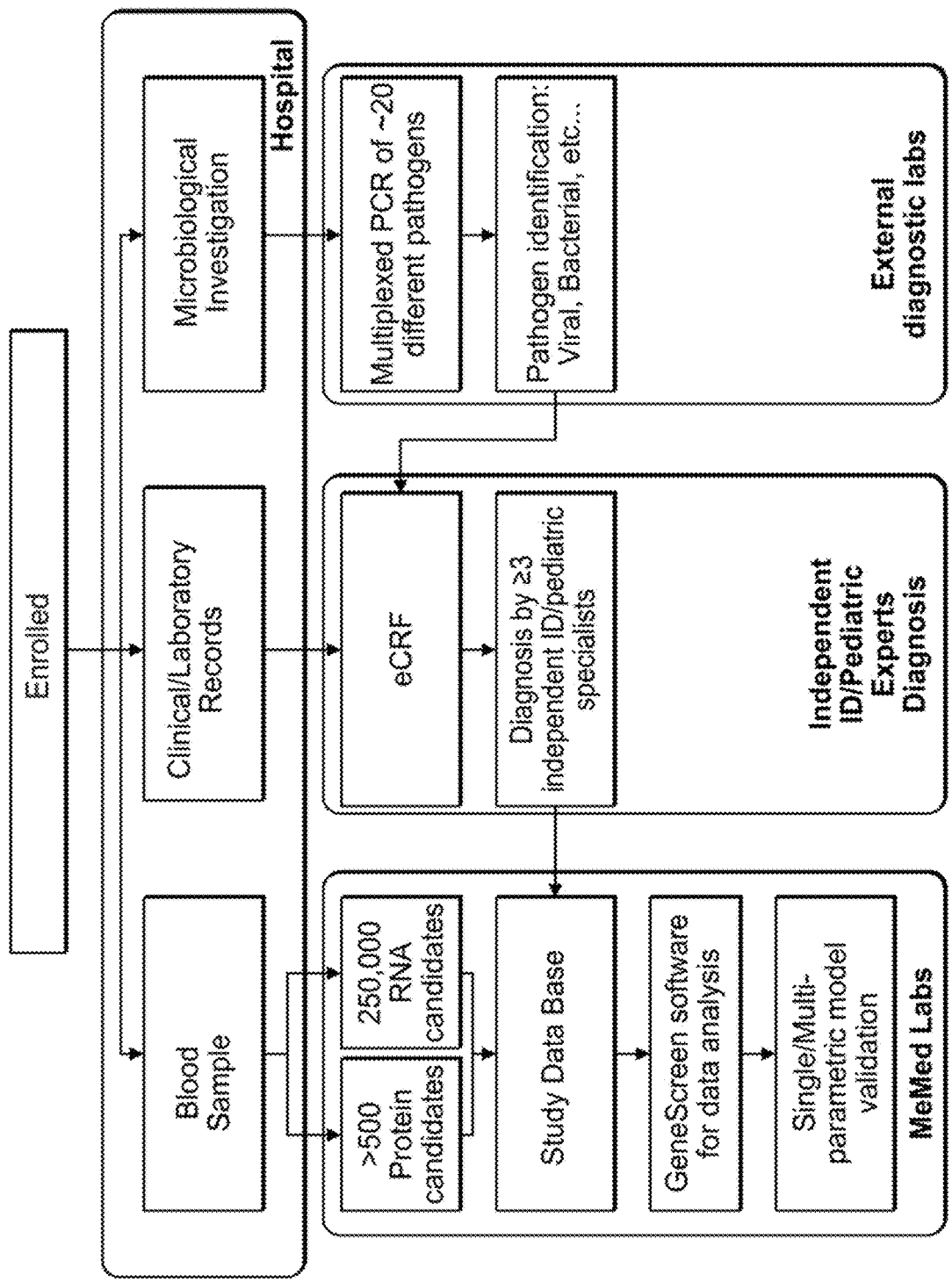

FIG. 1: Clinical study workflow.

Figure 2:
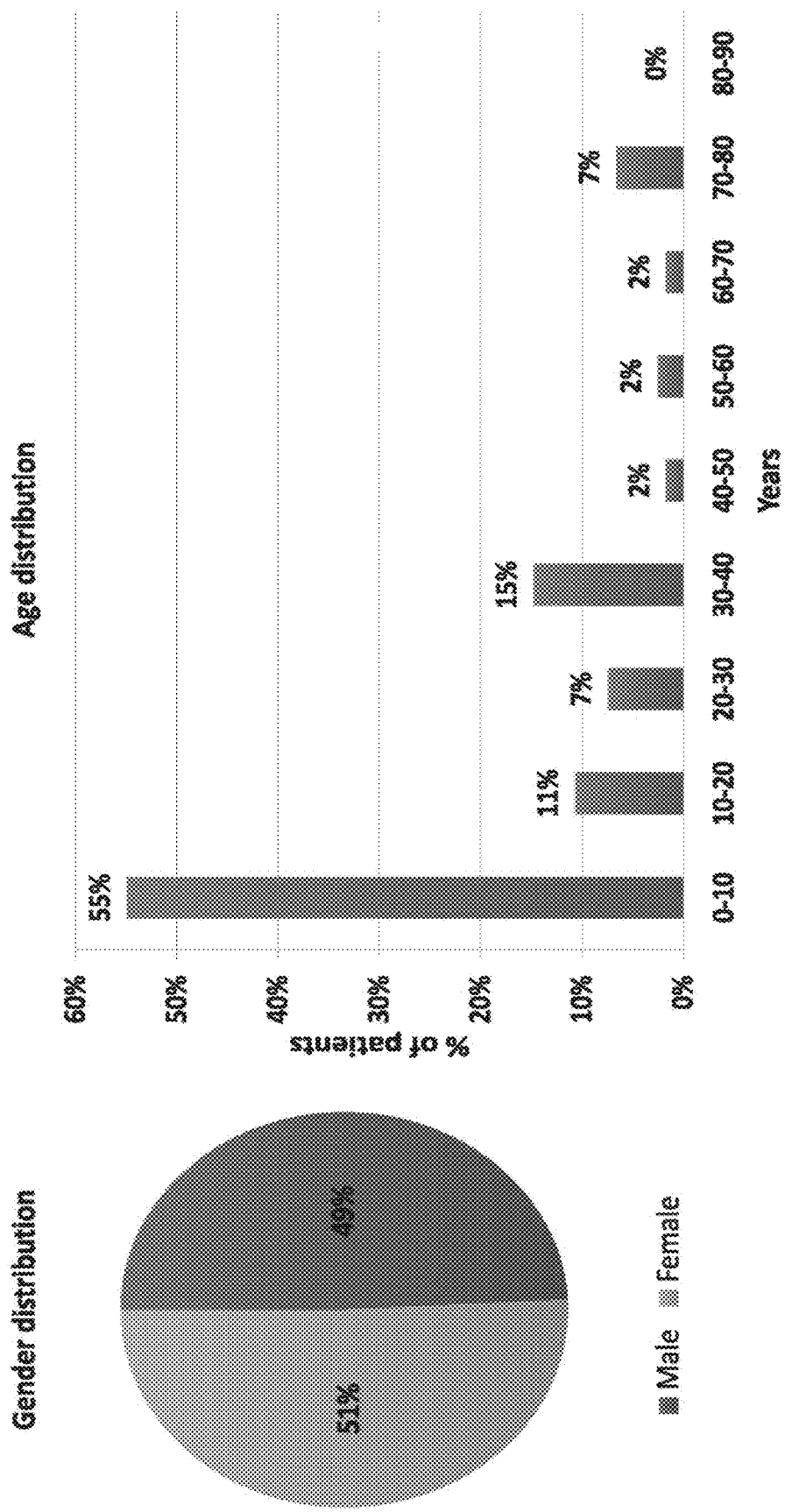

FIG. 2: Distribution of age and gender of the patients enrolled in the clinical study (N=122).

Figure 3:
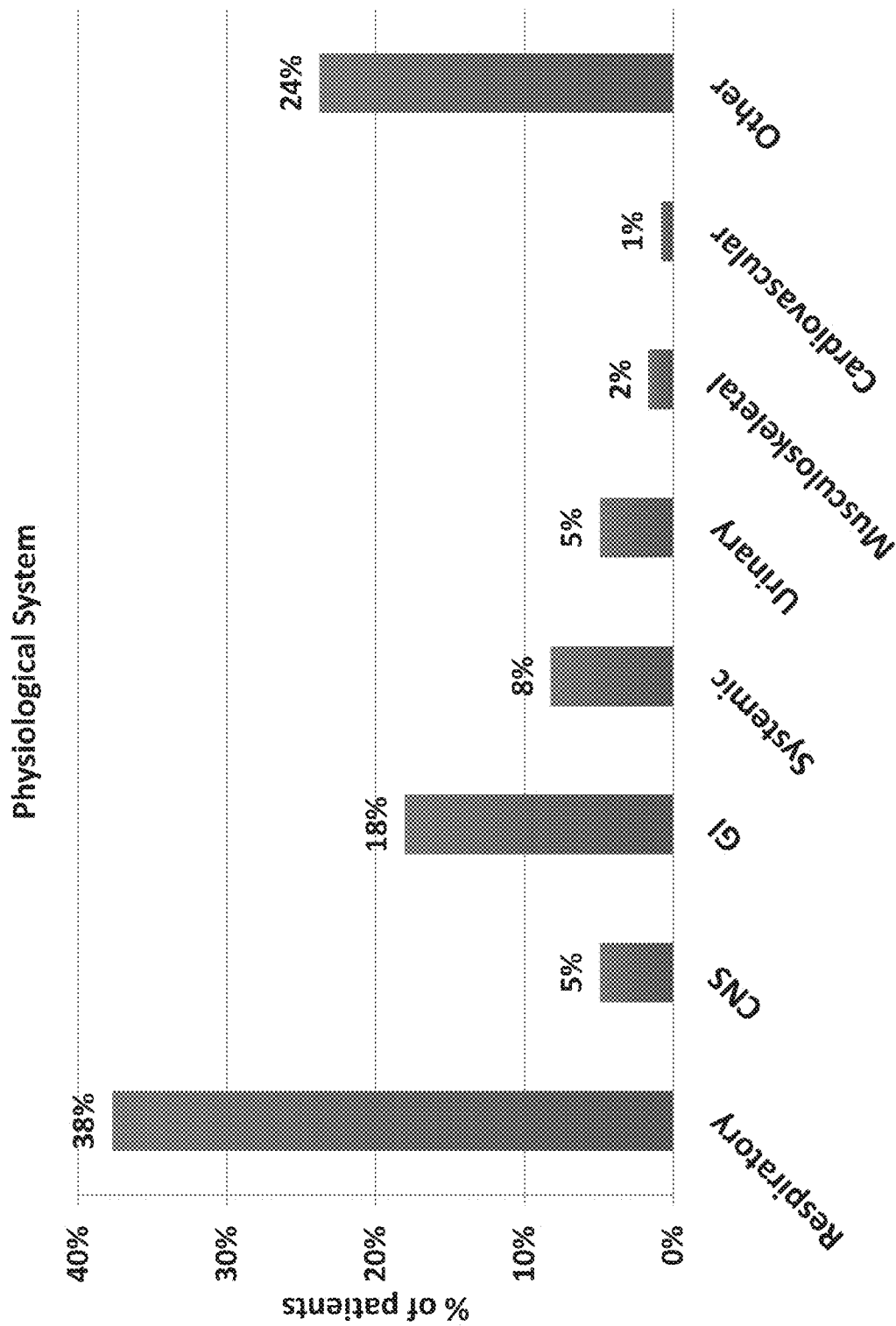

FIG. 3: Distribution of physiological systems of the patients enrolled in the clinical study.

Figure 4:
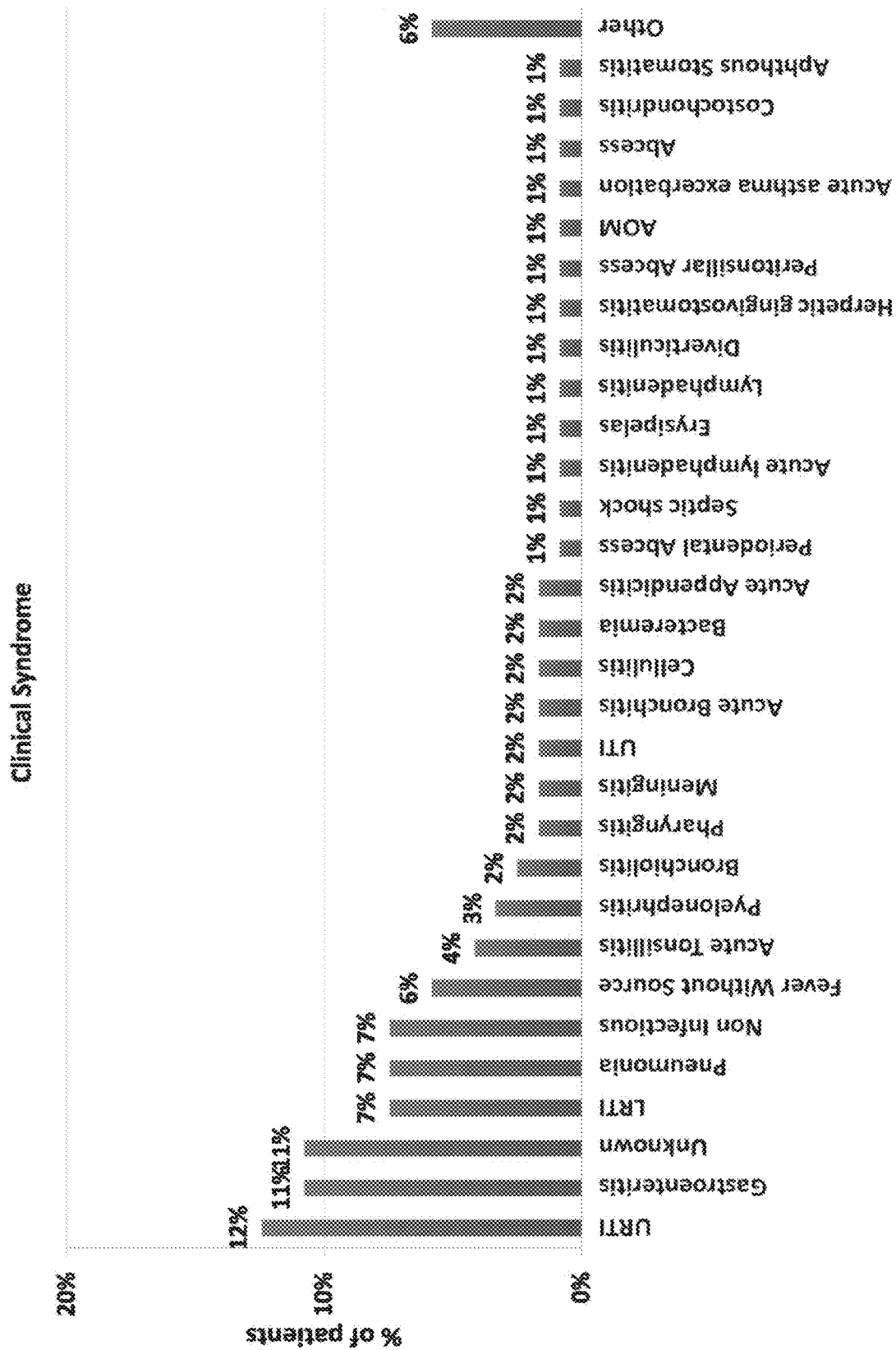

FIG. 4: Distribution of major clinical syndromes of the patients enrolled in the clinical study.

Figure 5:
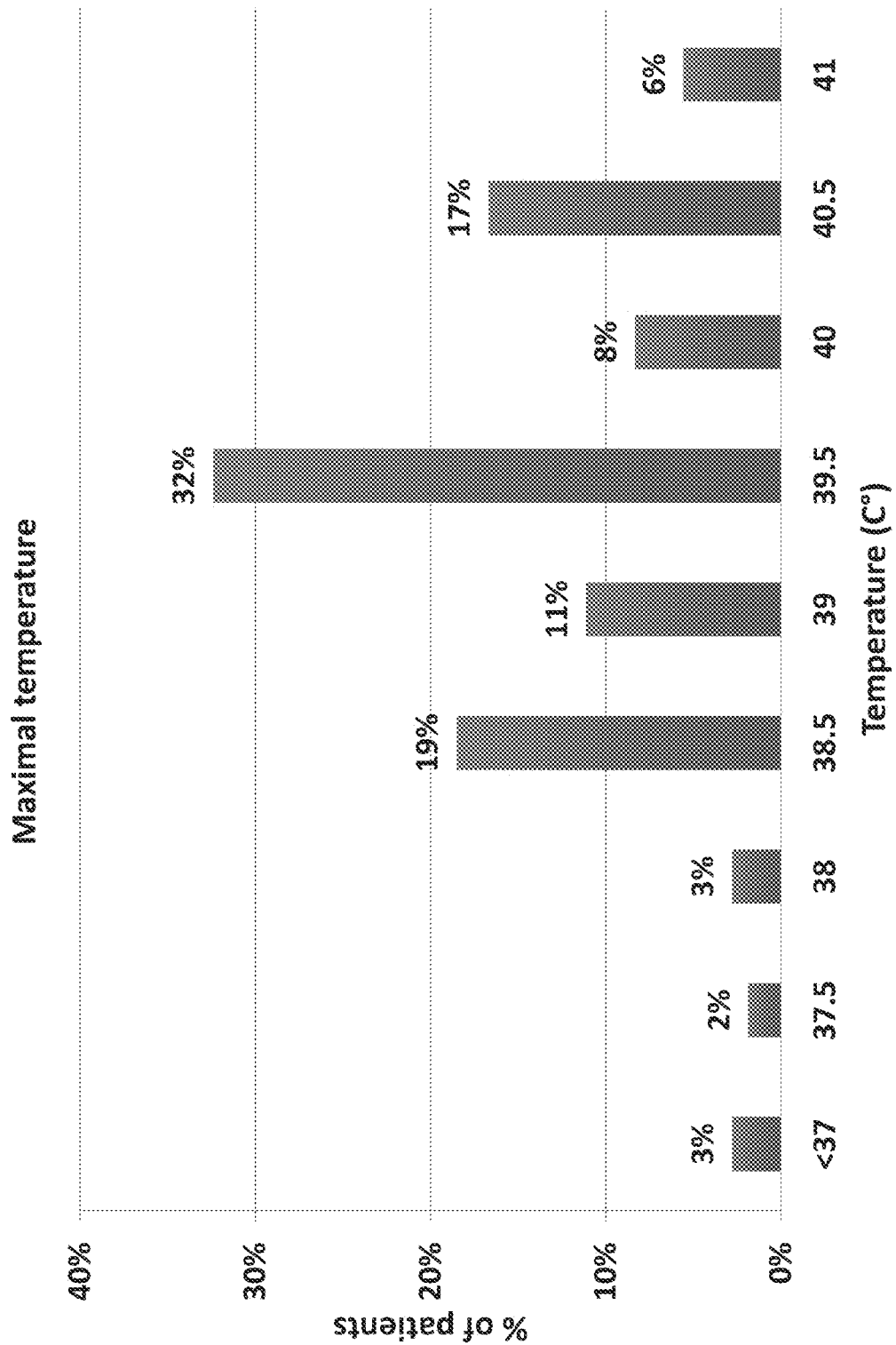

FIG. 5: Distribution of maximal body temperatures of the patients enrolled in the clinical study.

Figure 6:
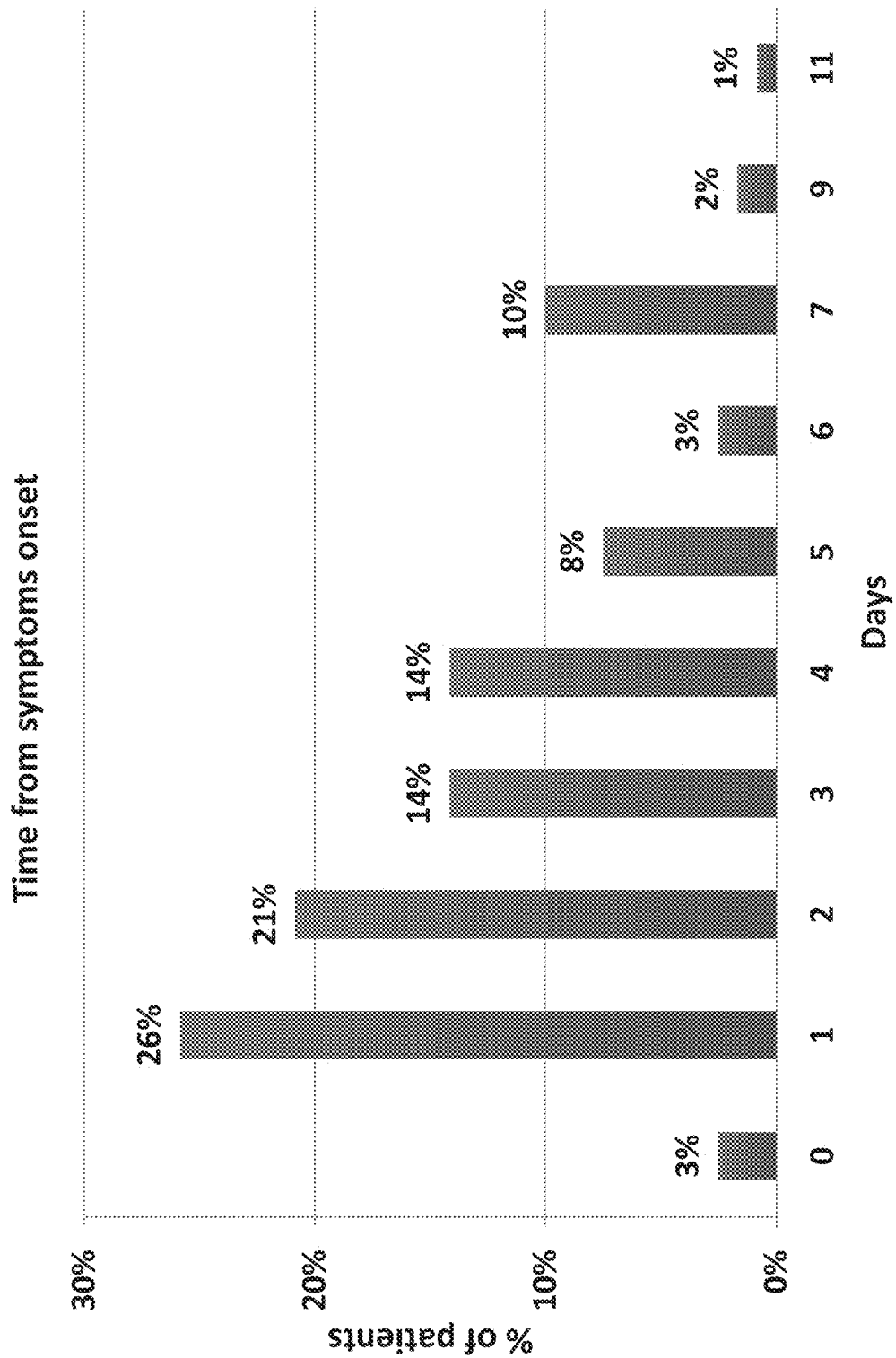

FIG. 6: Distribution of time from initiation of symptoms of the patients enrolled in the clinical study.

Figure 7:
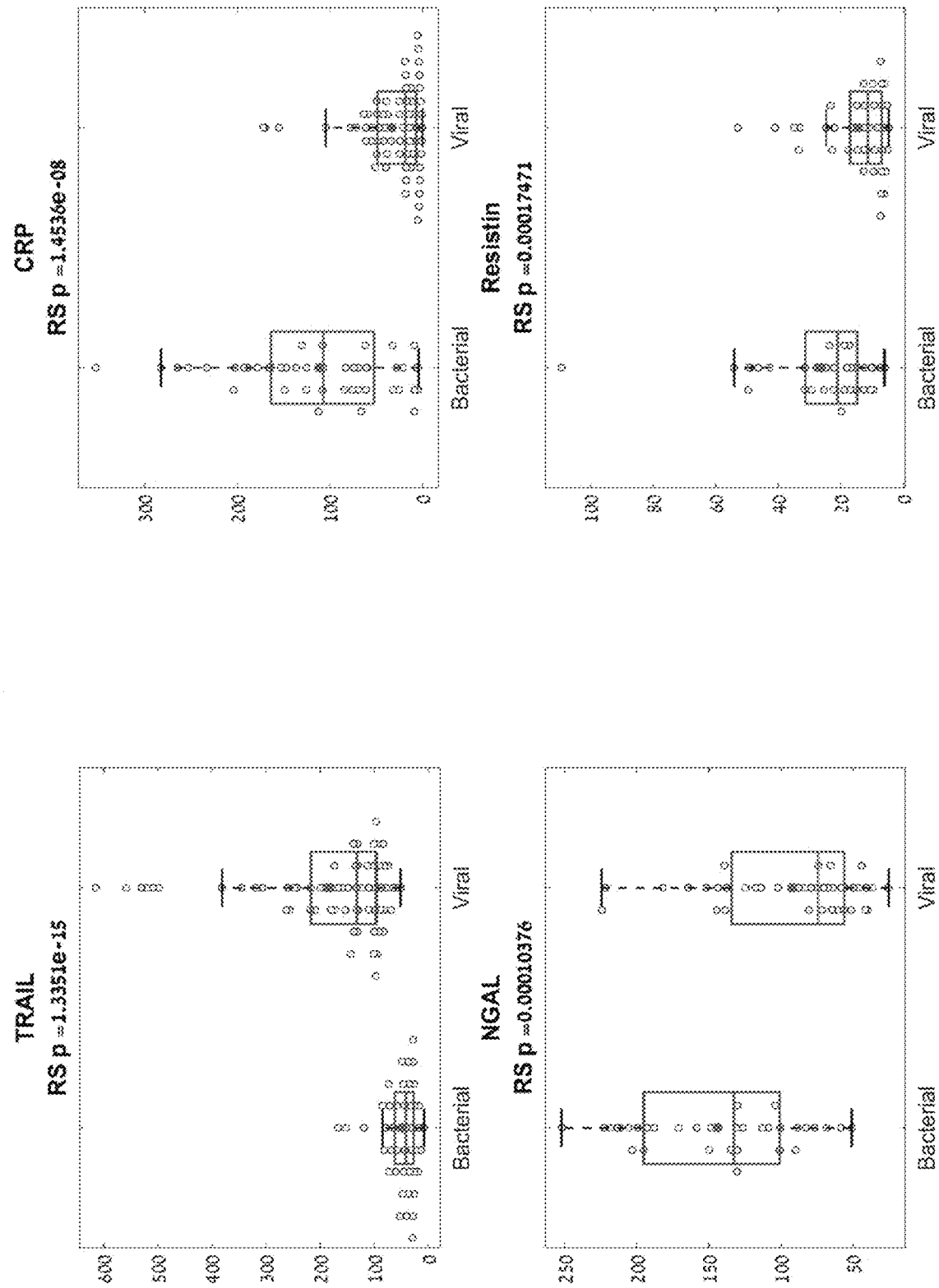
Figure 7:
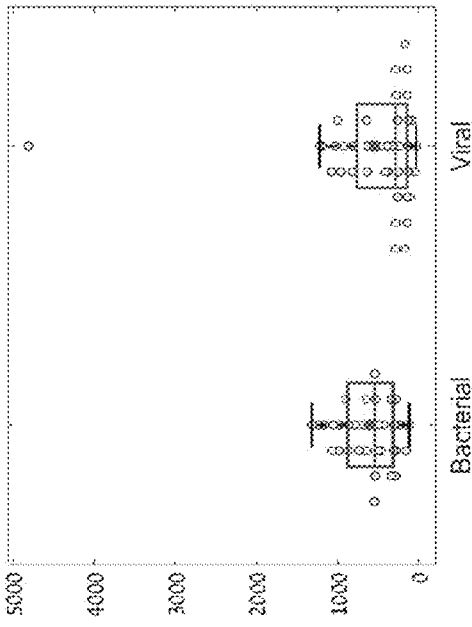
Figure 7:
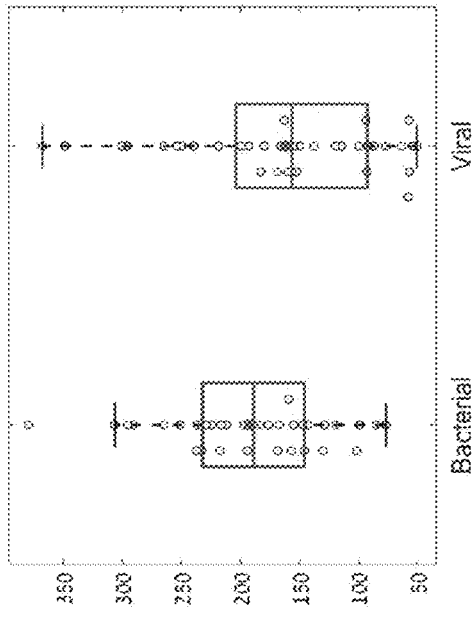
Figure 7:
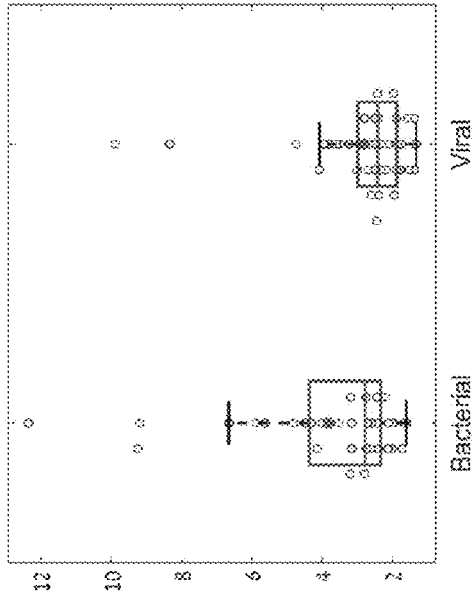
Figure 7:
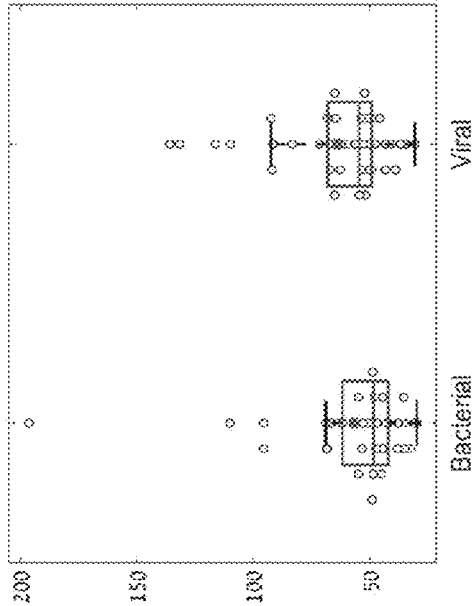
Figure 7:
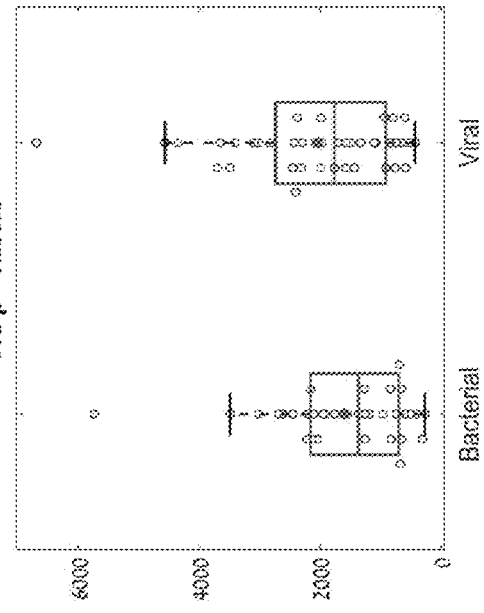
Figure 7:
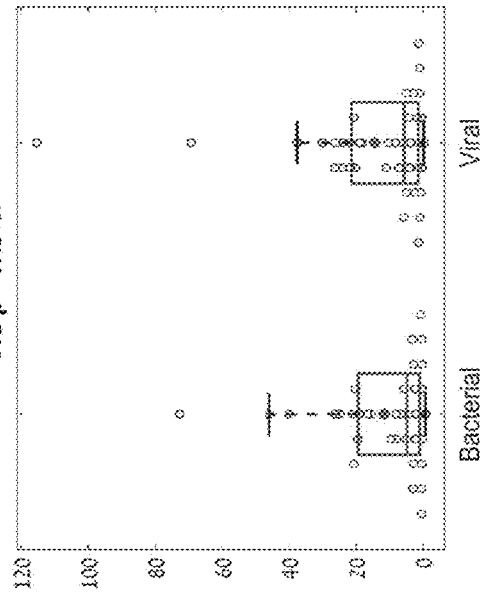
Figure 7:
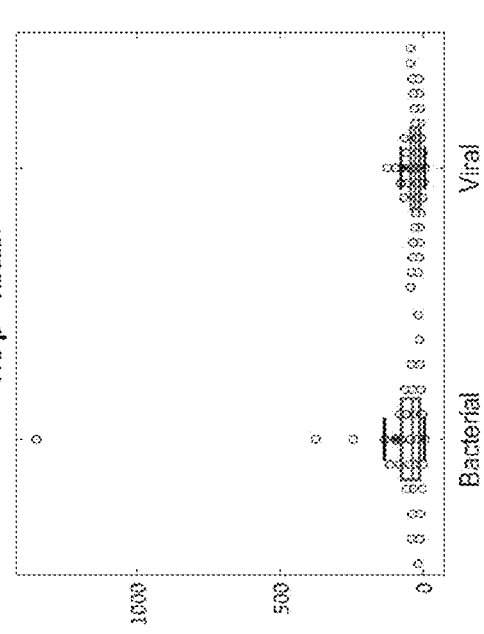
Figure 7:
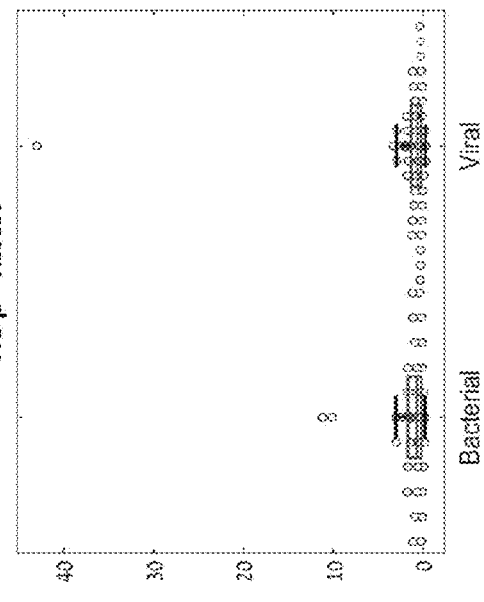
Figure 7:
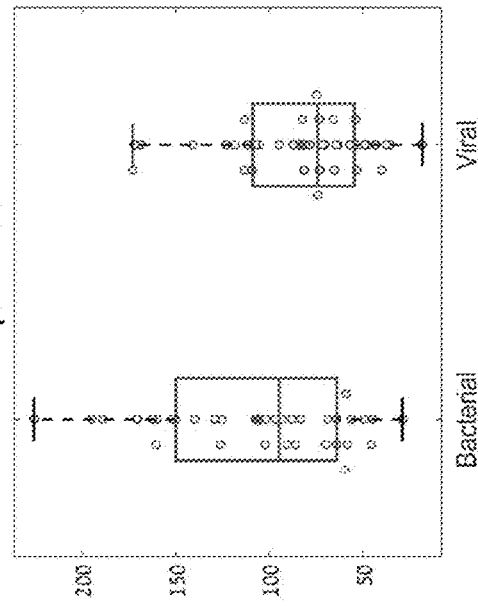
Figure 7:
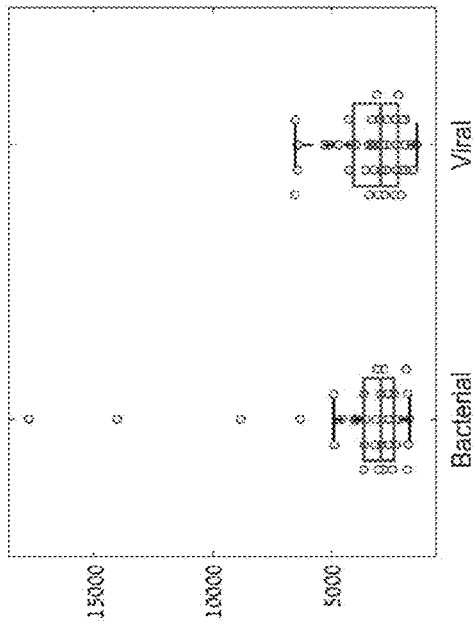
Figure 7:
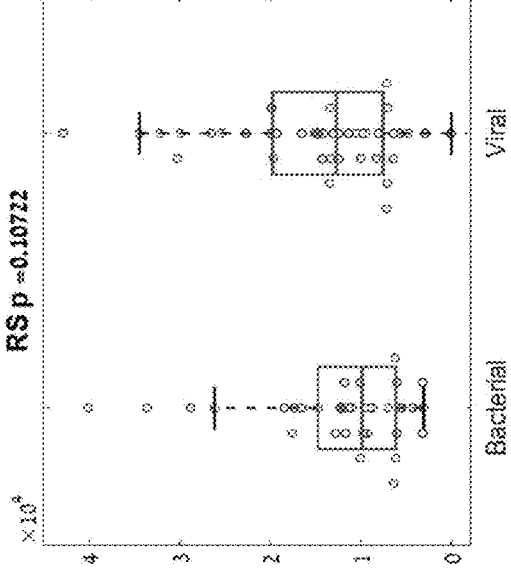
Figure 7:
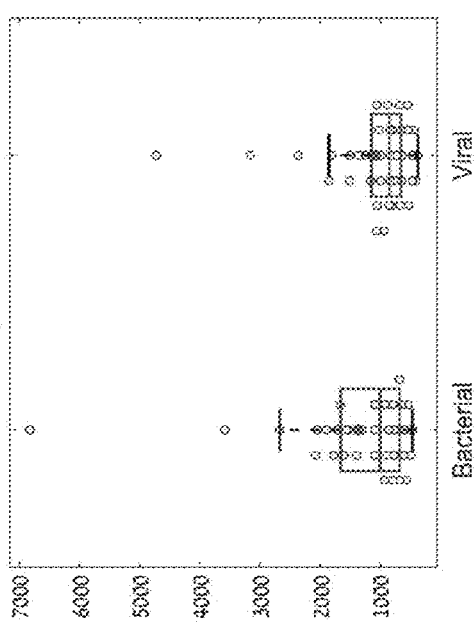
Figure 7:
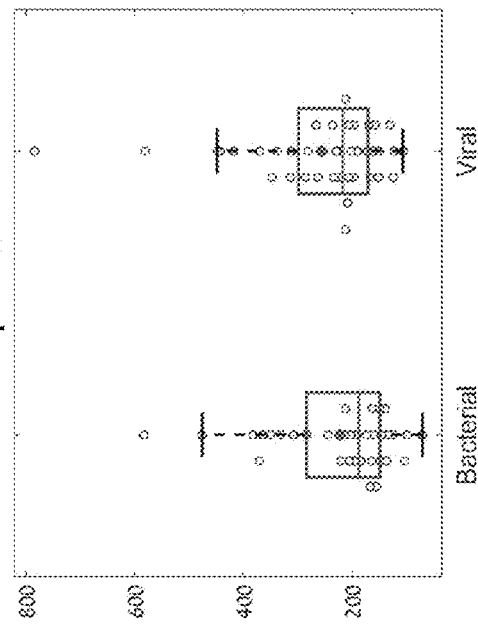
Figure 7:
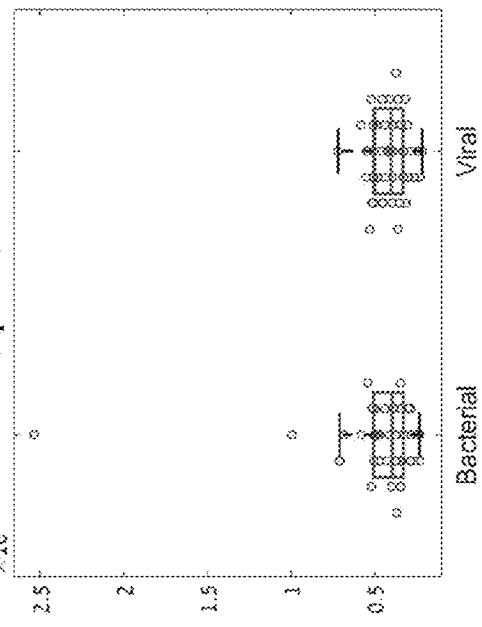
Figure 7:
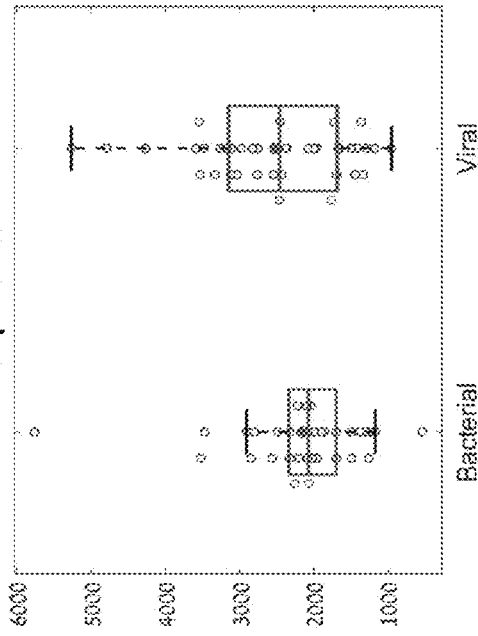
Figure 7:
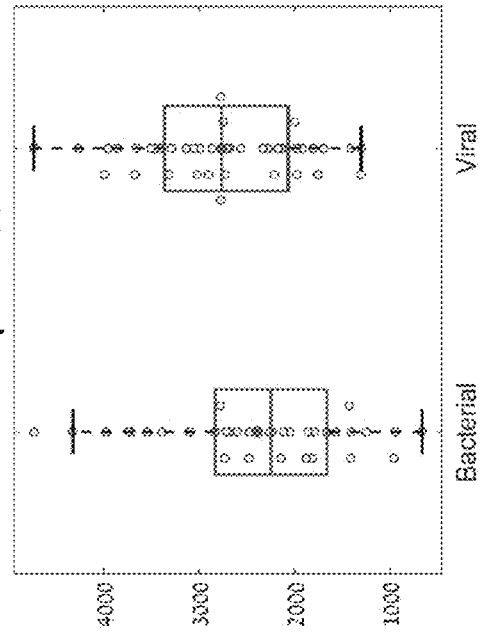

FIG. 7: Examples of determinants that differentiate between bacterial versus viral infected subjects.

Figure 8C:
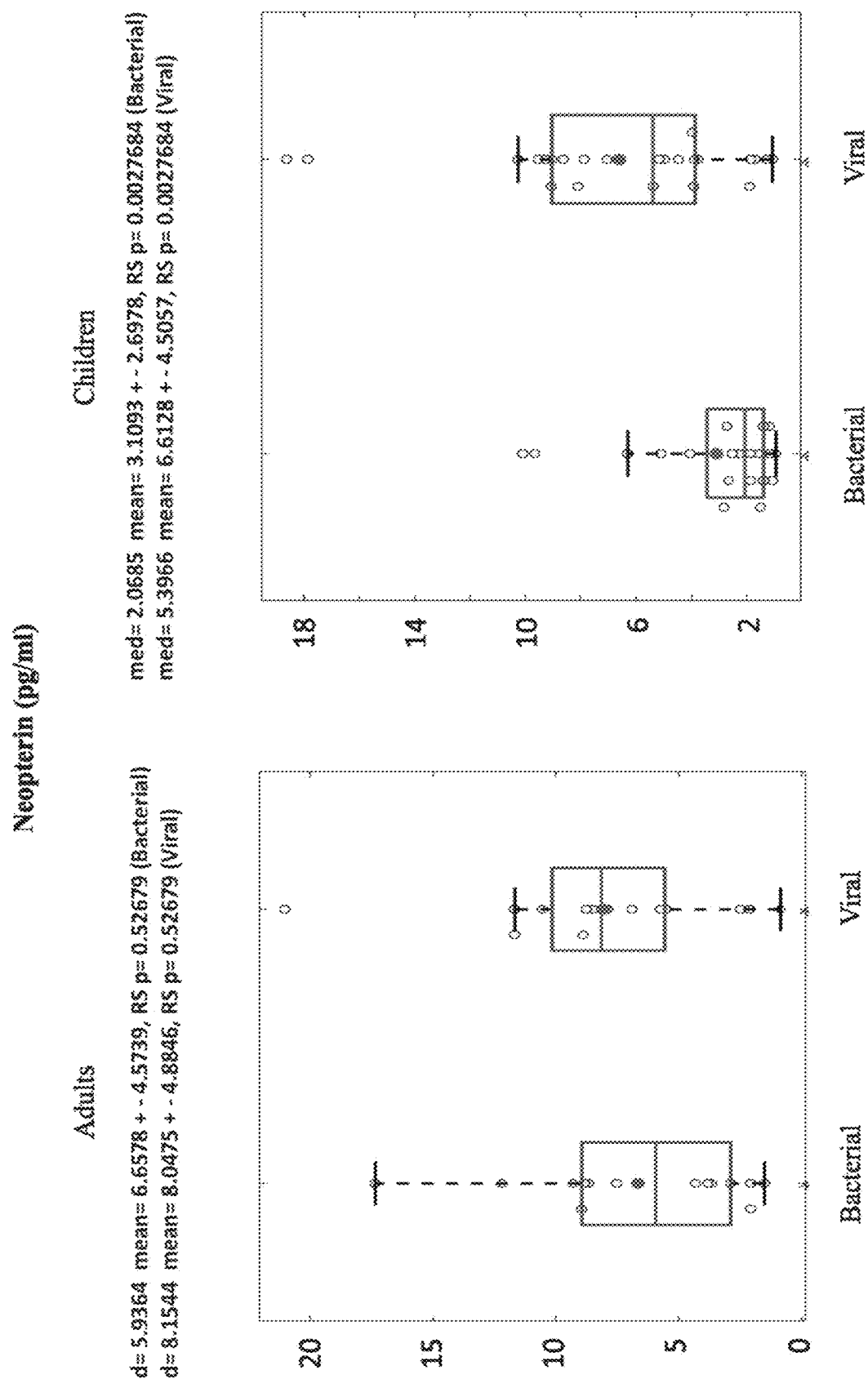

FIGS. 8A-8C. Examples of determinants which expression patterns in bacterial and viral patients differ between children and adults (A) Osteopontin; (B) NGAL; (C) Neopterin. Med=medians of bacterial and viral infected patients; mean=means±standard deviation of bacterial and viral infected patients; RS p=Wilcoxon ranksum P-value.

Figure 9:
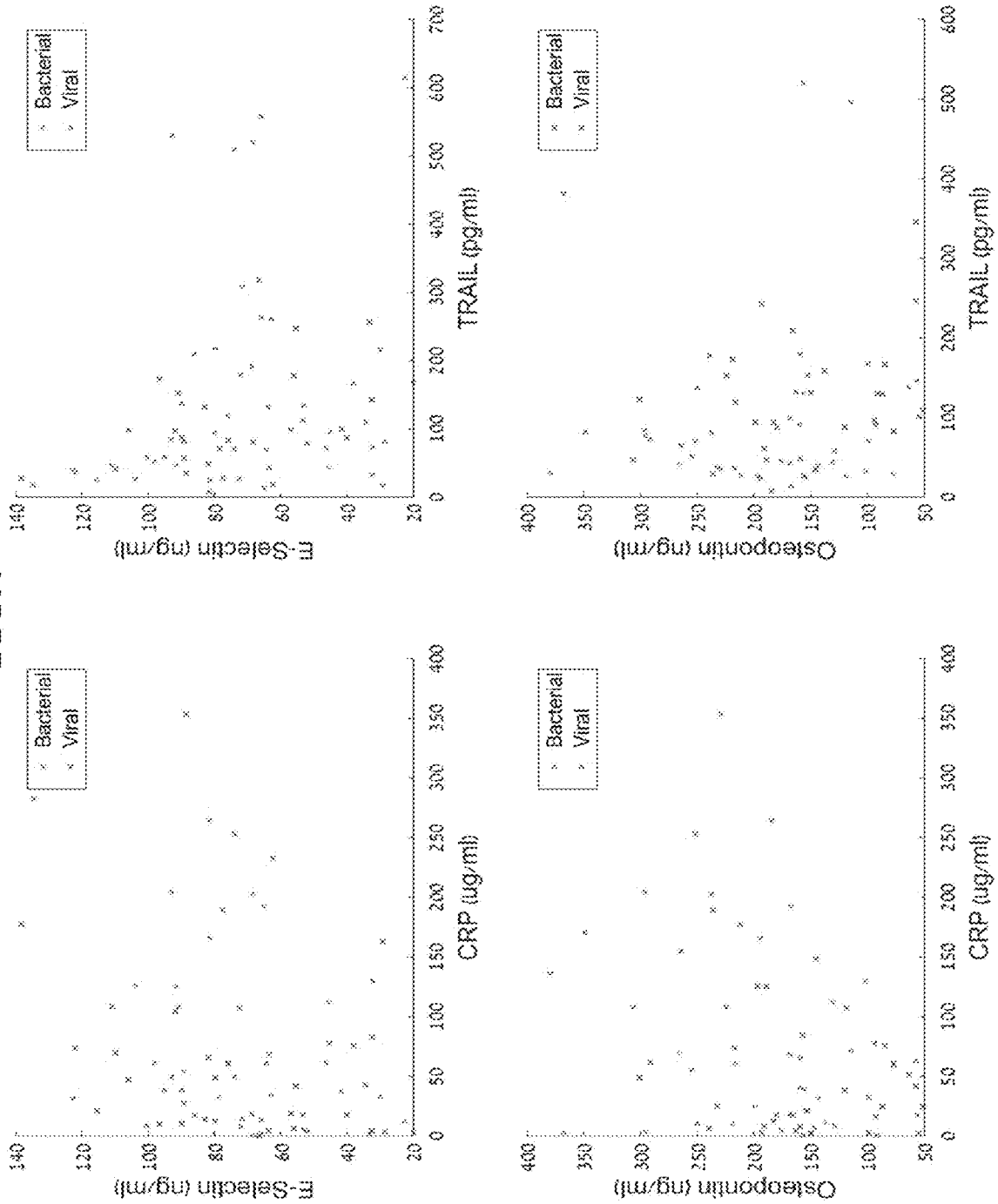
Figure 9:
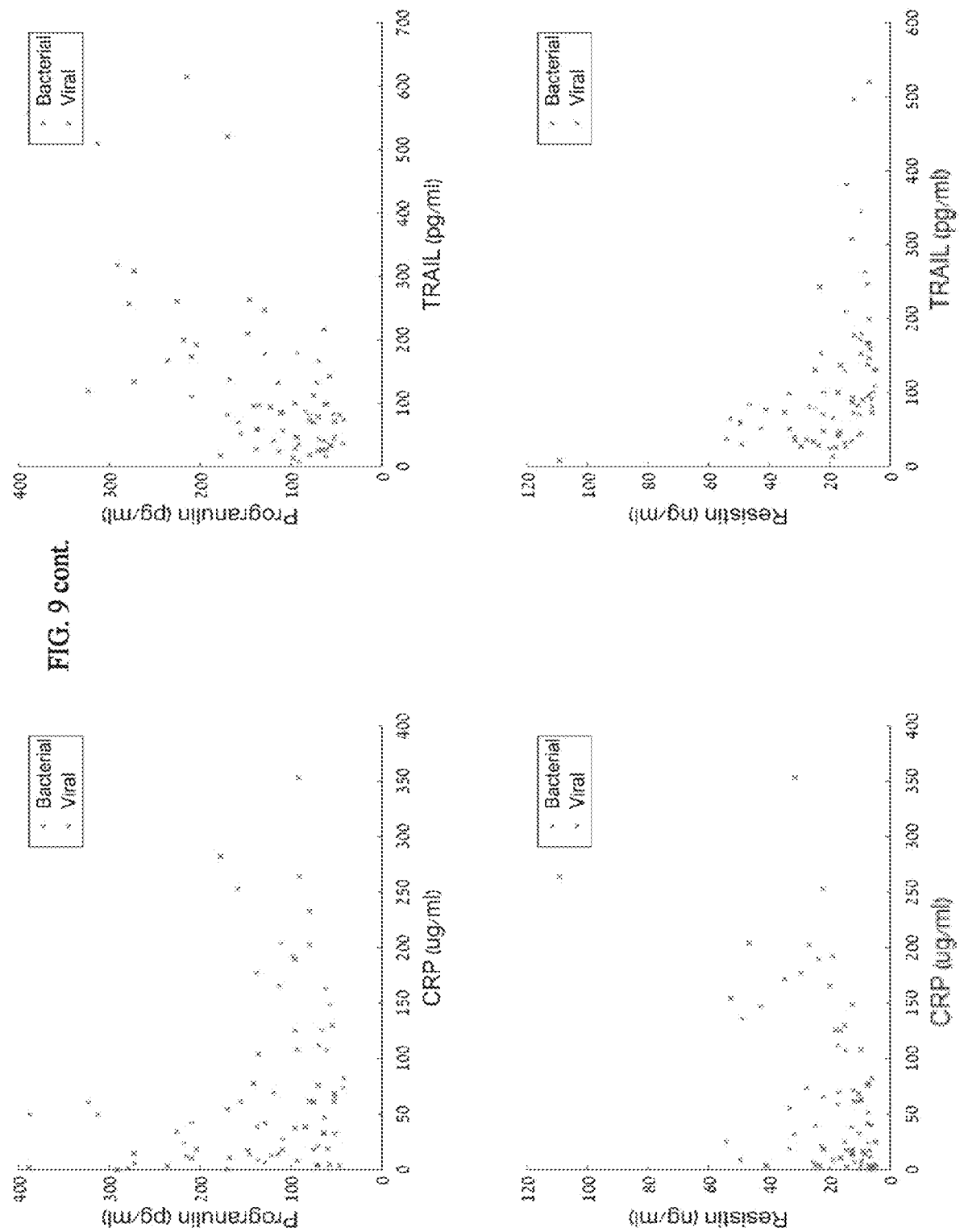
Figure 9:
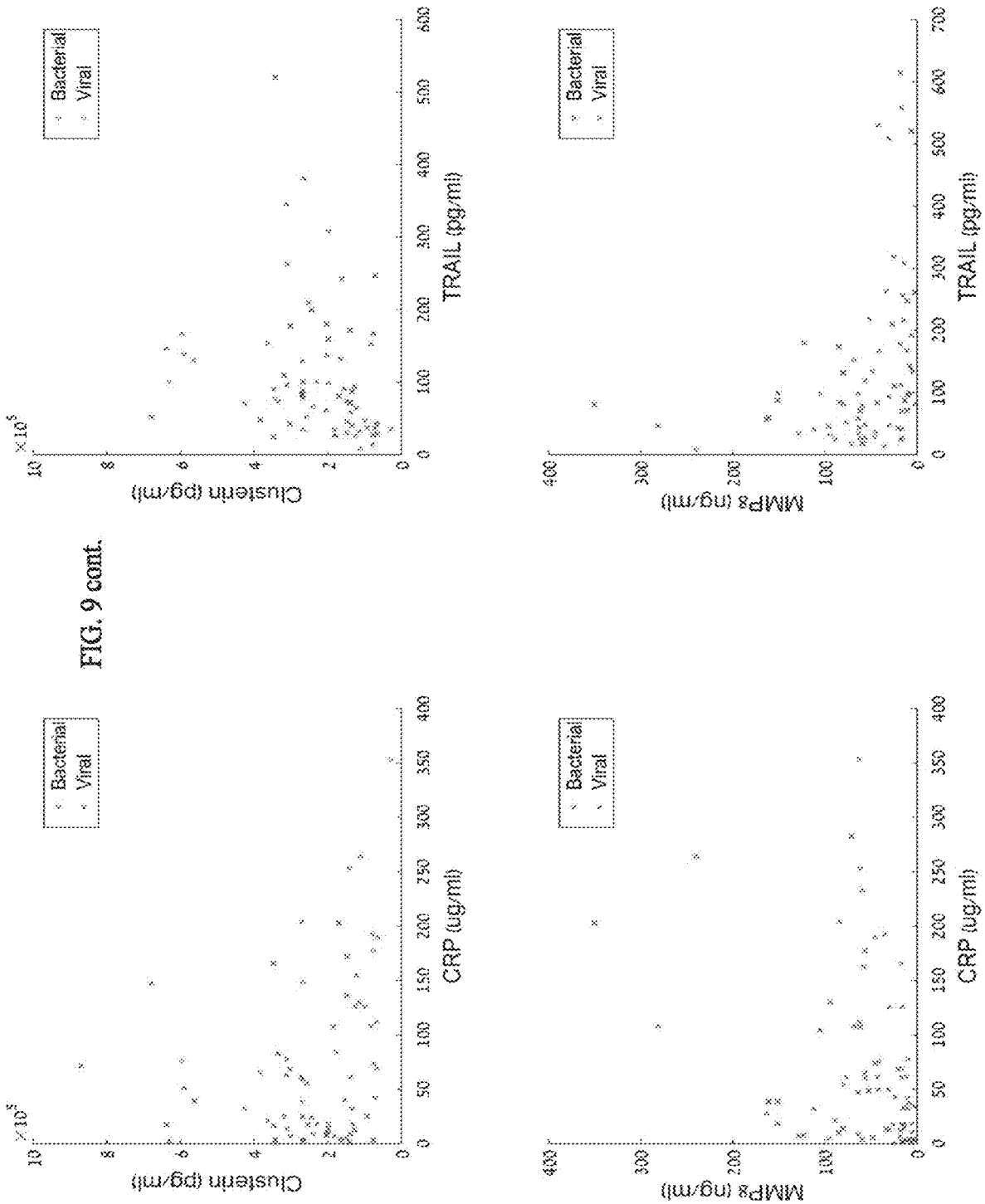
Figure 9:
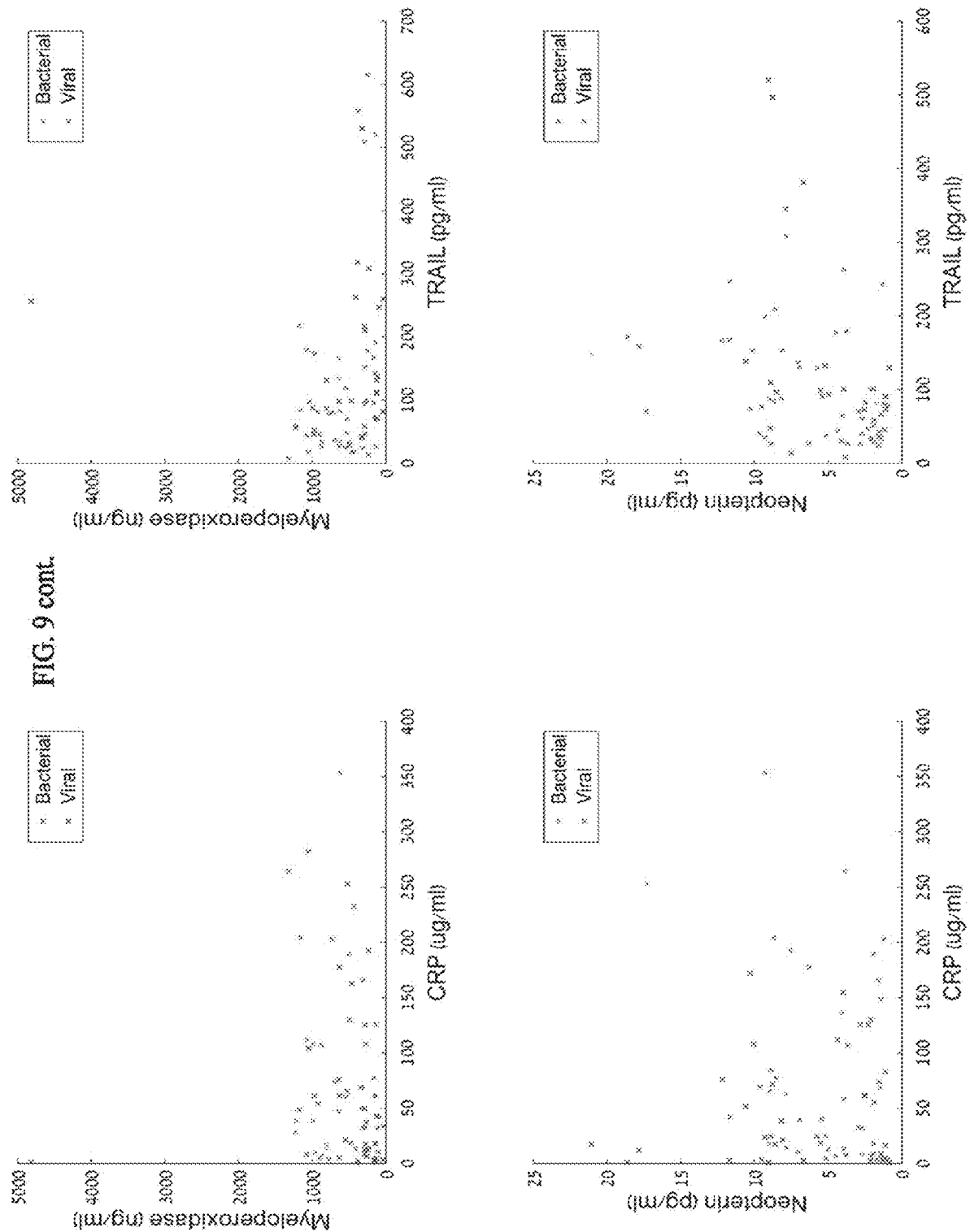
Figure 9:
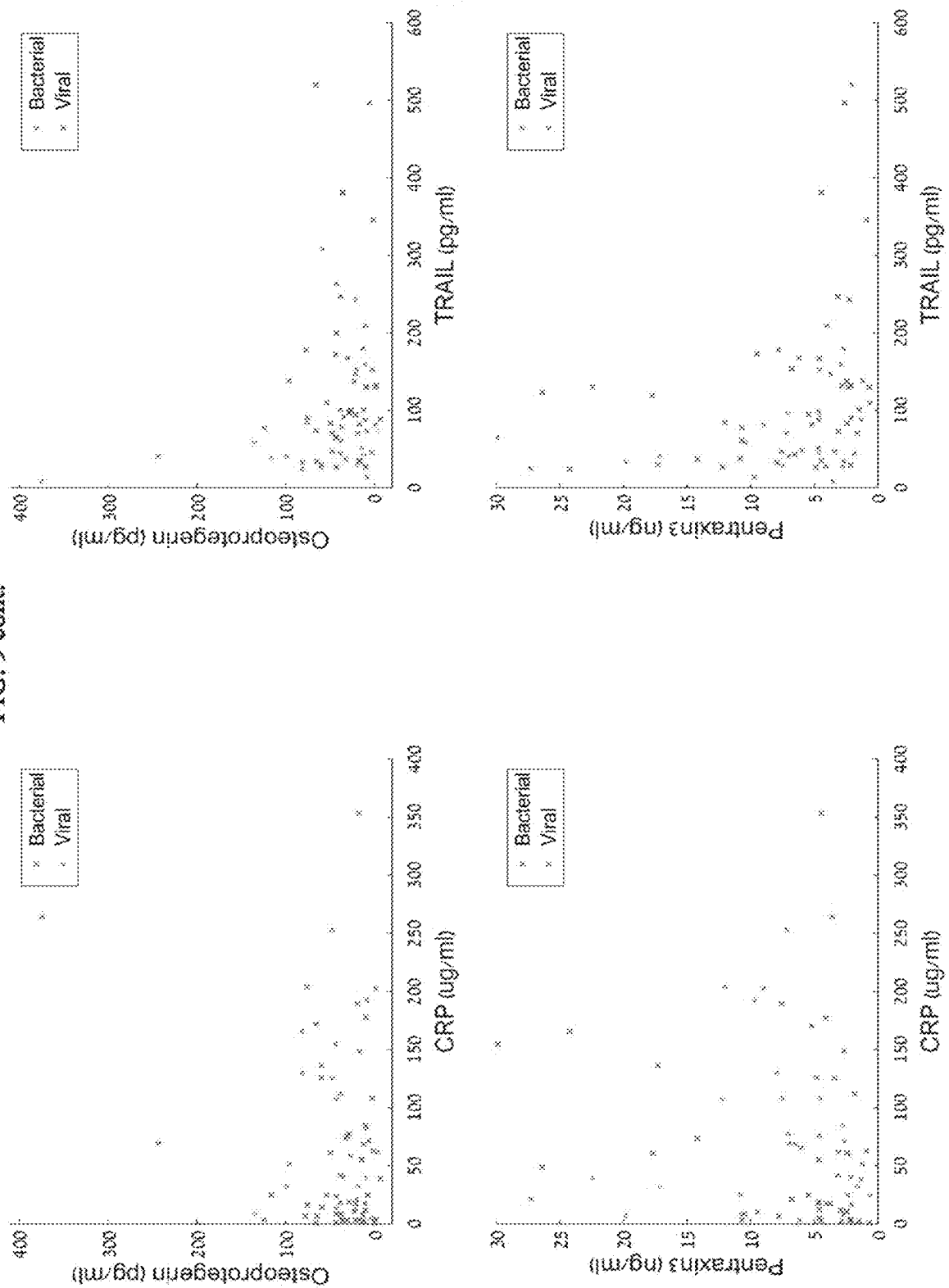
Figure 9:
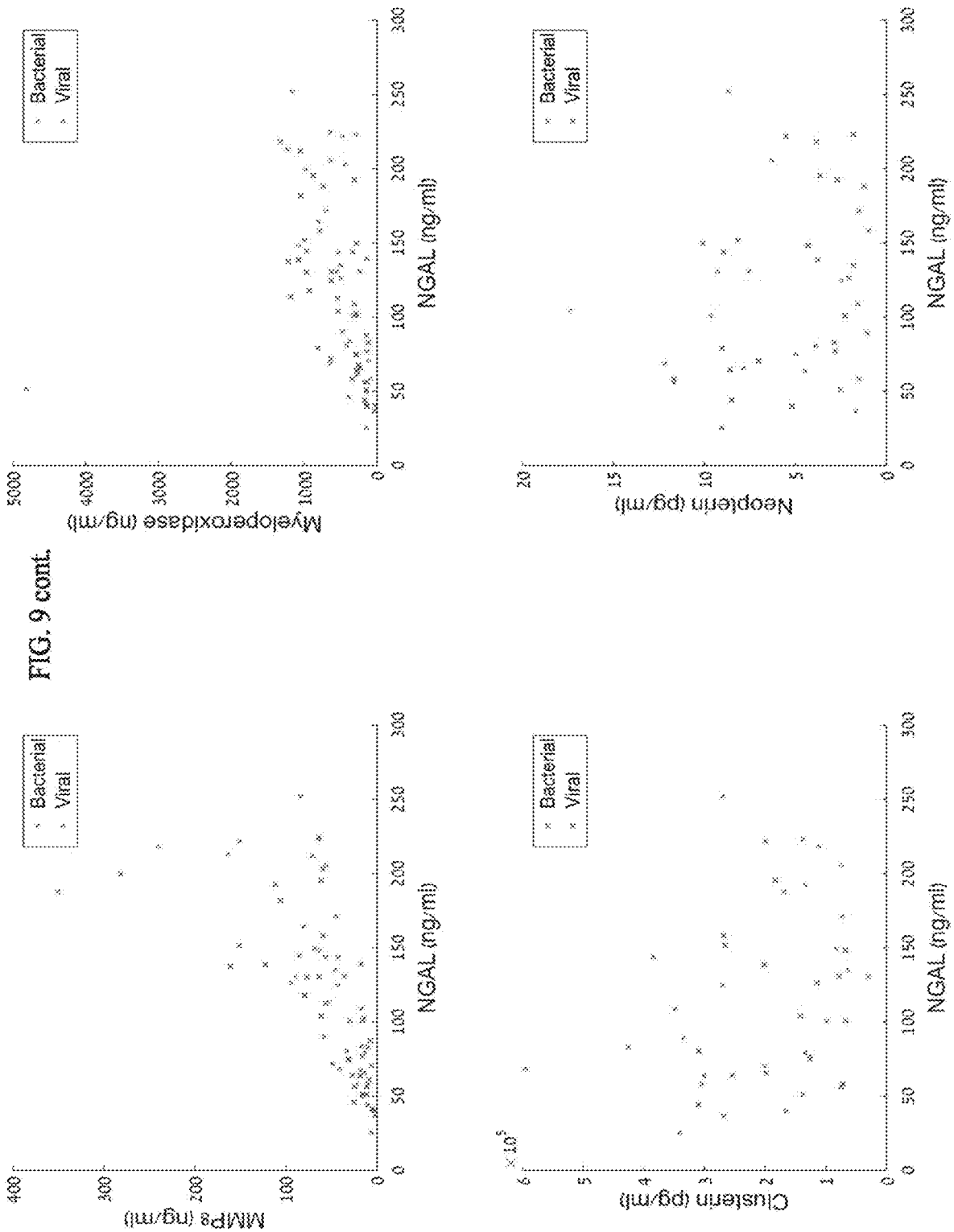
Figure 9:
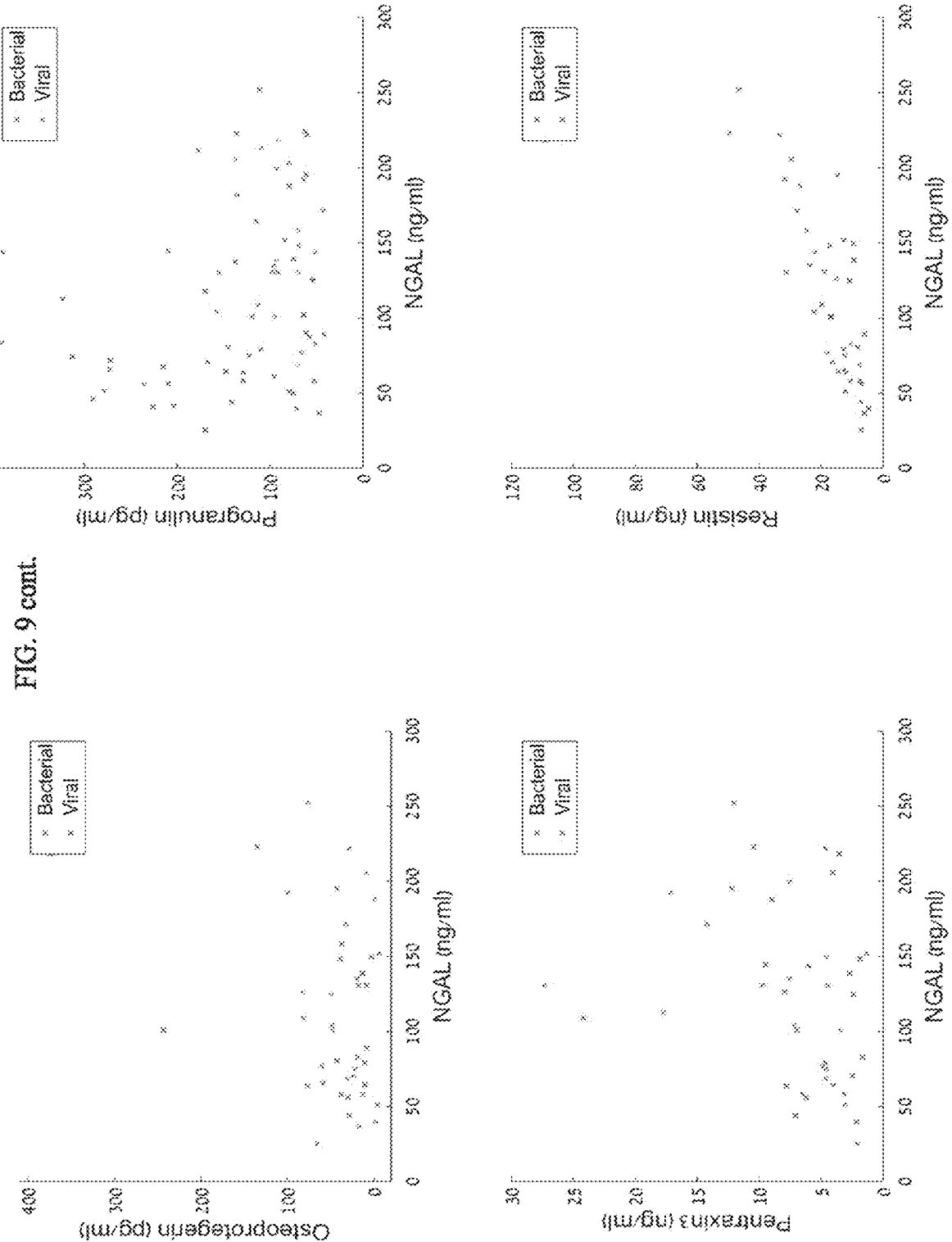

FIG. 9: Examples of expression patterns of pairs of determinants in bacterial (red) and viral (blue) infected subjects.

Figure 10:
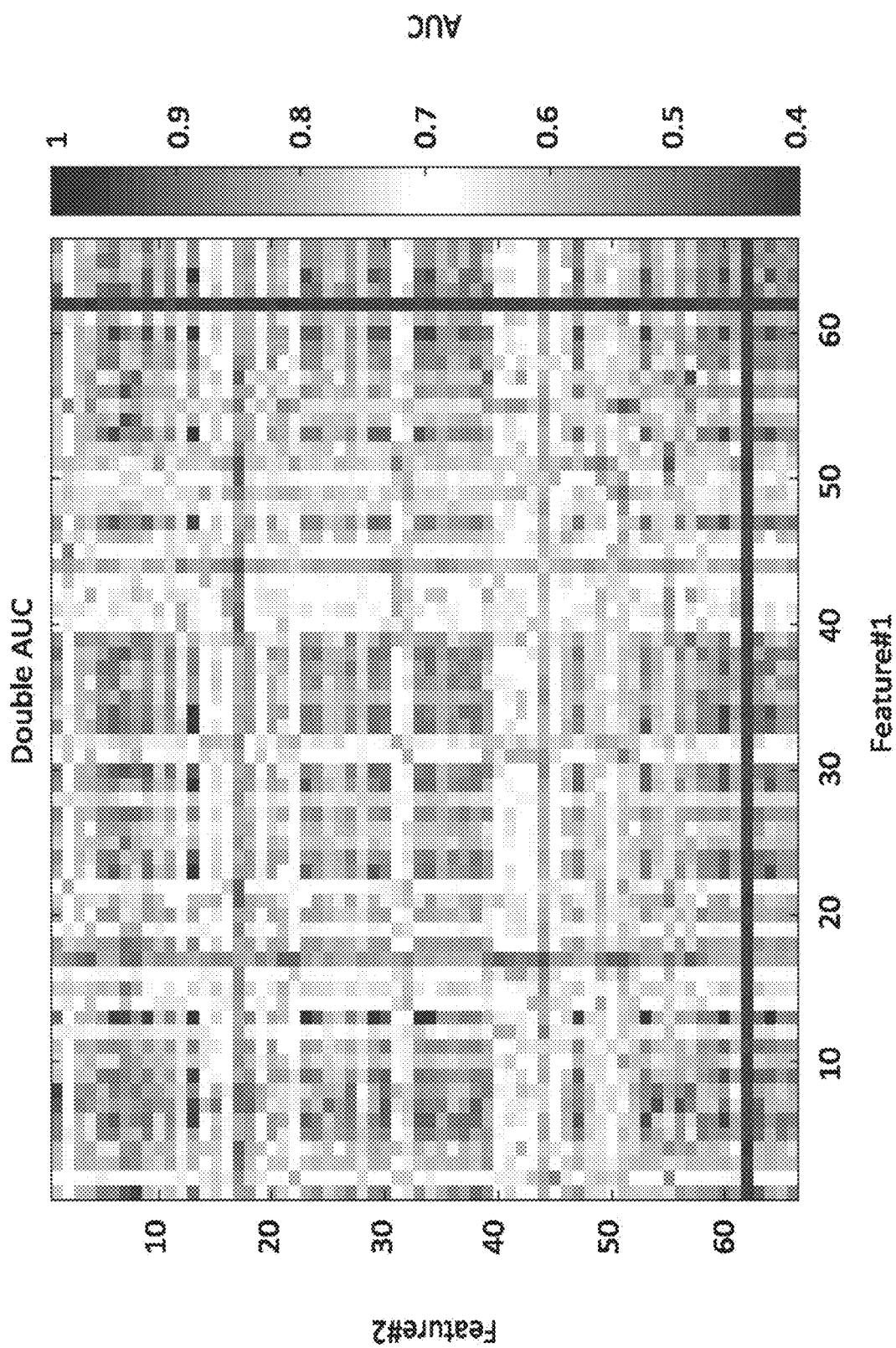

FIG. 10: Classification accuracy in terms of AUC of viral versus bacterial infected patients attained for pairs of determinants using a logistic regression model. Hot and cold colors indicate pairs of determinants whose combined classification accuracy is high or low respectively, as indicated in the legend.

Figure 11:
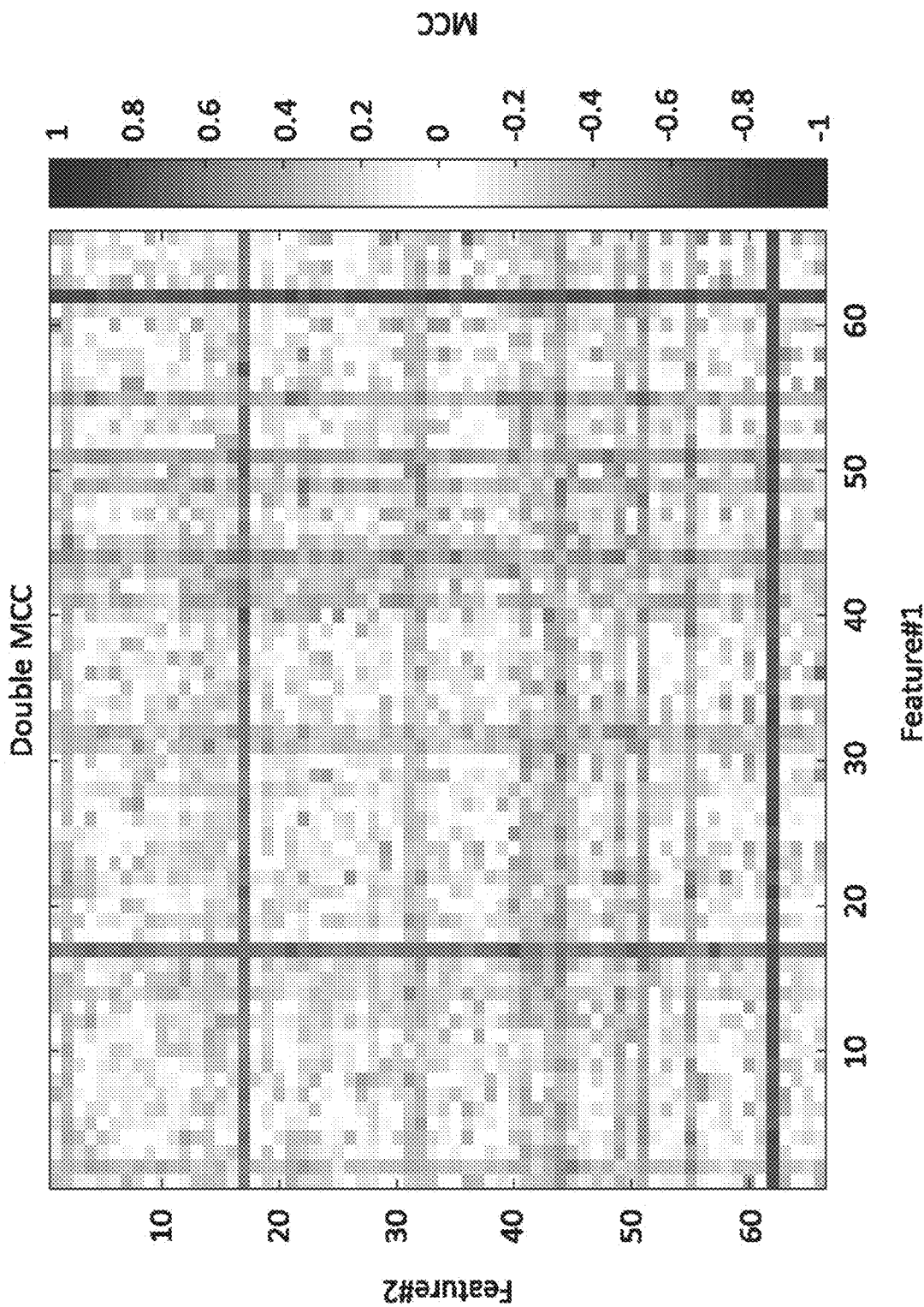

FIG. 11: Classification accuracy in terms of MCC of viral versus bacterial infected patients attained for pairs of determinants using a logistic regression model. Hot and cold colors indicate pairs of determinants whose combined classification accuracy is high or low respectively, as indicated in the legend.

Figure 12:
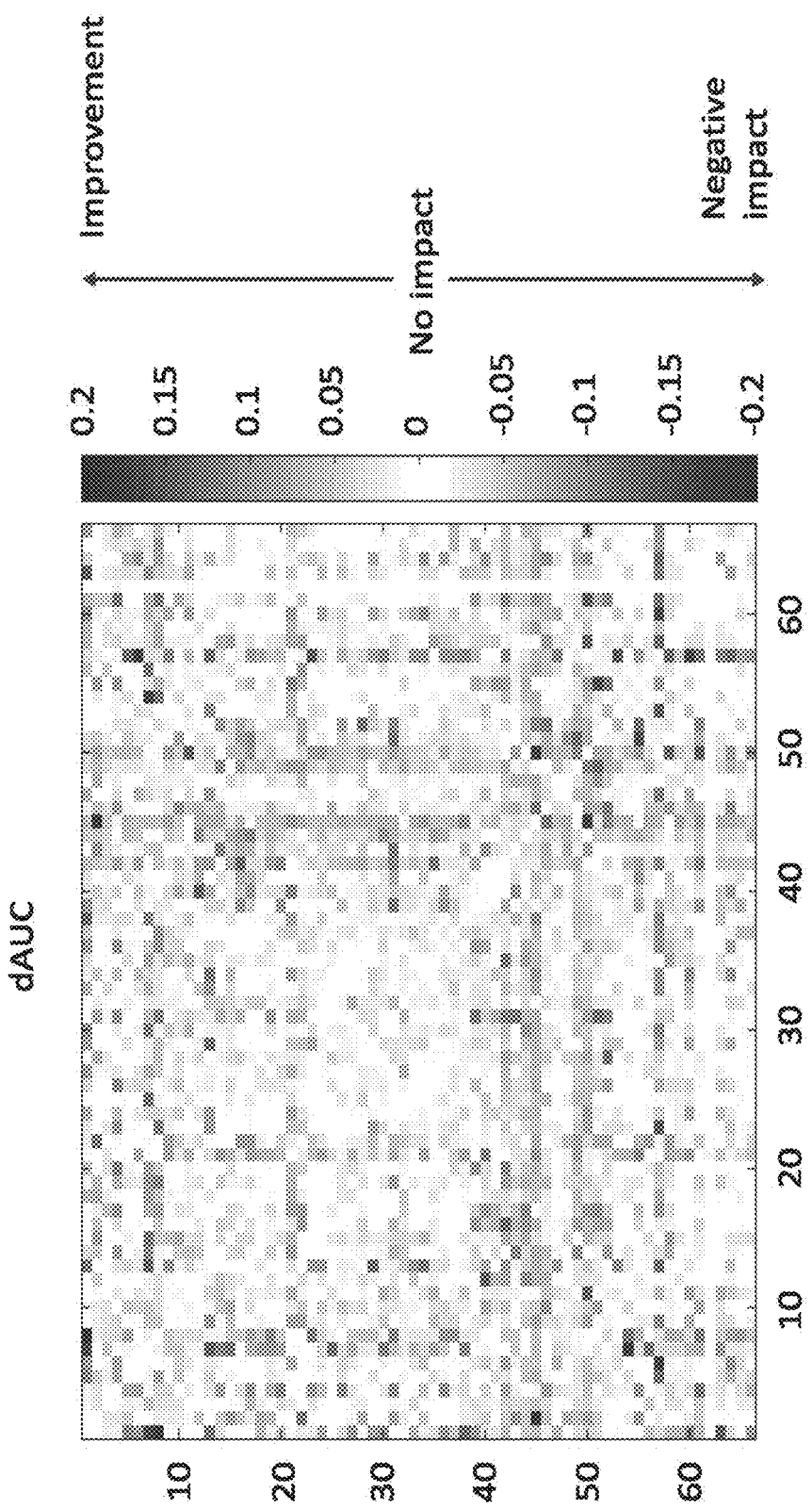

FIG. 12: Some determinant combinations exhibit an improved diagnostic accuracy (in terms of AUC) compared to that of the corresponding individual determinants, whereas other combinations exhibit a reduced accuracy. The change in classification accuracy (dAUC) for the determinants described in Table 4 (according to the serial numbers) is computed as follows: AUCi,j−max(AUCi, AUCj), where AUCi and AUCj correspond to the AUC obtained for determinant i and j individually and AUCi,j is obtained for the pair. Hot and cold colors indicate pairs of determinants whose combined classification accuracy compared to the individual determinant accuracy is higher and lower respectively.

Figure 13:
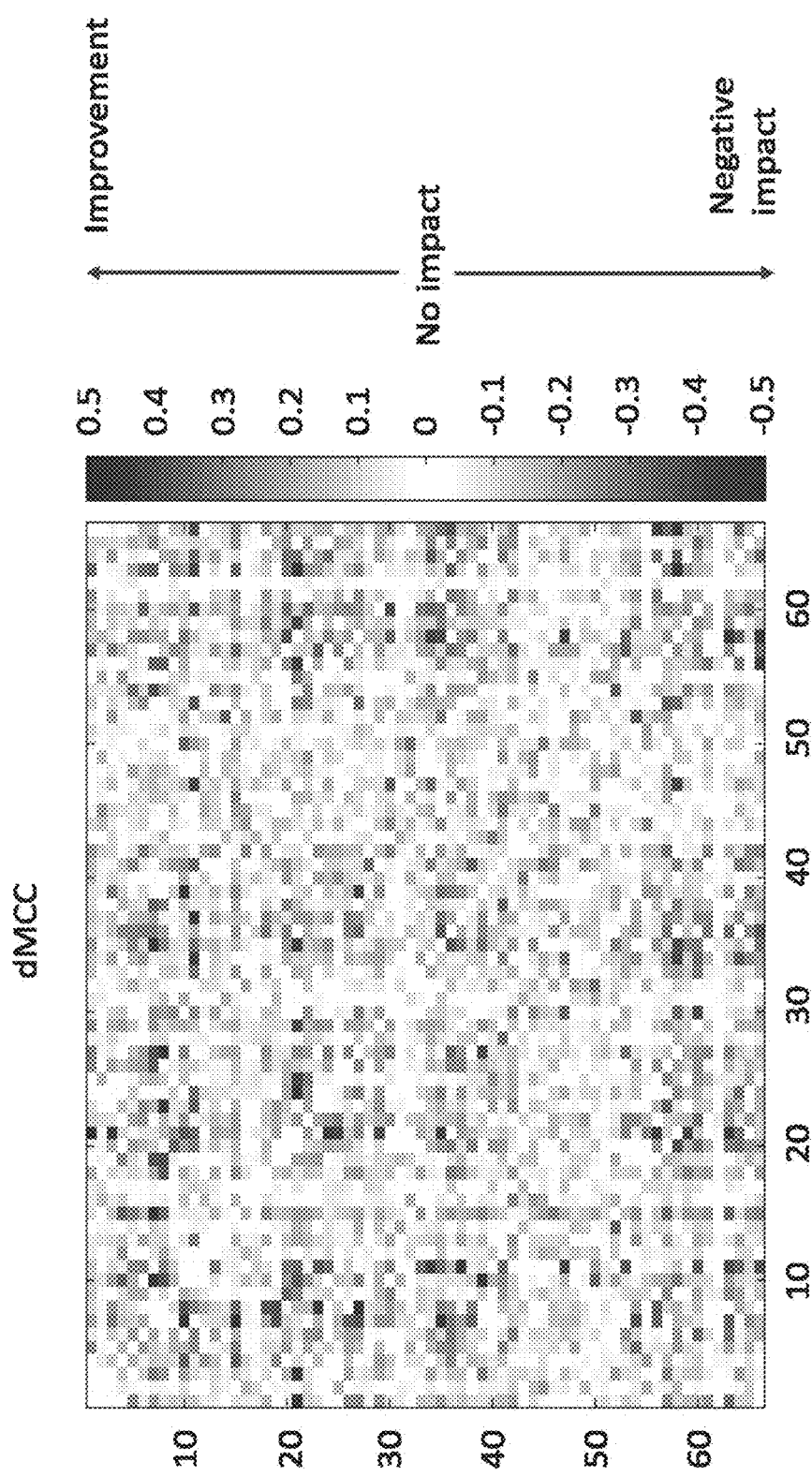

FIG. 13: Some determinant combinations exhibit an improved diagnostic accuracy (in terms of MCC) compared to that of the corresponding individual determinants, whereas other combinations exhibit a reduced accuracy. The change in classification accuracy (dMCC) for the determinants described in Table 4 (according to the serial numbers) is computed as follows: MCCi,j−max(MCCi, MCCj), where MCCi and MCCj correspond to the AUC obtained for determinant i and j individually and MCCi,j is obtained for the pair. Hot and cold colors indicate pairs of determinants whose combined classification accuracy compared to the individual determinant accuracy is higher and lower respectively.

Figure 14A:
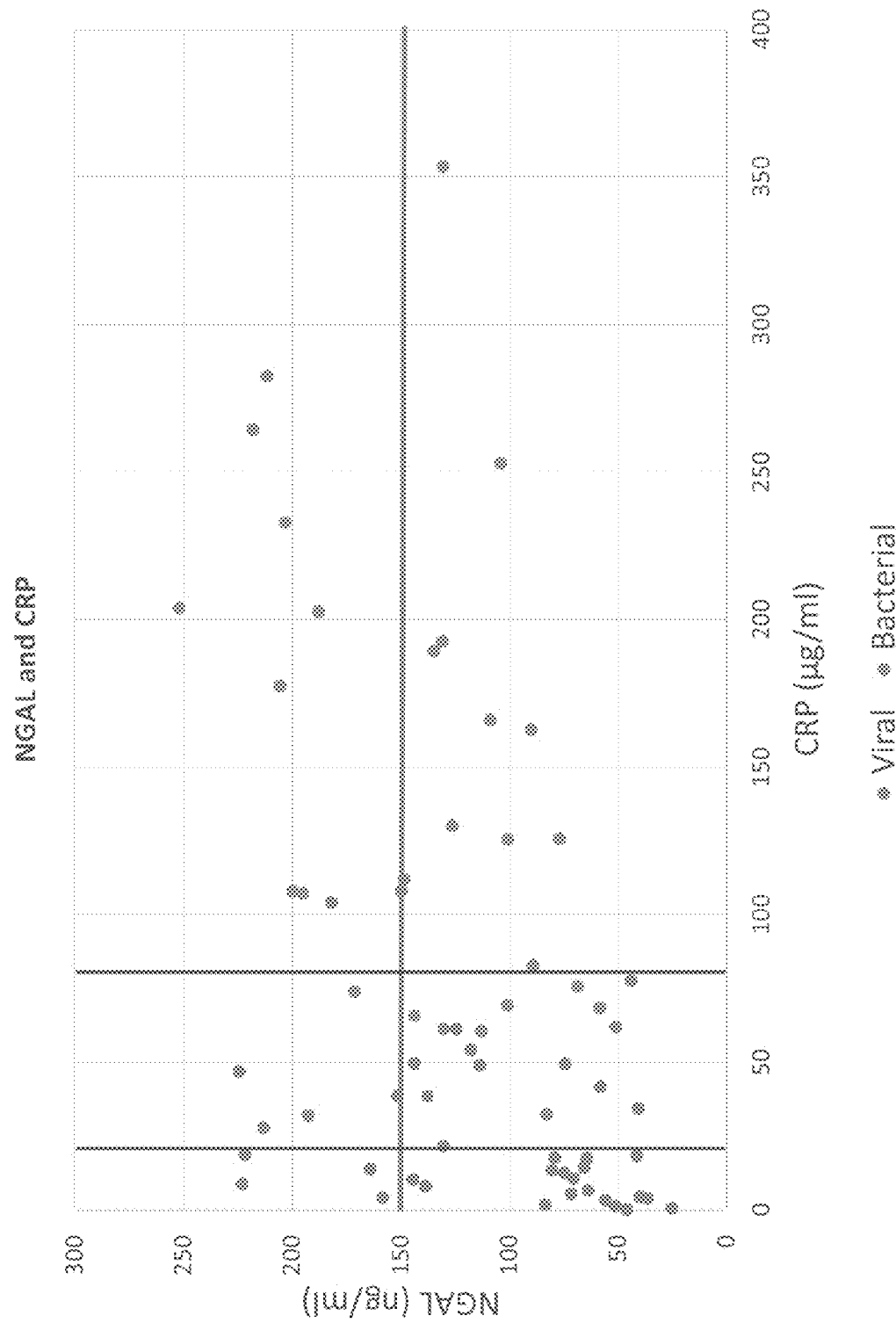
Figure 14B:
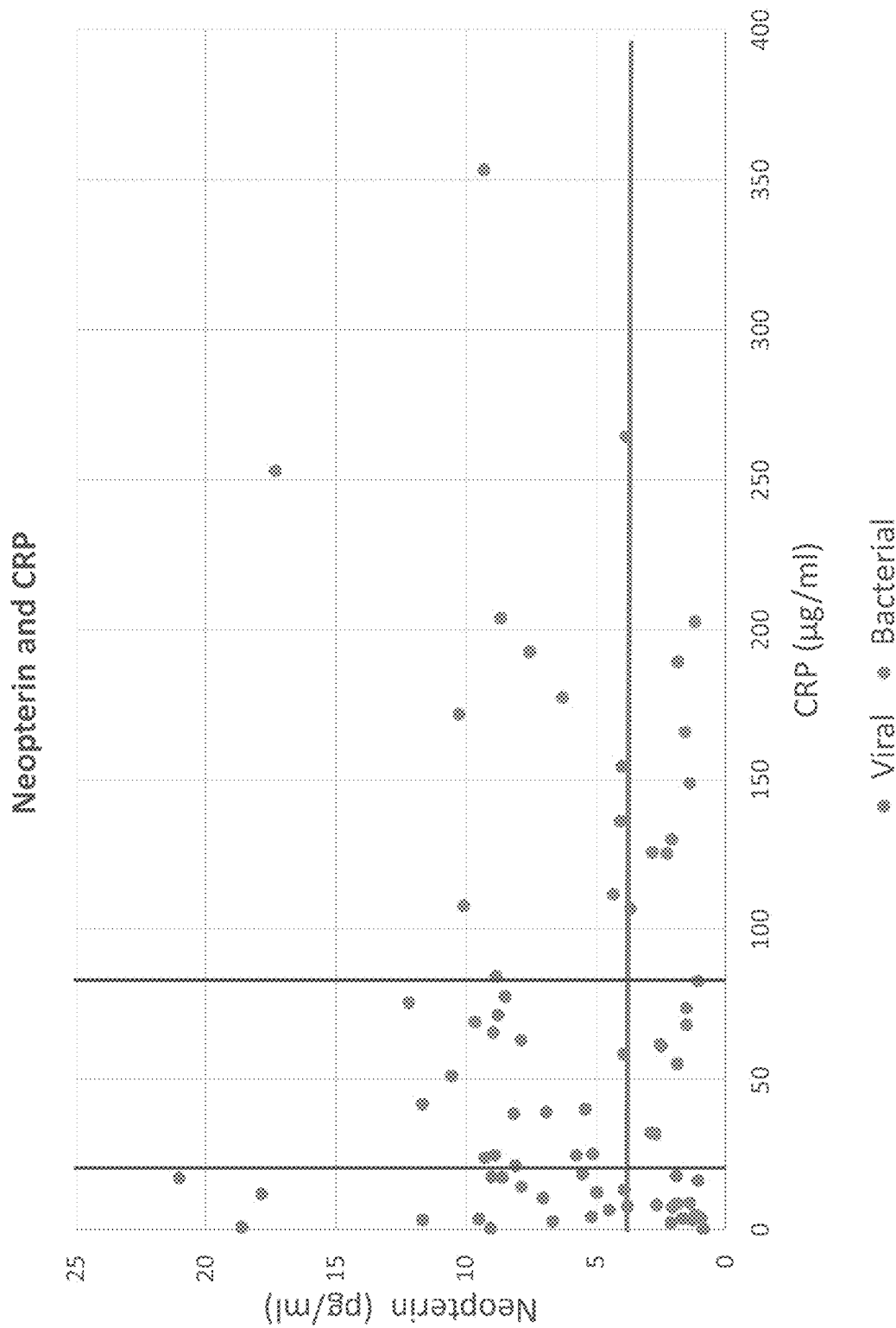

FIGS. 14A-14B: The levels of additional biomarkers can be combined with CRP to improve overall diagnostic performance. Routinely used CRP cutoffs (20 µg/ml and 80 µg/ml) are marked by red lines. (A) NGAL. An example of NGAL cutoff (150 ng/ml) is marked by a blue line. (B) Neopterin. An example of Neopterin cutoff (4 pg/ml) is marked by a blue line.

Figure 15A:
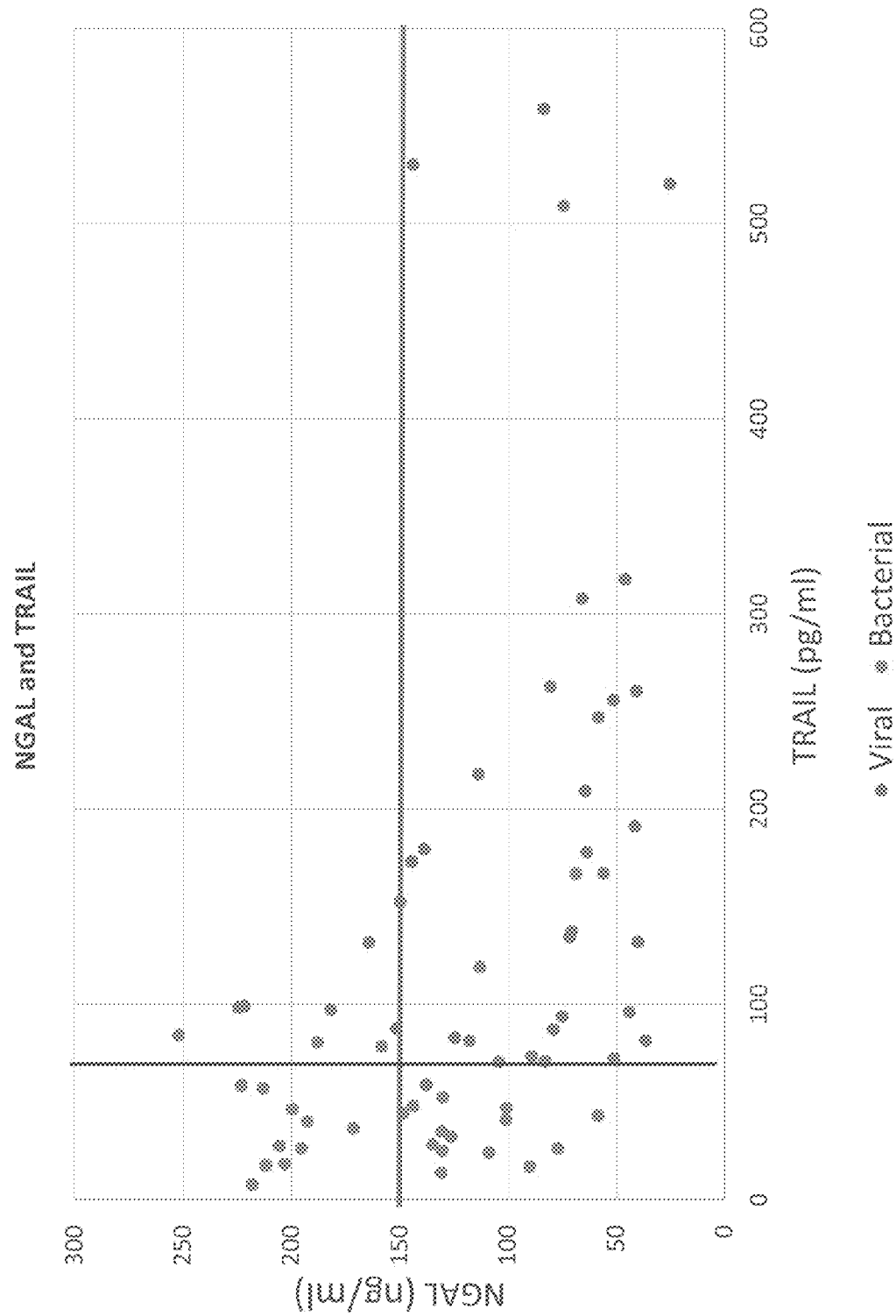
Figure 15B:
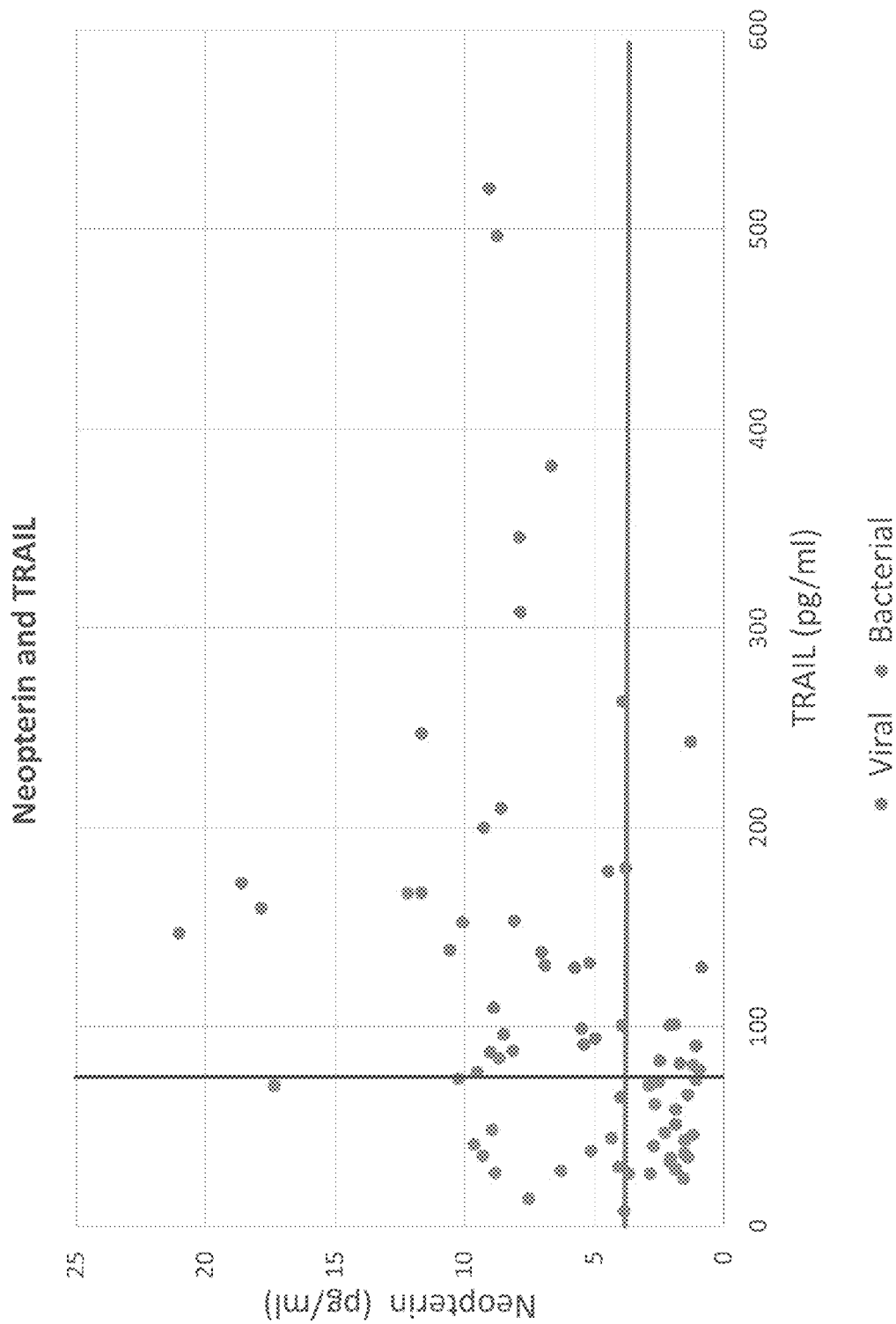

FIGS. 15A-15B: The levels of additional biomarkers can be combined with TRAIL to improve overall diagnostic performance. An example of TRAIL cutoff (70 pg/ml) is marked by a red line. (A) NGAL. An example of NGAL cutoff (150 ng/ml) is marked by a blue line. (B) Neopterin. An example of Neopterin cutoff (4 pg/ml) is marked by a blue line.

Figure 16A:
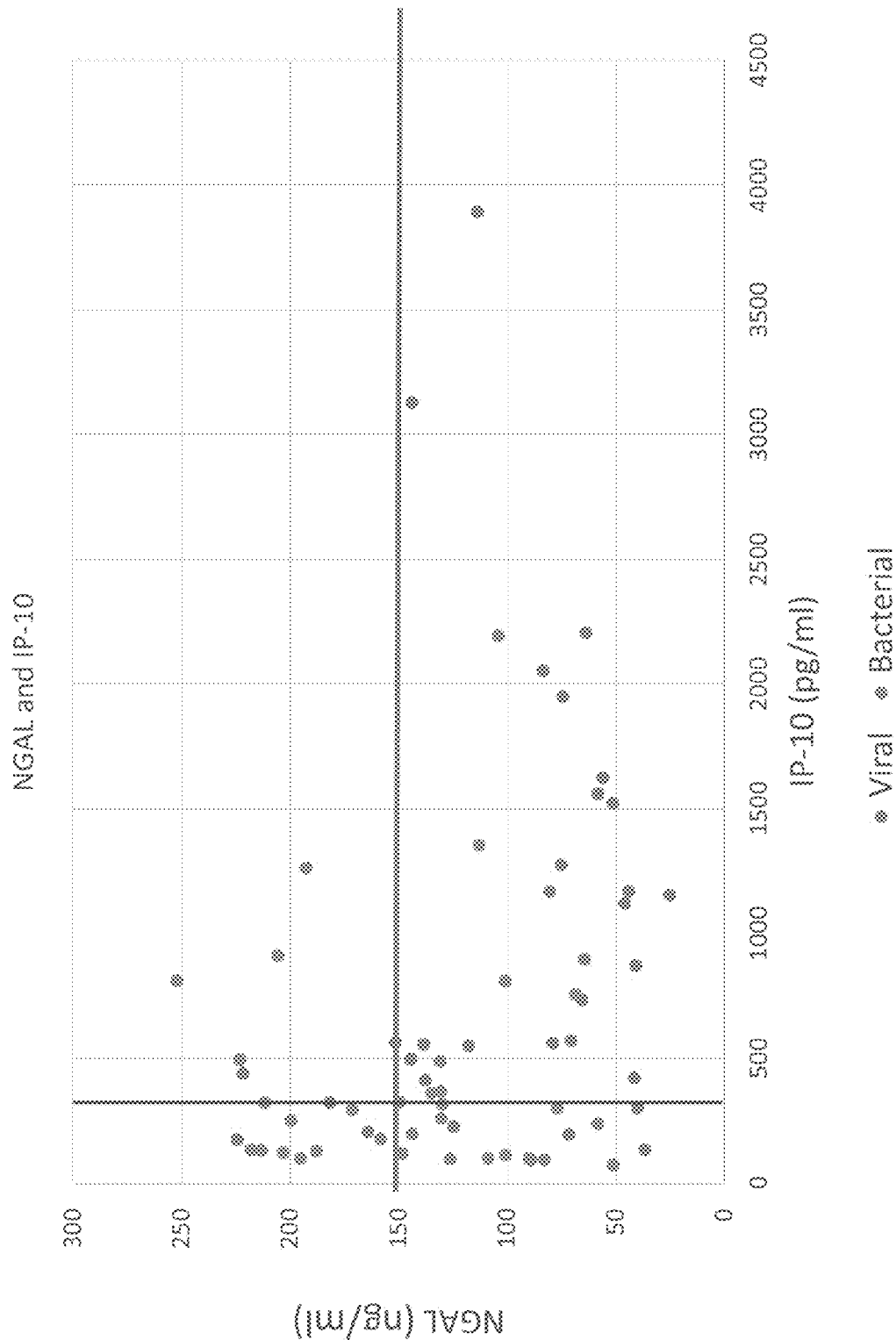
Figure 16B:
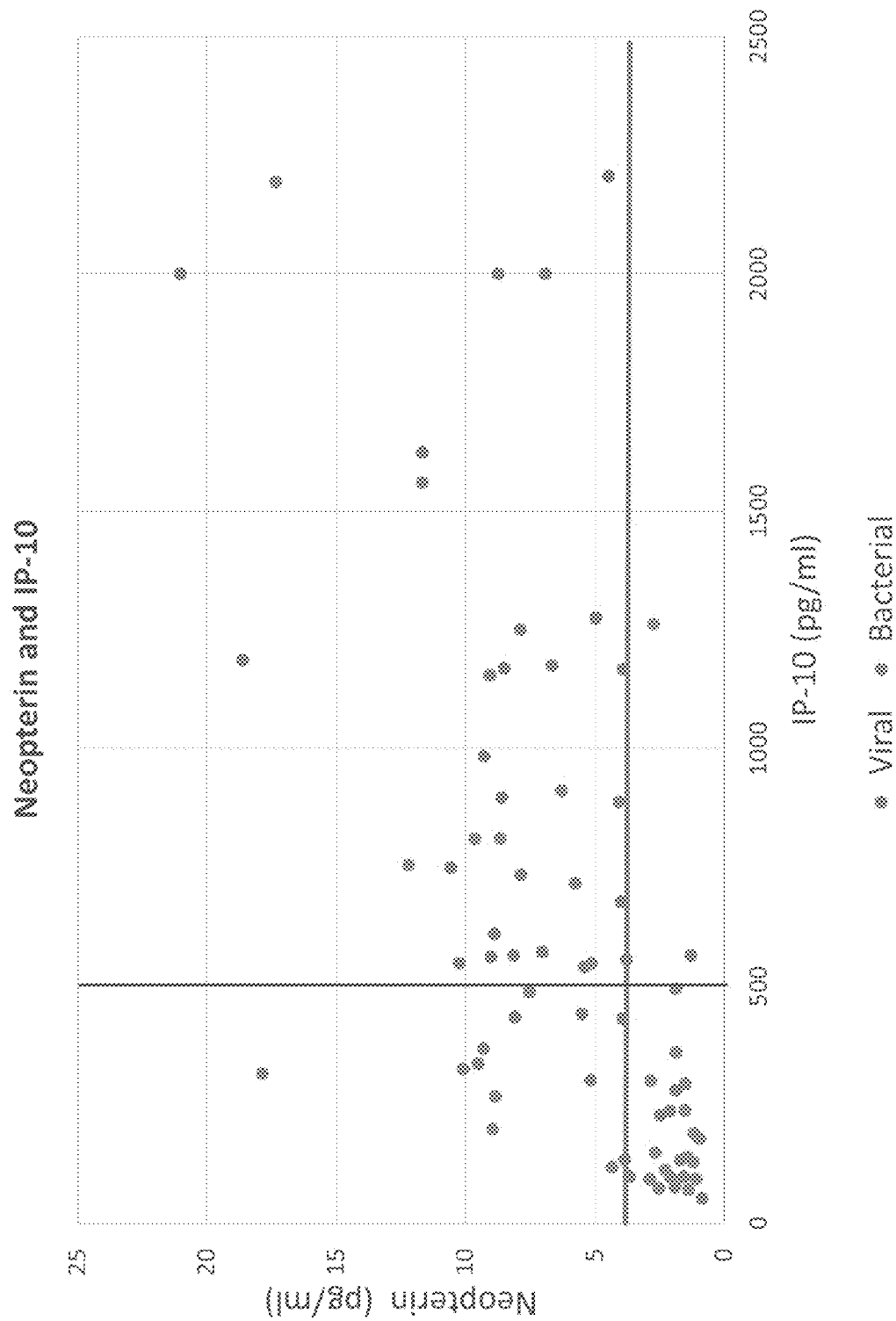

FIGS. 16A-16B: The levels of additional biomarkers can be combined with IP-10 to improve overall diagnostic performance. An example of IP-10 cutoff (500 pg/ml) is marked by a red line. (A) NGAL. An example of NGAL cutoff (150 ng/ml) is marked by a blue line. (B) Neopterin. An example of Neopterin cutoff (4 pg/ml) is marked by a blue line.

Figure 17A:
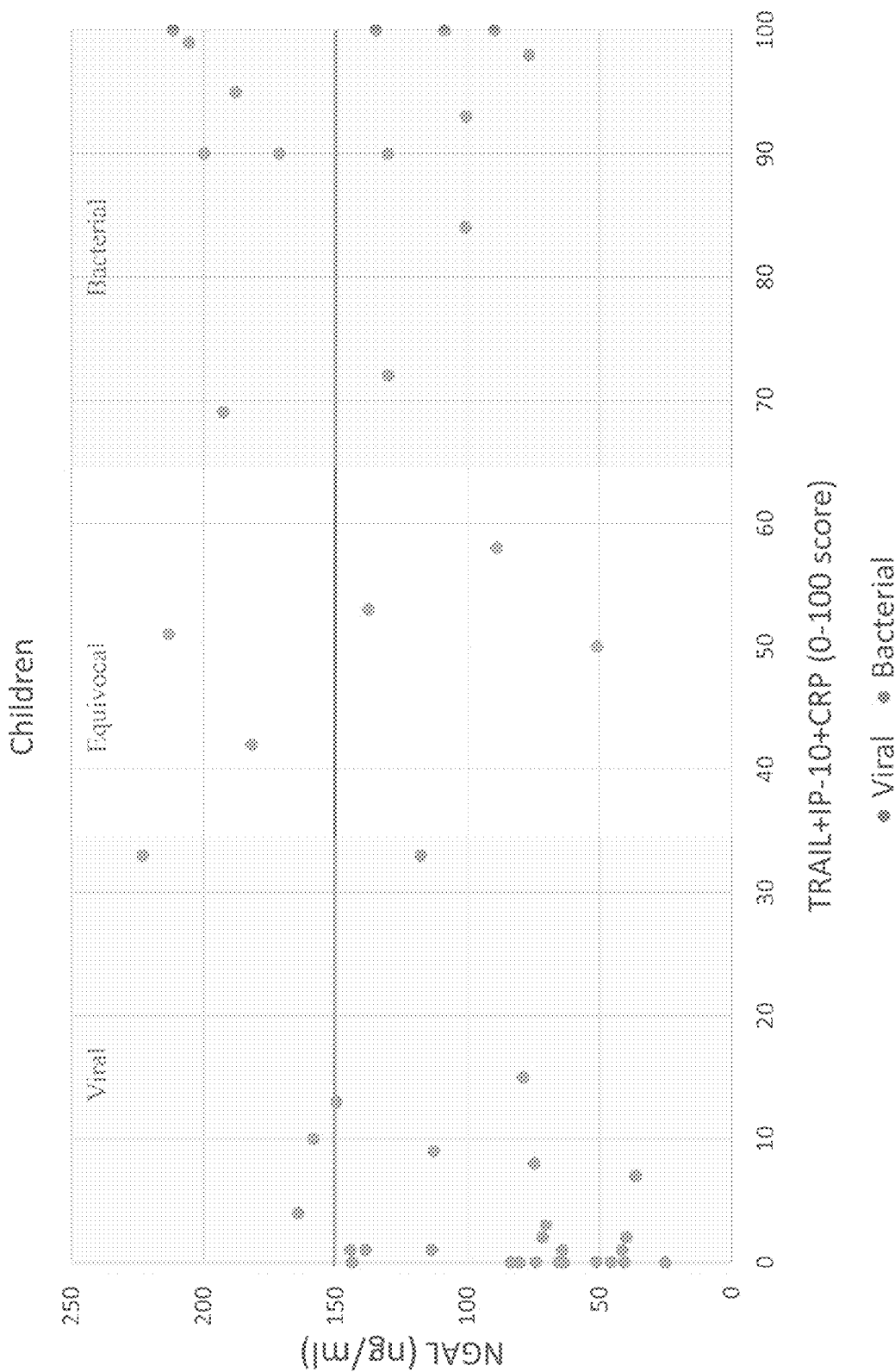
Figure 17B:
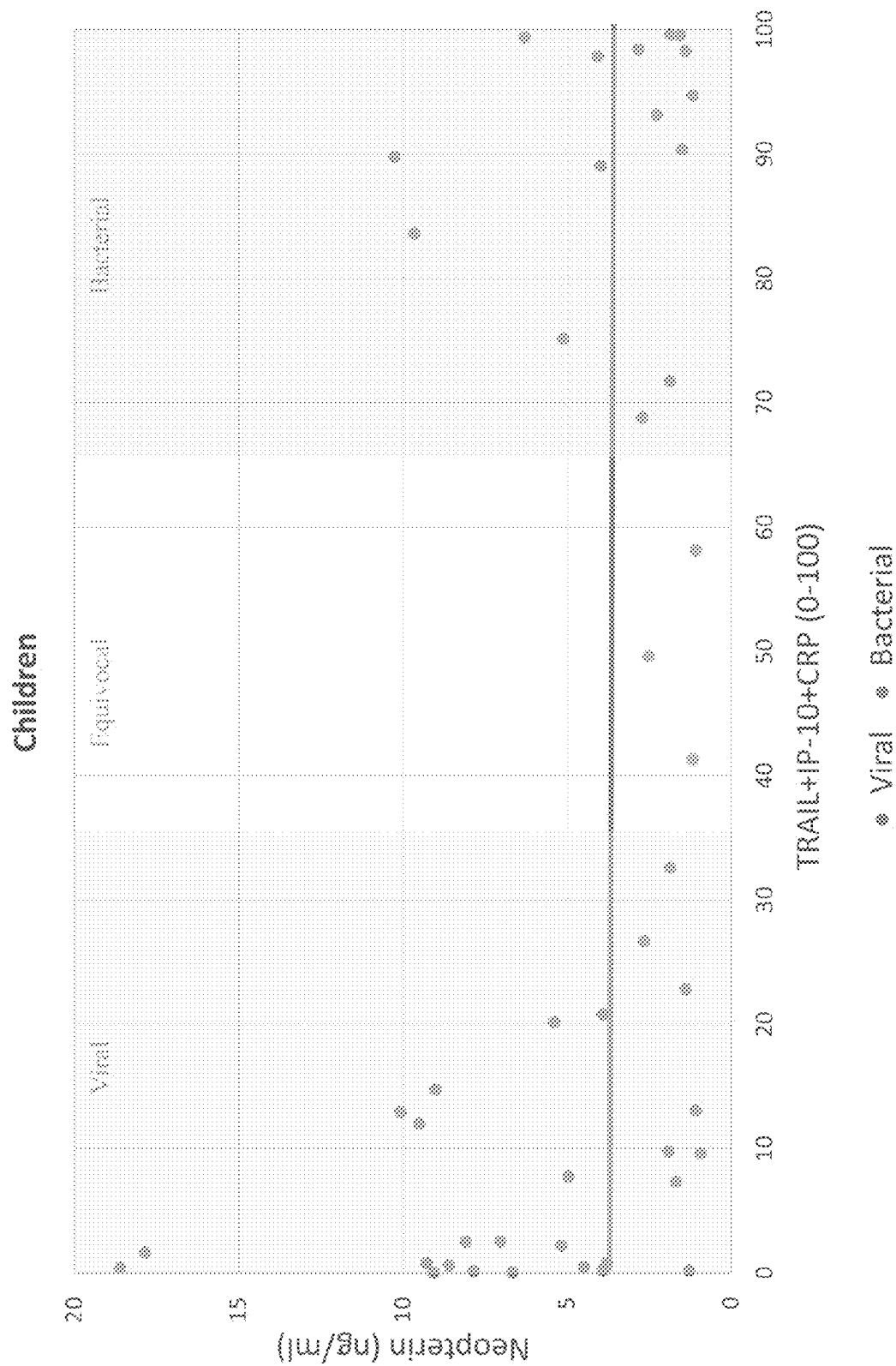

FIGS. 17A-17B: Additional biomarkers can be combined with the CRP-TRAIL-IP-10 signature to attain higher sensitivity (and lower specificity) when distinguishing between bacterial and viral infected children. Viral, bacterial, and equivocal immune scores generated by the CRP-TRAIL-IP-10 signature are marked by blue, red and gray areas respectively (Viral<35, Equivocal 35-65, Bacterial>65). (A) NGAL. An example of NGAL cutoff (150 ng/ml) is marked by a blue line. (B) Neopterin. An example of Neopterin cutoff (4 pg/ml) is marked by a blue line.

Figure 18A:
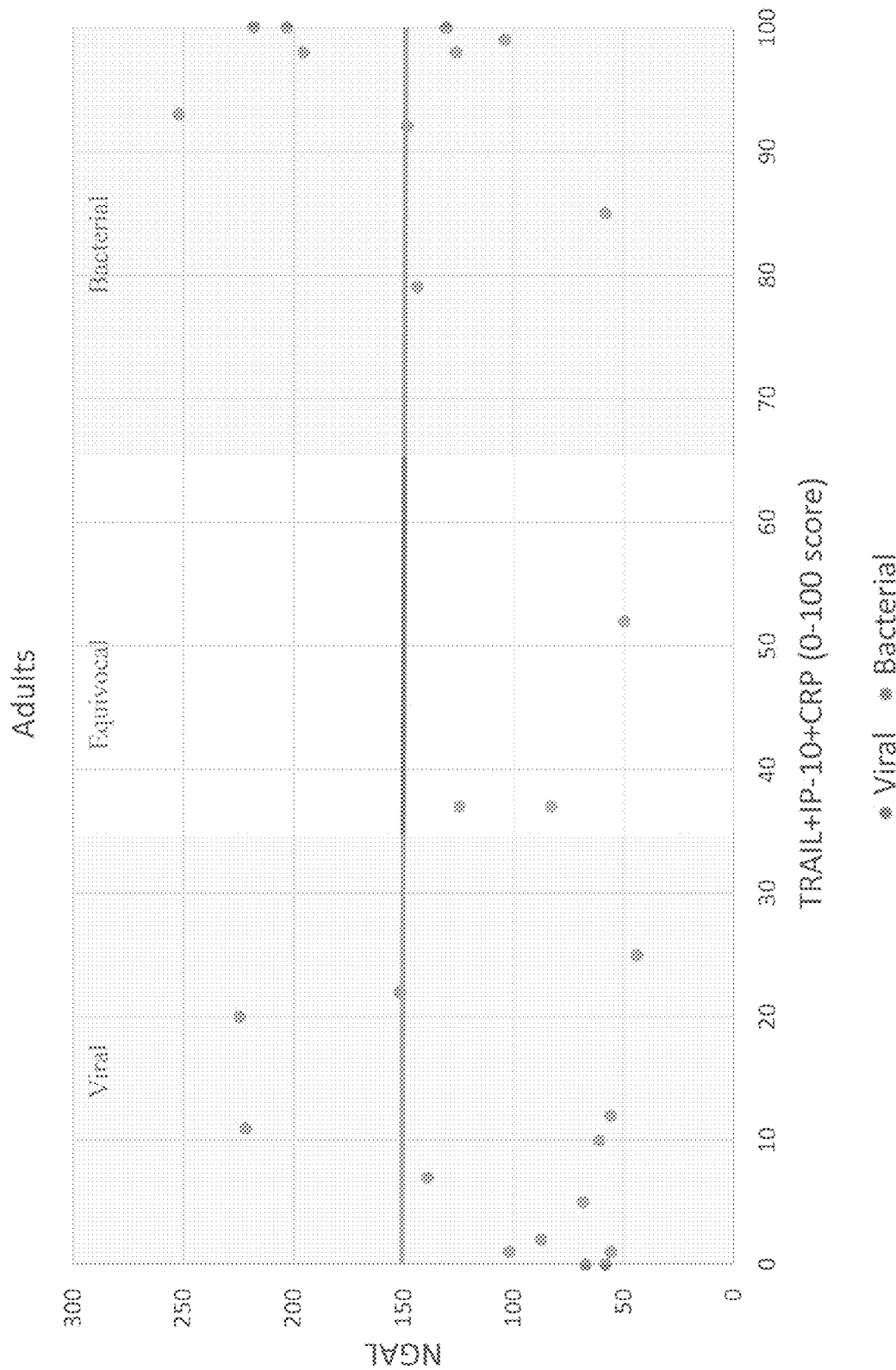
Figure 18B:
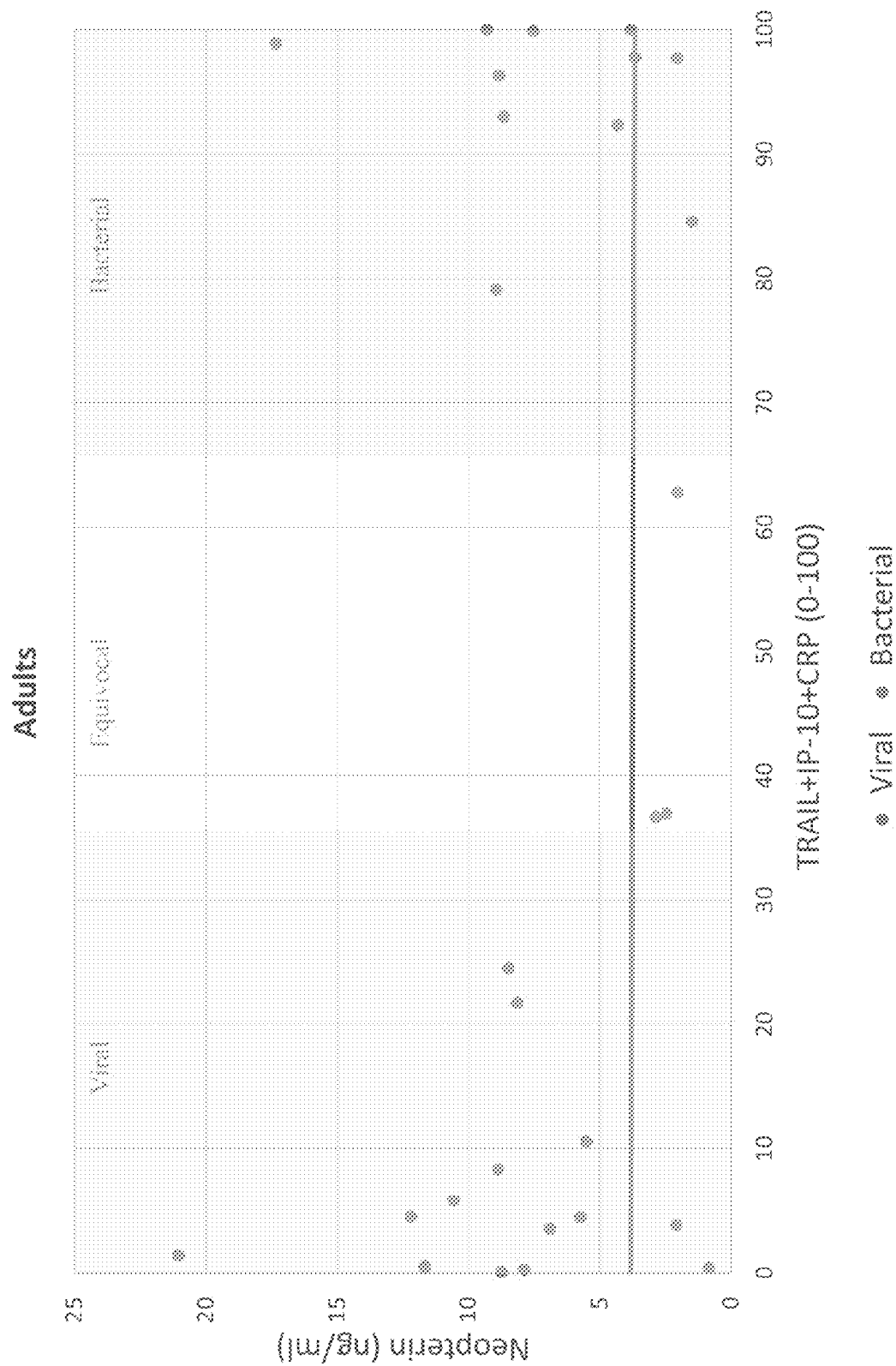

FIGS. 18A-18B: Additional biomarkers can be combined with the CRP-TRAIL-IP-10 signature to attain higher sensitivity (and lower specificity) when distinguishing between bacterial and viral infected adults. Viral, bacterial, and equivocal immune scores generated by the CRP-TRAIL-IP-10 signature are marked by blue, red and gray areas respectively (Viral<35, Equivocal 35-65, Bacterial>65). (A) NGAL. An example of NGAL cutoff (150 ng/ml) is marked by a blue line. (B) Neopterin. An example of Neopterin cutoff (4 pg/ml) is marked by a blue line.

DESCRIPTION OF SPECIFIC EMBODIMENTS OF THE INVENTION

The present invention, in some embodiments thereof, relates to the identification of signatures and determinants associated with bacterial, viral and mixed (i.e., bacterial and viral co-infections) infections. More specifically it was discovered that certain determinants are differentially expressed in a statistically significant manner in subjects with bacteria, viral or mixed (i.e., bacterial and viral co-infections) as well as non-infectious disease and healthy subjects.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Methods of distinguishing between bacterial and viral infections have been disclosed in International Patent Application WO2013/117746, to the present inventors. Seeking to expand the number of determinants that can aid in accurate diagnosis, the present inventors have now carried out additional clinical experiments and have identified other determinants that can be used for this aim.

Furthermore, the present inventors have now shown that analysis of some of these determinants in combination with previously disclosed determinants, or previously disclosed determinant combinations, improve the sensitivity of the diagnostic test, in some cases at a cost of reduced specificity.

Correct identification of bacterial patients is of high importance as these patients require antibiotic treatment and in some cases more aggressive management (hospitalization, additional diagnostic tests etc). Misclassification of bacterial patients increases the chance of morbidity and mortality. Therefore, increasing the sensitivity of a biomarker or diagnostic test that distinguishes between bacterial and viral infections may be desired, even though specificity may be reduced.

Whilst further reducing the present invention to practice, the present inventors have now found that for particular determinants, the threshold level for distinguishing between the different types of infections is age dependent. Thus, the present inventors conclude that for those determinants it is important to take into account the age of the tested subject.

Thus, according to a first aspect of the present invention there is provided a method for determining an infection type in a subject comprising measuring the concentration of a first determinant selected from the group consisting of the determinants which are set forth in Table 1 and a second determinant selected from the group of the determinants which are set forth in Table 2 in a sample derived from the subject, wherein the concentration is indicative of the infection type.

According to another aspect of the present invention there is provided a method of determining an infection type in a subject comprising measuring the concentration of only one determinant which is set forth in Table 1 in a subject derived sample, wherein the concentration is indicative of the infection type.

According to still another aspect of the present invention there is provided a method of determining an infection type in a subject comprising measuring the concentration of at least two determinants which are set forth in Table 1 in a sample derived from the subject, wherein the concentration is indicative of the infection type. In one aspect of the invention, these determinants include at least one that is set forth in Table 1 and at least one that is set forth in Table 2. In another aspect of the invention, these determinants include at least two that are set forth in Table 1.

TABLE 1

| DETERMINANT | RefSeq DNA sequence | RefSeq proteins |
|---|---|---|
| 4-1BB Ligand/TNFSF9 Tumor Necrosis Factor (Ligand) Superfamily, Member 9 | NC_000019.10, NT_011295.12, NC_018930.2 | NP_003802.1 |
| 4-1BB/TNFRSF9 tumor necrosis factor receptor superfamily, member 9 | NC_000001.11, NT_032977.10, NC_018912.2 | NP_001552.2 |
| a1-Acid Glycoprotein ORM2 (orosomucoid 2) | NC_000009.12, NC_018920.2, NT_008470.20 | NP_000598.2 |
| ACE/CD143 angiotensin I converting enzyme | NC_000017.11, NT_010783.16, NC_018928.2 | NP_000780.1, NP_001171528.1 NP_690043.1 |
| INHBA/Inhibin Beta A | NC_000007.14, NC_018918.2 NT_007819.18 | NP_002183.1 |
| Adiponectin/Acrp30 ADIPOQ (adiponectin, C1Q and collagen domain containing) | NC_000003.12, NT_005612.17, NC_018914.2 | NP_001171271.1, NP_004788.1 |
| a-Fetoprotein/AFP alpha-fetoprotein | NC_000004.12, NT_016354.20, NC_018915.2 | NP_001125.1 |
| AgRP/Agouti-related Protein agouti related neuropeptide | NC_000016.10, NT_010498.16, NC_018927.2 | NP_001129.1 |
| AKT1 v-akt murine thymoma viral oncogene homolog 1 | NC_000014.9, NT_026437.13, NC_018925.2 | NP_001014431.1 NP_001014432.1 NP_005154.2 |
| Angiogenin/ANG angiogenin, ribonuclease, RNase A family, 5 | NC_000014.9, NC_018925.2, NT_026437.13 | NP_001091046.1 NP_001136.1 |
| Angiopoietin-1 ANGPT1 | NC_000008.11, NT_008046.17, NC_018919.2 | NP_001137.2 NP_001186788.1 |
| Angiopoietin-2 ANGPT2 | NC_000008.11, NC_018919.2, NT_023736.18 | NP_001112359.1 NP_001112360.1 NP_001138.1 |
| Angiopoietin-like 3 ANGPTL3 | NC_000001.11, NC_018912.2, NT_032977.10 | NP_055310.1 |
| APP amyloid beta (A4) precursor protein | NC_000021.9, NC_018932.2, NT_011512.12 | NP_000475.1, NP_001129488.1 NP_001129601.1, NP_001129602.1 NP_001129603.1 NP_001191230.1 NP_001191231.1 NP_001191232.1, NP_958816.1 NP_958817.1 |
| APRIL/TNFSF13 tumor necrosis factor superfamily member 13 | NC_000017.11, NC_018928.2, NT_010718.17 | NP_001185551.1 NP_001185552.1 NP_001185553.1 NP_003799.1 NP_742084.1 NP_742085.1 |
| BAFF/TNFSF13B tumor necrosis factor superfamily member 13b | NC_000013.11, NT_009952.15, NC_018924.2 | NP_001139117.1 NP_006564.1 |
| BAFFR/TNFRSF13C tumor necrosis factor receptor superfamily member 13C | NC_000022.11, NC_018933.2, NT_011520.13 | NP_443177.1 |
| BCMA/TNFRSF17 tumor necrosis factor receptor superfamily member 17 | NC_000016.10, NC_018927.2, NT_010393.17 | NP_001183.2 |
| BDNF brain-derived neurotrophic factor | NC_000011.10, NT_009237.19, NC_018922.2 | NP_001137277.1 NP_001137278.1 NP_001137279.1 NP_001137280.1 NP_001137281.1 NP_001137282.1 NP_001137283.1 NP_001137284.1 NP_001137285.1 NP_001137286.1 NP_001137288.1 |
| | | NP_001700.2 NP_733927.1 NP_733928.1 NP_733929.1 NP_733930.1 NP_733931.1 |
| CTNNB1/Beta-catenin catenin beta 1 | NC_000003.12, NT_022517.19, NC_018914.2 | NP_001091679.1 NP_001091680.1 NP_001895.1 |
| BMP-2 bone morphogenetic protein 2 | NC_000020.11, NT_011387.9, NC_018931.2 | NP_001191.1 |
| BMP-4 bone morphogenetic protein 4 | NC_000014.9, NT_026437.13, NC_018925.2 | NP_001193.2 NP_570911.2 NP_570912.2 |
| BMP-7 bone morphogenetic protein 7 | NC_000020.11, NC_018931.2, NT_011362.11 | NP_001710.1 |
| Carbonic Anhydrase IX/CA9 | NC_000009.12, NT_008413.19, NC_018920.2 | NP_001207.2 |
| Cathepsin V CTSV | NC_000009.12, NC_018920.2, NT_008470.20 | NP_001188504.1 NP_001324.2 |
| CD14 CD14 molecule | NC_000005.10, NC_018916.2, NT_029289.12 | NP_000582.1 NP_001035110.1 NP_001167575.1 NP_001167576.1 |
| CD23/FCER2 Fc fragment of IgE, low affinity II, receptor for | NC_000019.10 NT_011295.12 NC_018930.2 | NP_001193948.2 NP_001207429.1 NP_001993.2 |
| CD27 Ligand/TNFSF7 CD70 molecule | NC_000019.10, NC_018930.2, NT_011295.12 | NP_001243.1 |
| CD27/TNFRSF7 CD27 molecule | NC_000012.12, NT_009759.17, NC_018923.2 | NP_001233.1 |
| CD30 Ligand/TNFSF8 tumor necrosis factor superfamily member 8 | NC_000009.12, NC_018920.2, NT_008470.20 | NP_001235.1 NP_001239219.1 |
| CD32/Fcg RII FCGR2A Fc fragment of IgG, low affinity IIa, receptor FCGR2B Fc fragment of IgG, low affinity IIb, receptor | NC_000001.11, NT_004487.20, NC_018912.2 | NP_001002273.1 NP_001002274.1 NP_001002275.1 NP_001177757.1 NP_003992.3 |
| Chemerin/RARRES2 retinoic acid receptor responder (tazarotene induced) 2 | NC_000007.14, NC_018918.2, NT_007933.16 | NP_002880.1 |
| CLU/Clusterin | NC_000008.11, NT_167187.2, NC_018919.2 | NP_001822.3 |
| CNTF ciliary neurotrophic factor | NC_000011.10, NC_018922.2, NT_167190.2 | NP_000605.1 |
| F3/Coagulation Factor III/Tissue Factor/CD142 coagulation factor III (thromboplastin, tissue factor) | NC_000001.11, NC_018912.2, NT_032977.10 | NP_001171567.1 NP_001984.1 |
| CFD/Complement Factor D/Adipsin | NC_000019.10, NC_018930.2, NT_011295.12, NT_187622.1 | NP_001919.2 |
| Corin corin, serine peptidase | NC_000004.12, NC_018915.2, NT_006238.12 | NP_001265514.1 NP_001265515.1 NP_006578.2 |
| CREB cAMP responsive element binding protein 1 (CREB1) | NC_000002.12, NT_005403.18, NC_018913.2 | NP_004370.1 NP_604391.1 |
| CXCL13/BLC/BCA-1 chemokine (C-X-C motif) ligand 13 | NC_000004.12, NT_016354.20, NC_018915.2 | NP_006410.1 |
| CXCL3 | NC_000004.12, | NP_002081.2 |

TABLE 1-continued

| DETERMINANT | RefSeq DNA sequence | RefSeq proteins |
|---|---|---|
| chemokine (C-X-C motif) ligand 3 | NC_018915.2, NT_016354.20 | |
| CXCL6/GCP-2 chemokine (C-X-C motif) ligand 6 | NC_000004.12, NC_018915.2, NT_016354.20 | NP_002984.1 |
| CXCL9/MIG chemokine (C-X-C motif) ligand 9 | NC_000004.12, NC_018915.2, NT_016354.20 | NP_002407.1 |
| Cystatin C CST3 | NC_000020.11, NC_018931.2, NT_011387.9 | NP_000090.1 NP_001275543.1 |
| DCR3/TNFRSF6B tumor necrosis factor receptor superfamily member 6b | NC_000020.11, NC_018931.2, NT_011362.11 | NP_003814.1 |
| Dkk-1 dickkopf WNT_signaling pathway inhibitor 1 | NC_000010.11, NC_018921.2, NT_030059.14 | NP_036374.1 |
| DLL1 delta-like 1 (*Drosophila*) | NC_000006.12, NT_025741.16, NT_187553.1, NC_018917.2 | NP_005609.3 |
| DPPIV/CD26 dipeptidyl-peptidase 4 | NC_000002.12, NT_005403.18, NC_018913.2 | NP_001926.2 |
| DR3/TNFRSF25 tumor necrosis factor receptor superfamily member 25 | NC_000001.11, NC_018912.2, NT_032977.10 | NP_001034753.1 NP_003781.1 NP_683866.1 NP_683867.1 NP_683868.1 NP_683871.1 |
| DR6/TNFRSF21 tumor necrosis factor receptor superfamily member 21 | NC_000006.12, NT_007592.16, NC_018917.2 | NP_055267.1 |
| E-Cadherin/CDH1 cadherin 1, type 1 | NC_000016.10, NT_010498.16, NC_018927.2 | NP_004351.1 |
| EDA ectodysplasin A | NC_000023.11, NT_011651.18, NC_018934.2 | NP_001005609.1 NP_001005610.2 NP_001005612.2 NP_001005613.1 NP_001390.1 |
| EDA2R/TNFRSF27 ectodysplasin A2 receptor | NC_000023.11, NT_011651.18, NC_018934.2 | NP_001186616.1 NP_001229239.1 NP_068555.1 |
| EDA-A1/Ectodysplasin A | NC_000023.11, NT_011651.18, NC_018934.2 | NP_001005609.1 NP_001005610.2 NP_001005612.2 NP_001005613.1 NP_001390.1 |
| EDAR ectodysplasin A receptor | NC_000002.12, NT_005403.18, NC_018913.2 | NP_071731.1 |
| EG-VEGF/PK1 PROK1 prokineticin 1 | NC_000001.11, NC_018912.2, NT_032977.10 | NP_115790.1 |
| Endoglin/CD105 ENG | NC_000009.12, NC_018920.2, NT_008470.20 | NP_000109.1, NP_001108225.1, NP_001265067.1 |
| Endostatin/COL18A1 collagen, type XVIII, alpha 1 | NC_000021.9, NC_018932.2, NT_011512.12 | NP_085059.2, NP_569711.2, NP_569712.2 |
| Endothelin-1/ET-1 EDN1 | NC_000006.12, NT_007592.16, NC_018917.2 | NP_001161791.1, NP_001946.3 |
| Endothelin-2 EDN2 | NC_000001.11, NC_018912.2, NT_032977.10 | NP_001289198.1, NP_001947.1 |
| Endothelin-3 EDN3 | NC_000020.11, NT_011362.11, NC_018931.2 | NP_001289384.1, NP_001289385.1, NP_996915.1, NP_996916.1, NP_996917.1 |
| EPCR PROCR protein C receptor, endothelial | NC_000020.11, NT_011362.11, NC_018931.2 | NP_006395.2 |
| ErbB2/Her2 erb-b2 receptor tyrosine kinase 2 | NC_000017.11, NC_018928.2, NT_010783.16 | NP_001005862.1, NP_001276865.1, NP_001276866.1, NP_001276867.1, NP_004439.2 |
| ErbB3/Her3 erb-b2 receptor tyrosine kinase 3 | NC_000012.12, NC_018923.2, NT_029419.13 | NP_001005915.1, NP_001973.2 |
| Erythropoietin/EPO | NC_000007.14, NC_018918.2, NT_007933.16 | NP_000790.2 |
| E-Selectin/CD62E SELE | NC_000001.11, NC_018912.2, NT_004487.20 | NP_000441.2 |
| Fas Ligand/TNFSF6 FASLG TNF superfamily, member 6 | NC_000001.11, NC_018912.2, NT_004487.20 | NP_000630.1, NP_001289675.1 |
| Fas/TNFRSF6/CD95 Fas cell surface death receptor | NC_000010.11 NT_030059.14 NC_018921.2 | NP_000034.1 NP_690610.1 NP_690611.1 |
| Fetuin A AHSG alpha-2-HS-glycoprotein | NC_000003.12, NC_018914.2, NT_005612.17 | NP_001613.2 |
| FGF acidic (FGF1) fibroblast growth factor 1 (acidic) | NC_000005.10, NT_029289.12, NC_018916.2 | NP_000791.1, NP_001138364.1, NP_001138406.1, NP_001138407.1, NP_001244134.1, NP_001244135.1, NP_001244136.1, NP_001244137.1, NP_001244138.1, NP_001244139.1, NP_001244140.1, NP_001244141.1, NP_149127.1, NP_149128.1 |
| FGF-19 fibroblast growth factor 19 | NC_000011.10, NC_018922.2, NT_167190.2 | NP_005108.1 |
| FGF-21 fibroblast growth factor 21 | NC_000019.10, NT_011109.17, NC_018930.2 | NP_061986.1 |
| Follistatin FST | NC_000005.10, NT_034772.7, NC_018916.2 | NP_006341.1, NP_037541.1 |
| FRS2 fibroblast growth factor receptor substrate 2 | NC_000012.12, NC_018923.2, NT_029419.13 | NP_001036020.1, NP_001265280.1, NP_001265282.1, NP_001265283.1, NP_001265284.1, NP_001265285.1, NP_001265286.1, NP_006645.3 |
| Gas6 growth arrest specific 6 | NC_000013.11, NC_018924.2, NT_024498.13 | NP_000811.1 |
| GDF-15 growth differentiation factor 15 | NC_000019.10, NC_018930.2, NT_011295.12 | NP_004855.2 |
| GITR Ligand/TNFSF18 tumor necrosis factor superfamily member 18 | NC_000001.11, NC_018912.2, NT_004487.20 | NP_005083.2 |
| GITR/TNFRSF18 tumor necrosis factor receptor superfamily member 18 | NC_000001.11, NC_018912.2, NT_032977.10 | NP_004186.1, NP_683699.1, NP_683700.1 |
| Granzyme A GZMA | NC_000005.10, NC_018916.2, NT_034772.7 | NP_006135.1 |
| Granzyme B GZMB | NC_000014.9, NT_026437.13, NC_018925.2 | NP_004122.2 |
| Granzyme H GZMH | NC_000014.9, NT_026437.13, NC_018925.2 | NP_001257709.1, NP_001257710.1, NP_219491.1 |

TABLE 1-continued

| DETERMINANT | RefSeq DNA sequence | RefSeq proteins |
|---|---|---|
| Granzyme K GZMK | NC_000005.10, NC_018916.2, NT_034772.7 | NP_002095.1 |
| Growth Hormone 1/GH1 | NC_000017.11, NT_010783.16, NC_018928.2 | NP_000506.2, NP_072053.1, NP_072054.1 |
| Growth Hormone 2/GH2 | NC_000017.11 NC_018928.2 NT_010783.16 | NP_002050.1 NP_072050.1 NP_072051.1 NP_072052.1 |
| GSK-3a glycogen synthase kinase 3 alpha | NC_000019.10, NC_018930.2, NT_011109.17 | NP_063937.2 NP_001139628.1, NP_002084.2 |
| GSK-3b glycogen synthase kinase 3 beta | NC_000003.12, NT_005612.17, NC_018914.2 | |
| APRIL/TNFSF13 tumor necrosis factor superfamily member 13 | NC_000017.11 NC_018928.2 NT_010718.17 | NP_001185551.1 NP_001185552.1 NP_001185553.1 NP_003799.1 NP_742084.1 NP_742085.1 |
| CD134/OX40/TNFRSF4 tumor necrosis factor receptor superfamily member 4 | NC_000001.11 NT_032977.10 NC_018912.2 | NP_003318.1 |
| CD137/4-1BB/TNFRSF9 tumor necrosis factor receptor superfamily member 9 | NC_000001.11 NT_032977.10 NC_018912.2 | NP_001552.2 |
| TWEAK/TNFSF12 tumor necrosis factor superfamily member 12 | NC_000017.11 NC_018928.2 NT_010718.17 | NP_003800.1 |
| HGF hepatocyte growth factor | NC_000007.14, NT_007933.16, NC_018918.2 | NP_000592.3, NP_001010931.1, NP_001010932.1, NP_001010933.1, NP_001010934.1 |
| HGFR HGFR/MET | NC_000007.14 NT_007933.16 NC_018918.2 | NP_000236.2 NP_001120972.1 |
| HIF-1a hypoxia inducible factor 1, alpha subunit (basic helix-loop-helix transcription factor) | NC_000014.9, NC_018925.2, NT_026437.13 | NP_001230013.1, NP_001521.1, NP_851397.1 |
| Histone H2AX H2AFX H2A histonefamily member X | NC_000011.10, NC_018922.2, NT_033899.9 | NP_002096.1 |
| HSPB1 heat shock protein family B (small) member 1 | NC_000007.14, NC_018918.2, NT_007933.16 | NP_001531.1 |
| HSPB2 heat shock protein family B (small) member 2 | NC_000011.10, NC_018922.2, NT_033899.9 | NP_001532.1 |
| HSPB3 heat shock protein family B (small) member 3 | NC_000005.10, NC_018916.2, NT_034772.7 | NP_006299.1 |
| HVEM/TNFRSF14 tumor necrosis factor receptor superfamily, member 14 | NC_000001.11 NT_032977.10 NT_187515.1, NC_018912.2 | NP_001284534.1, NP_003811.2 |
| ICAM-1/CD54 intercellular adhesion molecule 1 | NC_000019.10, NC_018930.2, NT_011295.12 | NP_000192.2 |
| IFNB interferon, beta 1, fibroblast | NC_000009.12, NC_018920.2, NT_008413.19 | NP_002167.1 |
| IFNW1 interferon, omega 1 | NC_000009.12, NC_018920.2, NT_008413.19 | NP_002168.1 |
| IGFBP-3 insulin like growth factor binding protein 3 | NC_000007.14, NC_018918.2, NT_007819.18 NC_000012.12, | NP_000589.2, NP_001013416.1 NP_000609.1, |
| IGF-I insulin like growth factor 1 | NT_029419.13, NC_018923.2 | NP_001104753.1, NP_001104754.1, NP_001104755.1 |
| IkB-alpha/NFKBIA nuclear factor of kappa light polypeptide gene enhancer in B-cells inhibitor, alpha | NC_000014.9, NC_018925.2, NT_026437.13 | NP_065390.1 |
| IL-1 (IL1B) interleukin 1 beta | NC_000002.12, NT_005403.18, NC_018913.2 | NP_000567.1 |
| IL-17A interleukin 17A | NC_000006.12, NC_018917.2, NT_007592.16 | NP_002181.1 |
| IL-17F interleukin 17F | NC_000006.12, NT_007592.16, NC_018917.2 | NP_443104.1 |
| IL-18/IL-1F4 interleukin 18 | NC_000011.10, NT_033899.9, NC_018922.2 | NP_001230140.1, NP_001553.1 |
| IL-19 interleukin 19 | NC_000001.11, NT_004487.20, NC_018912.2 | NP_037503.2, NP_715639.1 |
| IL-1A/IL1F1/IL1 interleukin 1 alpha | NC_000002.12, NC_018913.2, NT_005403.18 | NP_000566.3 |
| IL-22 interleukin 22 | NC_000012.12, NC_018923.2, NT_029419.13 | NP_065386.1 |
| KGF/FGF-7 fibroblast growth factor 7 | NC_000015.10, NC_018926.2, NT_010194.18 | NP_002000.1 |
| Leptin R (Leptin Receptor) LEPR | NC_000001.11, NC_018912.2, NT_032977.10 | NP_001003679.1, NP_001003680.1, NP_001185616.1, NP_001185617.1, NP_001185618.1, NP_002294.2 |
| Leptin/OB LEP | NC_000007.14, NT_007933.16, NC_018918.2 | NP_000221.1 |
| LIGHT/TNFSF14 tumor necrosis factor superfamily member 14 | NC_000019.10, NT_011295.12, NC_018930.2 | NP_003798.2, NP_742011.2 |
| Lipocalin-2/NGAL LCN2 | NC_000009.12, NC_018920.2, NT_008470.20 | NP_005555.2 |
| LOX-1/OLR1 oxidized low density lipoprotein (lectin-like) receptor 1 | NC_000012.12, NT_009714.18, NC_018923.2 | NP_001166103.1, NP_001166104.1, NP_002534.1 |
| LRG/LRG1 leucine-rich alpha-2-glycoprotein 1 | NC_000019.10, NC_018930.2, NT_011295.12 | NP_443204.1 |
| Lymphotoxin beta/TNFSF3 LTB | NC_000006.12, NC_018917.2, NT_007592.16, NT_113891.3, NT_167244.2, NT_167245.2, NT_167246.2, NT_167247.2, NT_167248.2, NT_167249.2 | NP_002332.1, NP_033666.1 |
| MAPK8 mitogen-activated protein kinase 8 | NC_000010.11, NT_030059.14, NC_018921.2 | NP_001265476.1, NP_001265477.1, NP_002741.1, NP_620634.1, NP_620637.1 |
| MBL mannose-binding lectin (protein C) 2, soluble | NC_000010.11, NT_030059.14, NC_018921.2 | NP_000233.1 |
| MEK1/MAP2K1 mitogen-activated protein kinase kinase 1 | NC_000015.10 NT_010194.18 NC_018926.2 | NP_002746.1 |

TABLE 1-continued

| DETERMINANT | RefSeq DNA sequence | RefSeq proteins |
|---|---|---|
| MEK2/MAP2K2 mitogen-activated protein kinase kinase 2 | NC_000019.10 NT_011295.12 NC_018930.2 | NP_109587.1 |
| MIF macrophage migration inhibitory factor (glycosylation-inhibiting factor) | NC_000022.11, NC_018933.2, NT_011520.13, NT_187633.1 | NP_002406.1 |
| MMP-1 matrix metallopeptidase 1 | NC_000011.10, NC_018922.2, NT_033899.9 | NP_001139410.1, NP_002412.1 |
| MMP-13 matrix metallopeptidase 13 | NC_000011.10, NC_018922.2, NT_033899.9 | NP_002418.1 |
| MMP-2 matrix metallopeptidase 2 | NC_000016.10, NC_018927.2, NT_010498.16 | NP_001121363.1, NP_001289437.1, NP_001289438.1, NP_001289439.1, NP_004521.1 |
| MMP-3 matrix metallopeptidase 3 | NC_000011.10, NC_018922.2, NT_033899.9 | NP_002413.1 |
| MMP-7 matrix metallopeptidase 7 | NC_000011.10, NC_018922.2, NT_033899.9 | NP_002414.1 |
| MMP-8 matrix metallopeptidase 8 | NC_000011.10, NT_033899.9, NC_018922.2 | NP_001291370.1, NP_001291371.1, NP_002415.1 |
| Myeloperoxidase/MPO | NC_000017.11, NT_010783.16, NC_018928.2 | NP_000241.1 |
| NAPSA napsin A aspartic peptidase | NC_000019.10, NT_011109.17, NC_018930.2 | NP_004842.1 |
| NGFB nerve growth factor (beta polypeptide) | NC_000001.11, NT_032977.10, NC_018912.2 | NP_002497.2 |
| NGFR/TNFRSF16 nerve growth factor receptor | NC_000017.11, NC_018928.2, NT_010783.16 | NP_002498.1 |
| NT-3/Ntf3 neurotrophin 3 | NC_000012.12, NT_009759.17, NC_018923.2 | NP_001096124.1, NP_002518.1 |
| NT-4/NTF4 neurotrophin 4 | NC_000019.10, NT_011109.17, NC_018930.2 | NP_006170.1 |
| OSM/Oncostatin M | NC_000022.11, NT_011520.13, NC_018933.2 | NP_065391.1 |
| Osteopontin/OPN/SPP1 secreted phosphoprotein 1 | NC_000004.12, NC_018915.2, NT_016354.20 | NP_000573.1, NP_001035147.1, NP_001035149.1, NP_001238758.1, NP_001238759.1 |
| Osteoprotegerin/TNFRSF11B tumor necrosis factor receptor superfamily member 11b | NC_000008.11, NC_018919.2, NT_008046.17 | NP_002537.3 |
| OX40/TNFRSF4 tumor necrosis factor receptor superfamily member 4 | NC_000001.11, NT_032977.10, NC_018912.2 | NP_003318.1 |
| OX40L/TNFSF4 tumor necrosis factor superfamily member 4 | NC_000001.11, NT_004487.20, NC_018912.2 | NP_001284491.1, NP_003317.1 |
| p38/MAPK14 mitogen-activated protein kinase 14 | NC_000006.12, NT_007592.16, NC_018917.2 | NP_001306.1, NP_620581.1, NP_620582.1, NP_620583.1 |
| P70S6 Kinase Alpha/ P70S6K1/RPS6KB1 ribosomal protein S6 kinase, 70 kDa, polypeptide 1 | NC_000017.11 NT_010783.16 NC_018928.2 | NP_001258971.1 NP_001258972.1 NP_001258973.1 NP_001258989.1 NP_003152.1 |
| Pappalysin-1/PAPP-A pregnancy-associated plasma protein A, pappalysin 1 | NC_000009.12, NT_008470.20, NC_018920.2 | NP_002572.2 |
| Pentraxin 3/TSG-14/PTX3 | NC_000003.12, NC_018914.2, NT_005612.17 | NP_002843.2 |
| Periostin/OSF-2/POSTN periostin, osteoblast specific factor | NC_000013.11, NT_024524.15, NC_018924.2 | NP_001129406.1, NP_001129407.1, NP_001129408.1, NP_001273594.1, NP_001273595.1, NP_001273596.1, NP_006466.2 |
| PI3/Elafin peptidase inhibitor 3, skin-derived | NC_000020.11, NC_018931.2, NT_011362.11 | NP_002629.1 |
| PIGF phosphatidylinositol glycan anchor biosynthesis class F | NC_000002.12, NT_022184.16, NC_018913.2 | NP_002634.1, NP_775097.1 |
| Pref-1/DLK-1/FA1 delta-like 1 homolog (Drosophila) | NC_000014.9, NC_018925.2, NT_026437.13 | NP_003827.3 |
| Pro-Cathepsin B cathepsin B/CTSB | NC_000008.11 NT_077531.5 NC_018919.2 | |
| Progranulin/GRN granulin | NC_000017.11, NT_010783.16, NC_018928.2 | NP_002078.1 |
| Pro-MMP-10 (Stromelysin-2/ MMP10) matrix metallopeptidase 10 | NC_000011.10 NC_018922.2 NT_033899.9 | |
| Proprotein Convertase 9/PCSK9 proprotein convertase subtilisin/kexin type 9 | NC_000001.11, NT_032977.10, NC_018912.2 | NP_777596.2 |
| P-Selectin/CD62P/SELP selectin P | NC_000001.11, NT_004487.20, NC_018912.2 | NP_002996.2 |
| RANK/TNFRSF11A tumor necrosis factor receptor superfamily member 11a | NC_000018.10, NT_010966.15, NC_018929.2 | NP_001257878.1, NP_001257879.1, NP_001257880.1, NP_001265197.1, NP_003830.1 |
| RBP4 retinol binding protein 4 | NC_000010.11, NC_018921.2, NT_030059.14 | NP_006735.2 |
| Relaxin-2/RLN2 Relaxin 2 | NC_000009.12, NT_008413.19, NC_018920.2 | NP_005050.2, NP_604390.1 |
| RELT/TNFRSF19L RELT tumor necrosis factor receptor | NC_000011.10, NT_167190.2, NC_018922.2 | NP_116260.2, NP_689408.1 |
| RETN Resistin | NC_000019.10, NC_018930.2, NT_011295.12 | NP_001180303.1, NP_065148.1 |
| CD14 CD14 molecule | NC_000005.10, NC_018916.2, NT_029289.12 | NP_000582.1, NP_001035110.1, NP_001167575.1, NP_001167576.1 |
| KIT/SCFR/c-kit v-kit Hardy-Zuckerman 4 feline sarcoma viral oncogene homolog | NC_000004.12, NT_022853.16, NC_018915.2 | NP_000213.1, NP_001087241.1 |
| SERPINE1/Serpin E1/PAI-1 serpin peptidase inhibitor, clade E (nexin, plasminogen activator inhibitor type 1), member 1 | NC_000007.14, NC_018918.2, NT_007933.16 | NP_000593.1 |
| SLPI secretory leukocyte peptidase inhibitor | NC_000020.11, NC_018931.2, NT_011362.11 | NP_003055.1 |
| ST2/IL1RL1 interleukin 1 receptor-like 1 | NC_000002.12, NT_005403.18, NC_018913.2 | NP_001269337.1, NP_003847.2, NP_057316.3 |
| STAT2 signal transducer and activator of transcription 2 | NC_000012.12, NT_029419.13, NC_018923.2 | NP_005410.1, NP_938146.1 |

TABLE 1-continued

| DETERMINANT | RefSeq DNA sequence | RefSeq proteins |
|---|---|---|
| STAT3 signal transducer and activator of transcription 3 (acute-phase response factor) | NC_000017.11, NT_010783.16, NC_018928.2 | NP_003141.2, NP_644805.1, NP_998827.1 |
| STAT4 signal transducer and activator of transcription 4 | NC_000002.12, NT_005403.18, NC_018913.2 | NP_001230764.1, NP_003142.1 |
| STAT5A signal transducer and activator of transcription 5A | NC_000017.11, NT_010783.16, NC_018928.2 | NP_001275647.1, NP_001275648.1, NP_001275649.1, NP_003143.2 |
| STAT5B signal transducer and activator of transcription 5B | NC_000017.11, NT_010783.16, NC_018928.2 | NP_036580.2 |
| STAT6 signal transducer and activator of transcription 6, interleukin-4 induced | NC_000012.12, NT_029419.13, NC_018923.2 | NP_001171549.1, NP_001171550.1, NP_001171551.1, NP_001171552.1, NP_003144.3 |
| TAC1/Substance P tachykinin precursor 1 | NC_000007.14, NC_018918.2, NT_007933.16 | NP_003173.1, NP_054702.1, NP_054703.1, NP_054704.1 |
| SFTPD/Surfactant Protein D | NC_000010.11, NT_030059.14, NC_018921.2 | NP_003010.4 |
| Survivin/BIRC5 baculoviral IAP repeat containing 5 | NC_000017.11, NT_010783.16, NC_018928.2 | NP_001012270.1, NP_001012271.1, NP_001159.2 |
| TACI/TNFRSF13B tumor necrosis factor receptor superfamily member 13B | NC_000017.11, NC_018928.2, NT_010718.17 | NP_036584.1 |
| TFPI tissue factor pathway inhibitor | NC_000002.12, NT_005403.18, NC_018913.2 | NP_001027452.1, NP_006278.1 |
| TfR/Transferrin Receptor | NC_000003.12, NT_005612.17, NC_018914.2, | NP_001121620.1, NP_003225.2 |
| TGFB1 (TGF-b1) transforming growth factor beta 1 | NC_000019.10, NT_011109.17, NC_018930.2 | NP_000651.3 |
| TGFB2/TGF-Beta2 (TGF-b2) transforming growth factor beta 2 | NC_000001.11, NC_018912.2, NT_004487.20 | NP_001129071.1, NP_003229.1 |
| THBS2/Thrombospondin-2 | NC_000006.12, NC_018917.2, NT_025741.16 | NP_003238.2 |
| Tie-1/TIE1 tyrosine kinase with immunoglobulin-like and EGF-like domains 1 | NC_000001.11, NT_032977.10, NC_018912.2 | NP_001240286.1, NP_005415.1 |
| TEK/Tie-2 TEK tyrosine kinase, endothelial | NC_000009.12, NT_008413.19, NC_018920.2 | NP_000450.2, NP_001277006.1, NP_001277007.1 |
| TIMP4/TIMP-4 TIMP metallopeptidase inhibitor 4 | NC_000003.12, NC_018914.2, NT_022517.19 | NP_003247.1 |
| TL1A/TNFSF15 tumor necrosis factor superfamily member 15 | NC_000009.12, NC_018920.2, NT_008470.20 | NP_001191273.1, NP_005109.2 |
| LTBR/TNFRSF3 lymphotoxin beta receptor | NC_000012.12, NT_009759.17, NC_018923.2 | NP_001257916.1, NP_002333.1 |
| MTOR mechanistic target of rapamycin (serine/threonine kinase) | NC_000001.11 NT_032977.10 NC_018912.2 | NP_004949.1 |
| PLAT/TPA plasminogen activator, tissue | NC_000008.11, NC_018919.2, NT_167187.2 | NP_000921.1, NP_127509.1 |
| TRAIL-R1/TNFRSF10A tumor necrosis factor receptor superfamily member 10a | NC_000008.11, NC_018919.2, NT_167187.2 | NP_003835.3 |
| TRAIL-R2/TNFRSF10B tumor necrosis factor receptor superfamily member 10b | NC_000008.11, NT_167187.2, NC_018919.2 | NP_003833.4, NP_671716.2 |
| TRAILR3/TNFRSF10C | NC_000008.11, | NP_003832.2 |
| tumor necrosis factor receptor superfamily member 10c, decoy without an intracellular domain | NC_018919.2, NT_167187.2 | |
| TRAILR4/TNFRSF10D tumor necrosis factor receptor superfamily member 10d, decoy with truncated death domain | NC_000008.11, NC_018919.2, NT_167187.2 | NP_003831.2 |
| TRANCE/TNFSF11 tumor necrosis factor superfamily member 11 | NC_000013.11, NT_024524.15, NC_018924.2 | NP_003692.1, NP_143026.1 |
| NTRK1/TrkA neurotrophic tyrosine kinase, receptor, type 1 | NC_000001.11, NC_018912.2, NT_004487.20 | NP_001007793.1, NP_001012331.1, NP_002520.2 |
| TROY/TNFRSF19 tumor necrosis factor receptor superfamily member 19 | NC_000013.11, NT_024524.15, NC_018924.2 | NP_001191387.1, NP_001191388.1, NP_061117.2, NP_683760.1 |
| TWEAK/TNFSF12 tumor necrosis factor superfamily member 12 | NC_000017.11, NC_018928.2, NT_010718.17 | NP_003800.1 |
| TWEAKR/TNFRSF12A tumor necrosis factor receptor superfamily member 12A | NC_000016.10, NC_018927.2, NT_010393.17 | NP_057723.1 |
| PLAUR/Upar plasminogen activator, urokinase receptor | NC_000019.10, NT_011109.17, NC_018930.2 | NP_001005376.1, NP_001005377.1, NP_001287966.1, NP_002650.1 |
| VCAM1/CD106 vascular cell adhesion molecule 1 | NC_000001.11, NC_018912.2, NT_032977.10 | NP_001069.1, NP_001186763.1, NP_542413.1 |
| VEGFC vascular endothelial growth factor C | NC_000004.12, NC_018915.2, NT_016354.20, | NP_005420.1 |
| FIGF/VEGF-D c-fos induced growth factor (vascular endothelial growth factor D) | NC_000023.11, NC_018934.2, NT_167197.2 | NP_004460.1 |
| GC/Vitamin D Binding Protein group-specific component (vitamin D binding protein) | NC_000004.12, NT_016354.20, NC_018915.2 | NP_000574.2, NP_001191235.1, NP_001191236.1 |
| Neopterin | NA | NA |
| cGMP | NA | NA |
| Leukotriene | NA | NA |
| Cotisol | NA | NA |
| Hyaloyronan | NA | NA |
| Prostaglandin E2 | NA | NA |
| Prostaglandin | NA | NA |
| Testosterone | NA | NA |

TABLE 2

CRP
TRAIL
IP-10
IL1R/IL1R1/IL1RA
Procalcitonin (PCT)
SAA/SAA1
TREM1
TREM2
RSAD2
MX1

In some cases, the determinants which are gene products are identified based on the official letter abbreviation or gene symbol assigned by the international Human Genome Organization Naming Committee (HGNC).

In some embodiments the level of additional parameters may be analyzed such as absolute Neutrophil count (ANC), ALC, Neu (%), Lymphocyte percentage (Lym (%)), Monocyte percentage (Mono (%)), Maximal temperature, Time from symptoms, Age, Creatinine (Cr), Potassium (K), Pulse and Urea.

In other embodiments, the level of different parameters may be analyzed, such as those selected from the group consisting of: ARG1, ARPC2, ATP6V0B, BILI (BILIRUBIN), BRI3BP, CCL19-MIP3B, CES1, CORO1A, EOS (%), HERC5, IFI6, IFIT3, KIAA0082, LIPT1, LRDD, MCP-2, NA (Sodium), PARP9, PTEN, QARS, RAB13, RPL34, SART3, TRIM22, UBE2N, WBC (Whole Blood Count), XAF1 and ZBP1.

In still other embodiment, the level of traditional laboratory risk factors and clinical parameters are also measured. These factors and parameters are further described herein below.

Additional determinants which may be measured together with those disclosed herein are provided in International Patent Application WO2013/117746, the contents of which is incorporated herein by reference and International Patent Application IL2015/050823, the contents of which are incorporated herein by reference.

The present invention, in some embodiments thereof: (i) enables accurate differentiation between a broad range of bacterial versus viral infections; (ii) enables rapid diagnosis (within minutes); (iii) avoids the "false positive" identification of non-pathogenic bacteria that are part of the body's natural flora, (iv) allows for accurate differentiation between mixed and pure viral infections and (v) allows diagnosis in cases where the pathogen is inaccessible.

To address the clinical challenge of mixed infection diagnosis and treatment, some aspects of the present invention include a method for differentiating between mixed infections (which require Abx treatment despite the presence of a virus) and pure viral infections (which do not require Abx treatment).

Some aspects of the present invention also address the challenge of "false-positive" diagnostics due to non-pathogenic strains of bacteria that are part of the body's natural flora. This is achieved by measuring biomarkers derived from the host rather than the pathogen.

Another aspect of the present invention enables the diagnosis of different infections, which is invariant to the presence or absence of colonizers (e.g. bacteria and viruses that are part of the natural flora). This addresses one of the major challenges in infectious disease diagnostics today: "false-positives" due to colonizers.

Importantly, some aspects of the current invention do not require direct access to the pathogen, because the immune system circulates in the entire body, thereby facilitating diagnosis in cases in which the pathogen is inaccessible.

Another aspect of the present invention is the fraction in which the biomarkers are measured, which affects the ease by which the assay can be performed in the clinical settings, and especially the point-of-care. For example, it is easier to measure proteins in the serum or plasma fraction compared to nucleic acids or intracellular proteins in the leukocytes fraction (the latter requires an additional experimental step in which leukocytes are isolated from the whole blood sample, washed and lysed). Accordingly, some aspects of the present invention also describe serum and plasma based protein signatures that are easily measurable using various immunoassays available in clinical settings.

Other aspects of the invention provide methods for identifying subjects who have an infection by the detection of determinants associated with an infection, including those subjects who are asymptomatic for the infection. These signatures and determinants are also useful for monitoring subjects undergoing treatments and therapies for infection, and for selecting or modifying diagnostics, therapies and treatments that would be efficacious in subjects having an infection.

Exemplary determinants measured in the present invention are described herein below.

CRP: C-reactive protein; additional aliases of CRP include without limitation RP11-419N10.4 and PTX1.

An exemplary amino acid sequence of human CRP is set forth below in SEQ ID NO: 1.

TRAIL: The protein encoded by this gene is a cytokine that belongs to the tumor necrosis factor (TNF) ligand family. The present invention contemplates measuring either the soluble and/or the membrane form of this protein. In one embodiment, only the soluble form of this protein is measured. Additional names of the gene include without limitations APO2L, TNF-related apoptosis-inducing ligand, TNFSF10 and CD253. This protein binds to several members of the TNF receptor superfamily such as TNFRSF10A/TRAILR1, TNFRSF10B/TRAILR2, TNFRSF10C/TRAILR3, TNFRSF10D/TRAILR4, and possibly also to TNFRSF11B/OPG.

Exemplary amino acid sequences of TRAIL are set forth in SEQ ID NOs: 2 or 3.

IP10: This gene encodes a chemokine of the CXC subfamily and ligand for the receptor CXCR3. Additional names of the gene include without limitations: CXCL10, Gamma-IP10, INP10 and chemokine (C-X-C motif) ligand 10.

An exemplary amino acid sequence of human IP10 is set forth in SEQ ID NO: 4.

IL1RA: The protein encoded by this gene is a cytokine receptor that belongs to the interleukin 1 receptor family. Additional names of the gene include without limitations: CD121A, IL-1RT1, p80, CD121a antigen, CD121A, IL1R and IL1ra.

PCT: Procalcitonin (PCT) is a peptide precursor of the hormone calcitonin, the latter being involved with calcium homeostasis.

TREM1: Triggering receptor expressed on myeloid cells 1; additional aliases of TREM1 are CD354 and TREM-1.

RSAD2: Radical S-adenosyl methionine domain containing 2; additional aliases of RSAD2 include without limitation 2510004L01Rik, cig33, cig5 and vig1.

MX1/MXA: myxovirus (influenza virus) resistance 1; additional aliases of MX1 include without limitation IFI-78K, IFI78, MX and MxA.

TRAILR3/TNFRSF10C: The protein encoded by this gene is a member of the TNF-receptor superfamily.

Exemplary amino acid sequences of this protein are set forth in SEQ ID NOs: 5 or 6.

TRAILR4/TNFRSF10D: The protein encoded by this gene is a member of the TNF-receptor superfamily.

Exemplary amino acid sequences of this protein are set forth in SEQ ID NOs: 7 or 8.

TRAIL-R1/TNFRSF10A: The protein encoded by this gene is a member of the TNF-receptor superfamily. Exemplary amino acid sequences of this protein are set forth in SEQ ID NOs: 9, 10 or 11.

TRAIL-R2/TNFRSF10B: The protein encoded by this gene is a member of the TNF-receptor superfamily, and contains an intracellular death domain. Exemplary amino acid sequences of this protein are set forth in SEQ ID NOs; 12, 13 or 14.

NGAL: Neutrophil gelatinase-associated lipocalin (NGAL) is also known as Lipocalin-2 (LCN2), also known as oncogene 24p3. An exemplary amino acid sequence of NGAL is set forth in SEQ ID NO: 15.

MMP8: Matrix metalloproteinase 8 (MMP8) is a collagen cleaving enzyme. Exemplary amino acid sequences of MMP8 are set forth in SEQ ID NOs: 16-18.

Neopterin: Neopterin is the catabolic product of guanosine triphosphate, a purine nucleotide. Neopterin belongs to the chemical group known as pteridines.

Cortisol: Cortisol is a steroid hormone, more specifically a glucocorticoid, which is produced by the zona fasciculata of the adrenal cortex. It is released in response to stress and a low level of blood glucose.

Definitions

As used herein, the term "determinant" refers to a polypeptide or chemical agent produced in the body which can serve as a marker for infection and/or infection type. In a particular embodiment, the determinant is not an RNA molecule.

In one embodiment, the determinant is a polypeptide.

In another embodiment, the determinant is a hormone.

In another embodiment, the determinant is a second messenger.

In still another embodiment, the determinant is a metabolite.

According to a particular embodiment, the determinants are soluble or secreted and are present outside the cellular interior in different body fluids such as serum, plasma, urine, CSF, sputum, sweat, stool, seminal fluid, etc.

"Traditional laboratory risk factors" encompass biomarkers isolated or derived from subject samples and which are currently evaluated in the clinical laboratory and used in traditional global risk assessment algorithms, such as absolute neutrophil count (abbreviated ANC), absolute lymphocyte count (abbreviated ALC), white blood count (abbreviated WBC), neutrophil % (defined as the fraction of white blood cells that are neutrophils and abbreviated Neu (%)), lymphocyte % (defined as the fraction of white blood cells that are lymphocytes and abbreviated Lym (%)), monocyte % (defined as the fraction of white blood cells that are monocytes and abbreviated Mon (%)), Sodium (abbreviated Na), Potassium (abbreviated K), Bilirubin (abbreviated Bili).

"Clinical parameters" encompass all non-sample or non-analyte biomarkers of subject health status or other characteristics, such as, without limitation, age (Age), ethnicity (RACE), gender (Sex), core body temperature (abbreviated "temperature"), maximal core body temperature since initial appearance of symptoms (abbreviated "maximal temperature"), time from initial appearance of symptoms (abbreviated "time from symptoms") or family history (abbreviated FamHX).

An "Infection Reference Expression Profile," is a set of values associated with two or more determinants resulting from evaluation of a biological sample (or population or set of samples).

A "subject with non-infectious disease" is one whose disease is not caused by an infectious disease agent (e.g. bacteria or virus). An "acute infection" is characterized by rapid onset of disease, a relatively brief period of symptoms, and resolution within days.

A "chronic infection" is an infection that develops slowly and lasts a long time. Viruses that may cause a chronic infection include Hepatitis C and HIV. One difference between acute and chronic infection is that during acute infection the immune system often produces IgM+ antibodies against the infectious agent, whereas the chronic phase of the infection is usually characteristic of IgM−/IgG+ antibodies. In addition, acute infections cause immune mediated necrotic processes while chronic infections often cause inflammatory mediated fibrotic processes and scaring (e.g. Hepatitis C in the liver). Thus, acute and chronic infections may elicit different underlying immunological mechanisms.

By infection type is meant to include bacterial infections, mixed infections, viral infections, no infection, infectious or non-infectious.

By "ruling in" an infection it is meant that the subject has that type of infection.

By "ruling out" an infection it is meant that the subject does not have that type of infection.

The "natural flora", or "colonizers" refers to microorganisms, such as bacteria or viruses, that may be present in healthy a-symptomatic subjects and in sick subjects.

An "anti-viral treatment" includes the administration of a compound, drug, regimen or an action that when performed by a subject with a viral infection can contribute to the subject's recovery from the infection or to a relief from symptoms. Examples of anti-viral treatments include without limitation the administration of the following drugs: oseltamivir, RNAi antivirals, monoclonal antibody respigams, zanamivir, and neuriminidase blocking agents.

"TP" is true positive, means positive test result that accurately reflects the tested-for activity. For example in the context of the present invention a TP, is for example but not limited to, truly classifying a bacterial infection as such.

"TN" is true negative, means negative test result that accurately reflects the tested-for activity. For example in the context of the present invention a TN, is for example but not limited to, truly classifying a viral infection as such.

"FN" is false negative, means a result that appears negative but fails to reveal a situation. For example in the context of the present invention a FN, is for example but not limited to, falsely classifying a bacterial infection as a viral infection.

"FP" is false positive, means test result that is erroneously classified in a positive category. For example in the context of the present invention a FP, is for example but not limited to, falsely classifying a viral infection as a bacterial infection.

"Sensitivity" is calculated by $TP/(TP+FN)$ or the true positive fraction of disease subjects.

"Specificity" is calculated by $TN/(TN+FP)$ or the true negative fraction of non-disease or normal subjects.

"Total accuracy" is calculated by $(TN+TP)/(TN+FP+TP+FN)$.

"Positive predictive value" or "PPV" is calculated by $TP/(TP+FP)$ or the true positive fraction of all positive test results. It is inherently impacted by the prevalence of the disease and pre-test probability of the population intended to be tested.

"Negative predictive value" or "NPV" is calculated by $TN/(TN+FN)$ or the true negative fraction of all negative test results. It also is inherently impacted by the prevalence of the disease and pre-test probability of the population intended to be tested. See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test.

"MCC" (Mathwes Correlation coefficient) is calculated as follows: $MCC=(TP*TN-FP*FN)/\{(TP+FN)*(TP+FP)*(TN+FP)*(TN+FN)\}^{0.5}$ where TP, FP, TN, FN are true-positives, false-positives, true-negatives, and false-negatives, respectively. Note that MCC values range between −1 to +1, indicating completely wrong and perfect classification, respectively. An MCC of 0 indicates random classification. MCC has been shown to be a useful for combining sensitivity and specificity into a single metric (Baldi, Brunak et al. 2000). It is also useful for measuring and optimizing classification accuracy in cases of unbalanced class sizes (Baldi, Brunak et al. 2000).

Often, for binary disease state classification approaches using a continuous diagnostic test measurement, the sensitivity and specificity is summarized by a Receiver Operating Characteristics (ROC) curve according to Pepe et al., "Limitations of the Odds Ratio in Gauging the Performance of a Diagnostic, Prognostic, or Screening Marker," Am. J. Epidemiol 2004, 159 (9): 882-890, and summarized by the Area Under the Curve (AUC) or c-statistic, an indicator that allows representation of the sensitivity and specificity of a test, assay, or method over the entire range of test (or assay) cut points with just a single value. See also, e.g., Shultz, "Clinical Interpretation Of Laboratory Procedures," chapter 14 in Teitz, Fundamentals of Clinical Chemistry, Burtis and Ashwood (eds.), 4$^{th}$ edition 1996, W.B. Saunders Company, pages 192-199; and Zweig et al., "ROC Curve Analysis: An Example Showing The Relationships Among Serum Lipid And Apolipoprotein Concentrations In Identifying Subjects With Coronory Artery Disease," Clin. Chem., 1992, 38(8): 1425-1428. An alternative approach using likelihood functions, odds ratios, information theory, predictive values, calibration (including goodness-of-fit), and reclassification measurements is summarized according to Cook, "Use and Misuse of the Receiver Operating Characteristic Curve in Risk Prediction," Circulation 2007, 115: 928-935.

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), Matheus correlation coefficient (MCC), or as a likelihood, odds ratio, Receiver Operating Characteristic (ROC) curve, Area Under the Curve (AUC) among other measures.

A "formula," "algorithm," or "model" is any mathematical equation, algorithmic, analytical or programmed process, or statistical technique that takes one or more continuous or categorical inputs (herein called "parameters") and calculates an output value, sometimes referred to as an "index" or "index value". Non-limiting examples of "formulas" include sums, ratios, and regression operators, such as coefficients or exponents, biomarker value transformations and normalizations (including, without limitation, those normalization schemes based on clinical-determinants, such as gender, age, or ethnicity), rules and guidelines, statistical classification models, and neural networks trained on historical populations. Of particular use in combining determinants are linear and non-linear equations and statistical classification analyses to determine the relationship between levels of determinants detected in a subject sample and the subject's probability of having an infection or a certain type of infection. In panel and combination construction, of particular interest are structural and syntactic statistical classification algorithms, and methods of index construction, utilizing pattern recognition features, including established techniques such as cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shrunken Centroids (SC), StepAIC, Kth-Nearest Neighbor, Boosting, Decision Trees, Neural Networks, Bayesian Networks, and Hidden Markov Models, among others. Other techniques may be used in survival and time to event hazard analysis, including Cox, Weibull, Kaplan-Meier and Greenwood models well known to those of skill in the art. Many of these techniques are useful either combined with a determinant selection technique, such as forward selection, backwards selection, or stepwise selection, complete enumeration of all potential panels of a given size, genetic algorithms, or they may themselves include biomarker selection methodologies in their own technique. These may be coupled with information criteria, such as Akaike's Information Criterion (AIC) or Bayes Information Criterion (BIC), in order to quantify the tradeoff between additional biomarkers and model improvement, and to aid in minimizing overfit. The resulting predictive models may be validated in other studies, or cross-validated in the study they were originally trained in, using such techniques as Bootstrap, Leave-One-Out (LOO) and 10-Fold cross-validation (10-Fold CV). At various steps, false discovery rates may be estimated by value permutation according to techniques known in the art. A "health economic utility function" is a formula that is derived from a combination of the expected probability of a range of clinical outcomes in an idealized applicable patient population, both before and after the introduction of a diagnostic or therapeutic intervention into the standard of care. It encompasses estimates of the accuracy, effectiveness and performance characteristics of such intervention, and a cost and/or value measurement (a utility) associated with each outcome, which may be derived from actual health system costs of care (services, supplies, devices and drugs, etc.) and/or as an estimated acceptable value per quality adjusted life year (QALY) resulting in each outcome. The sum, across all predicted outcomes, of the product of the predicted population size for an outcome multiplied by the respective outcome's expected utility is the total health economic utility of a given standard of care. The difference between (i) the total health economic utility calculated for the standard of care with the intervention versus (ii) the total health economic utility for the standard of care without the intervention results in an overall measure of the health economic cost or value of the intervention. This may itself be divided amongst the entire patient group being analyzed (or solely amongst the intervention group) to arrive at a cost per unit intervention, and to guide such decisions as market positioning, pricing, and assumptions of health system acceptance. Such health economic utility functions are commonly used to compare the cost-effectiveness of the intervention, but may also be transformed to estimate the acceptable value per QALY the health care system is willing to pay, or the acceptable cost-effective clinical performance characteristics required of a new intervention.

For diagnostic (or prognostic) interventions of the invention, as each outcome (which in a disease classifying diagnostic test may be a TP, FP, TN, or FN) bears a different cost, a health economic utility function may preferentially favor sensitivity over specificity, or PPV over NPV based on the clinical situation and individual outcome costs and value, and thus provides another measure of health economic performance and value which may be different from more direct clinical or analytical performance measures. These different measurements and relative trade-offs generally will converge only in the case of a perfect test, with zero error rate (a.k.a., zero predicted subject outcome misclassifications or FP and FN), which all performance measures will favor over imperfection, but to differing degrees.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's non-analyte clinical parameters or clinical-determinants.

"Analytical accuracy" refers to the reproducibility and predictability of the measurement process itself, and may be summarized in such measurements as coefficients of variation (CV), Pearson correlation, and tests of concordance and calibration of the same samples or controls with different times, users, equipment and/or reagents. These and other considerations in evaluating new biomarkers are also summarized in Vasan, 2006.

"Performance" is a term that relates to the overall usefulness and quality of a diagnostic or prognostic test, including, among others, clinical and analytical accuracy, other analytical and process characteristics, such as use characteristics (e.g., stability, ease of use), health economic value, and relative costs of components of the test. Any of these factors may be the source of superior performance and thus usefulness of the test, and may be measured by appropriate "performance metrics," such as AUC and MCC, time to result, shelf life, etc. as relevant.

A "sample" in the context of the present invention is a biological sample isolated from a subject and can include, by way of example and not limitation, whole blood, serum, plasma, saliva, mucus, breath, urine, CSF, sputum, sweat, stool, hair, seminal fluid, biopsy, rhinorrhea, tissue biopsy, cytological sample, platelets, reticulocytes, leukocytes, epithelial cells, or whole blood cells.

According to a particular embodiment the sample is a serum sample.

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is often considered highly significant at a p-value of 0.05 or less.

A "subject" in the context of the present invention may be a mammal (e.g. human dog, cat, horse, cow, sheep, pig, goat). According to another embodiment, the subject is a bird (e.g. chicken, turkey, duck, goose. According to a particular embodiment, the subject is a human. A subject can be male or female. A subject can be one who has been previously diagnosed or identified as having an infection, and optionally has already undergone, or is undergoing, a therapeutic intervention for the infection. Alternatively, a subject can also be one who has not been previously diagnosed as having an infection. For example, a subject can be one who exhibits one or more risk factors for having an infection.

In the context of the present invention the following abbreviations may be used: Antibiotics (Abx), Adverse Event (AE), Arbitrary Units (A.U.), Complete Blood Count (CBC), Case Report Form (CRF), Chest X-Ray (CXR), Electronic Case Report Form (eCRF), Food and Drug Administration (FDA), Good Clinical Practice (GCP), Gastrointestinal (GI), Gastroenteritis (GE), International Conference on Harmonization (ICH), Infectious Disease (ID), In vitro diagnostics (IVD), Lower Respiratory Tract Infection (LRTI), Myocardial infarction (MI), Polymerase chain reaction (PCR), Per-oss (P.O), Per-rectum (P.R), Standard of Care (SoC), Standard Operating Procedure (SOP), Urinary Tract Infection (UTI), Upper Respiratory Tract Infection (URTI).

Methods and Uses of the Invention

The methods disclosed herein are used to identify subjects with an infection or a specific infection type. By type of infection it is meant to include bacterial infections, viral infections, mixed infections, no infection (i.e., non-infectious). More specifically, some methods of the invention are used to distinguish subjects having a bacterial infection, a viral infection, a mixed infection (i.e., bacterial and viral co-infection), patients with a non-infectious disease and healthy individuals. Some methods of the present invention can also be used to monitor or select a treatment regimen for a subject who has a an infection, and to screen subjects who have not been previously diagnosed as having an infection, such as subjects who exhibit risk factors developing an infection. Some methods of the present invention are used to identify and/or diagnose subjects who are asymptomatic for an infection. "Asymptomatic" means not exhibiting the traditional signs and symptoms.

The term "Gram-positive bacteria" are bacteria that are stained dark blue by Gram staining. Gram-positive organisms are able to retain the crystal violet stain because of the high amount of peptidoglycan in the cell wall.

The term "Gram-negative bacteria" are bacteria that do not retain the crystal violet dye in the Gram staining protocol.

The term "Atypical bacteria" are bacteria that do not fall into one of the classical "Gram" groups. They are usually, though not always, intracellular bacterial pathogens. They include, without limitations, Mycoplasmas spp., *Legionella* spp. Rickettsiae spp., and Chlamydiae spp.

As used herein, infection is meant to include any infectious agent of viral or bacterial origin. The bacterial infection may be the result of gram-positive, gram-negative bacteria or atypical bacteria.

A subject having an infection is identified by measuring the amounts (including the presence or absence) of an effective number (which can be one or more) of determinants in a subject-derived sample. A clinically significant alteration in the level of the determinant is determined. Alternatively, the amounts are compared to a reference value. Alterations in the amounts and patterns of expression determinants in the subject sample compared to the reference value are then identified. In various embodiments, two, three, four, five, six, seven, eight, nine, ten or more determinants are measured. In various embodiments not more than two, no more than three, no more than four determinants are measured.

In some embodiments, the combination of determinants comprise measurements of a first determinant which is set forth in Table 1 and a second determinant which is set forth in Table 2.

According to a particular embodiment, the first determinant is a1 Acid Glycoprotein, Adiponectin, Angiogenin, Angiopoietin1, Angiopoietin2, APRIL, BAFF, BDNF, CD 23, CD14, CD142, CD27, CD95, Clusterin, Complement factor D, Corin, CXCL13, Cystatin C, Dkk1, E Cadherin, E Selectin, Endostatin, Fetuin A, GCP2, GDF15, ICAM1, IGFBP3, IL18, IL19, Leptin, Leptin R, LIGHT, MBL, MIF, MMP2, MMP3, MMP7, MMP8, Myeloperoxidase, Neopterin, NGAL, Osteopontin, Osteoprotegerin, P Selectin, PCSK9, Pentraxin3, Pro Cathepsin B, Progranulin, ProMMP10, Prostaglandin E2, RBP4, Resistin, SLPI, Substance P, TFPI, TGF B1, Thrombospondin2, Tie2, uPAR, VCAM1, VEGF C or Vitamin D Binding Protein. In another embodiment, the first determinant is NGAL, Resistin, MMP8, Pentraxin3, E Selectin, MMP7, Myeloperoxidase, Osteopontin, PCSK9, Pro Cathepsin B, a1 Acid Glycoprotein, GDF15, Progranulin, Adiponectin, Clusterin, Corin, Neopterin, Cystatin C, CD27, E Cadherin, Complement factor D, IGFBP3, GCP2, RBP4, CD14 or ProMMP10.

In yet another embodiment, the first determinant is NGAL, MMP8 or Neopterin.

According to another embodiment, the second determinant is CRP, TRAIL or IP-10.

In one embodiment, the present inventors contemplate analyzing no more than two determinants to distinguish between bacterial and viral infections.

Exemplary pairs include, but are not limited to CRP and NGAL; CRP and MMP8; CRP and Neopterin; TRAIL and NGAL; TRAIL and MMP8 TRAIL and Neopterin; IP-10 and NGAL; IP-10 and MMP8; IP-10 and Neopterin; IL1R and NGAL; IL1R and MMP8; IL1R and Neopterin; PCT and NGAL; PCT and MMP8; PCT and Neopterin; SAA and NGAL; SAA and MMP8; SAA and Neopterin. TREM1 and NGAL; TREM1 and MMP8; TREM1 and Neopterin; TREM2 and NGAL; TREM2 and MMP8; TREM2 and Neopterin; MX1 and NGAL; MX1 and MMP8; MX1 and Neopterin; RSAD2 and NGAL; RSAD2 and MMP8; RSAD2 and Neopterin.

Additional contemplated exemplary pairs include CRP and TRAILR3/TNFRSF10C, CRP and TRAILR4/TNFRSF10D, CRP and TRAIL-R1/TNFRSF10A and CRP and TRAIL-R2/TNFRSF10B.

Other exemplary pairs include TRAIL and TRAILR3/TNFRSF10C; TRAIL and TRAILR4/TNFRSF10D; TRAIL and TRAIL-R1/TNFRSF10A; and TRAIL and TRAIL-R2/TNFRSF10B.

Other exemplary pairs include IP10 and TRAILR3/TNFRSF10C, IP10 and TRAILR4/TNFRSF10D, IP10 and TRAIL-R1/TNFRSF10A and IP10 and TRAIL-R2/TNFRSF10B.

Other exemplary pairs include Neopterin and PCT; or NGAL and PCT.

Other exemplary pairs include IL1-Ra and TRAILR3/TNFRSF10C, IL1-Ra and TRAILR4/TNFRSF10D, IL1-Ra and TRAIL-R1/TNFRSF10A, and IL1-Ra and TRAIL-R2/TNFRSF10B.

Other exemplary pairs include PCT and TRAILR3/TNFRSF10C, PCT and TRAILR4/TNFRSF10D, PCT and TRAIL-R1/TNFRSF10A and PCT and TRAIL-R2/TNFRSF10B.

Other exemplary pairs include sTREM and TRAILR3/TNFRSF10C, sTREM and TRAILR4/TNFRSF10D, sTREM and TRAIL-R1/TNFRSF10A and, sTREM and TRAIL-R2/TNFRSF10B.

Other exemplary pairs include RSAD2 and TRAILR3/TNFRSF10C, RSAD2 and TRAILR4/TNFRSF10D, RSAD2 and TRAIL-R1/TNFRSF10A, and RSAD2 and TRAIL-R2/TNFRSF10B.

Other exemplary pairs include MX1 and TRAILR3/TNFRSF10C, MX1 and TRAIL-R1/TNFRSF10A, MX1 and TRAIL-R2/TNFRSF10B, and MX1 and TRAILR4/TNFRSF10D.

Additional pairs contemplated by the present inventors include TRAIL and MX1; TRAIL and RSAD2; TRAIL and sTREM; and TRAIL and IL1-Ra.

Exemplary pairs include CRP and NGAL, CRP and a1-Acid Glycoprotein/ORM1, CRP and IL18, CRP and CXCL6, CRP and MBL, CRP and OSM/Oncostatin M, CRP and TNFSF14 and CRP and CD14.

Other exemplary pairs include TRAIL and NGAL, TRAIL and a1-Acid Glycoprotein/ORM1, TRAIL and IL18, TRAIL and CXCL6, TRAIL and MBL, TRAIL and OSM/Oncostatin M, TRAIL and TNFSF14 and TRAIL and CD14.

Other exemplary pairs include IP10 and NGAL, IP10 and a1-Acid Glycoprotein/ORM1, IP10 and IL18, IP10 and CXCL6, IP10 and MBL, IP10 and OSM/Oncostatin M, IP10 and TNFSF14 and IP10 and CD14.

Other exemplary pairs include IL1-Ra and NGAL, IL1-Ra and a1-Acid Glycoprotein/ORM1, IL1-Ra and IL18, IL1-Ra and CXCL6, IL1-Ra and MBL, IL1-Ra and OSM/Oncostatin M, IL1-Ra and TNFSF14 and IL1-Ra and CD14.

Other exemplary pairs include PCT and NGAL, PCT and a1-Acid Glycoprotein/ORM1, PCT and IL18, PCT and CXCL6, PCT and MBL, PCT and OSM/Oncostatin M, PCT and TNFSF14 and PCT and CD14.

Other exemplary pairs include sTREM and NGAL, sTREM and a1-Acid Glycoprotein/ORM1, sTREM and IL18, sTREM and CXCL6, sTREM and MBL, sTREM and OSM/Oncostatin M, sTREM and TNFSF14 and sTREM and CD14.

Other exemplary pairs include RSAD2 and NGAL, RSAD2 and a1-Acid Glycoprotein/ORM1, RSAD2 and IL18, RSAD2 and CXCL6, RSAD2 and MBL, RSAD2 and OSM/Oncostatin M, RSAD2 and TNFSF14 and RSAD2 and CD14.

Other exemplary pairs include MX1 and NGAL, MX1 and a1-Acid Glycoprotein/ORM1, MX1 and IL18, MX1 and CXCL6, MX1 and MBL, MX1 and OSM/Oncostatin M, MX1 and TNFSF14 and MX1 and CD14.

It will be appreciated that 2, 3, 4 or more determinants from group 2 may be measured together with at least 1 determinant from group 1.

Thus for example TRAIL and CRP may be measured together with neopterin; TRAIL and CRP may be measured together with NGAL; TRAIL and CRP may be measured together with MMP8; TRAILR3/TNFRSF10C; TRAIL and CRP may be measured together with TRAILR4/TNFRSF10D; TRAIL and CRP may be measured together with TRAIL-R1/TNFRSF10A; and TRAIL and CRP may be measured together with TRAIL-R2/TNFRSF10B.

Alternatively, TRAIL and IP10 may be measured together with neopterin; TRAIL and IP10 may be measured together with NGAL; TRAIL and IP10 may be measured together with MMP8; TRAIL and IP10 may be measured together with TRAILR3/TNFRSF10C; TRAIL and IP10 may be measured together with TRAILR4/TNFRSF10D; TRAIL and IP10 may be measured together with TRAIL-R1/TNFRSF10A; and TRAIL and IP10 may be measured together with TRAIL-R2/TNFRSF10B.

Alternatively, CRP and IP10 may be measured together with neopterin; CRP and IP10 may be measured together with NGAL; CRP and IP10 may be measured together with MMP8; CRP and IP10 may be measured together with TRAILR3/TNFRSF10C; CRP and IP10 may be measured together with TRAIL-R1/TNFRSF10A; and CRP and IP10 may be measured together with TRAIL-R2/TNFRSF10B.

Thus for example TRAIL and CRP may be measured together with NGAL; TRAIL and CRP may be measured together with a1-Acid Glycoprotein/ORM1; TRAIL and CRP may be measured together with IL18; TRAIL and CRP may be measured together with CXCL6; TRAIL and CRP may be measured together with MBL; TRAIL and CRP may be measured together with OSM/Oncostatin M; TRAIL and CRP may be measured together with TNFSF14 and TRAIL and CRP may be measured together with CD14.

Alternatively TRAIL and IP10 may be measured together with NGAL; TRAIL and IP10 may be measured together with a1-Acid Glycoprotein/ORM1; TRAIL and IP10 may be measured together with IL18; TRAIL and IP10 may be measured together with CXCL6; TRAIL and IP10 may be measured together with MBL; TRAIL and IP10 may be measured together with OSM/Oncostatin M; TRAIL and IP10 may be measured together with TNFSF14 and TRAIL and IP10 may be measured together with CD14.

Alternatively CRP and IP10 may be measured together with NGAL, CRP and IP10 may be measured together with a1-Acid Glycoprotein/ORM1; CRP and IP10 may be measured together with IL18; CRP and IP10 may be measured together with CXCL6; CRP and IP10 may be measured together with MBL; CRP and IP10 may be measured together with OSM/Oncostatin M; CRP and IP10 may be measured together with TNFSF14 and CRP and IP10 may be measured together with CD14.

According to another embodiment 3 proteins from Table 2 are measured with at least one determinant in Table 1. Exemplary combinations include TRAIL, CRP and IP10 may be measured together with NGAL; TRAIL, CRP and IP10 may be measured together with neopterin; TRAIL, CRP and IP10 may be measured together with MMP8; TRAIL, CRP and IP10 may be measured together with TRAILR3/TNFRSF10C; TRAIL, CRP and IP10 may be measured together with TRAILR4/TNFRSF10D; TRAIL, CRP and IP10 may be measured together with TRAIL-R1/TNFRSF10A; TRAIL, CRP and IP10 may be measured together with TRAIL-R2/TNFRSF10B.

Exemplary combinations include TRAIL, CRP and IP10 may be measured together with NGAL; TRAIL, CRP and IP10 may be measured together with a1-Acid Glycoprotein/ORM1; TRAIL, CRP and IP10 may be measured together with IL18; TRAIL, CRP and IP10 may be measured together with CXCL6; TRAIL, CRP and IP10 may be measured together with MBL; TRAIL, CRP and IP10 may be measured together with OSM/Oncostatin M; TRAIL, CRP and IP10 may be measured together with TNFSF14; and TRAIL, CRP and IP10 may be measured together with CD14.

In other embodiments, the combination of determinants comprise measurements of at least two determinants which are set forth in Table 1.

According to a particular embodiment, at least one of the determinants in Table 1 is MMP-8, NGAL, or neopterin. Other contemplated combinations include TRAILR3/TNFRSF10C, TRAILR4/TNFRSF10D, TRAIL-R1/TNFRSF10A, TRAIL-R2/TNFRSF10B.

According to yet another embodiment, both the determinants in Table 1 are selected from the group consisting of: MMP-8, NGAL, neopterin, TRAILR3/TNFRSF10C, TRAILR4/TNFRSF10D, TRAIL-R1/TNFRSF10A and TRAIL-R2/TNFRSF10B.

Particular combinations include MMP-8 and NGAL; MMP-8 and neopterin or NGAL and neopterin.

In some embodiments, the determinant measurements further comprise measurements of one or more clinical-determinants selected from the group consisting of ANC, ALC, Neu (%), Lym (%), Mono (%), Maximal temperature, Time from symptoms, Age, Creatinine (Cr), Potassium (K), Pulse and Urea.

In some embodiments, the determinants or clinical-determinants further comprise measurements of one or more polypeptide or clinical-determinants selected from the group consisting of ARG1, ARPC2, ATP6V0B, BILI (Bilirubin), BRI3BP, CCL19-MIP3B, CES1, CORO1A, EOS (%), HERC5, IFI6, IFIT3, KIAA0082, LIPT1, LRDD, MCP-2, NA (Sodium), PARP9, PTEN, QARS, RAB13, RPL34, SART3, TRIM22, UBE2N, WBC (Whole Blood Count), XAF1 and ZBP1.

In various aspects the method distinguishes a virally infected subject from either a subject with non-infectious disease or a healthy subject; a bacterially infected subject, from either a subject with non-infectious disease or a healthy subject; a subject with an infectious disease from either a subject with an non-infectious disease or a healthy subject; a bacterially infected subject from a virally infected subject; a mixed infected subject from a virally infected subject; a mixed infected subject from a bacterially infected subject and a bacterially or mixed infected and subject from a virally infected subject.

In one aspect the method distinguishes a bacterially infected subject from a virally infected subject by measuring a first determinant set forth in Table 1 and a second determinant as set forth in Table 2.

Exemplary pairs are provided herein above.

In one aspect the method distinguishes a bacterially infected subject from a virally infected subject by measuring at least two determinants set forth in Table 1.

Exemplary pairs are provided herein above.

In another aspect the method distinguishes between a bacterial or mixed infected subject and a virally infected subject by measuring a first determinant set forth in Table 1 and a second determinant as set forth in Table 2.

Exemplary pairs are provided herein above.

In another aspect the method distinguishes between a bacterial or mixed infected subject and a virally infected subject by measuring at least two determinants set forth in Table 1.

Exemplary pairs of determinants from Table 1 include NGAL and MMP8; NGAL and Neopterin; and MMP8 and Neopterin.

In another aspect the method distinguishes between a subject with an infectious disease and a subject with a non-infectious disease or a healthy subject by measuring a first determinant set forth in Table 1 and a second determinant as set forth in Table 2.

Exemplary pairs are provided herein above.

In another aspect the method distinguishes between a subject with an infectious disease and a subject with a non-infectious disease or a healthy subject by measuring at least two determinants set forth in Table 1.

Exemplary pairs are provided herein above.

In specific embodiments the invention includes determining if a subject does not have a bacterial infection (i.e. ruling out a bacterial infection).

For example, a bacterial infection may be ruled out if the polypeptide concentration of TRAIL determined is higher than a pre-determined first threshold value. Optionally, the method further includes determining if a subject has a viral infection (i.e., ruling in a viral infection). A viral infection is rule in if the polypeptide concentration of TRAIL is higher than a pre-determined second threshold value.

In another specific embodiment the invention includes determining if a subject does not have a viral infection (i.e. ruling out a viral infection). A viral infection is ruled out if the polypeptide concentration of TRAIL determined is lower than a pre-determined first threshold value. Optionally, the method further includes determining if a subject has a bacterial infection (i.e., ruling in a bacterial infection). A bacterial infection is rule in if the polypeptide concentration of TRAIL is lower than a pre-determined second threshold value.

Indicative levels of some exemplary determinants which correspond to particular infection types are set forth in Table 3.

TABLE 3

| Determinant | Bacterial | Viral |
|---|---|---|
| Fas/TNFRSF6 | + | +++ |
| Fas Ligand/TNFSF6 | + | +++ |
| TWEAK/TNFSF12 | + | +++ |
| 4-1BB/TNFRSF9 | + | +++ |
| OX40/TNFRSF4 | + | +++ |
| CD30 Ligand/TNFSF8 | + | +++ |
| TRANCE/TNFSF11 | + | +++ |
| GITR Ligand/TNFSF18 | + | +++ |
| GITR/TNFRSF18 | + | +++ |
| DCR3/TNFRSF6B | + | +++ |
| HVEM/TNFRSF14 | + | +++ |
| TWEAKR/TNFRSF12A | + | +++ |
| TACI/TNFRSF13B | + | +++ |
| BCMA/TNFRSF17 | + | +++ |
| NGFR/TNFRSF16 | + | +++ |
| DR6/TNFRSF21 | + | +++ |
| RANK/TNFRSF11A | + | +++ |
| EDA2R/TNFRSF27 | + | +++ |
| RELT/TNFRSF19L | + | +++ |
| OX40L/TNFSF4 | + | +++ |
| TNFRSF3 | + | +++ |
| 4-1BB Ligand/TNFSF9 | + | +++ |
| DR3/TNFRSF25 | + | +++ |
| TL1A/TNFSF15 | + | +++ |
| TROY/TNFRSF19 | + | +++ |
| BAFFR/TNFRSF13C | + | +++ |
| CD27 Ligand/TNFSF7 | + | +++ |
| TRAILR3/TNFRSF10C | − | +++ |
| TRAILR4/TNFRSF10D | − | +++ |
| TRAIL-R1/TNFRSF10A | − | +++ |
| TRAIL-R2/TNFRSF10B | − | +++ |

For TRAILR3/TNFRSF10C, a bacterial infection may be ruled in if the polypeptide concentration is below a predetermined level. A bacterial infection may be ruled out if the polypeptide concentration is above a predetermined level. A viral infection may be ruled in if the polypeptide concentration is above a predetermined level.

For TRAILR4/TNFRSF10D, a bacterial infection may be ruled in if the polypeptide concentration is below a predetermined level. A bacterial infection may be ruled out if the polypeptide concentration is above a predetermined level. A viral infection may be ruled in if the polypeptide concentration is above a predetermined level.

For TRAIL-R1/TNFRSF10A, a bacterial infection may be ruled in if the polypeptide concentration is below a predetermined level. A bacterial infection may be ruled out if the polypeptide concentration is above a predetermined level. A viral infection may be ruled in if the polypeptide concentration is above a predetermined level.

For TRAIL-R2/TNFRSF10B, a bacterial infection may be ruled in if the polypeptide concentration is below a predetermined level. A bacterial infection may be ruled out if the polypeptide concentration is above a predetermined level. A viral infection may be ruled in if the polypeptide concentration is above a predetermined level.

For MMP8, a bacterial infection may be ruled in if the polypeptide concentration is above a predetermined level. A bacterial infection may be ruled out if the polypeptide concentration is below a predetermined level. A viral infection may be ruled in if the polypeptide concentration is below a predetermined level.

For NGAL, a bacterial infection may be ruled in if the polypeptide concentration is above a predetermined level. A bacterial infection may be ruled out if the polypeptide concentration is below a predetermined level. A viral infection may be ruled in if the polypeptide concentration is below a predetermined level.

For neopterin, a bacterial infection may be ruled in if the concentration thereof is below a predetermined level. A bacterial infection may be ruled out if the concentration thereof is above a predetermined level. A viral infection may be ruled in if the concentration thereof is above a predetermined level.

For a1-Acid Glycoprotein/ORM1, a bacterial infection may be ruled in if the polypeptide concentration is above a predetermined level. A bacterial infection may be ruled out if the polypeptide concentration is below a predetermined level. A viral infection may be ruled in if the polypeptide concentration is above a first predetermined level and below a second predetermined level.

For IL18, a bacterial infection may be ruled in if the polypeptide concentration is above a predetermined level. A bacterial infection may be ruled out if the polypeptide concentration is below a predetermined level. A viral infection may be ruled in if the polypeptide concentration is above a first predetermined level and below a second predetermined level.

For CXCL6, a bacterial infection may be ruled in if the polypeptide concentration is above a predetermined level. A bacterial infection may be ruled out if the polypeptide concentration is below a predetermined level. A viral infection may be ruled in if the polypeptide concentration is above a first predetermined level and below a second predetermined level.

For MBL, a bacterial infection may be ruled in if the polypeptide concentration is above a predetermined level. A bacterial infection may be ruled out if the polypeptide concentration is below a predetermined level. A viral infection may be ruled in if the polypeptide concentration is above a first predetermined level and below a second predetermined level.

For OSM/Oncostatin M, a bacterial infection may be ruled in if the polypeptide concentration is above a predetermined level. A bacterial infection may be ruled out if the polypeptide concentration is below a predetermined level. A viral infection may be ruled in if the polypeptide concentration is above a first predetermined level and below a second predetermined level.

For TNFSF14, a bacterial infection may be ruled in if the polypeptide concentration is below a predetermined level. A bacterial infection may be ruled out if the polypeptide concentration is above a predetermined level. A viral infection may be ruled in if the polypeptide concentration is above a predetermined level.

For CD14. a bacterial infection may be ruled in if the polypeptide concentration is above a predetermined level. A bacterial infection may be ruled out if the polypeptide concentration is below a predetermined level. A viral infection may be ruled in if the polypeptide concentration is above a first predetermined level and below a second predetermined level.

For example, a subject may be diagnosed as having a viral infection when the determinant levels of TRAIL, IP-10, Progranulin, Adiponectin, Clusterin, Corin, Neopterin, Cystatin C, CD27, E Cadherin, Complement factor D, IGFBP3, GCP2, RBP4, CD14 and/or ProMMP10, are at least 5%, 10%, 20%, 30%, 40%, 50%, 100%, 200%, 300%, or 400% higher than a bacterially-infected subject reference value.

For example, a subject may be diagnosed as having a bacterial infection when the polypeptide levels of CRP, NGAL, Resistin, MMP8, Pentraxin3, IL1R, E Selectin, MMP7, Myeloperoxidase, Osteopontin, PCSK9, Pro Cathepsin B, α1 Acid Glycoprotein, GDF15, are at least 5%, 10%, 20%, 30%, 40%, 50%, 100%, 200%, 300%, or 400% higher than a virally-infected subject reference value.

For example a subject may be diagnosed as having a bacterial infection when the determinant levels of TRAIL, IP-10, Progranulin, Adiponectin, Clusterin, Corin, Neopterin, Cystatin C, CD27, E Cadherin, Complement factor D, IGFBP3, GCP2, RBP4, CD14, ProMMP10 are 90%, 80%, 70%, 60%, 50%, 40%, 30%, 20%, 10%, 5%, 1% or less of a virally-infected subject or a healthy subject reference value.

For example a subject may be diagnosed as having a viral infection when the polypeptide levels of CRP, NGAL, Resistin, MMP8, Pentraxin3, IL1R, E Selectin, MMP7, Myeloperoxidase, Osteopontin, PCSK9, Pro Cathepsin B, α1 Acid Glycoprotein, GDF15, are 90%, 80%, 70%, 60%, 50%, 40%, 30%, 20%, 10%, 5%, 1% or less than a bacterially-infected subject or a healthy subject reference value.

In other embodiments the invention includes a method of distinguishing between a bacterial infection and a viral infection in a subject by measuring the polypeptide concentration of TRAIL and NGAL in a subject derived sample, applying a pre-determined mathematical function on the concentrations of TRAIL and NGAL to compute a score and comparing the score to a predetermined reference value. Optionally, one or more of CRP, PCT or IP10 is also measured. These additional measurements may be integrated into the score.

In other embodiments the invention includes a method of distinguishing between a bacterial infection and a viral infection in a subject by measuring the polypeptide concentration of TRAIL and MMP-8 in a subject derived sample, applying a pre-determined mathematical function on the concentrations of TRAIL and MMP-8 to compute a score and comparing the score to a predetermined reference value. Optionally, one or more of CRP, NGAL, PCT or IP10 is also measured. These additional measurements may be integrated into the score.

In other embodiments the invention includes a method of distinguishing between a bacterial infection and a viral infection in a subject by measuring the concentration of TRAIL and neopterin in a subject derived sample, applying a pre-determined mathematical function on the concentrations of TRAIL and neopterin to compute a score and comparing the score to a predetermined reference value. Optionally, one or more of CRP, NGAL, PCT or IP10 is also measured. These additional measurements may be integrated into the score.

In other embodiments the invention includes a method of distinguishing between a bacterial infection and a viral infection in a subject by measuring the polypeptide concentration of TRAIL and TRAILR3/TNFRSF10C in a subject derived sample, applying a pre-determined mathematical function on the concentrations of TRAIL and TRAILR3/TNFRSF10C to compute a score and comparing the score to a predetermined reference value. Optionally, one or more of CRP or IP10, NGAL, PCT is also measured. These additional measurements may be integrated into the score.

In another embodiment, the invention provides a method of distinguishing between a bacterial or mixed infection, and a viral infection in a subject by measuring the polypeptide concentration of TRAIL and TRAILR3/TNFRSF10C in a subject derived sample, applying a pre-determined mathematical function on the concentrations of TRAIL and TRAILR3/TNFRSF10C to compute a score and comparing the score to a predetermined reference value. Optionally, one or more of CRP, NGAL, PCT or IP10 is also measured. These additional measurements may be integrated into the score.

In other embodiments the invention includes a method of distinguishing between a bacterial infection and a viral infection in a subject by measuring the polypeptide concentration of TRAIL and TRAIL-R1/TNFRSF10A in a subject derived sample, applying a pre-determined mathematical function on the concentrations of TRAIL and TRAIL-R1/TNFRSF10A to compute a score and comparing the score to a predetermined reference value. Optionally, one or more of CRP, NGAL, PCT or IP10 is measured. These additional measurements may be integrated into the score.

In another embodiment, the invention provides a method of distinguishing between a bacterial or mixed infection, and a viral infection in a subject by measuring the polypeptide concentration of TRAIL and TRAIL-R1/TNFRSF10A in a subject derived sample, applying a pre-determined mathematical function on the concentrations of TRAIL and TRAIL-R1/TNFRSF10A to compute a score and comparing the score to a predetermined reference value. Optionally, one or more of CRP, NGAL, PCT or IP10 is also measured. These additional measurements may be integrated into the score.

In other embodiments the invention includes a method of distinguishing between a bacterial infection and a viral infection in a subject by measuring the polypeptide concentration of TRAIL and TRAILR4/TNFRSF10D in a subject derived sample, applying a pre-determined mathematical function on the concentrations of TRAIL and TRAILR4/TNFRSF10D to compute a score and comparing the score to a predetermined reference value. Optionally, one or more of CRP, NGAL, PCT or IP10 is measured. These additional measurements may be integrated into the score.

In another embodiment, the invention provides a method of distinguishing between a bacterial or mixed infection, and a viral infection in a subject by measuring the polypeptide concentration of TRAIL and TRAILR4/TNFRSF10D in a subject derived sample, applying a pre-determined mathematical function on the concentrations of TRAIL and TRAILR4/TNFRSF10D to compute a score and comparing the score to a predetermined reference value. Optionally, one or more CRP, NGAL, PCT or IP10 is also measured. These additional measurements may be integrated into the score.

In other embodiments the invention includes a method of distinguishing between a bacterial infection and a viral infection in a subject by measuring the polypeptide concentration of TRAIL and TRAIL-R2/TNFRSF10B in a subject derived sample, applying a pre-determined mathematical function on the concentrations of TRAIL and TRAIL-R2/TNFRSF10B to compute a score and comparing the score to a predetermined reference value. Optionally, one or more of CRP, NGAL, PCT or IP10 is also measured. These additional measurements may be integrated into the score.

In another embodiment, the invention provides a method of distinguishing between a bacterial or mixed infection, and a viral infection in a subject by measuring the polypeptide concentration of TRAIL and TRAIL-R2/TNFRSF10B in a subject derived sample, applying a pre-determined mathematical function on the concentrations of TRAIL and TRAIL-R2/TNFRSF10B to compute a score and comparing the score to a predetermined reference value. Optionally, one or more CRP, NGAL, PCT or IP10 is also measured. These additional measurements may be integrated into the score.

In another embodiment, the invention provides a method of distinguishing between a bacterial or mixed infection, and a viral infection in a subject by measuring the polypeptide concentration of TRAIL, IP10, CRP and at least one of neopterin, MMP8 or NGAL in a subject derived sample, applying a pre-determined mathematical function on the concentrations of each to compute a score and comparing the score to a predetermined reference value. Further information on generating pre-determined mathematical functions in general and for CRP, IP10 and TRAIL in particular are provided in International Patent Application IL2015/050823, the contents of which are incorporated herein by reference.

A reference value can be relative to a number or value derived from population studies, including without limitation, such subjects having the same infection, subject having the same or similar age range, subjects in the same or similar ethnic group, or relative to the starting sample of a subject undergoing treatment for an infection. Such reference values can be derived from statistical analyses and/or risk prediction data of populations obtained from mathematical algorithms and computed indices of infection. Reference determinant indices can also be constructed and used using algorithms and other methods of statistical and structural classification.

In one embodiment of the present invention, the reference value is the amount (i.e. level) of determinants in a control sample derived from one or more subjects who do not have an infection (i.e., healthy, and or non-infectious individuals). In a further embodiment, such subjects are monitored and/or periodically retested for a diagnostically relevant period of time ("longitudinal studies") following such test to verify continued absence of infection. Such period of time may be one day, two days, two to five days, five days, five to ten days, ten days, or ten or more days from the initial testing date for determination of the reference value. Furthermore, retrospective measurement of determinants in properly banked historical subject samples may be used in establishing these reference values, thus shortening the study time required.

A reference value can also comprise the amounts of determinants derived from subjects who show an improvement as a result of treatments and/or therapies for the infection. A reference value can also comprise the amounts of determinants derived from subjects who have confirmed infection by known techniques.

An example of a bacterially infected reference value index value is the mean or median concentrations of that determinant in a statistically significant number of subjects having been diagnosed as having a bacterial infection.

An example of a virally infected reference value is the mean or median concentrations of that determinant in a statistically significant number of subjects having been diagnosed as having a viral infection.

Exemplary bacterial and viral reference values are provided in Table 4 for each of the determinants (presented as the mean and/or the median).

In another embodiment, the reference value is an index value or a baseline value. An index value or baseline value is a composite sample of an effective amount of determinants from one or more subjects who do not have an infection. A baseline value can also comprise the amounts of determinants in a sample derived from a subject who has shown an improvement in treatments or therapies for the infection. In this embodiment, to make comparisons to the subject-derived sample, the amounts of determinants are similarly calculated and compared to the index value. Optionally, subjects identified as having an infection, are chosen to receive a therapeutic regimen to slow the progression or eliminate the infection.

Additionally, the amount of the determinant can be measured in a test sample and compared to the "normal control level," utilizing techniques such as reference limits, discrimination limits, or risk defining thresholds to define cutoff points and abnormal values. The "normal control level" means the level of one or more determinants or combined determinant indices typically found in a subject not suffering from an infection. Such normal control level and cutoff points may vary based on whether a determinant is used alone or in a formula combining with other determinants into an index. Alternatively, the normal control level can be a database of determinant patterns from previously tested subjects.

The effectiveness of a treatment regimen can be monitored by detecting a determinant in an effective amount (which may be one or more) of samples obtained from a subject over time and comparing the amount of determinants detected. For example, a first sample can be obtained prior to the subject receiving treatment and one or more subsequent samples are taken after or during treatment of the subject.

For example, the methods of the invention can be used to discriminate between bacterial, viral and mixed infections (i.e. bacterial and viral co-infections.) This will allow patients to be stratified and treated accordingly.

In a specific embodiment of the invention a treatment recommendation (i.e., selecting a treatment regimen) for a subject is provided by identifying the type infection (i.e., bacterial, viral, mixed infection or no infection) in the subject according to the method of any of the disclosed methods and recommending that the subject receive an antibiotic treatment if the subject is identified as having bacterial infection or a mixed infection; or an anti-viral treatment is if the subject is identified as having a viral infection.

In another embodiment, the methods of the invention can be used to prompt additional targeted diagnosis such as pathogen specific PCRs, chest-X-ray, cultures etc. For example, a diagnosis that indicates a viral infection according to embodiments of this invention, may prompt the usage of additional viral specific multiplex-PCRs, whereas a diagnosis that indicates a bacterial infection according to embodiments of this invention may prompt the usage of a bacterial specific multiplex-PCR. Thus, one can reduce the costs of unwarranted expensive diagnostics.

In a specific embodiment, a diagnostic test recommendation for a subject is provided by identifying the infection type (i.e., bacterial, viral, mixed infection or no infection) in the subject according to any of the disclosed methods and recommending a test to determine the source of the bacterial infection if the subject is identified as having a bacterial infection or a mixed infection; or a test to determine the source of the viral infection if the subject is identified as having a viral infection.

Some aspects of the present invention also comprise a kit with a detection reagent that binds to one or more determinant. Also provided by the invention is an array of detection reagents, e.g., antibodies that can bind to one or more determinants. In one embodiment, the kit contains antibodies that bind at least one determinant which appears in Table 1 and at least one polypeptide which appears in Table 2. In another embodiment, the kit contains antibodies that bind at least two determinants which appears in Table 1.

According to an exemplary embodiment, the kit (or array) does not detect more than 2 determinants, does not detect more than 3 determinants, does not detect more than 4 determinants, does not detect more than 5 determinants.

Thus, the kit may comprise antibodies which specifically recognize two different determinants, three different determinants, four different determinants, five different determinants, six different determinants, seven different determinants, eight different determinants, nine different determinants or ten or more different determinants. Preferably, the kit does not contain antibodies which recognize more than 20 different determinants, 30 different determinants, 40 different determinants, 50 different determinants, 100 different determinants or 200 different determinants.

Preferably, the concentration of the determinants is measured within about 24 hours after sample is obtained. Alternatively, the concentration of the polypeptide-determinant is measured in a sample that was stored at 12° C. or lower, when storage begins less than 24 hours after the sample is obtained.

In some embodiments the sample could have been stored in either room temperature, 4° C., −20° C. or −80° C. before measurement is performed.

In some embodiments the sample could have been stored for 1, 2, 3, 4, 5, 10, 12, 15, 20 or 24 hours before measurement is performed.

In some embodiments the sample may be stored for less than 5 minutes, 10 minutes, 20 minutes, 30 minutes, 45 minutes or 60 minutes before measurement is performed.

In some embodiments the sample is collected in a serum separator tube (SST). Following collection, the sample may be left at room temperature for at least 5, 10, 12, 15, 20, 25 30 minutes to allow blood clotting and then centrifuged for about 5-30 minutes (e.g. at least 5, 10, 12, 15, 20, 25, or 30 minutes) at 1200×g or at about 3000 RPM.

According to a specific embodiment, the kit comprises antibodies for detection of CRP and TRAILR3/TNFRSF10C, CRP and TRAILR4/TNFRSF10D, CRP and TRAIL-R1/TNFRSF10A, CRP and TRAIL-R2/TNFRSF10B, CRP and NGAL, CRP and neopterin or CRP and MMP8.

According to a specific embodiment, the kit comprises antibodies for detection of TRAIL and TRAILR3/TNFRSF10C, TRAIL and TRAILR4/TNFRSF10D, TRAIL and TRAIL-R1/TNFRSF10A, TRAIL and TRAIL-R2/TNFRSF10B, TRAIL and NGAL, TRAIL and neopterin or TRAIL and MMP8.

According to a specific embodiment, the kit comprises antibodies for detection of IP10 and TRAILR3/TNFRSF10C, IP10 and TRAILR4/TNFRSF10D, IP10 and TRAIL-R1/TNFRSF10A, IP10 and TRAIL-R2/TNFRSF10B, IP10 and neopterin, IP10 and NGAL or IP10 and MMP8.

According to a specific embodiment, the kit comprises antibodies for detection of IL1-Ra and TRAILR3/TNFRSF10C, IL1-Ra and TRAILR4/TNFRSF10D, IL1-Ra and TRAIL-R1/TNFRSF10A, IL1-Ra and TRAIL-R2/TNFRSF10B, IL1-Ra and neopterin, IL1Ra and NGAL or IL1Ra and MMP8.

According to a specific embodiment, the kit comprises antibodies for detection of PCT and TRAILR3/TNFRSF10C, PCT and TRAILR4/TNFRSF10D, PCT and TRAIL-R1/TNFRSF10A, PCT and TRAIL-R2/TNFRSF10B, PCT and neopterin, PCT and NGAL or PCT and MMP8.

According to a specific embodiment, the kit comprises antibodies for detection of sTREM and TRAILR3/TNFRSF10C, sTREM and TRAILR4/TNFRSF10D, sTREM and TRAIL-R1/TNFRSF10A, sTREM and TRAIL-R2/TNFRSF10B, sTREM and neopterin, sTREM and NGAL or sTREM and MMP8.

According to a specific embodiment, the kit comprises antibodies for detection of RSAD2 and TRAILR3/TNFRSF10C, RSAD2 and TRAILR4/TNFRSF10D, RSAD2 and TRAIL-R1/TNFRSF10A, RSAD2 and TRAIL-R2/TNFRSF10B, RSAD2 and neopterin, RSAD2 and NGAL or RSAD2 and MMP8.

According to a specific embodiment, the kit comprises antibodies for detection of MX1 and TRAILR3/TNFRSF10C, MX1 and TRAILR4/TNFRSF10D, MX1 and TRAIL-R1/TNFRSF10A, MX1 and TRAIL-R2/TNFRSF10B, MX1 and neopterin, MX1 and NGAL or MX1 and MMP8.

According to a specific embodiment, the kit comprises antibodies for detection of TRAIL and MX1; TRAIL and RSAD2; TRAIL and sTREM; and TRAIL and IL1-Ra.

According to a specific embodiment, the kit comprises antibodies for detection of TRAIL, CRP and TRAILR3/TNFRSF10C; TRAIL, CRP and TRAILR4/TNFRSF10D; TRAIL, CRP and TRAIL-R1/TNFRSF10A; TRAIL, CRP and TRAIL-R2/TNFRSF10B, TRAIL, CRP and neopterin; TRAIL, CRP and NGAL; or TRAIL, CRP and MMP8.

According to a specific embodiment, the kit comprises antibodies for detection of TRAIL, IP10 and TRAILR3/TNFRSF10C; TRAIL, IP10 and TRAILR4/TNFRSF10D; TRAIL, IP10 and TRAIL-R1/TNFRSF10A; TRAIL, IP10 and TRAIL-R2/TNFRSF10B; TRAIL, IP10 and neopterin; TRAIL, IP10 and NGAL; or TRAIL, IP10 and MMP8.

According to a specific embodiment, the kit comprises antibodies for detection of CRP, IP10 and TRAILR3/TNFRSF10C, CRP, IP10 and with TRAILR4/TNFRSF10D; CRP, IP10 and TRAIL-R1/TNFRSF10A; CRP, IP10 and TRAIL-R2/TNFRSF10B; CRP, IP10 and neopterin: CRP, IP10 and NGAL; or CRP, IP10 and MMP8.

According to a specific embodiment, the kit comprises antibodies for detection of TRAIL, CRP, IP10 and TRAILR3/TNFRSF10C; TRAIL, CRP, IP10 and TRAILR4/TNFRSF10D; TRAIL, CRP, IP10 and TRAIL-R1/TNFRSF10A; TRAIL, CRP, IP10 and TRAIL-R2/TNFRSF10B; TRAIL, CRP, IP10 and neopterin; TRAIL, CRP, IP10 and NGAL; or TRAIL, CRP, IP10 and MMP8.

According to a specific embodiment, the kit comprises antibodies for detection of CRP and NGAL, CRP and a1-Acid Glycoprotein/ORM1, CRP and IL18, CRP and CXCL6, CRP and MBL, CRP and OSM/Oncostatin M, CRP and TNFSF14 or CRP and CD14.

According to a specific embodiment, the kit comprises antibodies for detection of TRAIL and NGAL, TRAIL and a1-Acid Glycoprotein/ORM1, TRAIL and IL18, TRAIL and CXCL6, TRAIL and MBL, TRAIL and OSM/Oncostatin M, TRAIL and TNFSF14 or TRAIL and CD14.

According to a specific embodiment, the kit comprises antibodies for detection of IP10 and NGAL, IP10 and a1-Acid Glycoprotein/ORM1, IP10 and IL18, IP10 and CXCL6, IP10 and MBL, IP10 and OSM/Oncostatin M, IP10 and TNFSF14 or IP10 and CD14.

According to a specific embodiment, the kit comprises antibodies for detection of IL1-Ra and NGAL, IL1-Ra and a1-Acid Glycoprotein/ORM1, IL1-Ra and IL18, IL1-Ra and CXCL6, IL1-Ra and MBL, IL1-Ra and OSM/Oncostatin M, IL1-Ra and TNFSF14 or IL1-Ra and CD14.

According to a specific embodiment, the kit comprises antibodies for detection of PCT and NGAL, PCT and a1-Acid Glycoprotein/ORM1, PCT and IL18, PCT and CXCL6, PCT and MBL, PCT and OSM/Oncostatin M, PCT and TNFSF14 or PCT and CD14.

According to a specific embodiment, the kit comprises antibodies for detection of sTREM and NGAL, sTREM and a1-Acid Glycoprotein/ORM1, sTREM and IL18, sTREM and CXCL6, sTREM and MBL, sTREM and OSM/Oncostatin M, sTREM and TNFSF14 or sTREM and CD14.

According to a specific embodiment, the kit comprises antibodies for detection of RSAD2 and NGAL, RSAD2 and a1-Acid Glycoprotein/ORM1, RSAD2 and IL18, RSAD2 and CXCL6, RSAD2 and MBL, RSAD2 and OSM/Oncostatin M, RSAD2 and TNFSF14 or RSAD2 and CD14.

According to a specific embodiment, the kit comprises antibodies for detection of MX1 and NGAL, MX1 and a1-Acid Glycoprotein/ORM1, MX1 and IL18, MX1 and CXCL6, MX1 and MBL, MX1 and OSM/Oncostatin M, MX1 and TNFSF14 or MX1 and CD14.

According to a specific embodiment, the kit comprises antibodies for detection of TRAIL, CRP and NGAL; TRAIL, CRP and a1-Acid Glycoprotein/ORM1; TRAIL, CRP or IL18; TRAIL, CRP or CXCL6; TRAIL, CRP or MBL; TRAIL, CRP or OSM/Oncostatin M; TRAIL, CRP or TNFSF14, TRAIL, CRP or CD14.

According to a specific embodiment, the kit comprises antibodies for detection of TRAIL, IP10 and NGAL; TRAIL, IP10 and a1-Acid Glycoprotein/ORM1; TRAIL, IP10 and IL18; TRAIL, IP10 and CXCL6; TRAIL, IP10 and MBL; TRAIL, IP10 and OSM/Oncostatin M; TRAIL, IP10 and TNFSF14; or TRAIL, IP10 and CD14.

According to a specific embodiment, the kit comprises antibodies for detection of CRP, IP10 and NGAL, CRP, IP10 and with a1-Acid Glycoprotein/ORM1; CRP, IP10 and IL18; CRP, IP10 and CXCL6; CRP, IP10 and MBL; CRP, IP10 and OSM/Oncostatin M; CRP, IP10 and TNFSF14 or CRP, IP10 and CD14.

According to a specific embodiment, the kit comprises antibodies for detection of TRAIL, CRP, IP10 and NGAL; TRAIL, CRP, IP10 and a1-Acid Glycoprotein/ORM1; TRAIL, CRP, IP10 and IL18; TRAIL, CRP, IP10 and CXCL6; TRAIL, CRP, IP10 and MBL; TRAIL, CRP, IP10 and OSM/Oncostatin M; TRAIL, CRP, IP10 and TNFSF14; or TRAIL, CRP, IP10 and CD14.

In other embodiments, the kit comprises antibodies for detection of at least two polypeptide determinants which are set forth in Table 2.

According to a particular embodiment, at least one of the antibodies in the kit recognizes TRAILR3/TNFRSF10C.

According to a particular embodiment, at least one of the antibodies in the kit recognizes TRAILR4/TNFRSF10D.

According to a particular embodiment, at least one of the antibodies in the kit recognizes TRAIL-R1/TNFRSF10A.

According to a particular embodiment, at least one of the antibodies in the kit recognizes TRAIL-R2/TNFRSF10B.

According to a particular embodiment, at least one of the antibodies in the kit recognizes TRAILR3/TNFRSF10C, TRAILR4/TNFRSF10D, TRAIL-R1/TNFRSF10A, TRAIL-R2/TNFRSF10B or TRAIL (membrane form).

According to a particular embodiment, at least one of the antibodies in the kit recognizes neopterin.

According to a particular embodiment, at least one of the antibodies in the kit recognizes MMP8.

According to a particular embodiment, at least one of the antibodies in the kit recognizes NGAL.

Some aspects of the present invention can also be used to screen patient or subject populations in any number of settings. For example, a health maintenance organization, public health entity or school health program can screen a group of subjects to identify those requiring interventions, as described above, or for the collection of epidemiological data. Insurance companies (e.g., health, life or disability) may screen applicants in the process of determining coverage or pricing, or existing clients for possible intervention. Data collected in such population screens, particularly when tied to any clinical progression to conditions like infection, will be of value in the operations of, for example, health maintenance organizations, public health programs and insurance companies. Such data arrays or collections can be stored in machine-readable media and used in any number of health-related data management systems to provide improved healthcare services, cost effective healthcare, improved insurance operation, etc. See, for example, U.S. Patent Application No. 2002/0038227; U.S. Patent Application No. US 2004/0122296; U.S. Patent Application No. US 2004/0122297; and U.S. Pat. No. 5,018,067. Such systems can access the data directly from internal data storage or remotely from one or more data storage sites as further detailed herein.

A machine-readable storage medium can comprise a data storage material encoded with machine readable data or data arrays which, when using a machine programmed with instructions for using the data, is capable of use for a variety of purposes. Measurements of effective amounts of the biomarkers of the invention and/or the resulting evaluation of risk from those biomarkers can be implemented in computer programs executing on programmable computers, comprising, inter alia, a processor, a data storage system (including volatile and non-volatile memory and/or storage elements), at least one input device, and at least one output device. Program code can be applied to input data to perform the functions described above and generate output information. The output information can be applied to one or more output devices, according to methods known in the art. The computer may be, for example, a personal computer, microcomputer, or workstation of conventional design.

Each program can be implemented in a high level procedural or object oriented programming language to communicate with a computer system. However, the programs can be implemented in assembly or machine language, if desired. The language can be a compiled or interpreted language. Each such computer program can be stored on a storage media or device (e.g., ROM or magnetic diskette or others as defined elsewhere in this disclosure) readable by a general or special purpose programmable computer, for configuring and operating the computer when the storage media or device is read by the computer to perform the procedures described herein. The health-related data management system used in some aspects of the invention may also be considered to be implemented as a computer-readable storage medium, configured with a computer program, where the storage medium so configured causes a computer to operate in a specific and predefined manner to perform various functions described herein.

The determinants of the present invention, in some embodiments thereof, can be used to generate a "reference determinant profile" of those subjects who do not have an infection. The determinants disclosed herein can also be used to generate a "subject determinant profile" taken from subjects who have an infection. The subject determinant profiles can be compared to a reference determinant profile to diagnose or identify subjects with an infection. The subject determinant profile of different infection types can be compared to diagnose or identify the type of infection. The reference and subject determinant profiles of the present invention, in some embodiments thereof, can be contained in a machine-readable medium, such as but not limited to, analog tapes like those readable by a VCR, CD-ROM, DVD-ROM, USB flash media, among others. Such machine-readable media can also contain additional test results, such as, without limitation, measurements of clinical parameters and traditional laboratory risk factors. Alternatively or additionally, the machine-readable media can also comprise subject information such as medical history and any relevant family history. The machine-readable media can also contain information relating to other disease-risk algorithms and computed indices such as those described herein.

Performance and Accuracy Measures of the Invention.

The performance and thus absolute and relative clinical usefulness of the invention may be assessed in multiple ways as noted above. Amongst the various assessments of performance, some aspects of the invention are intended to provide accuracy in clinical diagnosis and prognosis. The accuracy of a diagnostic or prognostic test, assay, or method concerns the ability of the test, assay, or method to distinguish between subjects having an infection is based on whether the subjects have, a "significant alteration" (e.g., clinically significant and diagnostically significant) in the levels of a determinant. By "effective amount" it is meant that the measurement of an appropriate number of determinants (which may be one or more) to produce a "significant alteration" (e.g. level of expression or activity of a determinant) that is different than the predetermined cut-off point (or threshold value) for that determinant(s) and therefore indicates that the subject has an infection for which the determinant(s) is a determinant. The difference in the level of determinant is preferably statistically significant. As noted below, and without any limitation of the invention, achieving statistical significance, and thus the preferred analytical, diagnostic, and clinical accuracy, may require that combinations of several determinants be used together in panels and combined with mathematical algorithms in order to achieve a statistically significant determinant index.

In the categorical diagnosis of a disease state, changing the cut point or threshold value of a test (or assay) usually changes the sensitivity and specificity, but in a qualitatively inverse relationship. Therefore, in assessing the accuracy and usefulness of a proposed medical test, assay, or method for assessing a subject's condition, one should always take both sensitivity and specificity into account and be mindful of what the cut point is at which the sensitivity and specificity are being reported because sensitivity and specificity may vary significantly over the range of cut points. One way to achieve this is by using the MCC metric, which depends upon both sensitivity and specificity. Use of statistics such as AUC, encompassing all potential cut point values, is preferred for most categorical risk measures when using some aspects of the invention, while for continuous risk measures, statistics of goodness-of-fit and calibration to observed results or other gold standards, are preferred.

By predetermined level of predictability it is meant that the method provides an acceptable level of clinical or diagnostic accuracy. Using such statistics, an "acceptable degree of diagnostic accuracy", is herein defined as a test or assay (such as the test used in some aspects of the invention for determining the clinically significant presence of determinants, which thereby indicates the presence an infection type) in which the AUC (area under the ROC curve for the test or assay) is at least 0.60, desirably at least 0.65, more desirably at least 0.70, preferably at least 0.75, more preferably at least 0.80, and most preferably at least 0.85.

By a "very high degree of diagnostic accuracy", it is meant a test or assay in which the AUC (area under the ROC curve for the test or assay) is at least 0.75, 0.80, desirably at least 0.85, more desirably at least 0.875, preferably at least 0.90, more preferably at least 0.925, and most preferably at least 0.95.

Alternatively, the methods predict the presence or absence of an infection or response to therapy with at least 75% total accuracy, more preferably 80%, 85%, 90%, 95%, 97%, 98%, 99% or greater total accuracy.

Alternatively, the methods predict the presence of a bacterial infection or response to therapy with at least 75% sensitivity, more preferably 80%, 85%, 90%, 95%, 97%, 98%, 99% or greater sensitivity.

Alternatively, the methods predict the presence of a viral infection or response to therapy with at least 75% specificity, more preferably 80%, 85%, 90%, 95%, 97%, 98%, 99% or greater specificity. Alternatively, the methods predict the presence or absence of an infection or response to therapy with an MCC larger than 0.2, 0.3, 0.4, 0.5, 0.6, 0.7, 0.8, 0.9 or 1.0.

The predictive value of any test depends on the sensitivity and specificity of the test, and on the prevalence of the condition in the population being tested. This notion, based on Bayes' theorem, provides that the greater the likelihood that the condition being screened for is present in an individual or in the population (pre-test probability), the greater the validity of a positive test and the greater the likelihood that the result is a true positive. Thus, the problem with using a test in any population where there is a low likelihood of the condition being present is that a positive result has limited value (i.e., more likely to be a false positive). Similarly, in populations at very high risk, a negative test result is more likely to be a false negative.

As a result, ROC and AUC can be misleading as to the clinical utility of a test in low disease prevalence tested populations (defined as those with less than 1% rate of occurrences (incidence) per annum, or less than 10% cumulative prevalence over a specified time horizon).

A health economic utility function is an yet another means of measuring the performance and clinical value of a given test, consisting of weighting the potential categorical test outcomes based on actual measures of clinical and economic value for each. Health economic performance is closely related to accuracy, as a health economic utility function specifically assigns an economic value for the benefits of correct classification and the costs of misclassification of tested subjects. As a performance measure, it is not unusual to require a test to achieve a level of performance which results in an increase in health economic value per test (prior to testing costs) in excess of the target price of the test.

In general, alternative methods of determining diagnostic accuracy are commonly used for continuous measures, when a disease category has not yet been clearly defined by the relevant medical societies and practice of medicine, where thresholds for therapeutic use are not yet established, or where there is no existing gold standard for diagnosis of the pre-disease. For continuous measures of risk, measures of diagnostic accuracy for a calculated index are typically based on curve fit and calibration between the predicted continuous value and the actual observed values (or a historical index calculated value) and utilize measures such as R squared, Hosmer-Lemeshow P-value statistics and confidence intervals. It is not unusual for predicted values using such algorithms to be reported including a confidence interval (usually 90% or 95% CI) based on a historical observed cohort's predictions, as in the test for risk of future breast cancer recurrence commercialized by Genomic Health, Inc. (Redwood City, California).

In general, by defining the degree of diagnostic accuracy, i.e., cut points on a ROC curve, defining an acceptable AUC value, and determining the acceptable ranges in relative concentration of what constitutes an effective amount of the determinants of the invention allows for one of skill in the art to use the determinants to identify, diagnose, or prognose subjects with a pre-determined level of predictability and performance.

Furthermore, other unlisted biomarkers will be very highly correlated with the determinants (for the purpose of this application, any two variables will be considered to be "very highly correlated" when they have a Coefficient of Determination ($R^2$) of 0.5 or greater). Some aspects of the present invention encompass such functional and statistical equivalents to the aforementioned determinants. Furthermore, the statistical utility of such additional determinants is substantially dependent on the cross-correlation between multiple biomarkers and any new biomarkers will often be required to operate within a panel in order to elaborate the meaning of the underlying biology.

One or more of the listed determinants can be detected in the practice of the present invention, in some embodiments thereof. For example, two (2), three (3), four (4), five (5), ten (10), fifteen (15), twenty (20), forty (40), or more determinants can be detected.

In some aspects, all determinants listed herein can be detected. Preferred ranges from which the number of determinants can be detected include ranges bounded by any minimum selected from between one and, particularly two, three, four, five, six, seven, eight, nine ten, twenty, or forty. Particularly preferred ranges include two to five (2-5), two to ten (2-10), two to twenty (2-20), or two to forty (2-40).

Construction of Determinant Panels

Groupings of determinants can be included in "panels", also called "determinant-signatures", "determinant signatures", or "multi-determinant signatures." A "panel" within the context of the present invention means a group of biomarkers (whether they are determinants, clinical parameters, or traditional laboratory risk factors) that includes one or more determinants. A panel can also comprise additional biomarkers, e.g., clinical parameters, traditional laboratory risk factors, known to be present or associated with infection, in combination with a selected group of the determinants listed herein.

As noted above, many of the individual determinants, clinical parameters, and traditional laboratory risk factors listed, when used alone and not as a member of a multi-biomarker panel of determinants, have little or no clinical use in reliably distinguishing individual normal subjects, subjects at risk for having an infection (e.g., bacterial, viral or co-infection), and thus cannot reliably be used alone in classifying any subject between those three states. Even where there are statistically significant differences in their mean measurements in each of these populations, as commonly occurs in studies which are sufficiently powered, such biomarkers may remain limited in their applicability to an individual subject, and contribute little to diagnostic or prognostic predictions for that subject. A common measure of statistical significance is the p-value, which indicates the probability that an observation has arisen by chance alone; preferably, such p-values are 0.05 or less, representing a 5% or less chance that the observation of interest arose by chance. Such p-values depend significantly on the power of the study performed.

Despite this individual determinant performance, and the general performance of formulas combining only the traditional clinical parameters and few traditional laboratory risk factors, the present inventors have noted that certain specific combinations of two or more determinants can also be used as multi-biomarker panels comprising combinations of determinants that are known to be involved in one or more physiological or biological pathways, and that such information can be combined and made clinically useful through the use of various formulae, including statistical classification algorithms and others, combining and in many cases extending the performance characteristics of the combination beyond that of the individual determinants. These specific combinations show an acceptable level of diagnostic accuracy, and, when sufficient information from multiple determinants is combined in a trained formula, they often reliably achieve a high level of diagnostic accuracy transportable from one population to another.

The general concept of how two less specific or lower performing determinants are combined into novel and more useful combinations for the intended indications, is a key aspect of some embodiments of the invention. Multiple biomarkers can yield better performance than the individual components when proper mathematical and clinical algorithms are used; this is often evident in both sensitivity and specificity, and results in a greater AUC or MCC. Secondly, there is often novel unperceived information in the existing biomarkers, as such was necessary in order to achieve through the new formula an improved level of sensitivity or specificity. This hidden information may hold true even for biomarkers which are generally regarded to have suboptimal clinical performance on their own. In fact, the suboptimal performance in terms of high false positive rates on a single biomarker measured alone may very well be an indicator that some important additional information is contained within the biomarker results—information which would not be elucidated absent the combination with a second biomarker and a mathematical formula.

Several statistical and modeling algorithms known in the art can be used to both assist in determinant selection choices and optimize the algorithms combining these choices. Statistical tools such as factor and cross-biomarker correlation/covariance analyses allow more rationale approaches to panel construction. Mathematical clustering and classification tree showing the Euclidean standardized distance between the determinants can be advantageously used. Pathway informed seeding of such statistical classification techniques also may be employed, as may rational approaches based on the selection of individual determinants based on their participation across in particular pathways or physiological functions.

Ultimately, formula such as statistical classification algorithms can be directly used to both select determinants and to generate and train the optimal formula necessary to combine the results from multiple determinants into a single index. Often, techniques such as forward (from zero potential explanatory parameters) and backwards selection (from all available potential explanatory parameters) are used, and information criteria, such as AIC or BIC, are used to quantify the tradeoff between the performance and diagnostic accuracy of the panel and the number of determinants used. The position of the individual determinant on a forward or backwards selected panel can be closely related to its provision of incremental information content for the algorithm, so the order of contribution is highly dependent on the other constituent determinants in the panel.

Construction of Clinical Algorithms

Any formula may be used to combine determinant results into indices useful in the practice of the invention. As indicated above, and without limitation, such indices may indicate, among the various other indications, the probability, likelihood, absolute or relative risk, time to or rate of conversion from one to another disease states, or make predictions of future biomarker measurements of infection. This may be for a specific time period or horizon, or for remaining lifetime risk, or simply be provided as an index relative to another reference subject population.

Although various preferred formula are described here, several other model and formula types beyond those mentioned herein and in the definitions above are well known to one skilled in the art. The actual model type or formula used may itself be selected from the field of potential models based on the performance and diagnostic accuracy characteristics of its results in a training population. The specifics of the formula itself may commonly be derived from determinant results in the relevant training population. Amongst other uses, such formula may be intended to map the feature space derived from one or more determinant inputs to a set of subject classes (e.g. useful in predicting class membership of subjects as normal, having an infection), to derive an estimation of a probability function of risk using a Bayesian approach, or to estimate the class-conditional probabilities, then use Bayes' rule to produce the class probability function as in the previous case.

Preferred formulas include the broad class of statistical classification algorithms, and in particular the use of discriminant analysis. The goal of discriminant analysis is to predict class membership from a previously identified set of features. In the case of linear discriminant analysis (LDA), the linear combination of features is identified that maximizes the separation among groups by some criteria. Features can be identified for LDA using an eigengene based approach with different thresholds (ELDA) or a stepping algorithm based on a multivariate analysis of variance (MANOVA). Forward, backward, and stepwise algorithms can be performed that minimize the probability of no separation based on the Hotelling-Lawley statistic.

Eigengene-based Linear Discriminant Analysis (ELDA) is a feature selection technique developed by Shen et al. (2006). The formula selects features (e.g. biomarkers) in a multivariate framework using a modified eigen analysis to identify features associated with the most important eigenvectors. "Important" is defined as those eigenvectors that explain the most variance in the differences among samples that are trying to be classified relative to some threshold.

A support vector machine (SVM) is a classification formula that attempts to find a hyperplane that separates two classes. This hyperplane contains support vectors, data points that are exactly the margin distance away from the hyperplane. In the likely event that no separating hyperplane exists in the current dimensions of the data, the dimensionality is expanded greatly by projecting the data into larger dimensions by taking non-linear functions of the original variables (Venables and Ripley, 2002). Although not required, filtering of features for SVM often improves prediction. Features (e.g., biomarkers) can be identified for a support vector machine using a non-parametric Kruskal-Wallis (KW) test to select the best univariate features. A random forest (RF, Breiman, 2001) or recursive partitioning (RPART, Breiman et al., 1984) can also be used separately or in combination to identify biomarker combinations that are most important. Both KW and RF require that a number of features be selected from the total. RPART creates a single classification tree using a subset of available biomarkers.

Other formula may be used in order to pre-process the results of individual determinant measurements into more valuable forms of information, prior to their presentation to the predictive formula. Most notably, normalization of biomarker results, using either common mathematical transformations such as logarithmic or logistic functions, as normal or other distribution positions, in reference to a population's mean values, etc. are all well known to those skilled in the art. Of particular interest are a set of normalizations based on clinical-determinants such as time from symptoms, gender, race, or sex, where specific formula are used solely on subjects within a class or continuously combining a clinical-determinants as an input. In other cases, analyte-based biomarkers can be combined into calculated variables which are subsequently presented to a formula.

In addition to the individual parameter values of one subject potentially being normalized, an overall predictive formula for all subjects, or any known class of subjects, may itself be recalibrated or otherwise adjusted based on adjustment for a population's expected prevalence and mean biomarker parameter values, according to the technique outlined in D'Agostino et al., (2001) JAMA 286:180-187, or other similar normalization and recalibration techniques. Such epidemiological adjustment statistics may be captured, confirmed, improved and updated continuously through a registry of past data presented to the model, which may be machine readable or otherwise, or occasionally through the retrospective query of stored samples or reference to historical studies of such parameters and statistics. Additional examples that may be the subject of formula recalibration or other adjustments include statistics used in studies by Pepe, M. S. et al., 2004 on the limitations of odds ratios; Cook, N. R., 2007 relating to ROC curves. Finally, the numeric result of a classifier formula itself may be transformed post-processing by its reference to an actual clinical population and study results and observed endpoints, in order to calibrate to absolute risk and provide confidence intervals for varying numeric results of the classifier or risk formula.

Some determinants may exhibit trends that depends on the patient age (e.g. the population baseline may rise or fall as a function of age). One can use a 'Age dependent normalization or stratification' scheme to adjust for age related differences. Performing age dependent normalization, stratification or distinct mathematical formulas can be used to improve the accuracy of determinants for differentiating between different types of infections. For example, one skilled in the art can generate a function that fits the population mean levels of each determinant as function of age and use it to normalize the determinant of individual subjects levels across different ages. Another example is to stratify subjects according to their age and determine age specific thresholds or index values for each age group independently.

According to a particular embodiment, the set of normalizations, stratification or distinct mathematical formulas are based on age. As shown in FIGS. 8A-8C, particular determinants show an age dependent level of expression which further relate to infection type. These include neopterin, NGAL and osteopontin. Other determinants which show an age dependent level of expression during infection type are set forth in Table 5 herein below. Thus, the present invention contemplates different determinant thresholds depending on the age of the subject.

In one embodiment, there are different thresholds, normalizations or stratification if the subject is an adult (e.g. older than 18, 21, or 22 years) another if the subject is a child (e.g. younger than 18, 21 or 22 years).

In another embodiment, there are different thresholds, normalizations or stratification if the subject is an adult (e.g. older than 18, 21, or 22 years) another if the subject is an adolescent between 12 and 21 years, another if the subject is a child (between 2 and 12 years), another if the subject is an infant 29 days to less than 2 years of age, another if the subject is neonates (birth through the first 28 days of life).

In other embodiments, there are different thresholds, normalizations or stratification for a subject who is older than 70, 65, 60, 55, 50, 40, 30, 22, 21, 18, 12, 2, 1 year or older than 3, 2 and/or 1 month.

In other embodiments, there are different thresholds, normalizations or stratification for a subject who is younger than 70, 65, 60, 55, 50, 40, 30, 22, 21, 18, 12, 2, 1 year or older than 3, 2 and/or 1 month.

In specific embodiments the invention includes ruling out a bacterial infection in an adult subject if the polypeptide concentration of NGAL is lower than about 150, 140, 125, 100, 75, 50, 25 or even 10 ng/ml. Optionally, the method further includes ruling in a viral infection in the adult subject if the polypeptide concentration of NGAL is lower than 100, 90, 75, 50, 25 or even 10 ng/ml.

The invention may also include ruling out a viral infection in an adult subject if the polypeptide concentration of NGAL is higher than about 90, 100, 125, 150 or even 200 ng/ml. Optionally, the method further ruling in a bacterial infection in the adult subject if the polypeptide concentration of NGAL is higher than 125, 150, 175, 200, 250, 300, 400 or even 500 ng/ml.

In specific embodiments the invention includes ruling out a bacterial infection in an adolescent subject if the polypeptide concentration of NGAL is lower than about 150, 140, 125, 100, 75, 50, 25 or even 10 ng/ml. Optionally, the method further includes ruling in a viral infection in the adolescent subject if the polypeptide concentration of NGAL is lower than 100, 90, 75, 50, 25 or even 10 ng/ml.

The invention may also include ruling out a viral infection in an adolescent subject if the polypeptide concentration of NGAL is higher than about 90, 100, 125, 150 or even 200 ng/ml. Optionally, the method further ruling in a bacterial infection in the adolescent subject if the polypeptide concentration of NGAL is higher than 125, 150, 175, 200, 250, 300, 400 or even 500 ng/ml.

In specific embodiments the invention includes ruling out a bacterial infection in a child subject if the polypeptide concentration of NGAL is lower than about 150, 140, 125, 100, 75, 50, 25 or even 10 ng/ml. Optionally, the method further includes ruling in a viral infection in the child subject if the polypeptide concentration of NGAL is lower than 100, 90, 75, 50, 25 or even 10 ng/ml.

The invention may also include ruling out a viral infection in an child subject if the polypeptide concentration of NGAL is higher than about 90, 100, 125, 150 or even 200 ng/ml. Optionally, the method further ruling in a bacterial infection in the child subject if the polypeptide concentration of NGAL is higher than 125, 150, 175, 200, 250, 300, 400 or even 500 ng/ml.

In specific embodiments the invention includes ruling out a bacterial infection in an infant subject if the polypeptide concentration of NGAL is lower than about 150, 140, 125, 100, 75, 50, 25 or even 10 ng/ml. Optionally, the method further includes ruling in a viral infection in the infant subject if the polypeptide concentration of NGAL is lower than 100, 90, 75, 50, 25 or even 10 ng/ml.

The invention may also include ruling out a viral infection in an infant subject if the polypeptide concentration of NGAL is higher than about 90, 100, 125, 150 or even 200 ng/ml. Optionally, the method further ruling in a bacterial infection in the infant subject if the polypeptide concentration of NGAL is higher than 125, 150, 175, 200, 250, 300, 400 or even 500 ng/ml.

In specific embodiments the invention includes ruling out a bacterial infection in an adult subject if the concentration of Neopterin is higher than about 4, 5, 6, 7, 8, 10, 15, 20, 50, or even 100 pg/ml. Optionally, the method further includes ruling in a viral infection in the adult subject if the concentration of Neopterin is higher than about 4, 5, 6, 7, 8, 10, 15, 20, 50, or even 100 pg/ml.

The invention may also include ruling out a viral infection in an adult subject if the concentration of Neopterin is lower than about 7, 6, 5, 4, 3, 2 or even 1 pg/ml. Optionally, the method further ruling in a bacterial infection in the adult subject if the concentration of Neopterin is lower than about 7, 6, 5, 4, 3, 2 or even 1 pg/ml.

In specific embodiments the invention includes ruling out a bacterial infection in an adolescent subject if the concentration of Neopterin is higher than about 4, 5, 6, 7, 8, 10, 15, 20, 50, or even 100 pg/ml. Optionally, the method further includes ruling in a viral infection in the adolescent subject if the concentration of Neopterin is higher than about 4, 5, 6, 7, 8, 10, 15, 20, 50, or even 100 pg/ml.

The invention may also include ruling out a viral infection in an adolescent subject if the concentration of Neopterin is lower than about 7, 6, 5, 4, 3, 2 or even 1 pg/ml. Optionally, the method further ruling in a bacterial infection in the adolescent subject if the concentration of Neopterin is lower than about 7, 6, 5, 4, 3, 2 or even 1 pg/ml.

In specific embodiments the invention includes ruling out a bacterial infection in a child subject if the concentration of Neopterin is higher than about 4, 5, 6, 7, 8, 10, 15, 20, 50, or even 100 pg/ml. Optionally, the method further includes ruling in a viral infection in the child subject if the concentration of Neopterin is higher than about 4, 5, 6, 7, 8, 10, 15, 20, 50, or even 100 pg/ml.

The invention may also include ruling out a viral infection in a child subject if the concentration of Neopterin is lower than about 7, 6, 5, 4, 3, 2 or even 1 pg/ml.

Optionally, the method further ruling in a bacterial infection in the child subject if the concentration of Neopterin is lower than about 7, 6, 5, 4, 3, 2 or even 1 pg/ml.

In specific embodiments the invention includes ruling out a bacterial infection in an infant subject if the concentration of Neopterin is higher than about 4, 5, 6, 7, 8, 10, 15, 20, 50, or even 100 pg/ml. Optionally, the method further includes ruling in a viral infection in the infant subject if the concentration of Neopterin is higher than about 4, 5, 6, 7, 8, 10, 15, 20, 50, or even 100 pg/ml.

The invention may also include ruling out a viral infection in an infant subject if the concentration of Neopterin is lower than about 7, 6, 5, 4, 3, 2 or even 1 pg/ml. Optionally, the method further ruling in a bacterial infection in the infant subject if the concentration of Neopterin is lower than about 7, 6, 5, 4, 3, 2 or even 1 pg/ml.

Measurement of Determinants

The actual measurement of levels or amounts of the determinants can be determined at the protein or polypeptide level using any method known in the art.

For example, by measuring the levels of polypeptide encoded by the gene products described herein, or subcellular localization or activities thereof. Such methods are well known in the art and include, e.g., immunoassays based on antibodies to proteins, aptamers or molecular imprints. Any biological material can be used for the detection/quantification of the protein or its activity. Alternatively, a suitable method can be selected to determine the activity of proteins encoded by the marker genes according to the activity of each protein analyzed.

The determinants can be detected in any suitable manner, but are typically detected by contacting a sample from the subject with an antibody, which binds the determinant and then detecting the presence or absence of a reaction product. The antibody may be monoclonal, polyclonal, chimeric, or a fragment of the foregoing, as discussed in detail above, and the step of detecting the reaction product may be carried out with any suitable immunoassay. The sample from the subject is typically a biological sample as described above, and may be the same sample of biological sample used to conduct the method described above.

In one embodiment, the antibody which specifically binds the determinant is attached (either directly or indirectly) to a signal producing label, including but not limited to a radioactive label, an enzymatic label, a hapten, a reporter dye or a fluorescent label.

Immunoassays carried out in accordance with some embodiments of the present invention may be homogeneous assays or heterogeneous assays. In a homogeneous assay the immunological reaction usually involves the specific antibody (e.g., anti-determinant antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution. Immunochemical labels, which may be employed, include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are oligonucleotides, immunoblotting, immunofluorescence methods, immuno-precipitation, chemiluminescence methods, electrochemiluminescence (ECL) or enzyme-linked immunoassays.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al., titled "Methods for Modulating Ligand-Receptor Interactions and their Application," U.S. Pat. No. 4,659,678 to Forrest et al., titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label." The determinant can also be detected with antibodies using flow cytometry. Those skilled in the art will be familiar with flow cytometric techniques which may be useful in carrying out the methods disclosed herein (Shapiro 2005). These include, without limitation, Cytokine Bead Array (Becton Dickinson) and Luminex technology.

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., $^{35}$S, $^{125}$I, $^{131}$I), enzyme labels (e.g., horseradish peroxidase, alkaline phosphatase), and fluorescent labels (e.g., fluorescein, Alexa, green fluorescent protein, rhodamine) in accordance with known techniques.

Antibodies can also be useful for detecting post-translational modifications of determinant proteins, polypeptides, mutations, and polymorphisms, such as tyrosine phosphorylation, threonine phosphorylation, serine phosphorylation, glycosylation (e.g., O-GlcNAc). Such antibodies specifically detect the phosphorylated amino acids in a protein or proteins of interest, and can be used in immunoblotting, immunofluorescence, and ELISA assays described herein. These antibodies are well-known to those skilled in the art, and commercially available. Post-translational modifications can also be determined using metastable ions in reflector matrix-assisted laser desorption ionization-time of flight mass spectrometry (MALDI-TOF) (Wirth U. and Muller D. 2002).

For determinant-proteins, polypeptides, mutations, and polymorphisms known to have enzymatic activity, the activities can be determined in vitro using enzyme assays known in the art. Such assays include, without limitation, kinase assays, phosphatase assays, reductase assays, among many others. Modulation of the kinetics of enzyme activities can be determined by measuring the rate constant $K_M$ using known algorithms, such as the Hill plot, Michaelis-Menten equation, linear regression plots such as Lineweaver-Burk analysis, and Scatchard plot.

The term "metabolite" includes any chemical or biochemical product of a metabolic process, such as any compound produced by the processing, cleavage or consumption of a biological molecule (e.g., a protein, nucleic acid, carbohydrate, or lipid). Metabolites can be detected in a variety of ways known to one of skill in the art, including the refractive index spectroscopy (RI), ultra-violet spectroscopy (UV), fluorescence analysis, radiochemical analysis, near-infrared spectroscopy (near-IR), nuclear magnetic resonance spectroscopy (NMR), light scattering analysis (LS), mass spectrometry, pyrolysis mass spectrometry, nephelometry, dispersive Raman spectroscopy, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, NMR and IR detection. In this regard, other DETERMINANT analytes can be measured using the above-mentioned detection methods, or other methods known to the skilled artisan. For example, circulating calcium ions ($Ca^{2+}$) can be detected in a sample using fluorescent dyes such as the poly-amino carboxylic acid, Fluo series, Fura-2A, Rhod-2, the ratiometric calcium indicator Indo-1, among others. Other determinant metabolites can be similarly detected using reagents that are specifically designed or tailored to detect such metabolites.

Kits

Some aspects of the invention also include a determinant-detection reagent, or antibodies packaged together in the form of a kit. The kit may contain in separate containers an antibody (either already bound to a solid matrix or packaged separately with reagents for binding them to the matrix), control formulations (positive and/or negative), and/or a detectable label such as fluorescein, green fluorescent protein, rhodamine, cyanine dyes, Alexa dyes, luciferase, radiolabels, among others. The detectable label may be attached to a secondary antibody which binds to the Fc portion of the antibody which recognizes the determinant. Instructions (e.g., written, tape, VCR, CD-ROM, etc.) for carrying out the assay may be included in the kit. The assay may for example be in the form of a sandwich ELISA as known in the art.

For example, determinant detection reagents can be immobilized on a solid matrix such as a porous strip to form at least one determinant detection site. The measurement or detection region of the porous strip may include a plurality of sites. A test strip may also contain sites for negative and/or positive controls. Alternatively, control sites can be located on a separate strip from the test strip. Optionally, the different detection sites may contain different amounts of immobilized detection reagents, e.g., a higher amount in the first detection site and lesser amounts in subsequent sites. Upon the addition of test sample, the number of sites displaying a detectable signal provides a quantitative indication of the amount of determinants present in the sample. The detection sites may be configured in any suitably detectable shape and are typically in the shape of a bar or dot spanning the width of a test strip.

Suitable sources for antibodies for the detection of determinants include commercially available sources such as, for example, Abazyme, Abnova, AssayPro, Affinity Biologicals, AntibodyShop, Aviva bioscience, Biogenesis, Biosense Laboratories, Calbiochem, Cell Sciences, Chemicon International, Chemokine, Clontech, Cytolab, DAKO, Diagnostic BioSystems, eBioscience, Endocrine Technologies, Enzo Biochem, Eurogentec, Fusion Antibodies, Genesis Biotech, GloboZymes, Haematologic Technologies, Immunodetect, Immunodiagnostik, Immunometrics, Immunostar, Immunovision, Biogenex, Invitrogen, Jackson ImmunoResearch Laboratory, KMI Diagnostics, Koma Biotech, LabFrontier Life Science Institute, Lee Laboratories, Lifescreen, Maine Biotechnology Services, Mediclone, MicroPharm Ltd., ModiQuest, Molecular Innovations, Molecular Probes, Neoclone, Neuromics, New England Biolabs, Novocastra, Novus Biologicals, Oncogene Research Products, Orbigen, Oxford Biotechnology, Panvera, PerkinElmer Life Sciences, Pharmingen, Phoenix Pharmaceuticals, Pierce Chemical Company, Polymun Scientific, Polysiences, Inc., Promega Corporation, Proteogenix, Protos Immunoresearch, QED Biosciences, Inc., R&D Systems, Repligen, Research Diagnostics, Roboscreen, Santa Cruz Biotechnology, Seikagaku America, Serological Corporation, Serotec, SigmaAldrich, StemCell Technologies, Synaptic Systems GmbH, Technopharm, Terra Nova Biotechnology, TiterMax, Trillium Diagnostics, Upstate Biotechnology, US Biological, Vector Laboratories, Wako Pure Chemical Industries, and Zeptometrix. However, the skilled artisan can routinely make antibodies, against any of the polypeptide determinants described herein.

Another Company from which antibodies may be obtained is RnD.

We note that the fraction in which the polypeptide determinants reside affects the ease by which the assay can be performed at the clinical setting. For example, in the clinical setting, especially the point-of-care, it is often easier to measure determinants that are present in the serum or plasma fraction compared to intracellular determinants within the leukocytes fraction. This is because the latter requires an additional experimental step in which leukocytes are isolated from the whole blood sample, washed and lysed.

Examples of "Monoclonal antibodies for measuring TRAIL", include without limitation: Mouse, Monoclonal (55B709-3) IgG; Mouse, Monoclonal (2E5) IgG1; Mouse, Monoclonal (2E05) IgG1; Mouse, Monoclonal (M912292) IgG1 kappa; Mouse, Monoclonal (IIIF6) IgG2b; Mouse, Monoclonal (2E1-1B9) IgG1; Mouse, Monoclonal (RIK-2) IgG1, kappa; Mouse, Monoclonal M181 IgG1; Mouse, Monoclonal VI10E IgG2b; Mouse, Monoclonal MAB375 IgG1; Mouse, Monoclonal MAB687 IgG1; Mouse, Monoclonal HS501 IgG1; Mouse, Monoclonal clone 75411.11 Mouse IgG1; Mouse, Monoclonal T8175-50 IgG; Mouse, Monoclonal 2B2.108 IgG1; Mouse, Monoclonal B-T24 IgG1; Mouse, Monoclonal 55B709.3 IgG1; Mouse, Monoclonal D3 IgG1; Goat, Monoclonal C19 IgG; Rabbit, Monoclonal H257 IgG; Mouse, Monoclonal 500-M49 IgG; Mouse, Monoclonal 05-607 IgG; Mouse, Monoclonal B-T24 IgG1; Rat, Monoclonal (N2B2), IgG2a, kappa; Mouse, Monoclonal (1A7-2B7), IgG1; Mouse, Monoclonal (55B709.3), IgG and Mouse, Monoclonal B-S23*IgG1.

Soluble TRAIL and membrane TRAIL can be distinguished by using different measuring techniques and samples. For example, Soluble TRAIL can be measured without limitation in cell free samples such as serum or plasma. Membrane TRAIL can be measured in samples that contain cells using cell based assays including without limitation flow cytometry, ELISA, and other immunoassays.

Examples of "Monoclonal antibodies for measuring CRP", include without limitation: Mouse, Monoclonal (108-2A2); Mouse, Monoclonal (108-7G41D2); Mouse, Monoclonal (12D-2C-36), IgG1; Mouse, Monoclonal (1G1), IgG1; Mouse, Monoclonal (5A9), IgG2a kappa; Mouse, Monoclonal (63F4), IgG1; Mouse, Monoclonal (67A1), IgG1; Mouse, Monoclonal (8B-5E), IgG1; Mouse, Monoclonal (B893M), IgG2b, lambda; Mouse, Monoclonal (C1), IgG2b; Mouse, Monoclonal (C11F2), IgG; Mouse, Monoclonal (C2), IgG1; Mouse, Monoclonal (C3), IgG1; Mouse, Monoclonal (C4), IgG1; Mouse, Monoclonal (C5), IgG2a; Mouse, Monoclonal (C6), IgG2a; Mouse, Monoclonal (C7), IgG1; Mouse, Monoclonal (CRP103), IgG2b; Mouse, Monoclonal (CRP11), IgG1; Mouse, Monoclonal (CRP135), IgG1; Mouse, Monoclonal (CRP169), IgG2a;

Mouse, Monoclonal (CRP30), IgG1; Mouse, Monoclonal (CRP36), IgG2a; Rabbit, Monoclonal (EPR283Y), IgG; Mouse, Monoclonal (KT39), IgG2b; Mouse, Monoclonal (N-a), IgG1; Mouse, Monoclonal (N1G1), IgG1; Monoclonal (P5A9AT); Mouse, Monoclonal (55G1), IgG1; Mouse, Monoclonal (SB78c), IgG1; Mouse, Monoclonal (SB78d), IgG1 and Rabbit, Monoclonal (Y284), IgG.

Polyclonal antibodies for measuring determinants include without limitation antibodies that were produced from sera by active immunization of one or more of the following: Rabbit, Goat, Sheep, Chicken, Duck, Guinea Pig, Mouse, Donkey, Camel, Rat and Horse.

Examples of detection agents, include without limitation: scFv, dsFv, Fab, sVH, F(ab')$_2$, Cyclic peptides, Haptamers, A single-domain antibody, Fab fragments, Single-chain variable fragments, Affibody molecules, Affilins, Nanofitins, Anticalins, Avimers, DARPins, Kunitz domains, Fynomers and Monobody.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839, 153; 3,850,752; 3,850,578; 3,853,987; 3,867,517; 3,879, 262; 3,901,654; 3,935,074; 3,984,533; 3,996,345; 4,034, 074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Identifying Host-Proteome Signatures for Distinguishing Between Acute Bacterial and Viral Infections Patients were recruited as part of a multi-center, observational, prospective clinical study with the aim to develop and test a host proteins-signature for the purpose of rapid and accurate diagnosis of patients with viral and bacterial diseases.
Methods
Patient recruitment: A total of 122 patients were recruited of whom 111 had a suspected infectious disease and 11 had a non-infectious disease (control group). Informed consent was obtained from each participant or legal guardian, as applicable. Inclusion criteria for the infectious disease cohort included: clinical suspicion of an acute infectious disease, peak fever >37.5° C. since symptoms onset, and duration of symptoms ≤12 days. Inclusion criteria for the control group included: clinical impression of a non-infectious disease (e.g. trauma, stroke and myocardial infarction), or healthy subjects. Exclusion criteria included: evidence of any episode of acute infectious disease in the two weeks preceding enrollment; diagnosed congenital immune deficiency; current treatment with immunosuppressive or immunomodulatory therapy; active malignancy, proven or suspected human immunodeficiency virus (HIV)-1, hepatitis B virus (HBV), or hepatitis C virus (HCV) infection. Importantly, in order to enable broad generalization, antibiotic treatment at enrollment did not cause exclusion from the study. An overview of study workflow is depicted in FIG. 1.

Enrollment process and data collection: For each patient, the following baseline variables were recorded: demographics, physical examination, medical history (e.g. main complaints, underlying diseases, chronically-administered medications, comorbidities, time of symptom onset, and peak temperature), complete blood count (CBC) obtained at enrollment, and chemistry panel (e.g. creatinine, urea, electrolytes, and liver enzymes). A nasal swab was obtained from each patient for further microbiological investigation, and a blood sample was obtained for protein screening and validation. Additional samples were obtained as deemed appropriate by the physician (e.g. urine and stool samples in cases of suspected urinary tract infection [UTI], and gastroenteritis [GI] respectively). Radiological tests were obtained at the discretion of the physician (e.g. chest X-ray for suspected lower respiratory tract infection [LRTI]). All information was recorded in a custom electronic case report form (eCRF).

Establishing the reference standard: Currently, no single reference standard exists for determining bacterial and viral infections in a wide range of clinical syndromes. Therefore, a rigorous reference standard was created following recommendations of the Standards for Reporting of Diagnostic Accuracy (STARD) (Bossuyt et al. 2003). First, a thorough clinical and microbiological investigation was performed for each patient as described above. Then, all the data collected throughout the disease course was reviewed by a panel of up to three physicians that assigned one of the following diagnostic labels to each patient: (i) bacterial; (ii) viral; (iii) no apparent infectious disease or healthy (controls); and (iv) indeterminate. Importantly, the panel members were blinded to the labeling of their peers to prevent group pressure or influential personality bias as recommended by NHS-HTA (Rutjes et al. 2007), and to the results of the host-proteins measurements.

Samples, procedures and sample processing: Venous blood samples were stored at 4° C. for up to 5 hours, subsequently fractionated into plasma, serum and total leukocytes, and stored at −80° C. Nasal swabs and stool samples were stored at 4° C. for up to 72 hours and subsequently transported to a certified service laboratory for multiplex PCRs. Host-determinants were measured using enzyme-linked immunosorbent-assay (ELISA).

Statistical analysis Primary analysis was based on area under the receiver operating curve (AUC), Matthews correlation coefficient (MCC), sensitivity, specificity, total accuracy, positive predictive value (PPV), and negative predictive value (NPV). These measures are defined as follows:

$$\text{Sensitivity} = \frac{TP}{TP + FN}$$

$$\text{Specificity} = \frac{TN}{TN + FP}$$

$$\text{total accuracy} = \frac{TP + TN}{TP + FN + TN + FP}$$

$$PPV = \frac{TP}{TP + FP} = \frac{\text{sensitivity} \cdot \text{prevalence}}{\text{sensitivity} \cdot \text{prevalence} + (1 - \text{specificity}) \cdot (1 - \text{prevalence})}$$

$$NPV = \frac{TN}{TN + FN} = \frac{\text{specificity} \cdot (1 - \text{prevalence})}{\text{specificity} \cdot (1 - \text{prevalence}) + (1 - \text{sensitivity}) \cdot (\text{prevalence})}$$

$$MCC = \frac{TP \times TN - FP \times FN}{\sqrt{(TP + FP)(TP + FN)(TN + FP)(TN + FN)}}$$

P, N, TP, FP, TN, FN are positives, negatives, true-positives, false-positives, true-negatives, and false-negatives, respectively. Unless mentioned otherwise, positives and negatives refer to patients with bacterial and viral infections, respectively.

Results

Patients characteristics: The studied group of pediatric patients included 62 females (51%) and 60 males (49%)

aged 3 months to 79 years. The patients presented with a variety of clinical syndromes affecting different physiological systems (e.g., respiratory, urinal, central nervous system, systemic). Detailed characterization of studied patients is depicted in FIGS. 2-6.

Single DETERMINANTS can distinguish between bacterial (or mixed) and viral patients: The expression profiles of multiple DETERMINANTS measured in serum samples obtained from the described acute infection patients were studied (FIG. 7). Based on these measurements, a classifier was developed for distinguishing between bacterial and viral patients using logistic regression. It was further calculated for these determinants the measures of accuracy in distinguishing between bacterial and viral patients including AUC, MCC, total accuracy, sensitivity, specificity and Wilcoxon ranksum P-value (Table 4).

TABLE 4

| Number | Feature #1 | AUC | MCC | Total accuracy | Sensitivity | Specificity | PPV | NPV | ranksum P-value | Mean bacterial | Mean viral | Concentration units |
|---|---|---|---|---|---|---|---|---|---|---|---|---|
| 1 | a1 Acid Glycoprotein | 0.61 | −0.31 | 0.649 | 0.71 | 0.60 | 0.60 | 0.71 | 0.046554 | 3086569.8 | 3019442.3 | ng/ml |
| 2 | Adiponectin | 0.69 | 0.32 | 0.662 | 0.74 | 0.60 | 0.61 | 0.73 | 0.010312 | 7918.4 | 13110.0 | ng/ml |
| 3 | Angiogenin | 0.58 | 0.16 | 0.581 | 0.56 | 0.60 | 0.54 | 0.62 | 0.34813 | 300216.0 | 328195.0 | pg/ml |
| 4 | Angiopoietin1 | 0.57 | 0.11 | 0.575 | 0.50 | 0.64 | 0.55 | 0.60 | 0.44214 | 110144.2 | 98354.7 | pg/ml |
| 5 | Angiopoietin2 | 0.52 | 0.03 | 0.541 | 0.65 | 0.45 | 0.50 | 0.60 | 0.72039 | 3991.3 | 3283.8 | pg/ml |
| 6 | APRIL | 0.46 | −0.05 | 0.554 | 0.56 | 0.55 | 0.51 | 0.60 | 0.23495 | 1.5 | 1.9 | ng/ml |
| 7 | BAFF | 0.57 | −0.15 | 0.575 | 0.55 | 0.60 | 0.53 | 0.62 | 0.26059 | 2365.1 | 2444.3 | pg/ml |
| 8 | BDNF | 0.52 | −0.11 | 0.63 | 0.52 | 0.73 | 0.61 | 0.64 | 0.11424 | 15035 | 15219 | pg/ml |
| 9 | CD 23 | 0.52 | −0.16 | 0.622 | 0.56 | 0.68 | 0.59 | 0.64 | 0.34258 | 4645.3 | 4795.3 | pg/ml |
| 10 | CD14 | 0.60 | 0.24 | 0.618 | 0.67 | 0.58 | 0.59 | 0.66 | 0.26342 | 1762487.4 | 1841178.6 | pg/ml |
| 11 | CD142 | 0.57 | 0.11 | 0.528 | 0.74 | 0.32 | 0.51 | 0.57 | 0.45032 | 35.7 | 37.0 | pg/ml |
| 12 | CD27 | 0.66 | 0.17 | 0.622 | 0.65 | 0.60 | 0.58 | 0.67 | 0.027295 | 104 | 129 | U/ml |
| 13 | CD95 | 0.40 | −0.19 | 0.635 | 0.62 | 0.65 | 0.60 | 0.67 | 0.041434 | 5004.5 | 4744.0 | pg/ml |
| 14 | Clusterin | 0.69 | 0.30 | 0.689 | 0.63 | 0.74 | 0.69 | 0.69 | 0.009075 | 198900.7 | 285325.2 | pg/ml |
| 15 | Complement factor D | 0.62 | 0.34 | 0.662 | 0.77 | 0.58 | 0.61 | 0.74 | 0.10033 | 2155.0 | 2526.1 | ng/ml |
| 16 | Corin | 0.68 | 0.19 | 0.645 | 0.58 | 0.70 | 0.64 | 0.65 | 0.010336 | 1171.5 | 1647.9 | pg/ml |
| 17 | CRP | 0.82 | 0.60 | 0.82 | 0.76 | 0.86 | 0.79 | 0.84 | 7.02E−08 | 111.7 | 32.7 | μg/ml |
| 18 | CXCL13 | 0.57 | 0.09 | 0.514 | 0.77 | 0.30 | 0.48 | 0.60 | 0.82826 | 175.7 | 151.9 | pg/ml |
| 19 | Cystatin C | 0.67 | 0.24 | 0.632 | 0.72 | 0.55 | 0.59 | 0.69 | 0.034512 | 1411 | 1600 | ng/ml |
| 20 | Dkk1 | 0.57 | 0.19 | 0.486 | 0.71 | 0.30 | 0.46 | 0.55 | 0.53284 | 2564.2 | 2788.0 | pg/ml |
| 21 | E Cadherin | 0.64 | 0.18 | 0.452 | 0.27 | 0.62 | 0.38 | 0.49 | 0.09171 | 56.7 | 63.9 | ng/ml |
| 22 | E Selectin | 0.67 | 0.32 | 0.658 | 0.68 | 0.64 | 0.62 | 0.69 | 0.032367 | 81.4 | 64.2 | ng/ml |
| 23 | Endostatin | 0.48 | −0.12 | 0.592 | 0.58 | 0.60 | 0.57 | 0.62 | 0.11029 | 101.9 | 101.4 | ng/ml |
| 24 | Fetuin A | 0.54 | −0.18 | 0.622 | 0.57 | 0.67 | 0.61 | 0.63 | 0.16914 | 1712799.6 | 1836541.5 | ng/ml |
| 25 | GCP2 | 0.61 | 0.11 | 0.635 | 0.53 | 0.73 | 0.62 | 0.64 | 0.16503 | 222.0 | 257.1 | pg/ml |
| 26 | GDF15 | 0.60 | 0.20 | 0.5 | 0.47 | 0.53 | 0.46 | 0.54 | 0.4674 | 1376.3 | 1081.2 | pg/ml |
| 27 | ICAM1 | 0.54 | 0.07 | 0.526 | 0.50 | 0.55 | 0.50 | 0.55 | 1 | 1320.6 | 1131.4 | ng/ml |
| 28 | IGFBP3 | 0.62 | 0.22 | 0.622 | 0.71 | 0.55 | 0.57 | 0.69 | 0.10259 | 2390.6 | 2759.9 | ng/ml |
| 29 | IL18 | 0.53 | −0.27 | 0.654 | 0.55 | 0.75 | 0.68 | 0.64 | 0.007719 | 619.2 | 624.1 | pg/ml |
| 30 | IL19 | 0.50 | −0.01 | 0.527 | 0.41 | 0.63 | 0.48 | 0.56 | 0.95242 | 123 | 117 | pg/ml |
| 31 | IL1R | 0.69 | 0.29 | 0.662 | 0.56 | 0.75 | 0.66 | 0.67 | 0.0197 | 37.2 | 23.4 | pg/ml |
| 32 | IP-10 | 0.75 | 0.25 | 0.73 | 0.73 | 0.73 | 0.65 | 0.80 | 4.84E−05 | 428.6 | 870.6 | pg/ml |
| 33 | Leptin | 0.50 | −0.13 | 0.608 | 0.56 | 0.65 | 0.58 | 0.63 | 0.18755 | 7140.4 | 6613.1 | pg/ml |
| 34 | Leptin R | 0.53 | −0.10 | 0.622 | 0.47 | 0.75 | 0.62 | 0.63 | 0.081707 | 37.8 | 38.4 | ng/ml |
| 35 | LIGHT | 0.59 | 0.17 | 0.459 | 0.38 | 0.53 | 0.41 | 0.50 | 0.30281 | 188.2 | 169.7 | pg/ml |
| 36 | MBL | 0.52 | −0.21 | 0.635 | 0.56 | 0.70 | 0.61 | 0.65 | 0.033964 | 1390.6 | 1337.6 | ng/ml |
| 37 | MIF | 0.51 | −0.15 | 0.649 | 0.65 | 0.65 | 0.61 | 0.68 | 0.06286 | 109.4 | 117.7 | ng/ml |
| 38 | MMP2 | 0.51 | −0.02 | 0.539 | 0.58 | 0.50 | 0.51 | 0.57 | 0.50887 | 143.9 | 150.9 | ng/ml |
| 39 | MMP3 | 0.55 | −0.07 | 0.595 | 0.77 | 0.44 | 0.55 | 0.68 | 0.42303 | 11.7 | 14.4 | ng/ml |
| 40 | MMP7 | 0.66 | 0.21 | 0.625 | 0.64 | 0.62 | 0.58 | 0.67 | 0.03001 | 3.8 | 2.8 | ng/ml |
| 41 | MMP8 | 0.74 | 0.43 | 0.73 | 0.74 | 0.72 | 0.70 | 0.76 | 0.001119 | 80.0 | 40.3 | ng/ml |
| 42 | Myeloperoxidase | 0.65 | 0.05 | 0.486 | 0.54 | 0.44 | 0.46 | 0.52 | 0.63381 | 610.2 | 549.1 | ng/ml |
| 43 | Neopterin | 0.68 | 0.26 | 0.703 | 0.65 | 0.75 | 0.69 | 0.71 | 0.009685 | 4.6 | 7.2 | pg/ml |
| 44 | NGAL | 0.77 | 0.34 | 0.74 | 0.85 | 0.64 | 0.67 | 0.83 | 0.000159 | 144.1 | 92.2 | ng/ml |
| 45 | Osteopontin | 0.63 | 0.19 | 0.611 | 0.60 | 0.62 | 0.60 | 0.62 | 0.15573 | 191.7 | 161.7 | ng/ml |
| 46 | Osteoprotegerin | 0.59 | 0.17 | 0.595 | 0.53 | 0.65 | 0.56 | 0.62 | 0.46408 | 94.8 | 32.7 | pg/ml |
| 47 | P Selectin | 0.52 | −0.27 | 0.632 | 0.67 | 0.60 | 0.60 | 0.67 | 0.028534 | 82.9 | 80.0 | ng/ml |
| 48 | PCSK9 | 0.63 | 0.21 | 0.605 | 0.64 | 0.58 | 0.58 | 0.64 | 0.070271 | 563.6 | 483.0 | ng/ml |
| 49 | Pentraxin3 | 0.72 | 0.37 | 0.681 | 0.60 | 0.76 | 0.70 | 0.67 | 0.012377 | 8.9 | 5.6 | ng/ml |
| 50 | Pro Cathepsin B | 0.62 | 0.17 | 0.644 | 0.62 | 0.67 | 0.62 | 0.67 | 0.11253 | 106.0 | 83.2 | pg/ml |
| 51 | Progranulin | 0.75 | 0.44 | 0.726 | 0.79 | 0.67 | 0.68 | 0.79 | 0.000646 | 94.9 | 163.5 | pg/ml |
| 52 | ProMMP10 | 0.60 | 0.11 | 0.608 | 0.83 | 0.41 | 0.56 | 0.73 | 0.15611 | 1604.8 | 2049.9 | pg/ml |
| 53 | Prostaglandin E2 | 0.48 | −0.26 | 0.676 | 0.65 | 0.70 | 0.65 | 0.70 | 0.025815 | 30 | 30 | pg/ml |
| 54 | RBP4 | 0.61 | 0.19 | 0.608 | 0.65 | 0.58 | 0.56 | 0.66 | 0.19492 | 12112.3 | 14761.5 | ng/ml |
| 55 | Resistin | 0.76 | 0.34 | 0.716 | 0.71 | 0.73 | 0.69 | 0.74 | 0.002105 | 26.5 | 14.7 | ng/ml |
| 56 | SLPI | 0.55 | −0.10 | 0.645 | 0.72 | 0.58 | 0.61 | 0.70 | 0.081415 | 41716.5 | 42982.4 | pg/ml |
| 57 | Substance P | 0.46 | −0.28 | 0.658 | 0.59 | 0.72 | 0.65 | 0.67 | 0.028513 | 67 | 72 | pg/ml |
| 58 | TFPI | 0.54 | 0.00 | 0.556 | 0.54 | 0.57 | 0.54 | 0.57 | 0.49547 | 29307.8 | 27608.6 | pg/ml |
| 59 | TGF B1 | 0.53 | 0.03 | 0.566 | 0.81 | 0.35 | 0.53 | 0.67 | 0.47924 | 303 | 295 | pg/ml |
| 60 | Thrombospondin2 | 0.44 | −0.29 | 0.662 | 0.59 | 0.73 | 0.65 | 0.67 | 0.001689 | 45.3 | 41.7 | ng/ml |
| 61 | Tie2 | 0.57 | 0.23 | 0.622 | 0.53 | 0.70 | 0.60 | 0.64 | 0.62933 | 22.7 | 21.0 | ng/ml |
| 62 | TRAIL | 0.95 | 0.75 | 0.901 | 0.89 | 0.91 | 0.87 | 0.92 | 5.67E−15 | 49.5 | 182.9 | pg/ml |
| 63 | uPAR | 0.50 | −0.04 | 0.554 | 0.50 | 0.60 | 0.52 | 0.59 | 0.47073 | 4875.5 | 4144.9 | pg/ml |

TABLE 4-continued

| Number | Feature #1 | AUC | MCC | Total accuracy | Sensitivity | Specificity | PPV | NPV | ranksum P-value | Mean bacterial | Mean viral | Concentration units |
|---|---|---|---|---|---|---|---|---|---|---|---|---|
| 64 | VCAM1 | 0.45 | −0.06 | 0.658 | 0.56 | 0.75 | 0.67 | 0.65 | 0.02302 | 1228.0 | 1202.4 | ng/ml |
| 65 | VEGF C | 0.54 | −0.03 | 0.554 | 0.41 | 0.68 | 0.52 | 0.57 | 0.48079 | 8292.3 | 8632.7 | pg/ml |
| 66 | Vitamin D Binding Protein | 0.53 | −0.31 | 0.667 | 0.58 | 0.75 | 0.69 | 0.65 | 0.002578 | 185488.3 | 183031.6 | pg/ml |

Determinants Whose Accuracy for Distinguishing Between Bacterial (or Mixed) and Viral Infection Differs Between Children and Adults:

For each of the examined determinants, the present inventors performed measurements for both children (3 months-18 years) and adults (older than 18 years), and monitored the change in performance when distinguishing between bacterial and viral infections. Most of the determinants did not show an age dependent performance. However, the performance of some of the studied determinants was significantly dependent on age.

Examples of determinants for which expression patterns in bacterial (or mixed) and viral patients differ between children and adults are summarized in Table 5.

TABLE 5

| Protein | AUC All | AUC Adults | AUC Children | Delta AUC (adults vs children) |
|---|---|---|---|---|
| Myeloperoxidase | 0.65 | 0.78 | 0.43 | 0.35 |
| Osteopontin | 0.63 | 0.84 | 0.54 | 0.30 |
| Complement factor D | 0.62 | 0.83 | 0.59 | 0.25 |
| PCSK9 | 0.63 | 0.76 | 0.52 | 0.24 |
| IGFBP3 | 0.62 | 0.44 | 0.67 | 0.22 |
| GDF15 | 0.60 | 0.69 | 0.47 | 0.22 |
| Osteoprotegerin | 0.59 | 0.71 | 0.51 | 0.21 |
| Neopterin | 0.68 | 0.57 | 0.76 | 0.19 |
| SLPI | 0.55 | 0.75 | 0.56 | 0.19 |
| Progranulin | 0.75 | 0.64 | 0.82 | 0.18 |
| Adiponectin | 0.69 | 0.59 | 0.76 | 0.18 |
| E Cadherin | 0.64 | 0.54 | 0.71 | 0.18 |
| ICAM1 | 0.54 | 0.77 | 0.59 | 0.17 |
| CXCL13 | 0.57 | 0.70 | 0.53 | 0.17 |
| CD95 | 0.40 | 0.58 | 0.73 | 0.15 |
| LIGHT | 0.59 | 0.68 | 0.53 | 0.15 |
| Angiopoietin1 | 0.57 | 0.52 | 0.65 | 0.13 |
| Resistin | 0.76 | 0.84 | 0.71 | 0.13 |
| Angiogenin | 0.58 | 0.55 | 0.68 | 0.12 |
| Pro Cathepsin B | 0.62 | 0.68 | 0.58 | 0.10 |
| IL19 | 0.50 | 0.69 | 0.60 | 0.10 |
| NGAL | 0.77 | 0.71 | 0.81 | 0.09 |
| BAFF | 0.57 | 0.58 | 0.66 | 0.08 |
| RBP4 | 0.61 | 0.69 | 0.61 | 0.08 |
| MMP2 | 0.51 | 0.71 | 0.63 | 0.08 |
| CD27 | 0.66 | 0.71 | 0.65 | 0.07 |
| GCP2 | 0.61 | 0.65 | 0.59 | 0.06 |
| Clusterin | 0.69 | 0.68 | 0.74 | 0.06 |
| Cystatin C | 0.67 | 0.63 | 0.69 | 0.06 |

For example, Osteopontin is a highly distinctive marker in adults but not in children (FIG. 8A), while NGAL and Neopterin are much more distinctive markers in children than in adults (FIG. 8B-8C). For Neopterin, besides the changes in differential expression patterns, the actual cutoffs were changed as well as there was a shift up in Neopterin expression levels in adults (FIG. 8C; mean Neopterin levels in bacterial and viral patients were 5.9 and 8.1 pg/ml respectively in adults and only 2.1 and 5.4 pg/ml respectively in children). Importantly, the differences between accuracy levels in children and adults can lead to a reduced accuracy when considering the entire population (comprised of both children and adults) as it masks the differential expression of one of the age groups. Accordingly, for the determinants presented in Table 5, the AUC of a specific determinant for a specific age group (AUC Adults or AUC Children) was up to 0.33 higher than for the entire population (AUC All; see for example CD95 in which AUC children is 0.73 compared to an AUC of 0.4 for the entire population).

Combining different determinants to increase diagnostic accuracy: Next, the present inventors tested whether combining several determinants can improve diagnostic accuracy of single determinants. They used a linear logistic regression to develop a classifier for each pair of determinants (2145 combinations) and evaluated its ability to distinguish between bacterial (or mixed) and viral patients. FIG. 9 includes examples of scatter plots of pairs of determinants that differentiate between bacterial (red) vs viral (blue) infected subjects.

FIGS. 10 and 11 present the classification accuracy in terms of AUC and MCC (respectively) of viral versus bacterial infected patients attained for pairs of determinants using a logistic regression model.

Table 6 presents examples of pairs that demonstrated high accuracy improvement as calculated by the difference in AUC of the pair compared to the AUC of the single determinant (out of the same pair) with the highest AUC (delta AUC). Combining pairs of determinants generated an increase of up to 0.18 in AUC (when comparing AUC of single vs. pairs of determinants; e.g., combined AUC of 0.87 compared to AUC of 0.69 of the best single) and up to 0.27 in MCC (when comparing MCC of single vs. pairs of determinants; e.g., combined MCC of 0.61 compared to MCC of 0.34 of the best single), to generate highly discriminative combinations (AUCs between 0.75-0.96, average AUC 0.90, when testing the pairs summarized in Table 6).

TABLE 6

| Feature #1 | Feature #2 | AUC_1 | AUC_2 | Combined model AUC | Delta AUC | MCC_1 | MCC_2 | MCC | Delta MCC | Sensitivity | Specificity |
|---|---|---|---|---|---|---|---|---|---|---|---|
| Adiponectin | Osteopontin | 0.69 | 0.63 | 0.87 | 0.18 | 0.32 | 0.19 | 0.55 | 0.23 | 0.77 | 0.84 |
| Progranulin | Resistin | 0.75 | 0.76 | 0.92 | 0.16 | 0.44 | 0.34 | 0.63 | 0.20 | 0.92 | 0.83 |
| Pentraxin 3 | Progranulin | 0.72 | 0.75 | 0.87 | 0.13 | 0.37 | 0.44 | 0.45 | 0.01 | 0.85 | 0.67 |
| ProMMP10 | Resistin | 0.60 | 0.76 | 0.88 | 0.12 | 0.11 | 0.34 | 0.46 | 0.11 | 0.93 | 0.77 |

TABLE 6-continued

| Feature #1 | Feature #2 | AUC_1 | AUC_2 | Combined model AUC | Delta AUC | MCC_1 | MCC_2 | MCC | Delta MCC | Sensitivity | Specificity |
|---|---|---|---|---|---|---|---|---|---|---|---|
| IL1R | Progranulin | 0.69 | 0.75 | 0.87 | 0.12 | 0.29 | 0.44 | 0.49 | 0.05 | 0.92 | 0.72 |
| CRP | NGAL | 0.82 | 0.77 | 0.92 | 0.10 | 0.60 | 0.34 | 0.61 | 0.01 | 0.82 | 0.85 |
| E Cadherin | Resistin | 0.64 | 0.76 | 0.86 | 0.10 | 0.18 | 0.34 | 0.61 | 0.27 | 0.73 | 0.89 |
| CRP | Progranulin | 0.82 | 0.75 | 0.91 | 0.10 | 0.60 | 0.44 | 0.64 | 0.04 | 0.82 | 0.87 |
| CD27 | NGAL | 0.66 | 0.77 | 0.86 | 0.10 | 0.17 | 0.34 | 0.45 | 0.11 | 0.89 | 0.71 |
| IL19 | NGAL | 0.50 | 0.77 | 0.86 | 0.09 | −0.01 | 0.34 | 0.58 | 0.24 | 0.77 | 0.82 |
| Corin | NGAL | 0.68 | 0.77 | 0.86 | 0.09 | 0.19 | 0.34 | 0.55 | 0.21 | 0.78 | 0.83 |
| Angiopoietin1 | CRP | 0.57 | 0.82 | 0.91 | 0.09 | 0.11 | 0.60 | 0.64 | 0.04 | 0.88 | 0.87 |
| CRP | E Selectin | 0.82 | 0.67 | 0.91 | 0.09 | 0.60 | 0.32 | 0.56 | −0.04 | 0.77 | 0.85 |
| CRP | Substance P | 0.82 | 0.46 | 0.90 | 0.09 | 0.60 | −0.28 | 0.70 | 0.10 | 0.82 | 0.90 |
| CRP | MMP7 | 0.82 | 0.66 | 0.90 | 0.08 | 0.60 | 0.21 | 0.72 | 0.12 | 0.85 | 0.87 |
| CRP | Pro Cathepsin B | 0.82 | 0.62 | 0.90 | 0.08 | 0.60 | 0.17 | 0.67 | 0.07 | 0.79 | 0.90 |
| CRP | E Cadherin | 0.82 | 0.64 | 0.90 | 0.08 | 0.60 | 0.18 | 0.67 | 0.07 | 0.82 | 0.87 |
| BDNF | CRP | 0.52 | 0.82 | 0.90 | 0.08 | −0.11 | 0.60 | 0.59 | −0.02 | 0.82 | 0.83 |
| BAFF | CRP | 0.57 | 0.82 | 0.89 | 0.07 | −0.15 | 0.60 | 0.64 | 0.04 | 0.76 | 0.88 |
| CRP | MMP8 | 0.82 | 0.74 | 0.89 | 0.07 | 0.60 | 0.43 | 0.57 | −0.04 | 0.80 | 0.80 |
| NGAL | Resistin | 0.77 | 0.76 | 0.83 | 0.07 | 0.34 | 0.34 | 0.60 | 0.26 | 0.77 | 0.88 |
| Angiogenin | CRP | 0.58 | 0.82 | 0.88 | 0.06 | 0.16 | 0.60 | 0.59 | −0.01 | 0.88 | 0.75 |
| NGAL | PCSK9 | 0.77 | 0.63 | 0.83 | 0.06 | 0.34 | 0.21 | 0.53 | 0.19 | 0.78 | 0.77 |
| NGAL | Vitamin D Binding Protein | 0.77 | 0.53 | 0.82 | 0.06 | 0.34 | −0.31 | 0.40 | 0.06 | 0.89 | 0.71 |
| CRP | Neopterin | 0.82 | 0.68 | 0.88 | 0.06 | 0.60 | 0.26 | 0.46 | −0.15 | 0.88 | 0.70 |
| NGAL | SLPI | 0.77 | 0.55 | 0.82 | 0.06 | 0.34 | −0.10 | 0.38 | 0.05 | 0.78 | 0.77 |
| CRP | Resistin | 0.82 | 0.76 | 0.87 | 0.06 | 0.60 | 0.34 | 0.51 | −0.09 | 0.82 | 0.78 |
| NGAL | RBP4 | 0.77 | 0.61 | 0.82 | 0.05 | 0.34 | 0.19 | 0.45 | 0.11 | 0.81 | 0.71 |
| NGAL | Tie2 | 0.77 | 0.57 | 0.82 | 0.05 | 0.34 | 0.23 | 0.49 | 0.15 | 0.73 | 0.88 |
| CRP | Pentraxin 3 | 0.82 | 0.72 | 0.87 | 0.05 | 0.60 | 0.37 | 0.58 | −0.02 | 0.74 | 0.87 |
| NGAL | Progranulin | 0.77 | 0.75 | 0.81 | 0.05 | 0.34 | 0.44 | 0.47 | 0.03 | 0.85 | 0.71 |
| NGAL | ProMMP10 | 0.77 | 0.60 | 0.81 | 0.05 | 0.34 | 0.11 | 0.44 | 0.10 | 0.70 | 0.77 |
| CRP | MMP3 | 0.82 | 0.55 | 0.86 | 0.05 | 0.60 | −0.07 | 0.62 | 0.02 | 0.74 | 0.87 |
| CRP | ProMMP10 | 0.82 | 0.60 | 0.86 | 0.05 | 0.60 | 0.11 | 0.57 | −0.04 | 0.74 | 0.82 |
| NGAL | a1 Acid Glycoprotein | 0.77 | 0.61 | 0.81 | 0.05 | 0.34 | −0.31 | 0.45 | 0.11 | 0.85 | 0.77 |
| NGAL | TGF B1 | 0.77 | 0.53 | 0.81 | 0.04 | 0.34 | 0.03 | 0.35 | 0.01 | 0.78 | 0.72 |
| NGAL | Osteoprotegerin | 0.77 | 0.59 | 0.81 | 0.04 | 0.34 | 0.17 | 0.49 | 0.15 | 0.77 | 0.77 |
| NGAL | VCAM1 | 0.77 | 0.45 | 0.81 | 0.04 | 0.34 | −0.06 | 0.38 | 0.05 | 0.78 | 0.77 |
| CRP | IP-10 | 0.82 | 0.75 | 0.86 | 0.04 | 0.60 | 0.25 | 0.59 | −0.02 | 0.71 | 0.86 |
| NGAL | uPAR | 0.77 | 0.50 | 0.80 | 0.04 | 0.34 | −0.04 | 0.41 | 0.07 | 0.77 | 0.77 |
| CRP | TFPI | 0.82 | 0.54 | 0.85 | 0.04 | 0.60 | 0.00 | 0.53 | −0.07 | 0.77 | 0.81 |
| NGAL | Neopterin | 0.77 | 0.68 | 0.80 | 0.04 | 0.34 | 0.26 | 0.45 | 0.11 | 0.85 | 0.71 |
| NGAL | Prostaglandin E2 | 0.77 | 0.48 | 0.80 | 0.04 | 0.34 | −0.26 | 0.33 | −0.01 | 0.81 | 0.72 |
| CRP | Cystatin C | 0.82 | 0.67 | 0.85 | 0.04 | 0.60 | 0.24 | 0.55 | −0.05 | 0.69 | 0.88 |
| NGAL | P Selectin | 0.77 | 0.52 | 0.80 | 0.04 | 0.34 | −0.27 | 0.38 | 0.05 | 0.82 | 0.77 |
| NGAL | Pentraxin 3 | 0.77 | 0.72 | 0.80 | 0.04 | 0.34 | 0.37 | 0.58 | 0.22 | 0.74 | 0.87 |
| IP-10 | NGAL | 0.75 | 0.77 | 0.80 | 0.03 | 0.25 | 0.34 | 0.49 | 0.15 | 0.82 | 0.69 |
| CRP | Complement factor D | 0.82 | 0.62 | 0.85 | 0.03 | 0.60 | 0.34 | 0.59 | −0.01 | 0.74 | 0.93 |
| CRP | Myeloperoxidase | 0.82 | 0.65 | 0.85 | 0.03 | 0.60 | 0.05 | 0.59 | −0.01 | 0.77 | 0.82 |
| NGAL | Osteopontin | 0.77 | 0.63 | 0.79 | 0.03 | 0.34 | 0.19 | 0.44 | 0.10 | 0.85 | 0.67 |
| NGAL | Substance P | 0.77 | 0.46 | 0.79 | 0.03 | 0.34 | −0.28 | 0.33 | −0.01 | 0.82 | 0.66 |
| NGAL | Thrombospondin2 | 0.77 | 0.44 | 0.79 | 0.03 | 0.34 | −0.29 | 0.41 | 0.07 | 0.85 | 0.65 |
| NGAL | VEGF C | 0.77 | 0.54 | 0.79 | 0.03 | 0.34 | −0.03 | 0.46 | 0.12 | 0.69 | 0.78 |
| Angiopoietin1 | TRAIL | 0.57 | 0.95 | 0.96 | 0.01 | 0.11 | 0.75 | 0.78 | 0.03 | 0.91 | 0.95 |
| E Cadherin | TRAIL | 0.64 | 0.95 | 0.96 | 0.01 | 0.18 | 0.75 | 0.78 | 0.03 | 0.91 | 0.87 |
| Progranulin | TRAIL | 0.75 | 0.95 | 0.96 | 0.01 | 0.44 | 0.75 | 0.81 | 0.06 | 0.91 | 0.90 |
| CD14 | TRAIL | 0.60 | 0.95 | 0.95 | 0.01 | 0.24 | 0.75 | 0.75 | 0.00 | 0.86 | 0.90 |
| NGAL | Pro Cathepsin B | 0.77 | 0.62 | 0.77 | 0.00 | 0.34 | 0.17 | 0.25 | −0.09 | 0.88 | 0.58 |
| Pro Cathepsin B | TRAIL | 0.62 | 0.95 | 0.95 | 0.00 | 0.17 | 0.75 | 0.73 | −0.02 | 0.91 | 0.85 |
| Myeloperoxidase | TRAIL | 0.65 | 0.95 | 0.95 | 0.00 | 0.05 | 0.75 | 0.74 | −0.01 | 0.89 | 0.87 |
| Endostatinn | TRAIL | 0.48 | 0.95 | 0.95 | 0.00 | −0.12 | 0.75 | 0.77 | 0.02 | 0.86 | 0.93 |
| MMP8 | TRAIL | 0.74 | 0.95 | 0.95 | 0.00 | 0.43 | 0.75 | 0.71 | −0.04 | 0.89 | 0.90 |
| NGAL | TRAIL | 0.77 | 0.95 | 0.95 | 0.00 | 0.34 | 0.75 | 0.71 | −0.04 | 0.85 | 0.95 |
| PCSK9 | TRAIL | 0.63 | 0.95 | 0.95 | 0.00 | 0.21 | 0.75 | 0.72 | −0.03 | 0.86 | 0.93 |
| IL18 | TRAIL | 0.53 | 0.95 | 0.95 | 0.00 | −0.27 | 0.75 | 0.75 | 0.00 | 0.90 | 0.88 |
| IP-10 | TRAIL | 0.75 | 0.95 | 0.95 | 0.00 | 0.25 | 0.75 | 0.73 | −0.02 | 0.87 | 0.92 |
| MMP3 | TRAIL | 0.55 | 0.95 | 0.95 | 0.00 | −0.07 | 0.75 | 0.68 | −0.07 | 0.89 | 0.87 |
| TGF B1 | TRAIL | 0.53 | 0.95 | 0.95 | 0.00 | 0.03 | 0.75 | 0.74 | −0.01 | 0.92 | 0.85 |
| TRAIL | VCAM1 | 0.95 | 0.45 | 0.95 | 0.00 | 0.75 | −0.06 | 0.74 | −0.01 | 0.89 | 0.88 |
| ICAM1 | TRAIL | 0.54 | 0.95 | 0.95 | 0.00 | 0.07 | 0.75 | 0.77 | 0.02 | 0.94 | 0.85 |

TABLE 6-continued

| Feature #1 | Feature #2 | AUC_1 | AUC_2 | Combined model AUC | Delta AUC | MCC_1 | MCC_2 | MCC | Delta MCC | Sensitivity | Specificity |
|---|---|---|---|---|---|---|---|---|---|---|---|
| MMP2 | TRAIL | 0.51 | 0.95 | 0.95 | 0.00 | −0.02 | 0.75 | 0.74 | −0.01 | 0.86 | 0.95 |
| P Selectin | TRAIL | 0.52 | 0.95 | 0.95 | 0.00 | −0.27 | 0.75 | 0.74 | −0.01 | 0.86 | 0.93 |
| ProMMP 10 | TRAIL | 0.60 | 0.95 | 0.95 | 0.00 | 0.11 | 0.75 | 0.71 | −0.04 | 0.89 | 0.87 |
| TRAIL | Vitamin D Binding Protein | 0.95 | 0.53 | 0.95 | 0.00 | 0.75 | −0.31 | 0.77 | 0.02 | 0.87 | 0.95 |
| TRAIL | a1 Acid Glycoprotein | 0.95 | 0.61 | 0.95 | 0.00 | 0.75 | −0.31 | 0.77 | 0.02 | 0.85 | 0.95 |
| CRP | TRAIL | 0.82 | 0.95 | 0.95 | 0.00 | 0.60 | 0.75 | 0.77 | 0.02 | 0.91 | 0.91 |
| CXCL13 | TRAIL | 0.57 | 0.95 | 0.95 | 0.00 | 0.09 | 0.75 | 0.71 | −0.04 | 0.82 | 0.95 |
| E Selectin | TRAIL | 0.67 | 0.95 | 0.95 | 0.00 | 0.32 | 0.75 | 0.68 | −0.06 | 0.82 | 0.85 |
| Adiponectin | TRAIL | 0.69 | 0.95 | 0.95 | 0.00 | 0.32 | 0.75 | 0.76 | 0.01 | 0.91 | 0.88 |
| Clusterin | TRAIL | 0.69 | 0.95 | 0.95 | 0.00 | 0.30 | 0.75 | 0.76 | 0.01 | 0.89 | 0.90 |
| RBP4 | TRAIL | 0.61 | 0.95 | 0.95 | 0.00 | 0.19 | 0.75 | 0.74 | −0.01 | 0.85 | 0.93 |
| SLPI | TRAIL | 0.55 | 0.95 | 0.95 | 0.00 | −0.10 | 0.75 | 0.66 | −0.09 | 0.86 | 0.93 |
| Substance P | TRAIL | 0.46 | 0.95 | 0.95 | 0.00 | −0.28 | 0.75 | 0.71 | −0.04 | 0.82 | 0.92 |
| CD 23 | TRAIL | 0.52 | 0.95 | 0.94 | 0.00 | −0.16 | 0.75 | 0.68 | −0.07 | 0.88 | 0.90 |
| CD27 | TRAIL | 0.66 | 0.95 | 0.94 | 0.00 | 0.17 | 0.75 | 0.74 | −0.01 | 0.85 | 0.93 |
| CD95 | TRAIL | 0.40 | 0.95 | 0.94 | 0.00 | −0.19 | 0.75 | 0.71 | −0.04 | 0.85 | 0.90 |
| Cystatin C | TRAIL | 0.67 | 0.95 | 0.94 | 0.00 | 0.24 | 0.75 | 0.74 | −0.01 | 0.89 | 0.90 |
| Fetuin A | TRAIL | 0.54 | 0.95 | 0.94 | 0.00 | −0.18 | 0.75 | 0.71 | −0.04 | 0.86 | 0.95 |
| Leptin R | TRAIL | 0.53 | 0.95 | 0.94 | 0.00 | −0.10 | 0.75 | 0.77 | 0.02 | 0.85 | 0.95 |
| TRAIL | uPAR | 0.95 | 0.50 | 0.94 | 0.00 | 0.75 | −0.04 | 0.74 | −0.01 | 0.91 | 0.88 |
| Angiogenin | TRAIL | 0.58 | 0.95 | 0.94 | −0.01 | 0.16 | 0.75 | 0.76 | 0.01 | 0.85 | 0.95 |
| APRIL | TRAIL | 0.46 | 0.95 | 0.94 | −0.01 | −0.05 | 0.75 | 0.72 | −0.03 | 0.91 | 0.85 |
| Corin | TRAIL | 0.68 | 0.95 | 0.94 | −0.01 | 0.19 | 0.75 | 0.74 | −0.01 | 0.89 | 0.95 |
| GDF15 | TRAIL | 0.60 | 0.95 | 0.94 | −0.01 | 0.20 | 0.75 | 0.76 | 0.01 | 0.91 | 0.88 |
| IGFBP3 | TRAIL | 0.62 | 0.95 | 0.94 | −0.01 | 0.22 | 0.75 | 0.73 | −0.02 | 0.85 | 0.95 |
| IL19 | TRAIL | 0.50 | 0.95 | 0.94 | −0.01 | −0.01 | 0.75 | 0.74 | −0.01 | 0.88 | 0.85 |
| Leptin | TRAIL | 0.50 | 0.95 | 0.94 | −0.01 | −0.13 | 0.75 | 0.79 | 0.04 | 0.85 | 0.95 |
| LIGHT | TRAIL | 0.59 | 0.95 | 0.94 | −0.01 | 0.17 | 0.75 | 0.68 | −0.07 | 0.85 | 0.93 |
| MBL | TRAIL | 0.52 | 0.95 | 0.94 | −0.01 | −0.21 | 0.75 | 0.73 | −0.02 | 0.88 | 0.90 |
| MMP7 | TRAIL | 0.66 | 0.95 | 0.94 | −0.01 | 0.21 | 0.75 | 0.70 | −0.05 | 0.88 | 0.87 |
| Neopterin | TRAIL | 0.68 | 0.95 | 0.94 | −0.01 | 0.26 | 0.75 | 0.71 | −0.04 | 0.85 | 0.90 |
| Prostaglandin E2 | TRAIL | 0.48 | 0.95 | 0.94 | −0.01 | −0.26 | 0.75 | 0.71 | −0.04 | 0.88 | 0.88 |
| Resistin | TRAIL | 0.76 | 0.95 | 0.94 | −0.01 | 0.34 | 0.75 | 0.76 | 0.01 | 0.91 | 0.88 |
| TRAIL | Thrombospondin2 | 0.95 | 0.44 | 0.94 | −0.01 | 0.75 | −0.29 | 0.74 | −0.01 | 0.91 | 0.85 |
| BAFF | TRAIL | 0.57 | 0.95 | 0.94 | −0.01 | −0.15 | 0.75 | 0.73 | −0.02 | 0.88 | 0.88 |
| BDNF | TRAIL | 0.52 | 0.95 | 0.94 | −0.01 | −0.11 | 0.75 | 0.71 | −0.04 | 0.85 | 0.95 |
| Dkk1 | TRAIL | 0.57 | 0.95 | 0.94 | −0.01 | 0.19 | 0.75 | 0.71 | −0.04 | 0.85 | 0.93 |
| TRAIL | Tie2 | 0.95 | 0.57 | 0.94 | −0.01 | 0.75 | 0.23 | 0.77 | 0.02 | 0.85 | 0.95 |
| GCP2 | TRAIL | 0.61 | 0.95 | 0.94 | −0.01 | 0.11 | 0.75 | 0.68 | −0.07 | 0.88 | 0.90 |
| MIF | TRAIL | 0.51 | 0.95 | 0.94 | −0.01 | −0.15 | 0.75 | 0.73 | −0.02 | 0.88 | 0.90 |
| Osteoprotegerin | TRAIL | 0.59 | 0.95 | 0.94 | −0.01 | 0.17 | 0.75 | 0.76 | 0.01 | 0.88 | 0.90 |
| TRAIL | VEGF C | 0.95 | 0.54 | 0.94 | −0.01 | 0.75 | −0.03 | 0.73 | −0.02 | 0.88 | 0.88 |
| Angiopoietin2 | TRAIL | 0.52 | 0.95 | 0.94 | −0.01 | 0.03 | 0.75 | 0.68 | −0.07 | 0.88 | 0.88 |
| Complement factor D | TRAIL | 0.62 | 0.95 | 0.94 | −0.01 | 0.34 | 0.75 | 0.74 | −0.01 | 0.91 | 0.90 |
| IL1R | TRAIL | 0.69 | 0.95 | 0.94 | −0.01 | 0.29 | 0.75 | 0.71 | −0.04 | 0.88 | 0.88 |
| Osteopontin | TRAIL | 0.63 | 0.95 | 0.94 | −0.01 | 0.19 | 0.75 | 0.78 | 0.03 | 0.89 | 0.89 |
| Pentraxin 3 | TRAIL | 0.72 | 0.95 | 0.94 | −0.01 | 0.37 | 0.75 | 0.78 | 0.03 | 0.91 | 0.89 |
| TFPI | TRAIL | 0.54 | 0.95 | 0.94 | −0.01 | 0.00 | 0.75 | 0.72 | −0.02 | 0.89 | 0.92 |
| CD142 | TRAIL | 0.57 | 0.95 | 0.93 | −0.01 | 0.11 | 0.75 | 0.72 | −0.02 | 0.89 | 0.92 |
| NGAL | TFPI | 0.77 | 0.54 | 0.75 | −0.02 | 0.34 | 0.00 | 0.28 | −0.06 | 0.82 | 0.67 |

It is noted that some determinant combinations exhibited an improved diagnostic accuracy (in terms of AUC or MCC) compared to that of the corresponding individual determinants, whereas other combinations exhibit a reduced accuracy (FIGS. 12-13).

FIGS. 14A-16B and Tables 7-8 demonstrate the ability of NGAL and Neopterin to increase the sensitivity of CRP, TRAIL, and IP-10 using selected cutoffs. For example, combining NGAL (at a selected cutoff of 150 ng/ml) increased the sensitivity of CRP (at the routinely used cutoff of 80 μg/ml) from 0.59 to 0.74 (25% increase; Table 7). In this analysis a patient is classified as having a bacterial infection if his CRP levels were higher than 80 μg/ml OR his NGAL levels were higher than 150 ng/ml. Similarly, combining Neopterin (at a selected cutoff of 4 pg/ml) increased the sensitivity of CRP (at the routinely used cutoff of 80 μg/ml) from 0.56 to 0.88 (57% increase; Table 8). In this analysis a patient is classified as having a bacterial infection if his CRP levels were higher than 80 μg/ml or his Neopterin levels were lower than 4 pg/ml.

Table 7 provides data illustrating that levels of NGAL can be combined with other biomarkers to improve overall diagnostic performance (N=66). A patient was classified as having a bacterial infection in the following cases (according to the evaluated determinant): if his CRP levels were higher than the indicated cutoff (20 μg/ml or 80 μg/ml) OR his NGAL levels were higher than 150 ng/ml; if his TRAIL levels were lower than the indicated cutoff (70 pg/ml) OR his NGAL levels were higher than 150 ng/ml; if his IP-10 levels were lower than the indicated cutoff (500 pg/ml) OR his NGAL levels were higher than 150 ng/ml; if his CRP-TRAIL-IP-10 signature score was higher than 65 OR his NGAL levels were higher than 150 ng/ml.

TABLE 7

| Biomarker | Sensitivity (biomarker alone) | Specificity (biomarker alone) | Sensitivity (biomarker + NGAL 150 ng/ml cutoff) | Specificity (biomarker + NGAL 150 ng/ml cutoff) | Delta sensitivity | Delta specificity |
|---|---|---|---|---|---|---|
| CRP (20 µg/ml) | 0.94 | 0.63 | 1.00 | 0.56 | 0.06 | −0.06 |
| CRP (80 µg/ml) | 0.59 | 0.97 | 0.74 | 0.84 | 0.15 | −0.13 |
| TRAIL (70 pg/ml) | 0.71 | 0.97 | 0.79 | 0.81 | 0.09 | −0.16 |
| IP-10 (500 pg/ml) | 0.79 | 0.66 | 0.88 | 0.63 | 0.09 | −0.03 |
| CRP + TRAIL + IP-10 signature | 0.83 | 1.00 | 0.90 | 0.89 | 0.07 | −0.11 |

Table 8 below provides data showing that the levels of Neopterin can be combined with other biomarkers to improve overall diagnostic performance (N=74). A patient was classified as having a bacterial infection in the following cases (according to the evaluated determinant): if his CRP levels were higher than the indicated cutoff (20 µg/ml or 80 µg/ml) OR his Neopterin levels were lower than 4 pg/ml; if his TRAIL levels were lower than the indicated cutoff (70 pg/ml) OR his Neopterin levels were lower than 4 pg/ml; if his IP-0 levels were lower than the indicated cutoff (500 pg/ml) OR his Neopterin levels were lower than 4 pg/ml; if his CRP-TRAIL-IP-10 signature score was higher than 65 OR his Neopterin levels were lower than 4 pg/ml.

TABLE 8

| Biomarker | Sensitivity (biomarker alone) | Specificity (biomarker alone) | Sensitivity (biomarker + Neopterin 4 pg/ml cutoff) | Specificity (biomarker + Neopterin 4 pg/ml cutoff) | Delta sensitivity | Delta specificity |
|---|---|---|---|---|---|---|
| CRP (20 µg/ml) | 0.82 | 0.58 | 1.00 | 0.38 | 0.18 | −0.20 |
| CRP (80 µg/ml) | 0.56 | 0.95 | 0.88 | 0.68 | 0.32 | −0.28 |
| TRAIL (70 pg/ml) | 0.74 | 0.95 | 0.88 | 0.70 | 0.15 | −0.25 |
| IP-10 (500 pg/ml) | 0.76 | 0.68 | 0.79 | 0.58 | 0.03 | −0.10 |
| CRP + TRAIL + IP-10 signature | 0.79 | 0.92 | 0.94 | 0.68 | 0.15 | −0.25 |

FIGS. 17A-18B demonstrate the ability of NGAL and Neopterin to increase the sensitivity (at the expense of specificity) of the CRP, TRAIL, and IP-10 signature, using selected cutoff in children but not in adults (consistent with the findings described in FIGS. 8A-8C).

Next, the present inventors evaluated the diagnostic accuracy of triplets of determinants. They developed a linear logistic regression classifier for each triplet (45,760 combinations) and further calculated for these triplets the measures of accuracy in distinguishing between bacterial (or mixed) and viral patients including AUC, MCC, total accuracy, sensitivity, specificity and Wilcoxon ranksum P-value. Table 9 presents different determinant triplets with very high accuracy levels (AUCs between 0.89-0.99, average AUC 0.95) when tested on 111 infectious disease patients.

TABLE 9

| Feature #1 | Feature #2 | Feature #3 | AUC | ranksum P-value | MCC | Total accuracy | Sensitivity | Specificity |
|---|---|---|---|---|---|---|---|---|
| Angiogenin | CRP | Progranulin | 0.99 | 2.39E−05 | 0.76 | 0.91 | 0.92 | 0.89 |
| CRP | Complement factor D | NGAL | 0.99 | 3.52E−05 | 0.76 | 0.88 | 0.89 | 0.88 |
| CRP | Osteopontin | Pro Cathepsin B | 0.98 | 4.35E−06 | 0.69 | 0.86 | 0.89 | 0.80 |
| CRP | Pentraxin3 | Pro Cathepsin B | 0.98 | 3.38E−06 | 0.69 | 0.88 | 0.82 | 1.00 |
| CRP | Pentraxin3 | Progranulin | 0.98 | 4.35E−06 | 0.70 | 0.86 | 0.82 | 0.93 |
| APRIL | E Cadherin | TRAIL | 0.98 | 6.08E−06 | 0.73 | 0.86 | 0.85 | 0.89 |
| Angiopoietin1 | TGF B1 | TRAIL | 0.98 | 1.21E−06 | 0.77 | 0.89 | 0.93 | 0.83 |
| CD 23 | E Cadherin | TRAIL | 0.98 | 6.08E−06 | 0.62 | 0.84 | 0.81 | 0.89 |
| CD14 | E Cadherin | TRAIL | 0.98 | 1.02E−05 | 0.59 | 0.84 | 0.82 | 0.89 |
| CD95 | E Cadherin | TRAIL | 0.98 | 3.86E−06 | 0.67 | 0.89 | 0.81 | 1.00 |
| CRP | Complement factor D | Progranulin | 0.98 | 5.71E−07 | 0.77 | 0.91 | 0.92 | 0.89 |
| Dkk1 | E Cadherin | TRAIL | 0.98 | 7.62E−06 | 0.63 | 0.86 | 0.81 | 0.94 |
| E Cadherin | Endostatin | TRAIL | 0.98 | 9.13E−06 | 0.64 | 0.84 | 0.82 | 0.89 |

TABLE 9-continued

| Feature #1 | Feature #2 | Feature #3 | AUC | ranksum P-value | MCC | Total accuracy | Sensitivity | Specificity |
|---|---|---|---|---|---|---|---|---|
| E Cadherin | IL18 | TRAIL | 0.98 | 9.13E−06 | 0.53 | 0.82 | 0.82 | 0.83 |
| E Cadherin | Leptin | TRAIL | 0.98 | 1.32E−05 | 0.58 | 0.84 | 0.81 | 0.89 |
| E Cadherin | RBP4 | TRAIL | 0.98 | 6.38E−05 | 0.67 | 0.84 | 0.89 | 0.78 |
| E Cadherin | TRAIL | Thrombospondin2 | 0.98 | 6.08E−06 | 0.57 | 0.84 | 0.81 | 0.89 |
| E Cadherin | TRAIL | Tie2 | 0.98 | 7.62E−06 | 0.67 | 0.84 | 0.81 | 0.89 |
| E Cadherin | TRAIL | Vitamin D Binding Protein | 0.98 | 3.40E−06 | 0.54 | 0.89 | 0.82 | 1.00 |
| E Cadherin | TRAIL | uPAR | 0.98 | 1.06E−05 | 0.58 | 0.84 | 0.77 | 0.94 |
| Angiogenin | E Cadherin | TRAIL | 0.98 | 6.81E−06 | 0.62 | 0.84 | 0.81 | 0.89 |
| Angiopoietin1 | CD 23 | TRAIL | 0.98 | 2.72E−06 | 0.67 | 0.89 | 0.89 | 0.89 |
| Angiopoietin1 | Endostatin | TRAIL | 0.98 | 2.71E−06 | 0.68 | 0.87 | 0.89 | 0.83 |
| Angiopoietin1 | IGFBP3 | TRAIL | 0.98 | 1.92E−06 | 0.72 | 0.89 | 0.89 | 0.89 |
| Angiopoietin1 | P Selectin | TRAIL | 0.98 | 3.25E−07 | 0.86 | 0.96 | 0.96 | 0.94 |
| Angiopoietin2 | E Cadherin | TRAIL | 0.98 | 1.19E−06 | 0.57 | 0.82 | 0.81 | 0.83 |
| E Cadherin | GCP2 | TRAIL | 0.98 | 6.81E−06 | 0.72 | 0.86 | 0.89 | 0.83 |
| E Cadherin | GDF15 | TRAIL | 0.98 | 3.44E−06 | 0.62 | 0.89 | 0.81 | 1.00 |
| E Cadherin | IGFBP3 | TRAIL | 0.98 | 3.86E−06 | 0.67 | 0.89 | 0.85 | 0.94 |
| E Cadherin | MMP2 | TRAIL | 0.98 | 4.33E−06 | 0.68 | 0.84 | 0.82 | 0.89 |
| E Cadherin | Neopterin | TRAIL | 0.98 | 7.62E−06 | 0.58 | 0.89 | 0.81 | 1.00 |
| E Cadherin | SLPI | TRAIL | 0.98 | 7.36E−06 | 0.54 | 0.87 | 0.78 | 1.00 |
| Angiopoietin1 | IL18 | TRAIL | 0.98 | 2.42E−06 | 0.58 | 0.87 | 0.85 | 0.89 |
| Angiopoietin1 | MMP2 | TRAIL | 0.98 | 6.43E−05 | 0.64 | 0.87 | 0.89 | 0.83 |
| Angiopoietin1 | TRAIL | VCAM1 | 0.98 | 3.80E−06 | 0.72 | 0.87 | 0.89 | 0.83 |
| CD95 | CRP | NGAL | 0.98 | 1.97E−06 | 0.72 | 0.86 | 0.85 | 0.88 |
| Corin | E Cadherin | TRAIL | 0.98 | 3.04E−06 | 0.63 | 0.89 | 0.85 | 0.94 |
| Cystatin C | E Cadherin | TRAIL | 0.98 | 1.72E−06 | 0.77 | 0.89 | 0.89 | 0.89 |
| E Cadherin | TGF B1 | TRAIL | 0.98 | 8.20E−06 | 0.59 | 0.84 | 0.78 | 0.94 |
| Progranulin | TRAIL | Vitamin D Binding Protein | 0.98 | 3.80E−06 | 0.63 | 0.84 | 0.82 | 0.89 |
| APRIL | Angiopoietin1 | TRAIL | 0.98 | 1.19E−06 | 0.72 | 0.89 | 0.89 | 0.89 |
| APRIL | Progranulin | TRAIL | 0.98 | 3.06E−06 | 0.72 | 0.86 | 0.89 | 0.83 |
| Angiopoietin1 | GDF15 | TRAIL | 0.98 | 3.06E−06 | 0.67 | 0.89 | 0.89 | 0.89 |
| Angiopoietin1 | TRAIL | Thrombospondin2 | 0.98 | 2.72E−06 | 0.62 | 0.86 | 0.85 | 0.89 |
| Angiopoietin1 | TRAIL | Tie2 | 0.98 | 2.72E−06 | 0.72 | 0.89 | 0.92 | 0.83 |
| Angiopoietin1 | TRAIL | a1 Acid Glycoprotein | 0.98 | 6.08E−06 | 0.57 | 0.84 | 0.81 | 0.89 |
| CD 23 | Progranulin | TRAIL | 0.98 | 8.51E−06 | 0.62 | 0.82 | 0.77 | 0.89 |
| CRP | Leptin R | Progranulin | 0.98 | 9.32E−07 | 0.77 | 0.89 | 0.89 | 0.89 |
| CRP | Osteoprotegerin | Progranulin | 0.98 | 3.06E−06 | 0.67 | 0.89 | 0.85 | 0.94 |
| E Cadherin | IL19 | TRAIL | 0.98 | 7.62E−06 | 0.63 | 0.84 | 0.81 | 0.89 |
| E Cadherin | Resistin | TRAIL | 0.98 | 1.92E−06 | 0.77 | 0.91 | 0.92 | 0.89 |
| E Cadherin | TRAIL | a1 Acid Glycoprotein | 0.98 | 6.81E−06 | 0.67 | 0.86 | 0.85 | 0.89 |
| Angiopoietin1 | Cystatin C | TRAIL | 0.98 | 2.42E−06 | 0.72 | 0.87 | 0.85 | 0.89 |
| Angiopoietin1 | SLPI | TRAIL | 0.98 | 3.40E−06 | 0.58 | 0.87 | 0.82 | 0.94 |
| Angiopoietin1 | TRAIL | Vitamin D Binding Protein | 0.98 | 1.72E−06 | 0.63 | 0.89 | 0.85 | 0.94 |
| CD142 | Progranulin | TRAIL | 0.98 | 4.94E−06 | 0.80 | 0.91 | 0.89 | 0.93 |
| CRP | LIGHT | NGAL | 0.98 | 4.14E−05 | 0.66 | 0.84 | 0.81 | 0.88 |
| CRP | NGAL | uPAR | 0.98 | 8.19E−07 | 0.77 | 0.91 | 0.92 | 0.88 |
| E Cadherin | ICAM1 | TRAIL | 0.98 | 6.60E−06 | 0.68 | 0.84 | 0.85 | 0.83 |
| E Cadherin | P Selectin | TRAIL | 0.98 | 2.16E−06 | 0.77 | 0.89 | 0.89 | 0.89 |
| MMP2 | Progranulin | TRAIL | 0.98 | 3.92E−05 | 0.63 | 0.84 | 0.85 | 0.83 |
| P Selectin | Progranulin | TRAIL | 0.98 | 8.51E−07 | 0.68 | 0.91 | 0.96 | 0.83 |
| Pentraxin3 | Progranulin | TRAIL | 0.98 | 7.16E−06 | 0.70 | 0.88 | 0.85 | 0.93 |
| Progranulin | SLPI | TRAIL | 0.98 | 5.92E−06 | 0.54 | 0.84 | 0.82 | 0.89 |
| Angiogenin | Angiopoietin1 | TRAIL | 0.97 | 2.72E−06 | 0.72 | 0.86 | 0.85 | 0.89 |
| Angiopoietin1 | CD95 | TRAIL | 0.97 | 2.42E−06 | 0.67 | 0.86 | 0.85 | 0.89 |
| Angiopoietin1 | IL19 | TRAIL | 0.97 | 4.33E−06 | 0.72 | 0.89 | 0.92 | 0.83 |
| Angiopoietin1 | Leptin | TRAIL | 0.97 | 4.85E−06 | 0.67 | 0.86 | 0.85 | 0.89 |
| Angiopoietin1 | MBL | TRAIL | 0.97 | 1.34E−06 | 0.72 | 0.91 | 0.89 | 0.94 |
| Angiopoietin1 | RBP4 | TRAIL | 0.97 | 2.80E−05 | 0.67 | 0.86 | 0.89 | 0.83 |
| Angiopoietin1 | Resistin | TRAIL | 0.97 | 1.34E−06 | 0.81 | 0.93 | 0.96 | 0.89 |
| CD95 | Progranulin | TRAIL | 0.97 | 4.85E−06 | 0.62 | 0.84 | 0.81 | 0.89 |
| CRP | Progranulin | Resistin | 0.97 | 2.16E−06 | 0.67 | 0.86 | 0.89 | 0.83 |
| CXCL13 | E Cadherin | TRAIL | 0.97 | 6.08E−06 | 0.62 | 0.86 | 0.81 | 0.94 |
| Dkk1 | Progranulin | TRAIL | 0.97 | 6.81E−06 | 0.53 | 0.84 | 0.81 | 0.89 |
| E Cadherin | Leptin R | TRAIL | 0.97 | 3.86E−06 | 0.77 | 0.89 | 0.89 | 0.89 |
| E Cadherin | MIF | TRAIL | 0.97 | 9.32E−07 | 0.82 | 0.91 | 0.89 | 0.94 |
| E Cadherin | TRAIL | VEGF C | 0.97 | 3.86E−06 | 0.65 | 0.86 | 0.85 | 0.89 |
| Pro Cathepsin B | Prostaglandin E2 | TRAIL | 0.97 | 5.43E−06 | 0.77 | 0.91 | 0.89 | 0.94 |
| Angiopoietin1 | Corin | TRAIL | 0.97 | 1.72E−06 | 0.63 | 0.89 | 0.89 | 0.89 |
| Angiopoietin1 | PCSK9 | TRAIL | 0.97 | 1.72E−06 | 0.72 | 0.89 | 0.89 | 0.89 |
| CRP | IL19 | NGAL | 0.97 | 9.30E−07 | 0.66 | 0.91 | 0.85 | 1.00 |
| Endostatin | Progranulin | TRAIL | 0.97 | 1.02E−05 | 0.63 | 0.84 | 0.85 | 0.83 |
| PCSK9 | Progranulin | TRAIL | 0.97 | 4.75E−06 | 0.72 | 0.87 | 0.93 | 0.78 |
| Progranulin | TGF B1 | TRAIL | 0.97 | 6.60E−06 | 0.59 | 0.84 | 0.82 | 0.89 |

TABLE 9-continued

| Feature #1 | Feature #2 | Feature #3 | AUC | ranksum P-value | MCC | Total accuracy | Sensitivity | Specificity |
|---|---|---|---|---|---|---|---|---|
| Angiopoietin | Progranulin | TRAIL | 0.97 | 7.62E−06 | 0.57 | 0.84 | 0.81 | 0.89 |
| Angiopoietin1 | Angiopoietin2 | TRAIL | 0.97 | 3.86E−06 | 0.67 | 0.86 | 0.85 | 0.89 |
| Angiopoietin1 | Dkk1 | TRAIL | 0.97 | 1.92E−06 | 0.67 | 0.89 | 0.85 | 0.94 |
| Angiopoietin1 | GCP2 | TRAIL | 0.97 | 2.72E−06 | 0.67 | 0.86 | 0.89 | 0.83 |
| Angiopoietin1 | LIGHT | TRAIL | 0.97 | 1.19E−06 | 0.72 | 0.89 | 0.85 | 0.94 |
| Angiopoietin1 | Leptin R | TRAIL | 0.97 | 1.92E−06 | 0.76 | 0.89 | 0.92 | 0.83 |
| Angiopoietin1 | Neopterin | TRAIL | 0.97 | 3.06E−06 | 0.62 | 0.84 | 0.81 | 0.89 |
| Angiopoietin1 | TRAIL | uPAR | 0.97 | 3.06E−06 | 0.57 | 0.86 | 0.85 | 0.89 |
| Angiopoietin2 | Progranulin | TRAIL | 0.97 | 1.83E−05 | 0.62 | 0.84 | 0.81 | 0.89 |
| CD27 | E Cadherin | TRAIL | 0.97 | 6.08E−06 | 0.52 | 0.86 | 0.81 | 0.94 |
| CRP | E Cadherin | Resistin | 0.97 | 7.62E−06 | 0.67 | 0.86 | 0.89 | 0.83 |
| CRP | Neopterin | Pro Cathepsin B | 0.97 | 4.33E−06 | 0.73 | 0.91 | 0.92 | 0.89 |
| GDF15 | Progranulin | TRAIL | 0.97 | 6.08E−06 | 0.72 | 0.86 | 0.89 | 0.83 |
| IGFBP3 | Progranulin | TRAIL | 0.97 | 4.85E−06 | 0.57 | 0.86 | 0.85 | 0.89 |
| Progranulin | RBP4 | TRAIL | 0.97 | 3.83E−05 | 0.67 | 0.84 | 0.81 | 0.89 |
| Progranulin | Resistin | TRAIL | 0.97 | 6.81E−06 | 0.81 | 0.93 | 0.92 | 0.94 |
| Progranulin | TRAIL | Tie2 | 0.97 | 8.51E−06 | 0.62 | 0.84 | 0.85 | 0.83 |
| Angiopoietin1 | CD14 | TRAIL | 0.97 | 1.93E−06 | 0.63 | 0.87 | 0.85 | 0.89 |
| BDNF | CRP | IL19 | 0.97 | 1.70E−06 | 0.72 | 0.89 | 0.92 | 0.84 |
| BDNF | CRP | VEGF C | 0.97 | 2.28E−05 | 0.82 | 0.91 | 0.88 | 0.94 |
| CRP | E Selectin | Neopterin | 0.97 | 1.04E−05 | 0.76 | 0.91 | 0.92 | 0.88 |
| Corin | Progranulin | TRAIL | 0.97 | 3.40E−06 | 0.67 | 0.87 | 0.82 | 0.94 |
| E Cadherin | PCSK9 | TRAIL | 0.97 | 8.20E−06 | 0.55 | 0.84 | 0.78 | 0.94 |
| E Cadherin | TRAIL | VCAM1 | 0.97 | 4.33E−05 | 0.64 | 0.82 | 0.78 | 0.89 |
| Adiponectin | Angiopoietin1 | TRAIL | 0.97 | 4.33E−06 | 0.67 | 0.89 | 0.89 | 0.89 |
| Angiopoietin1 | MIF | TRAIL | 0.97 | 9.32E−07 | 0.76 | 0.89 | 0.89 | 0.89 |
| Angiopoietin1 | Pro Cathepsin B | TRAIL | 0.97 | 9.43E−11 | 0.80 | 0.90 | 0.91 | 0.90 |
| Angiopoietin1 | TRAIL | VEGF C | 0.97 | 1.19E−06 | 0.81 | 0.91 | 0.89 | 0.94 |
| Angiopoietin2 | Pro Cathepsin B | TRAIL | 0.97 | 1.18E−05 | 0.67 | 0.86 | 0.89 | 0.83 |
| CRP | E Cadherin | Neopterin | 0.97 | 9.51E−06 | 0.61 | 0.89 | 0.89 | 0.89 |
| CRP | E Selectin | Pentraxin3 | 0.97 | 4.35E−06 | 0.70 | 0.86 | 0.82 | 0.93 |
| CRP | MMP7 | Neopterin | 0.97 | 6.44E−06 | 0.58 | 0.86 | 0.88 | 0.83 |
| CRP | NGAL | Pentraxin3 | 0.97 | 9.15E−06 | 0.70 | 0.88 | 0.85 | 0.93 |
| CRP | Neopterin | Substance P | 0.97 | 1.70E−06 | 0.61 | 0.89 | 0.89 | 0.89 |
| CRP | Pro Cathepsin B | Resistin | 0.97 | 4.85E−06 | 0.67 | 0.86 | 0.81 | 0.94 |
| E Cadherin | MBL | TRAIL | 0.97 | 2.16E−06 | 0.77 | 0.91 | 0.89 | 0.94 |
| Progranulin | Prostaglandin E2 | TRAIL | 0.97 | 2.72E−06 | 0.72 | 0.89 | 0.89 | 0.89 |
| Progranulin | TFPI | TRAIL | 0.97 | 6.33E−06 | 0.75 | 0.88 | 0.85 | 0.93 |
| Progranulin | TRAIL | Thrombospondin2 | 0.97 | 5.43E−06 | 0.62 | 0.84 | 0.81 | 0.89 |
| Progranulin | TRAIL | a1 Acid Glycoprotein | 0.97 | 5.77E−05 | 0.62 | 0.84 | 0.85 | 0.83 |
| LIGHT | NGAL | TRAIL | 0.97 | 1.16E−05 | 0.76 | 0.91 | 0.92 | 0.88 |
| Angiopoietin1 | CRP | Neopterin | 0.97 | 2.72E−06 | 0.61 | 0.89 | 0.89 | 0.89 |
| CRP | Cystatin C | NGAL | 0.97 | 1.82E−06 | 0.71 | 0.86 | 0.85 | 0.88 |
| CRP | NGAL | Resistin | 0.97 | 1.83E−05 | 0.81 | 0.91 | 0.92 | 0.88 |
| IL19 | NGAL | TRAIL | 0.97 | 0.00044 | 0.61 | 0.86 | 0.85 | 0.88 |
| CRP | Neopterin | Progranulin | 0.97 | 6.08E−06 | 0.67 | 0.84 | 0.81 | 0.89 |
| Angiogenin | CRP | NGAL | 0.96 | 5.16E−06 | 0.72 | 0.86 | 0.85 | 0.88 |
| CRP | Dkk1 | NGAL | 0.96 | 3.72E−05 | 0.56 | 0.86 | 0.81 | 0.94 |
| CRP | MIF | NGAL | 0.96 | 2.84E−06 | 0.66 | 0.86 | 0.85 | 0.88 |
| E Cadherin | NGAL | TRAIL | 0.96 | 2.97E−10 | 0.76 | 0.92 | 0.88 | 0.95 |
| Angiopoietin1 | NGAL | TRAIL | 0.96 | 2.04E−10 | 0.75 | 0.92 | 0.88 | 0.95 |
| CRP | NGAL | TFPI | 0.96 | 7.16E−06 | 0.66 | 0.86 | 0.82 | 0.93 |
| NGAL | Progranulin | TRAIL | 0.96 | 9.60E−10 | 0.80 | 0.92 | 0.91 | 0.92 |
| CRP | NGAL | Neopterin | 0.96 | 3.61E−06 | 0.62 | 0.86 | 0.89 | 0.82 |
| Complement factor D | NGAL | TRAIL | 0.96 | 1.83E−05 | 0.71 | 0.88 | 0.85 | 0.94 |
| CD27 | CRP | NGAL | 0.96 | 9.25E−06 | 0.66 | 0.86 | 0.89 | 0.82 |
| CRP | MBL | NGAL | 0.96 | 4.07E−06 | 0.62 | 0.88 | 0.92 | 0.82 |
| CRP | NGAL | Osteoprotegerin | 0.96 | 8.24E−06 | 0.62 | 0.81 | 0.77 | 0.88 |
| Neopterin | Progranulin | TRAIL | 0.96 | 1.19E−05 | 0.57 | 0.82 | 0.77 | 0.89 |
| CRP | NGAL | Osteopontin | 0.96 | 1.67E−05 | 0.56 | 0.83 | 0.85 | 0.80 |
| Angiopoietin2 | CRP | NGAL | 0.96 | 4.58E−06 | 0.66 | 0.86 | 0.89 | 0.82 |
| CRP | Corin | NGAL | 0.96 | 3.40E−06 | 0.68 | 0.87 | 0.89 | 0.83 |
| CRP | GCP2 | NGAL | 0.96 | 5.81E−06 | 0.53 | 0.84 | 0.89 | 0.77 |
| Corin | NGAL | TRAIL | 0.96 | 1.26E−05 | 0.68 | 0.87 | 0.85 | 0.89 |
| CD142 | CRP | NGAL | 0.96 | 8.10E−06 | 0.60 | 0.83 | 0.82 | 0.87 |
| CRP | IL18 | NGAL | 0.96 | 4.18E−05 | 0.57 | 0.84 | 0.89 | 0.77 |
| APRIL | CRP | NGAL | 0.96 | 5.81E−06 | 0.57 | 0.81 | 0.81 | 0.82 |
| CRP | CXCL13 | NGAL | 0.96 | 7.34E−06 | 0.61 | 0.84 | 0.85 | 0.82 |
| CRP | Leptin | NGAL | 0.96 | 2.55E−05 | 0.53 | 0.81 | 0.77 | 0.88 |
| CRP | NGAL | RBP4 | 0.96 | 1.63E−05 | 0.57 | 0.86 | 0.92 | 0.77 |
| CRP | NGAL | VEGF C | 0.96 | 3.86E−06 | 0.62 | 0.84 | 0.81 | 0.89 |
| Neopterin | Pro Cathepsin B | TRAIL | 0.96 | 1.83E−05 | 0.63 | 0.86 | 0.81 | 0.94 |
| CRP | Neopterin | ProMMP10 | 0.95 | 4.66E−06 | 0.61 | 0.91 | 0.96 | 0.82 |
| CRP | NGAL | TRAIL | 0.95 | 6.20E−09 | 0.64 | 0.84 | 0.88 | 0.80 |
| CRP | Endostatin | NGAL | 0.95 | 2.92E−06 | 0.63 | 0.86 | 0.89 | 0.82 |

TABLE 9-continued

| Feature #1 | Feature #2 | Feature #3 | AUC | ranksum P-value | MCC | Total accuracy | Sensitivity | Specificity |
|---|---|---|---|---|---|---|---|---|
| CD95 | NGAL | TRAIL | 0.95 | 1.46E−05 | 0.66 | 0.91 | 0.89 | 0.94 |
| Cystatin C | NGAL | TRAIL | 0.95 | 3.76E−05 | 0.57 | 0.82 | 0.78 | 0.88 |
| CRP | MMP3 | Neopterin | 0.95 | 3.69E−06 | 0.61 | 0.86 | 0.85 | 0.88 |
| CRP | MMP8 | Neopterin | 0.95 | 9.21E−06 | 0.57 | 0.82 | 0.78 | 0.88 |
| CRP | Myeloperoxidase | Neopterin | 0.95 | 7.35E−06 | 0.51 | 0.89 | 0.93 | 0.82 |
| NGAL | Prostaglandin E2 | TRAIL | 0.95 | 2.80E−05 | 0.62 | 0.86 | 0.85 | 0.89 |
| CRP | NGAL | a1 Acid Glycoprotein | 0.95 | 1.04E−05 | 0.57 | 0.84 | 0.89 | 0.77 |
| Clusterin | NGAL | TRAIL | 0.95 | 0.000101 | 0.71 | 0.86 | 0.89 | 0.82 |
| Myeloperoxidase | NGAL | TRAIL | 0.95 | 2.59E−09 | 0.68 | 0.89 | 0.88 | 0.90 |
| NGAL | Pro Cathepsin B | TRAIL | 0.95 | 2.87E−09 | 0.69 | 0.86 | 0.82 | 0.90 |
| MMP8 | NGAL | TRAIL | 0.95 | 7.69E−09 | 0.64 | 0.90 | 0.85 | 0.95 |
| NGAL | ProMMP10 | TRAIL | 0.95 | 4.48E−09 | 0.67 | 0.88 | 0.85 | 0.90 |
| NGAL | TRAIL | VEGF C | 0.95 | 3.45E−05 | 0.72 | 0.86 | 0.89 | 0.83 |
| Adiponectin | CRP | NGAL | 0.95 | 9.25E−06 | 0.57 | 0.86 | 0.92 | 0.77 |
| CRP | GDF15 | NGAL | 0.95 | 9.25E−06 | 0.57 | 0.84 | 0.89 | 0.77 |
| CRP | IL1R | NGAL | 0.95 | 5.81E−06 | 0.57 | 0.81 | 0.81 | 0.82 |
| E Selectin | NGAL | TRAIL | 0.95 | 3.89E−05 | 0.66 | 0.89 | 0.85 | 0.92 |
| IP-10 | NGAL | TRAIL | 0.95 | 3.18E−09 | 0.68 | 0.89 | 0.82 | 0.95 |
| Leptin | NGAL | TRAIL | 0.95 | 0.000204 | 0.62 | 0.81 | 0.81 | 0.82 |
| NGAL | P Selectin | TRAIL | 0.95 | 3.76E−05 | 0.71 | 0.86 | 0.89 | 0.82 |
| CRP | Leptin R | NGAL | 0.95 | 5.43E−06 | 0.58 | 0.82 | 0.73 | 0.94 |
| CRP | NGAL | Prostaglandin E2 | 0.95 | 4.33E−06 | 0.53 | 0.82 | 0.77 | 0.89 |
| CRP | Clusterin | NGAL | 0.95 | 5.16E−06 | 0.53 | 0.84 | 0.89 | 0.77 |
| CRP | Fetuin A | NGAL | 0.95 | 5.81E−06 | 0.53 | 0.86 | 0.92 | 0.77 |
| CRP | IGFBP3 | NGAL | 0.95 | 1.16E−05 | 0.57 | 0.86 | 0.92 | 0.77 |
| CXCL13 | NGAL | TRAIL | 0.95 | 4.38E−05 | 0.56 | 0.81 | 0.77 | 0.88 |
| MMP2 | NGAL | TRAIL | 0.95 | 0.00088 | 0.62 | 0.84 | 0.89 | 0.77 |
| NGAL | Pentraxin3 | TRAIL | 0.95 | 7.37E−05 | 0.70 | 0.86 | 0.85 | 0.87 |
| NGAL | RBP4 | TRAIL | 0.95 | 0.000364 | 0.71 | 0.86 | 0.89 | 0.82 |
| NGAL | TRAIL | VCAM1 | 0.95 | 0.000273 | 0.57 | 0.80 | 0.82 | 0.77 |
| CD14 | Neopterin | TRAIL | 0.95 | 2.74E−09 | 0.65 | 0.88 | 0.88 | 0.88 |
| CXCL13 | Neopterin | TRAIL | 0.95 | 1.70E−09 | 0.65 | 0.88 | 0.85 | 0.90 |
| MMP8 | Neopterin | TRAIL | 0.95 | 0.00017 | 0.57 | 0.82 | 0.78 | 0.88 |
| Leptin R | NGAL | TRAIL | 0.94 | 1.64E−05 | 0.62 | 0.86 | 0.85 | 0.89 |
| MMP3 | NGAL | TRAIL | 0.94 | 3.91E−09 | 0.72 | 0.89 | 0.82 | 0.95 |
| NGAL | TGF B1 | TRAIL | 0.94 | 5.82E−05 | 0.72 | 0.87 | 0.93 | 0.78 |
| Neopterin | PCSK9 | TRAIL | 0.94 | 4.10E−09 | 0.65 | 0.85 | 0.85 | 0.85 |
| CRP | MMP3 | NGAL | 0.94 | 2.25E−09 | 0.64 | 0.85 | 0.94 | 0.77 |
| Angiopoietin2 | NGAL | TRAIL | 0.94 | 0.000152 | 0.66 | 0.86 | 0.92 | 0.77 |
| BAFF | NGAL | TRAIL | 0.94 | 6.85E−09 | 0.64 | 0.90 | 0.84 | 0.95 |
| CRP | NGAL | P Selectin | 0.94 | 4.15E−06 | 0.55 | 0.86 | 0.93 | 0.77 |
| CRP | NGAL | Thrombospondin2 | 0.94 | 5.81E−06 | 0.53 | 0.86 | 0.92 | 0.77 |
| CRP | NGAL | Tie2 | 0.94 | 7.34E−06 | 0.53 | 0.81 | 0.85 | 0.77 |
| GCP2 | NGAL | TRAIL | 0.94 | 3.94E−05 | 0.71 | 0.86 | 0.89 | 0.82 |
| IL18 | NGAL | TRAIL | 0.94 | 5.13E−05 | 0.62 | 0.84 | 0.85 | 0.82 |
| MMP7 | NGAL | TRAIL | 0.94 | 1.20E−08 | 0.63 | 0.90 | 0.84 | 0.95 |
| NGAL | Osteoprotegerin | TRAIL | 0.94 | 7.43E−05 | 0.71 | 0.86 | 0.89 | 0.82 |
| NGAL | PCSK9 | TRAIL | 0.94 | 6.97E−05 | 0.62 | 0.84 | 0.85 | 0.82 |
| NGAL | Substance P | TRAIL | 0.94 | 2.44E−08 | 0.70 | 0.86 | 0.88 | 0.84 |
| APRIL | Neopterin | TRAIL | 0.94 | 7.18E−09 | 0.66 | 0.85 | 0.85 | 0.85 |
| Adiponectin | Neopterin | TRAIL | 0.94 | 1.05E−09 | 0.73 | 0.88 | 0.88 | 0.88 |
| Leptin R | Neopterin | TRAIL | 0.94 | 2.77E−09 | 0.67 | 0.88 | 0.85 | 0.90 |
| Myeloperoxidase | Neopterin | TRAIL | 0.94 | 0.00014 | 0.57 | 0.82 | 0.85 | 0.77 |
| Neopterin | TRAIL | VCAM1 | 0.94 | 2.39E−09 | 0.73 | 0.88 | 0.88 | 0.88 |
| BDNF | NGAL | TRAIL | 0.94 | 7.88E−09 | 0.66 | 0.90 | 0.84 | 0.95 |
| CD 23 | NGAL | TRAIL | 0.94 | 4.70E−05 | 0.67 | 0.86 | 0.89 | 0.83 |
| Angiopoietin2 | Neopterin | TRAIL | 0.94 | 6.99E−09 | 0.62 | 0.84 | 0.82 | 0.85 |
| CRP | Neopterin | TRAIL | 0.94 | 5.19E−09 | 0.78 | 0.92 | 0.91 | 0.93 |
| Clusterin | Neopterin | TRAIL | 0.94 | 1.61E−09 | 0.70 | 0.88 | 0.85 | 0.90 |
| Fetuin A | Neopterin | TRAIL | 0.94 | 4.16E−09 | 0.68 | 0.85 | 0.85 | 0.85 |
| Neopterin | TRAIL | Thrombospondin2 | 0.94 | 8.51E−09 | 0.65 | 0.86 | 0.82 | 0.90 |
| CRP | ICAM1 | NGAL | 0.94 | 1.03E−05 | 0.53 | 0.82 | 0.85 | 0.77 |
| Angiopoietin | NGAL | TRAIL | 0.94 | 0.000124 | 0.71 | 0.86 | 0.89 | 0.82 |
| Endostatin | NGAL | TRAIL | 0.94 | 0.000104 | 0.71 | 0.86 | 0.89 | 0.82 |
| ICAM1 | NGAL | TRAIL | 0.94 | 4.17E−05 | 0.62 | 0.84 | 0.85 | 0.82 |
| IGFBP3 | NGAL | TRAIL | 0.94 | 6.03E−05 | 0.61 | 0.86 | 0.92 | 0.77 |
| NGAL | Resistin | TRAIL | 0.94 | 9.14E−05 | 0.66 | 0.86 | 0.89 | 0.82 |
| NGAL | SLPI | TRAIL | 0.94 | 0.000127 | 0.62 | 0.84 | 0.85 | 0.82 |
| NGAL | TFPI | TRAIL | 0.94 | 0.000238 | 0.59 | 0.81 | 0.78 | 0.87 |
| NGAL | TRAIL | Thrombospondin2 | 0.94 | 6.03E−05 | 0.66 | 0.86 | 0.89 | 0.82 |
| NGAL | TRAIL | Vitamin D Binding Protein | 0.94 | 7.71E−05 | 0.66 | 0.86 | 0.89 | 0.82 |
| NGAL | TRAIL | a1 Acid Glycoprotein | 0.94 | 0.000112 | 0.61 | 0.86 | 0.85 | 0.88 |
| BAFF | CRP | Neopterin | 0.94 | 7.53E−06 | 0.60 | 0.82 | 0.80 | 0.84 |
| CD142 | Neopterin | TRAIL | 0.94 | 1.11E−08 | 0.72 | 0.91 | 0.87 | 0.94 |

TABLE 9-continued

| Feature #1 | Feature #2 | Feature #3 | AUC | ranksum P-value | MCC | Total accuracy | Sensitivity | Specificity |
|---|---|---|---|---|---|---|---|---|
| Endostatin | Neopterin | TRAIL | 0.94 | 2.74E−09 | 0.65 | 0.88 | 0.85 | 0.90 |
| ICAM1 | Neopterin | TRAIL | 0.94 | 1.29E−09 | 0.73 | 0.88 | 0.88 | 0.88 |
| MMP2 | Neopterin | TRAIL | 0.94 | 2.09E−09 | 0.68 | 0.86 | 0.85 | 0.88 |
| Neopterin | Osteoprotegerin | TRAIL | 0.94 | 1.93E−09 | 0.63 | 0.87 | 0.82 | 0.90 |
| Neopterin | P Selectin | TRAIL | 0.94 | 1.59E−09 | 0.75 | 0.89 | 0.88 | 0.90 |
| Neopterin | TFPI | TRAIL | 0.94 | 2.11E−08 | 0.72 | 0.87 | 0.87 | 0.88 |
| CD 23 | CRP | NGAL | 0.94 | 4.85E−06 | 0.53 | 0.82 | 0.81 | 0.83 |
| Angiogenin | Neopterin | TRAIL | 0.94 | 2.09E−09 | 0.65 | 0.88 | 0.85 | 0.90 |
| Leptin | Neopterin | TRAIL | 0.94 | 1.59E−09 | 0.68 | 0.88 | 0.85 | 0.90 |
| MBL | Neopterin | TRAIL | 0.94 | 1.93E−09 | 0.76 | 0.88 | 0.88 | 0.88 |
| Neopterin | Pentraxin3 | TRAIL | 0.94 | 7.93E−08 | 0.72 | 0.87 | 0.90 | 0.84 |
| Neopterin | RBP4 | TRAIL | 0.94 | 1.21E−09 | 0.71 | 0.88 | 0.85 | 0.90 |
| Neopterin | TRAIL | a1 Acid Glycoprotein | 0.94 | 1.13E−09 | 0.74 | 0.87 | 0.85 | 0.88 |
| CD14 | CRP | NGAL | 0.94 | 8.23E−06 | 0.53 | 0.86 | 0.93 | 0.77 |
| CRP | MMP2 | NGAL | 0.94 | 1.99E−05 | 0.53 | 0.84 | 0.89 | 0.77 |
| APRIL | NGAL | TRAIL | 0.94 | 4.88E−05 | 0.71 | 0.86 | 0.89 | 0.82 |
| Angiogenin | NGAL | TRAIL | 0.94 | 0.000124 | 0.71 | 0.86 | 0.89 | 0.82 |
| CRP | NGAL | Vitamin D Binding Protein | 0.94 | 6.56E−06 | 0.52 | 0.86 | 0.96 | 0.71 |
| MBL | NGAL | TRAIL | 0.94 | 3.53E−05 | 0.71 | 0.91 | 0.89 | 0.94 |
| NGAL | TRAIL | Tie2 | 0.94 | 6.69E−05 | 0.71 | 0.86 | 0.89 | 0.82 |
| NGAL | TRAIL | uPAR | 0.94 | 0.000112 | 0.66 | 0.84 | 0.85 | 0.82 |
| BDNF | CRP | Neopterin | 0.94 | 2.71E−06 | 0.60 | 0.84 | 0.88 | 0.79 |
| CD95 | Neopterin | TRAIL | 0.94 | 3.14E−09 | 0.65 | 0.85 | 0.85 | 0.85 |
| Dkk1 | Neopterin | TRAIL | 0.94 | 4.10E−09 | 0.70 | 0.86 | 0.85 | 0.88 |
| IL18 | Neopterin | TRAIL | 0.94 | 1.29E−09 | 0.68 | 0.87 | 0.88 | 0.85 |
| IL1R | Neopterin | TRAIL | 0.94 | 5.01E−09 | 0.68 | 0.86 | 0.88 | 0.85 |
| MIF | Neopterin | TRAIL | 0.94 | 1.95E−09 | 0.67 | 0.88 | 0.85 | 0.90 |
| Neopterin | ProMMP10 | TRAIL | 0.94 | 5.69E−05 | 0.57 | 0.84 | 0.85 | 0.82 |
| Neopterin | Resistin | TRAIL | 0.94 | 6.12E−09 | 0.65 | 0.88 | 0.85 | 0.90 |
| Neopterin | SLPI | TRAIL | 0.94 | 6.12E−09 | 0.68 | 0.88 | 0.85 | 0.90 |
| Neopterin | TRAIL | Tie2 | 0.94 | 2.24E−09 | 0.68 | 0.88 | 0.85 | 0.90 |
| Neopterin | TRAIL | VEGF C | 0.94 | 4.18E−09 | 0.66 | 0.85 | 0.82 | 0.87 |
| Neopterin | TRAIL | uPAR | 0.94 | 3.84E−09 | 0.65 | 0.86 | 0.82 | 0.90 |
| CD142 | NGAL | TRAIL | 0.94 | 0.000127 | 0.64 | 0.83 | 0.85 | 0.80 |
| CRP | NGAL | TGF B1 | 0.94 | 4.78E−05 | 0.50 | 0.80 | 0.85 | 0.72 |
| CD 23 | Neopterin | TRAIL | 0.94 | 4.48E−09 | 0.67 | 0.88 | 0.85 | 0.90 |
| CD27 | Neopterin | TRAIL | 0.94 | 3.07E−09 | 0.65 | 0.87 | 0.82 | 0.90 |
| GCP2 | Neopterin | TRAIL | 0.94 | 3.14E−09 | 0.70 | 0.86 | 0.85 | 0.88 |
| GDF15 | Neopterin | TRAIL | 0.94 | 4.39E−09 | 0.65 | 0.86 | 0.82 | 0.90 |
| IGFBP3 | Neopterin | TRAIL | 0.94 | 2.56E−09 | 0.67 | 0.88 | 0.85 | 0.90 |
| IL19 | Neopterin | TRAIL | 0.94 | 5.36E−09 | 0.70 | 0.85 | 0.85 | 0.85 |
| Neopterin | Osteopontin | TRAIL | 0.94 | 1.16E−07 | 0.72 | 0.89 | 0.87 | 0.91 |
| Neopterin | Prostaglandin E2 | TRAIL | 0.94 | 3.91E−09 | 0.67 | 0.85 | 0.91 | 0.80 |
| Neopterin | Substance P | TRAIL | 0.94 | 5.76E−05 | 0.53 | 0.82 | 0.81 | 0.83 |
| Neopterin | TRAIL | Vitamin D Binding Protein | 0.94 | 1.05E−09 | 0.68 | 0.88 | 0.85 | 0.90 |
| CRP | NGAL | SLPI | 0.94 | 1.28E−05 | 0.53 | 0.84 | 0.89 | 0.77 |
| CRP | NGAL | VCAM1 | 0.94 | 1.28E−05 | 0.53 | 0.86 | 0.93 | 0.77 |
| Dkk1 | NGAL | TRAIL | 0.94 | 6.03E−05 | 0.61 | 0.84 | 0.85 | 0.82 |
| Fetuin A | NGAL | TRAIL | 0.94 | 0.000152 | 0.66 | 0.86 | 0.89 | 0.82 |
| GDF15 | NGAL | TRAIL | 0.94 | 0.000101 | 0.66 | 0.84 | 0.85 | 0.82 |
| MIF | NGAL | TRAIL | 0.94 | 2.84E−05 | 0.66 | 0.86 | 0.85 | 0.88 |
| LIGHT | Neopterin | TRAIL | 0.94 | 2.56E−09 | 0.67 | 0.88 | 0.85 | 0.90 |
| CRP | NGAL | Substance P | 0.94 | 1.54E−09 | 0.61 | 0.85 | 0.91 | 0.79 |
| NGAL | Osteopontin | TRAIL | 0.94 | 4.22E−05 | 0.70 | 0.88 | 0.85 | 0.93 |
| Corin | Neopterin | TRAIL | 0.94 | 3.18E−09 | 0.70 | 0.88 | 0.85 | 0.90 |
| Neopterin | TGF B1 | TRAIL | 0.94 | 7.19E−09 | 0.64 | 0.85 | 0.82 | 0.87 |
| CD27 | NGAL | TRAIL | 0.93 | 0.000168 | 0.66 | 0.84 | 0.85 | 0.82 |
| Complement factor D | Neopterin | TRAIL | 0.93 | 2.69E−09 | 0.68 | 0.88 | 0.85 | 0.90 |
| Cystatin C | Neopterin | TRAIL | 0.93 | 3.14E−09 | 0.71 | 0.86 | 0.85 | 0.88 |
| CRP | IP-10 | NGAL | 0.93 | 3.64E−09 | 0.61 | 0.82 | 0.79 | 0.85 |
| BAFF | Neopterin | TRAIL | 0.93 | 9.24E−05 | 0.53 | 0.80 | 0.80 | 0.79 |
| IP-10 | Neopterin | TRAIL | 0.93 | 2.69E−09 | 0.63 | 0.87 | 0.82 | 0.90 |
| CD14 | NGAL | TRAIL | 0.93 | 0.000115 | 0.57 | 0.82 | 0.74 | 0.94 |
| CRP | NGAL | PCSK9 | 0.93 | 8.23E−06 | 0.53 | 0.84 | 0.89 | 0.77 |
| IL1R | NGAL | TRAIL | 0.93 | 0.000168 | 0.57 | 0.79 | 0.81 | 0.77 |
| NGAL | Neopterin | TRAIL | 0.93 | 0.000124 | 0.51 | 0.79 | 0.73 | 0.88 |
| E Selectin | Neopterin | TRAIL | 0.93 | 0.000137 | 0.41 | 0.81 | 0.77 | 0.88 |
| MMP3 | Neopterin | TRAIL | 0.93 | 5.13E−05 | 0.52 | 0.82 | 0.82 | 0.82 |
| CRP | MMP7 | NGAL | 0.93 | 2.59E−08 | 0.68 | 0.84 | 0.81 | 0.87 |
| CRP | NGAL | Progranulin | 0.93 | 3.24E−08 | 0.58 | 0.80 | 0.82 | 0.79 |
| BAFF | CRP | NGAL | 0.93 | 2.91E−08 | 0.63 | 0.81 | 0.81 | 0.82 |
| CRP | NGAL | ProMMP10 | 0.93 | 1.31E−08 | 0.55 | 0.82 | 0.85 | 0.80 |
| CRP | NGAL | Pro Cathepsin B | 0.93 | 5.31E−09 | 0.64 | 0.83 | 0.85 | 0.82 |

TABLE 9-continued

| Feature #1 | Feature #2 | Feature #3 | AUC | ranksum P-value | MCC | Total accuracy | Sensitivity | Specificity |
|---|---|---|---|---|---|---|---|---|
| CRP | Myeloperoxidase | NGAL | 0.93 | 2.36E−08 | 0.58 | 0.81 | 0.82 | 0.80 |
| NGAL | Progranulin | Resistin | 0.93 | 4.61E−05 | 0.67 | 0.86 | 0.84 | 0.88 |
| BDNF | Neopterin | TRAIL | 0.92 | 6.22E−05 | 0.64 | 0.82 | 0.80 | 0.84 |
| MMP7 | Neopterin | TRAIL | 0.92 | 0.000573 | 0.51 | 0.81 | 0.83 | 0.78 |
| CRP | E Cadherin | NGAL | 0.92 | 1.71E−07 | 0.63 | 0.82 | 0.79 | 0.84 |
| CRP | MMP8 | NGAL | 0.92 | 1.31E−08 | 0.61 | 0.82 | 0.85 | 0.80 |
| CRP | E Selectin | NGAL | 0.92 | 1.12E−08 | 0.61 | 0.81 | 0.77 | 0.85 |
| Angiogenin1 | CRP | NGAL | 0.92 | 8.49E−09 | 0.69 | 0.86 | 0.82 | 0.90 |
| Neopterin | Progranulin | Resistin | 0.92 | 9.51E−06 | 0.63 | 0.89 | 0.92 | 0.83 |
| BDNF | CRP | NGAL | 0.92 | 1.58E−08 | 0.60 | 0.80 | 0.84 | 0.76 |
| CRP | Neopterin | Pentraxin3 | 0.91 | 5.41E−07 | 0.50 | 0.79 | 0.90 | 0.69 |
| CRP | Neopterin | TFPI | 0.91 | 4.69E−07 | 0.56 | 0.78 | 0.77 | 0.78 |
| Corin | NGAL | Vitamin D Binding Protein | 0.91 | 0.000127 | 0.38 | 0.77 | 0.74 | 0.82 |
| CRP | Neopterin | Osteopontin | 0.91 | 1.17E−06 | 0.60 | 0.79 | 0.74 | 0.84 |
| CD27 | IL1R | NGAL | 0.91 | 0.000137 | 0.58 | 0.79 | 0.77 | 0.82 |
| IL1R | IP-10 | NGAL | 0.91 | 8.25E−05 | 0.62 | 0.81 | 0.81 | 0.82 |
| Complement factor D | NGAL | Vitamin D Binding Protein | 0.91 | 8.25E−05 | 0.76 | 0.88 | 0.89 | 0.88 |
| CD27 | LIGHT | NGAL | 0.91 | 0.000101 | 0.57 | 0.81 | 0.77 | 0.88 |
| CD142 | CRP | Neopterin | 0.91 | 4.06E−07 | 0.62 | 0.84 | 0.77 | 0.91 |
| Adiponectin | CRP | Neopterin | 0.90 | 6.15E−08 | 0.61 | 0.81 | 0.76 | 0.85 |
| CRP | Neopterin | Osteoprotegerin | 0.90 | 5.68E−08 | 0.56 | 0.84 | 0.88 | 0.80 |
| Corin | NGAL | ProMMP10 | 0.90 | 0.000226 | 0.49 | 0.80 | 0.77 | 0.83 |
| NGAL | Pentraxin3 | Progranulin | 0.90 | 0.000682 | 0.41 | 0.78 | 0.85 | 0.67 |
| Cystatin C | IL1R | NGAL | 0.90 | 0.000101 | 0.58 | 0.84 | 0.85 | 0.82 |
| CRP | Neopterin | Resistin | 0.90 | 1.54E−07 | 0.56 | 0.82 | 0.85 | 0.80 |
| Corin | MMP8 | NGAL | 0.90 | 0.000226 | 0.58 | 0.82 | 0.81 | 0.83 |
| CRP | Corin | Neopterin | 0.90 | 1.39E−07 | 0.61 | 0.79 | 0.76 | 0.82 |
| CRP | IP-10 | Neopterin | 0.90 | 1.17E−07 | 0.51 | 0.78 | 0.79 | 0.78 |
| Angiogenin | CRP | Neopterin | 0.90 | 1.07E−07 | 0.61 | 0.81 | 0.82 | 0.80 |
| Angiopoietin2 | CRP | Neopterin | 0.90 | 1.73E−07 | 0.45 | 0.78 | 0.88 | 0.70 |
| Complement factor D | IP-10 | NGAL | 0.89 | 0.000364 | 0.53 | 0.81 | 0.77 | 0.88 |
| Corin | NGAL | Pentraxin3 | 0.89 | 0.000375 | 0.62 | 0.82 | 0.84 | 0.79 |
| LIGHT | NGAL | Vitamin D Binding Protein | 0.89 | 0.000204 | 0.66 | 0.84 | 0.85 | 0.82 |
| CRP | Complement factor D | Neopterin | 0.89 | 8.66E−08 | 0.56 | 0.82 | 0.79 | 0.85 |
| CD27 | MMP7 | NGAL | 0.89 | 0.001991 | 0.50 | 0.78 | 0.74 | 0.82 |
| CD27 | NGAL | Pentraxin3 | 0.89 | 0.001565 | 0.56 | 0.79 | 0.79 | 0.79 |
| E Cadherin | Neopterin | Resistin | 0.89 | 0.000226 | 0.60 | 0.82 | 0.89 | 0.72 |
| IL1R | Neopterin | Progranulin | 0.89 | 0.000187 | 0.49 | 0.77 | 0.77 | 0.78 |
| Adiponectin | Neopterin | Osteopontin | 0.89 | 2.46E−06 | 0.52 | 0.79 | 0.73 | 0.84 |
| Adiponectin | LIGHT | NGAL | 0.89 | 0.000331 | 0.49 | 0.81 | 0.85 | 0.77 |
| CD27 | Corin | NGAL | 0.89 | 0.00053 | 0.42 | 0.74 | 0.69 | 0.82 |
| Complement factor D | IL1R | NGAL | 0.89 | 9.14E−05 | 0.41 | 0.81 | 0.85 | 0.77 |
| IL19 | IP-10 | NGAL | 0.89 | 0.000185 | 0.47 | 0.77 | 0.69 | 0.88 |
| IL19 | NGAL | Resistin | 0.89 | 6.03E−05 | 0.58 | 0.79 | 0.77 | 0.82 |
| IP-10 | NGAL | Pentraxin3 | 0.89 | 0.001134 | 0.60 | 0.81 | 0.82 | 0.80 |
| CRP | Neopterin | VCAM1 | 0.89 | 3.96E−07 | 0.45 | 0.81 | 0.70 | 0.90 |

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of treating a viral infection in a subject comprising:
    (a) measuring the concentration of NGAL and the concentration of TRAIL in a sample derived of the subject; and
    (b) treating the subject with an anti-viral agent when said concentration of NGAL is below 150 ng/ml and said concentration of TRAIL is above 70 pg/ml.

2. The method of claim 1, further comprising measuring the concentration of IP-10.

3. The method of claim 1, wherein the sample is whole blood or a fraction thereof.

4. The method of claim 1, wherein said viral infection is an acute infection.

5. The method of claim 1, wherein the subject is a child.

6. The method of claim 1, wherein no more than three determinants are measured, wherein said determinants are markers of infection.

7. The method of claim 1, wherein no more than four determinants are measured, wherein said determinants are markers of infection.

8. A method of treating an infection in a subject comprising:
    (a) measuring the concentration of NGAL and the concentration of TRAIL in a sample derived of the subject; and
    (b) treating the subject with:
        (i) an anti-viral agent when said concentration of NGAL is below 150 ng/ml and said concentration of TRAIL is higher than 70 pg/ml; or
        (ii) an antibiotic agent when said concentration of NGAL is above 150 ng/ml and said concentration of TRAIL is below 70 pg/ml.

* * * * *

SEQUENCE LISTING

```
Sequence total quantity: 18
SEQ ID NO: 1            moltype = AA  length = 224
FEATURE                 Location/Qualifiers
source                  1..224
                        mol_type = protein
                        organism = Homo sapiens
SEQUENCE: 1
MEKLLCFLVL TSLSHAFGQT DMSRKAFVFP KESDTSYVSL KAPLTKPLKA FTVCLHFYTE    60
```

```
LSSTRGYSIF SYATKRQDNE ILIFWSKDIG YSFTVGGSEI LFEVPEVTVA PVHICTSWES   120
ASGIVEFWVD GKPRVRKSLK KGYTVGAEAS IILGQEQDSF GGNFEGSQSL VGDIGNVNMW   180
DFVLSPDEIN TIYLGGPFSP NVLNWRALKY EVQGEVFTKP QLWP                   224

SEQ ID NO: 2              moltype = AA   length = 187
FEATURE                   Location/Qualifiers
REGION                    1..187
                          note = amino acid sequences of soluble TRAIL
source                    1..187
                          mol_type = protein
                          organism = synthetic construct
SEQUENCE: 2
TSEETISTVQ EKQQNISPLV RERGPQRVAA HITGTRGRSN TLSSPNSKNE KALGRKINSW   60
ESSRSGHSFL SNLHLRNGEL VIHEKGFYYI YSQTYFRFQE EIKENTKNDK QMVQYIYKYT   120
SYPDPILLMK SARNSCWSKD AEYGLYSIYQ GGIFELKEND RIFVSVTNEH LIDMDHEASF   180
FGAFLVG                                                            187

SEQ ID NO: 3              moltype = AA   length = 168
FEATURE                   Location/Qualifiers
REGION                    1..168
                          note = amino acid sequences of soluble TRAIL
source                    1..168
                          mol_type = protein
                          organism = synthetic construct
SEQUENCE: 3
VRERGPQRVA AHITGTRGRS NTLSSPNSKN EKALGRKINS WESSRSGHSF LSNLHLRNGE   60
LVIHEKGFYY IYSQTYFRFQ EEIKENTKND KQMVQYIYKY TSYPDPILLM KSARNSCWSK   120
DAEYGLYSIY QGGIFELKEN DRIFVSVTNE HLIDMDHEAS FFGAFLVG                168

SEQ ID NO: 4              moltype = AA   length = 98
FEATURE                   Location/Qualifiers
source                    1..98
                          mol_type = protein
                          organism = Homo sapiens
SEQUENCE: 4
MNQTAILICC LIFLTLSGIQ GVPLSRTVRC TCISISNQPV NPRSLEKLEI IPASQFCPRV   60
EIIATMKKKG EKRCLNPESK AIKNLLKAVS KERSKRSP                           98

SEQ ID NO: 5              moltype = AA   length = 258
FEATURE                   Location/Qualifiers
REGION                    1..258
                          note = amino acid sequences of TRAILR3/ TNFRSF10C
source                    1..258
                          mol_type = protein
                          organism = synthetic construct
SEQUENCE: 5
ARIPKTLKFV VVIVAVLLPV LAYSATTARQ EEVPQQTVAP QQQRHSFKGE ECPAGSHRSE   60
HTGACNPCTE GVDYTNASNN EPSCFPCTVC KSDQKHKSSC TMTRDTVCQC KEGTFRNENS   120
PEMCRKCSRC PSGEVQVSNC TSWDDIQCVE EFGANATVET PAAEETMNTS PGTPAPAAEE   180
TMNTSPGTPA PAAEETMTTS PGTPAPAAEE TMTTSPGTPA PAAEETMTTS PGTPASSHYL   240
SCTIVGIIVL IVLLIVFV                                                258

SEQ ID NO: 6              moltype = AA   length = 259
FEATURE                   Location/Qualifiers
REGION                    1..259
                          note = amino acid sequences of TRAILR3/ TNFRSF10C
source                    1..259
                          mol_type = protein
                          organism = synthetic construct
SEQUENCE: 6
MARIPKTLKF VVVIVAVLLP VLAYSATTAR QEEVPQQTVA PQQQRHSFKG EECPAGSHRS   60
EHTGACNPCT EGVDYTNASN NEPSCFPCTV CKSDQKHKSS CTMTRDTVCQ CKEGTFRNEN   120
SPEMCRKCSR CPSGEVQVSN CTSWDDIQCV EEFGANATVE TPAAEETMNT SPGTPAPAAE   180
ETMNTSPGTP APAAEETMTT SPGTPAPAAE ETMTTSPGTP APAAEETMTT SPGTPASSHY   240
LSCTIVGIIV LIVLLIVFV                                               259

SEQ ID NO: 7              moltype = AA   length = 385
FEATURE                   Location/Qualifiers
REGION                    1..385
                          note = amino acid sequences of TRAILR4/ TNFRSF10D
source                    1..385
                          mol_type = protein
                          organism = synthetic construct
SEQUENCE: 7
MGLWGQSVPT ASSARAGRYP GARTASGTRP WLLDPKILKF VVFIVAVLLP VRVDSATIPR   60
QDEVPQQTVA PQQQRRSLKE EECPAGSHRS EYTGACNPCT EGVDYTIASN NLPSCLLCTV   120
CKSGQTNKSS CTTTRDTVCQ CEKGSFQDKN SPEMCRTCRT GCPRGMVKVS NCTPRSDIKC   180
KNESAASSGK TPAAEETVTT ILGMLASPYH YLIIIVVLVI ILAVVVVGFS CRKKFISYLK   240
GICSGGGGGP ERVHRVLFRR RSCPSRVPGA EDNARNETLS NRYLQPTQVS EQEIQGQELA   300
```

```
ELTGVTVESP EEPQRLLEQA EAEGCQRRRL LVPVNDADSA DISTLLDASA TLEEGHAKET   360
IQDQLVGSEK LFYEEDEAGS ATSCL                                        385

SEQ ID NO: 8              moltype = AA  length = 386
FEATURE                   Location/Qualifiers
REGION                    1..386
                          note = amino acid sequences of TRAILR4/ TNFRSF10D
source                    1..386
                          mol_type = protein
                          organism = synthetic construct
SEQUENCE: 8
MGLWGQSVPT ASSARAGRYP GARTASGTRP WLLDPKILKF VVFIVAVLLP VRVDSATIPR   60
QDEVPQQTVA PQQQRRSLKE EECPAGSHRS EYTGACNPCT EGVDYTIASN NLPSCLLCTV   120
CKSGQTNKSS CTTTRDTVCQ CEKGSFQDKN SPEMCRTCRT GCPRGMVKVS NCTPRSDIKC   180
KNESAASSTG KTPAAEETVT TILGMLASPY HYLIIIVVLV IILAVVVGF SCRKKFISYL    240
KGICSGGGGG PERVHRVLFR RRSCPSRVPG AEDNARNETL SNRYLQPTQV SEQEIQGQEL   300
AELTGVTVEL PEEPQRLLEQ AEAEGCQRRR LLVPVNDADS ADISTLLDAS ATLEEGHAKE   360
TIQDQLVGSE KLFYEEDEAG SATSCL                                       386

SEQ ID NO: 9              moltype = AA  length = 468
FEATURE                   Location/Qualifiers
REGION                    1..468
                          note = amino acid sequences of TRAIL-R1/ TNFRSF10A
source                    1..468
                          mol_type = protein
                          organism = synthetic construct
SEQUENCE: 9
MAPPPARVHL GAFLAVTPNP GSAASGTEAA AATPSKVWGS SAGRIEPRGG GRGALPTSMG   60
QHGPSARARA GRAPGPRPAR EASPRLRVHK TFKFVVVGVL LQVVPSSAAT IKLHDQSIGT   120
QQWEHSPLGE LCPPGSHRSE HPGACNRCTE GVGYTNASNN LFACLPCTAC KSDEEERSPC   180
TTTRNTACQC KPGTFRNDNS AEMCRKCSRG CPRGMVKVKD CTPWSDIECV HKESGNGHNI   240
WVILVVTLVV PLLLVAVLIV CCCIGSGCGG DPKCMDRVCF WRLGLLRPG AEDNAHNEIL    300
SNADSLSTFV SEQQMESQEP ADLTGVTVQS PGEAQCLLGP AEAEGSQRRR LLVPANGADP   360
TETLMLFFDK FANIVPFDSW DQLMRQLDLT KNEIDVVRAG TAGPGDALYA MLMKWVNKTG   420
RNASIHTLLD ALERMEERHA REKIQDLLVD SGKFIYLEDG TGSAVSLE                468

SEQ ID NO: 10             moltype = AA  length = 468
FEATURE                   Location/Qualifiers
REGION                    1..468
                          note = amino acid sequences of TRAIL-R1/ TNFRSF10A
source                    1..468
                          mol_type = protein
                          organism = synthetic construct
SEQUENCE: 10
MAPPPARVHL GAFLAVTPNP GSAASGTEAA AATPSKVWGS SAGRIEPRGG GRGALPTSMG   60
QHGPSARARA GRAPGPRPAR EASPRLRVHK TFKFVVVGVL LQVVPSSAAT IKLHDQSIGT   120
QQWEHSPLGE LCPPGSHRSE HPGACNRCTE GVGYTNASNN LFACLPCTAC KSDEEERSPC   180
TTTRNTACQC KPGTFRNDNS AEMCRKCSRG CPRGMVKVKD CTPWSDIECV HKESGNGHNI   240
WVILVVTLVV PLLLVAVLIV CCCIGSGCGG DPKCMDRVCF WRLGLLRPG AEDNAHNEIL    300
SNADSLSTFV SEQQMESQEP ADLTGVTVQS PGEAQCLLGP AEAEGSQRRR LLVPANGADP   360
TETLMLFFDK FANIVPFDSW DQLMRQLDLT KNEIDVVRAG TAGPGDALYA MLMKWVNKTG   420
RNASIHTLLD ALERMEERHA REKIQDLLVD SGKFIYLEDG TGSAVSLE                468

SEQ ID NO: 11             moltype = AA  length = 310
FEATURE                   Location/Qualifiers
REGION                    1..310
                          note = amino acid sequences of TRAIL-R1/ TNFRSF10A
source                    1..310
                          mol_type = protein
                          organism = synthetic construct
SEQUENCE: 11
MAPPPARVHL ACKSDEEERS PCTTTRNTAC QCKPGTFRND NSAEMCRKCS RGCPRGMVKV   60
KDCTPWSDIE CVHKESGNGH NIWVILVVTL VVPLLLVAVL IVCCCIGSGC GGDPKCMDRV   120
CFWRLGLLRG PGAEDNAHNE ILSNADSLST FVSEQQMESQ EPADLTGVTV QSPGEAQCLL   180
GPAEAEGSQR RRLLVPANGA DPTETLMLFF DKFANIVPFD SWDQLMRQLD LTKNEIDVVR   240
AGTAGPGDAL YAMLMKWVNK TGRNASIHTL LDALERMEER HAREKIQDLL VDSGKFIYLE   300
DGTGSAVSLE                                                         310

SEQ ID NO: 12             moltype = AA  length = 440
FEATURE                   Location/Qualifiers
REGION                    1..440
                          note = amino acid sequences of TRAIL-R2/ TNFRSF10B
source                    1..440
                          mol_type = protein
                          organism = synthetic construct
SEQUENCE: 12
MEQRGQNAPA ASGARKRHGP GPREARGARP GPRVPKTLVL VVAAVLLLVS AESALITQQD   60
LAPQQRAAPQ QKRSSPSEGL CPPGHHISED GRDCISCKYG QDYSTHWNDL LFCLRCTRCD   120
SGEVELSPCT TTRNTVCQCE EGTFREEDSP EMCRKCRTGC PRGMVKVGDC TPWSDIECVH   180
```

```
KESGTKHSGE VPAVEETVTS SPGTPASPCS LSGIIIGVTV AAVVLIVAVF VCKSLLWKKV    240
LPYLKGICSG GGGDPERVDR SSQRPGAEDN VLNEIVSILQ PTQVPEQEME VQEPAEPTGV    300
NMLSPGESEH LLEPAEAERS QRRRLLVPAN EGDPTETLRQ CFDDFADLVP FDSWEPLMRK    360
LGLMDNEIKV AKAEAAGHRD TLYTMLIKWV NKTGRDASVH TLLDALETLG ERLAKQKIED    420
HLLSSGKFMY LEGNADSAMS                                               440

SEQ ID NO: 13           moltype = AA  length = 440
FEATURE                 Location/Qualifiers
REGION                  1..440
                        note = amino acid sequences of TRAIL-R2/ TNFRSF10B
source                  1..440
                        mol_type = protein
                        organism = synthetic construct
SEQUENCE: 13
MEQRGQNAPA ASGARKRHGP GPREARGARP GPRVPKTLVL VVAAVLLLVS AESALITQQD    60
LAPQQRAAPQ QKRSSPSEGL CPPGHHISED GRDCISCKYG QDYSTHWNDL LFCLRCTRCD    120
SGEVELSPCT TTRNTVCQCE EGTFREEDSP EMCRKCRTGC PRGMVKVGDC TPWSDIECVH    180
KESGTKHSGE VPAVEETVTS SPGTPASPCS LSGIIIGVTV AAVVLIVAVF VCKSLLWKKV    240
LPYLKGICSG GGGDPERVDR SSQRPGAEDN VLNEIVSILQ PTQVPEQEME VQEPAEPTGV    300
NMLSPGESEH LLEPAEAERS QRRRLLVPAN EGDPTETLRQ CFDDFADLVP FDSWEPLMRK    360
LGLMDNEIKV AKAEAAGHRD TLYTMLIKWV NKTGRDASVH TLLDALETLG ERLAKQKIED    420
HLLSSGKFMY LEGNADSAMS                                               440

SEQ ID NO: 14           moltype = AA  length = 411
FEATURE                 Location/Qualifiers
REGION                  1..411
                        note = amino acid sequences of TRAIL-R2/ TNFRSF10B
source                  1..411
                        mol_type = protein
                        organism = synthetic construct
SEQUENCE: 14
MEQRGQNAPA ASGARKRHGP GPREARGARP GPRVPKTLVL VVAAVLLLVS AESALITQQD    60
LAPQQRAAPQ QKRSSPSEGL CPPGHHISED GRDCISCKYG QDYSTHWNDL LFCLRCTRCD    120
SGEVELSPCT TTRNTVCQCE EGTFREEDSP EMCRKCRTGC PRGMVKVGDC TPWSDIECVH    180
KESGIIIGVT VAAVVLIVAV FVCKSLLWKK VLPYLKGICS GGGGDPERVD RSSQRPGAED    240
NVLNEIVSIL QPTQVPEQEM EVQEPAEPTG VNMLSPGESE HLLEPAEAER SQRRRLLVPA    300
NEGDPTETLR QCFDDFADLV PFDSWEPLMR KLGLMDNEIK VAKAEAAGHR DTLYTMLIKW    360
VNKTGRDASV HTLLDALETL GERLAKQKIE DHLLSSGKFM YLEGNADSAM S             411

SEQ ID NO: 15           moltype = AA  length = 198
FEATURE                 Location/Qualifiers
REGION                  1..198
                        note = Amino acid sequence of NGAL
source                  1..198
                        mol_type = protein
                        organism = synthetic construct
SEQUENCE: 15
MPLGLLWLGL ALLGALHAQA QDSTSDLIPA PPLSKVPLQQ NFQDNQFQGK WYVVGLAGNA    60
ILREDKDPQK MYATIYELKE DKSYNVTSVL FRKKKCDYWI RTFVPGCQPG EFTLGNIKSY    120
PGLTSYLVRV VSTNYNQHAM VFFKKVSQNR EYFKITLYGR TKELTSELKE NFIRFSKSLG    180
LPENHIVFPV PIDQCIDG                                                 198

SEQ ID NO: 16           moltype = AA  length = 444
FEATURE                 Location/Qualifiers
REGION                  1..444
                        note = Amino acid sequences of MMP8
source                  1..444
                        mol_type = protein
                        organism = synthetic construct
SEQUENCE: 16
MQQIPQEKSI NDYLEKFYQL PSNQYQSTRK NGTNVIVEKL KEMQRFFGLN VTGKPNEETL    60
DMMKKPRCGV PDSGGFMLTP GNPKWERTNL TYRIRNYTPQ LSEAEVERAI KDAFELWSVA    120
SPLIFTRISQ GEADINIAFY QRDHGDNSPF DGPNGILAHA FQPGQGIGGD AHFDAEETWT    180
NTSANYNLFL VAAHEFGHSL GLAHSSDPGA LMYPNYAFRE TSNYSLPQDD IDGIQAIYGL    240
SSNPIQPTGP STPKPCDPSL TFDAITTLRG EILFFKDRYF WRRHPQLQRV EMNFISLFWP    300
SLPTGIQAAY EDFDRDLIFL FKGNQYWALS GYDILQGYPK DISNYGFPSS VQAIDAAVFY    360
RSKTYFFVND QFWRYDNQRQ FMEPGYPKSI SGAFPGIESK VDAVFQQEHF FHVFSGPRYY    420
AFDLIAQRVT RVARGNKWLN CRYG                                          444

SEQ ID NO: 17           moltype = AA  length = 444
FEATURE                 Location/Qualifiers
REGION                  1..444
                        note = Amino acid sequences of MMP8
source                  1..444
                        mol_type = protein
                        organism = synthetic construct
SEQUENCE: 17
MQQIPQEKSI NDYLEKFYQL PSNQYQSTRK NGTNVIVEKL KEMQRFFGLN VTGKPNEETL    60
DMMKKPRCGV PDSGGFMLTP GNPKWERTNL TYRIRNYTPQ LSEAEVERAI KDAFELWSVA    120
```

```
SPLIFTRISQ GEADINIAFY QRDHGDNSPF DGPNGILAHA FQPGQGIGGD AHFDAEETWT 180
NTSANYNLFL VAAHEFGHSL GLAHSSDPGA LMYPNYAFRE TSNYSLPQDD IDGIQAIYGL 240
SSNPIQPTGP STPKPCDPSL TFDAITTLRG EILFFKDRYF WRRHPQLQRV EMNFISLFWP 300
SLPTGIQAAY EDFDRDLIFL FKGNQYWALS GYDILQGYPK DISNYGFPSS VQAIDAAVFY 360
RSKTYFFVND QFWRYDNQRQ FMEPGYPKSI SGAFPGIESK VDAVFQQEHF FHVFSGPRYY 420
AFDLIAQRVT RVARGNKWLN CRYG                                     444

SEQ ID NO: 18          moltype = AA  length = 467
FEATURE                Location/Qualifiers
REGION                 1..467
                       note = Amino acid sequences of MMP8
source                 1..467
                       mol_type = protein
                       organism = synthetic construct
SEQUENCE: 18
MFSLKTLPFL LLLHVQISKA FPVSSKEKNT KTVQDYLEKF YQLPSNQYQS TRKNGTNVIV 60
EKLKEMQRFF GLNVTGKPNE ETLDMMKKPR CGVPDSGGFM LTPGNPKWER TNLTYRIRNY 120
TPQLSEAEVE RAIKDAFELW SVASPLIFTR ISQGEADINI AFYQRDHGDN SPFDGPNGIL 180
AHAFQPGQGI GGDAHFDAEE TWTNTSANYN LFLVAAHEFG HSLGLAHSSD PGALMYPNYA 240
FRETSNYSLP QDDIDGIQAI YGLSSNPIQP TGPSTPKPCD PSLTFDAITT LRGEILFFKD 300
RYFWRRHPQL QRVEMNFISL FWPSLPTGIQ AAYEDFDRDL IFLFKGNQYW ALSGYDILQG 360
YPKDISNYGF PSSVQAIDAA VFYRSKTYFF VNDQFWRYDN QRQFMEPGYP KSISGAFPGI 420
ESKVDAVFQQ EHFFHVFSGP RYYAFDLIAQ RVTRVARGNK WLNCRYG            467
```